US010195189B2

(12) United States Patent
Atuegbu et al.

(10) Patent No.: US 10,195,189 B2
(45) Date of Patent: Feb. 5, 2019

(54) 2-PHENETHENYLTETRAHYDRO ISOQUINOLINES USEFUL AS ANTI-HIV COMPOUNDS

(71) Applicant: Prosetta Antiviral, Inc., San Franscisco, CA (US)

(72) Inventors: Andy Atuegbu, Dublin, CA (US); Dennis Solas, San Francisco, CA (US); Clarence R. Hurt, Los Altos, CA (US); Anatoliy Kitaygorodskyy, San Francisco, CA (US)

(73) Assignee: Prosetta Antiviral, Inc., San Francisco, CA (US)

( * ) Notice: Subject to any disclaimer, the term of this patent is extended or adjusted under 35 U.S.C. 154(b) by 0 days.

(21) Appl. No.: 15/536,104

(22) PCT Filed: Dec. 15, 2015

(86) PCT No.: PCT/US2015/065893
§ 371 (c)(1),
(2) Date: Jun. 14, 2017

(87) PCT Pub. No.: WO2016/100391
PCT Pub. Date: Jun. 23, 2016

(65) Prior Publication Data
US 2017/0368051 A1    Dec. 28, 2017

Related U.S. Application Data

(60) Provisional application No. 62/092,115, filed on Dec. 15, 2014.

(51) Int. Cl.
| | | |
|---|---|---|
| A61K 31/472 | (2006.01) | |
| C07D 217/02 | (2006.01) | |
| C07D 217/04 | (2006.01) | |
| C07D 217/06 | (2006.01) | |
| C07D 401/06 | (2006.01) | |

(52) U.S. Cl.
CPC .......... *A61K 31/472* (2013.01); *C07D 217/02* (2013.01); *C07D 217/04* (2013.01); *C07D 217/06* (2013.01); *C07D 401/06* (2013.01)

(58) Field of Classification Search
CPC .............................. C07D 215/02; C07D 217/02
See application file for complete search history.

(56) References Cited

U.S. PATENT DOCUMENTS

| | | | | |
|---|---|---|---|---|
| 8,227,459 | B2 * | 7/2012 | Plattner ................. | C07D 417/14 514/224.8 |
| 9,518,022 | B2 * | 12/2016 | Atuegbu ............. | C07D 217/02 |
| 2012/0157435 | A1 * | 6/2012 | Hurt ................... | A61K 31/5415 514/210.21 |
| 2012/0238543 | A1 * | 9/2012 | Hurt ..................... | C07D 279/18 514/210.21 |
| 2012/0270854 | A1 * | 10/2012 | Hurt .................... | A61K 31/5415 514/210.21 |
| 2012/0302556 | A1 * | 11/2012 | Hurt ...................... | C07D 279/20 514/225.8 |
| 2016/0168100 | A1 * | 6/2016 | Atuegbu .............. | C07D 217/02 514/307 |

FOREIGN PATENT DOCUMENTS

WO    WO 2012/145567 A1    10/2012

OTHER PUBLICATIONS

A. Brossi et al., 44 Helvetica Chimica Acta 1558-1565 (1961).*
CAS Registry Nos. (Mar. 2014).*
X. Liu et al., 17 Organic Letters, 2396-2399 (2015).*
U.S. Appl. No. 11/903,494, filed Sep. 20, 2007, now abandoned.
U.S. Appl. No. 10/346,654, filed Jan. 17, 2003, now U.S. Pat. No. 7,348,134.
U.S. Appl. No. 10/243,509, filed Sep. 13, 2002, now U.S. Pat. No. 7,638,269.
U.S. Appl. No. 10/040,206, filed Jan. 2, 2002, now abandoned.
U.S. Appl. No. 09/020,144, filed Feb. 6, 1998, now U.S. Pat. No. 6,593,103.
U.S. Appl. No. 10/527,973, filed Aug. 2, 2006, now abandoned.
U.S. Appl. No. 11/473,460, filed Jun. 22, 2006, now abandoned; U.S. Pat Pub No. 2007-0015211 (Jan. 18, 2007).
U.S. Appl. No. 11/567,142, filed Dec. 5, 2006, now abandoned; U.S. Pat Pub No. 2007-0202537 (Aug. 30, 2007).
U.S. Appl. No. 11/955,337, filed Dec. 12, 2007, now abandoned; U.S. Pat Pub No. 2009-0155761(Jun. 18, 2009).
U.S. Appl. No. 12/062,491, filed Apr. 3, 2008, now U.S. Pat. No. 8,227,459; U.S. Pat Pub. No. 2011-0178071 (Oct. 16, 2008).
U.S. Appl. No. 12/699,831, filed Feb. 3, 2010, now abandoned; U.S. Pat Pub. No. 2010-0211327 (Aug. 19, 2010).
U.S. Appl. No. 13/099,006, filed May 2, 2011, now U.S. Appl. No. 8,785,434; U.S. Pat Pub. No. 2012-0157435 (Jun. 21, 2012).
U.S. Appl. No. 13/316,423, filed Dec. 9, 2011, now U.S. Pat. No. 8,796,448.
U.S. Appl. No. 13/423,141, filed Mar. 16, 2012, now U.S. Pat. No. 8,759,336; U.S. Pat Pub. No. 2012-0238543 (Sep. 20, 2012).
U.S. Appl. No. 13/433,378, filed Mar. 29, 2012, now U.S. Pat. No. 8,809,317; U.S. Pat Pub. No. 2012-0302556 (Nov. 29, 2012).
U.S. Appl. No. 13/451,608, filed Apr. 20, 2012, now U.S. Pat. No. 8,828,986; U.S. Pat Pub. No. 2012-0270854 (Oct. 25, 2012).
U.S. Appl. No. 13/457,481, filed Apr. 26, 2012, now abandoned; U.S. Pat Pub. No. 2012-0301904 (Nov. 29, 2012).
U.S. Appl. No. 13/566,897, filed Aug, 3, 2012, now abandoned; U.S. Pat Pub. No. 2013-0053267 (Feb. 28, 2013).

(Continued)

*Primary Examiner* — Alexander R Pagano
(74) *Attorney, Agent, or Firm* — Morgan, Lewis & Bockius LLP

(57) ABSTRACT

This invention provides, among other things, tetrahydroisoquinolines useful for treating viral infections, pharmaceutical formulations containing such compounds, as well as methods of inhibiting the replication of a virus, such as HIV, or treating a disease, such as AIDS.

31 Claims, No Drawings

(56) References Cited

OTHER PUBLICATIONS

U.S. Appl. No. 13/950,232, filed Jul. 24, 2013, now abandoned; U.S. Pat Pub. No. 2014-0106365 (Apr. 17, 2014).
U.S. Appl. No. 14/677,819, filed Apr. 2, 2015 U.S. Pat Pub. No. 2015-0226748 (Aug. 13, 2015).
U.S. Appl. No. 14/970,393, filed Dec. 15, 2015, now U.S. Pat. No. 9,518,022 U.S. Pat Pub. No. 2016-0168100 (Jun. 16, 2016).
U.S. Appl. No. 15/427,993, filed Feb. 8, 2017 U.S. Pat Pub. No. 2017-0159097 (Jun. 8, 2017).
Czarnocki, et al. "(R)•2•Alkoxycarbonyl-1-formyl-1,2,3,4-tetrahydro-6, 7-dimethoxyisoquinolines from d-(−)-Tartaric Acid: Synthesis of (S)-Homolaudanosine and (S)-2,3,9, 10, 11-Pentamethoxyhomoprotoberberine", J. Chem. Soc., Chem. Commun., 1987, pp. 493-494.
Santangelo Freel, et al. "Synthesis and Structure Activity Relationship of Tetrahydroisoquinoline-Based Potentiators of GluN2C and GluN2D Containing N-Methyl-D-aspartate Receptors", Journal of Medicinal Chemistry, pp. 5351-5381.
XP-002753935 Database CAPLUS—Chemical Abstract, 2 pages.
Saito, et al. "Reissert-Like Alkenylation of Azaaromatic Compounds with Alkenylzirconocene Chloride Complexes", Heterocycles, vol. 86, No. 1, 2012, pp. 267-280.
XP-002753936 Database CAPLUS—Chemical Abstract, 2 pages.
Morimoto, et al. "Asymmetric Synthesis of (S)-Norlaudanosine and (S)-Tetrahydrohomopapverine by Catalytic Asymmetric Hydrogenation with Chiral Diphosphine-Iridium(I)-Phthalimide Complex Catalysts[1]", Heterocycles, vol. 43, No. 12, 1996, pp. 2557-2560.

\* cited by examiner

2-PHENETHENYLTETRAHYDRO ISOQUINOLINES USEFUL AS ANTI-HIV COMPOUNDS

CROSS-REFERENCE TO RELATED APPLICATIONS

This application is a National Stage of International Patent Application No. PCT/US2015/065893 filed Dec. 15, 2015 and published as WO 2016/100391 A1, which claims priority to U.S. Provisional Application No. 62/092,115 filed Dec. 15, 2014, the entire contents of which applications is incorporated herein for all purposes by this reference.

BACKGROUND OF THE INVENTION

There is a need in the art to discover new compounds useful as antivirals.

It has now been discovered that certain tetrahydroisoquinolines are surprisingly effective antivirals. This, and other uses of these compounds are described herein.

SUMMARY OF THE INVENTION

This invention provides, among other things, novel compounds useful for treating viral infections, pharmaceutical formulations containing such compounds, as well as methods of inhibiting the replication of a virus or treating a disease.

In an exemplary embodiment, the invention provides a compound of the formula which is:

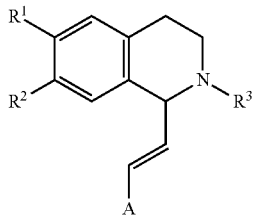

in which
- $R^1$ is H or unsubstituted alkoxy or phenyl substituted alkoxy,
- $R^2$ is H or $CF_3$ or unsubstituted alkoxy or phenyl substituted alkoxy,
- $R^3$ is H or —C(O)OR$^4$ or —C(O)R$^4$ or —C(O)NR$^4$R$^5$, wherein
- $R^4$ and $R^5$ are independently selected from unsubstituted alkyl, unsubstituted phenyl, or unsubstituted pyridinyl;
- A is substituted or unsubstituted phenyl.

Also provided are hydrates, salts and solvates of these compounds.

In an exemplary embodiment, there is provided a pharmaceutical formulation comprising a compound of the invention and a pharmaceutically acceptable diluent or carrier.

Also provided is a method of treating a subject infected with a lentivirus, e.g., human immunodeficiency virus (HIV). The method comprises, administering to the subject a therapeutically effective amount of a compound of the invention.

Other embodiments, objects and advantages of the invention are apparent from the detailed description that follows.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis (diphenylphosphino) ferroceneldichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R' C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR" C(O)$_2$R', —NR''''-C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR" C(O)$_2$R', —NR''''-C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted $C_1$ or $C_2$ or $C_3$ or $C_4$ or $C_5$ or $C_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are all encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (5)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the animal. Representative carriers include water, oils, both vegetable and mineral, cream bases, lotion bases, ointment bases and the like. These bases include suspending agents, thickeners, penetration enhancers, and the like. Their formulation is well known to those in the pharmaceutical arts. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Salt counterion", as used herein, refers to positively charged ions that associate with a compound of the invention. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

II. Introduction

The invention provides tetrahydroisoquinolines, as well as pharmaceutical formulations containing such compounds or combinations of these compounds with at least one additional therapeutically effective agent, can be used for, among other things, treating viral infections.

III. The Compounds

III. a)

In one aspect, the invention provides a compound of the invention. In an exemplary embodiment, the invention is a compound described herein. In an exemplary embodiment, the invention is a compound according to a formula described herein.

In an exemplary embodiment, the invention provides a compound of the formula which is:

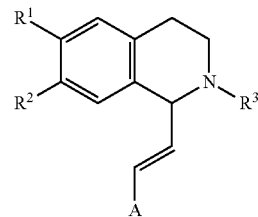

in which
  $R^1$ is H or unsubstituted alkoxy or phenyl substituted alkoxy,
  $R^2$ is H or $CF_3$ or unsubstituted alkoxy or phenyl substituted alkoxy,
  $R^3$ is H or —C(O)OR$^4$ or —C(O)R$^4$ or —C(O)NR$^4$R$^5$,
    wherein
      $R^4$ and $R^5$ are independently selected from unsubstituted alkyl, unsubstituted phenyl, or unsubstituted pyridinyl;

A is substituted or unsubstituted phenyl or substituted or unsubstituted pyrazole or substituted or unsubstituted pyridinyl or substituted or unsubstituted thienyl or substituted or unsubstituted pyrimidinyl or substituted or unsubstituted pyrrole or substituted or unsubstituted thiazolyl Also provided are hydrates, salts and solvates of these compounds.

In an exemplary embodiment, A, R² and R³ are as described herein, and R¹ is —CH₃. In an exemplary embodiment, A, R² and R³ are as described herein, and R¹ is

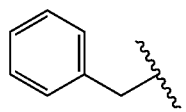

In an exemplary embodiment, A, R² and R³ are as described herein, and R¹ is H.

In an exemplary embodiment, A, R¹ and R³ are as described herein, and R² is —CH₃. In an exemplary embodiment, A, R¹ and R³ are as described herein, and R² is

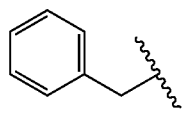

In an exemplary embodiment, A, R¹ and R³ are as described herein, and R² is H.

In an exemplary embodiment, A, R¹ and R² are as described herein, and R³ is H. In an exemplary embodiment, A, R¹ and R² are as described herein, and R³ is —C(O)OCH₃. In an exemplary embodiment, A, R¹ and R² are as described herein, and R³ is —C(O)OC(CH₃)₃. In an exemplary embodiment, A, R¹ and R² are as described herein, and R³ is

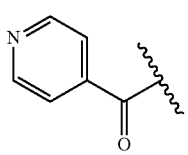

In an exemplary embodiment, A, R¹ and R² are as described herein, and R³ is

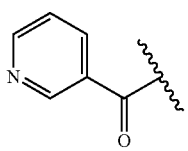

In an exemplary embodiment, A, R¹ and R² are as described herein, and R³ is

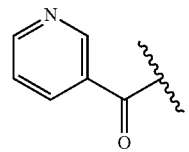

In an exemplary embodiment, A, R¹ and R² are as described herein, and R³ is

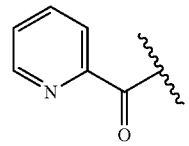

In an exemplary embodiment, A, R¹ and R² are as described herein, and R³ is

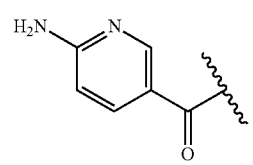

In an exemplary embodiment, A, R¹ and R² are as described herein, and R³ is

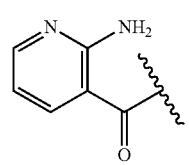

In an exemplary embodiment, A, R¹ and R² are as described herein, and R³ is

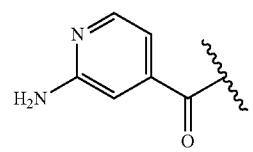

In an exemplary embodiment, A, R¹ and R² are as described herein, and R³ is

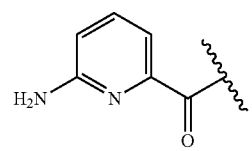

In an exemplary embodiment, A, R¹ and R² are as described herein, and R³ is

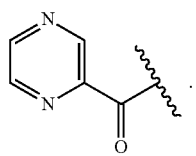 [SMILES: *C(=O)c1cnccn1]

In an exemplary embodiment, A, $R^1$ and $R^2$ are as described herein, and $R^3$ is —C(O)NH$_2$. In an exemplary embodiment, A, $R^1$ and $R^2$ are as described herein, and $R^3$ is —C(O)NHC(CH$_3$)$_3$. In an exemplary embodiment, A, $R^1$ and $R^2$ are as described herein, and $R^3$ is —(CH$_2$)$_n$CH$_3$, wherein n is an integer selected from 0 or 1 or 2 or 3 or 4 or 5. In an exemplary embodiment, A, $R^1$ and $R^2$ are as described herein, and $R^3$ is —(CH$_2$)$_n$CH$_3$, wherein n is an integer selected from 6 or 7 or 8 or 9 or 10. In an exemplary embodiment, A, $R^1$ and $R^2$ are as described herein, and $R^3$ is —(CH$_2$)$_n$CH$_3$, wherein n is an integer selected from 2 or 3 or 4. In an exemplary embodiment, A, $R^1$ and $R^2$ are as described herein, and $R^3$ is —(CH$_2$)$_3$CH$_3$. In an exemplary embodiment, A, $R^1$ and $R^2$ are as described herein, and $R^3$ is —CH$_3$.

In an exemplary embodiment, $R^1$, $R^2$ and $R^3$ are as described herein, and A is

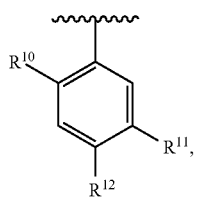

wherein each $R^{10}$, $R^{11}$ and $R^{12}$ is independently selected from H or halogen or unsubstituted alkyl or halogen-substituted alkyl or unsubstituted alkoxy or phenyl-substituted alkoxy. In an exemplary embodiment, $R^{11}$ and $R^{12}$ are as described herein, and $R^{10}$ is —CH$_3$. In an exemplary embodiment, $R^{11}$ and $R^{12}$ are as described herein, and $R^{10}$ is —CH$_2$CH$_3$. In an exemplary embodiment, $R^{11}$ and $R^{12}$ are as described herein, and $R^{10}$ is tert-butyl. In an exemplary embodiment, and $R^{12}$ are as described herein, and $R^{10}$ is —CF$_3$. In an exemplary embodiment, $R^{11}$ and $R^{12}$ are as described herein, and $R^{10}$ is —OBn. In an exemplary embodiment, and $R^{12}$ are as described herein, and $R^{10}$ is halogen. In an exemplary embodiment, $R^{11}$ and $R^{12}$ are as described herein, and $R^{10}$ is Cl. In an exemplary embodiment, $R^{11}$ and $R^{12}$ are as described herein, and $R^{10}$ is H. In an exemplary embodiment, $R^{10}$ and $R^{12}$ are as described herein, and $R^{11}$ is —OCH$_3$. In an exemplary embodiment, $R^{10}$ and $R^{12}$ are as described herein, and $R^{11}$ is —OBn. In an exemplary embodiment, $R^{10}$ and $R^{12}$ are as described herein, and $R^{11}$ is H. In an exemplary embodiment, $R^{10}$ and $R^{11}$ are as described herein, and $R^{12}$ is —OCH$_3$. In an exemplary embodiment, $R^{10}$ and $R^{11}$ are as described herein, and $R^{12}$ is —OBn. In an exemplary embodiment, $R^{10}$ and $R^{11}$ are as described herein, and $R^{12}$ is halogen. In an exemplary embodiment, $R^{10}$ and $R^{11}$ are as described herein, and $R^{12}$ is H. In an exemplary embodiment, $R^{10}$ is unsubstituted C$_1$-C$_6$ alkoxy, $R^{11}$ is H, and $R^{12}$ is unsubstituted C$_1$-C$_6$ alkoxy. In an exemplary embodiment, $R^{10}$ is methoxy, is H, and $R^{12}$ is unsubstituted C$_1$-C$_6$ alkoxy. In an exemplary embodiment, $R^{10}$ is unsubstituted C$_1$-C$_6$ alkoxy, $R^{11}$ is H, and $R^{12}$ is methoxy. In an exemplary embodiment, $R^{10}$ is methoxy, is H, and $R^{12}$ is methoxy. In an exemplary embodiment, $R^{10}$ is H, $R^{11}$ is unsubstituted C$_1$-C$_6$ alkoxy, and $R^{12}$ is unsubstituted C$_1$-C$_6$ alkoxy. In an exemplary embodiment, $R^{10}$ is H, $R^{11}$ is methoxy, and $R^{12}$ is unsubstituted C$_1$-C$_6$ alkoxy. In an exemplary embodiment, $R^{10}$ is H, is unsubstituted C$_1$-C$_6$ alkoxy, and $R^{12}$ is methoxy. In an exemplary embodiment, $R^{10}$ is $R^{11}$ is methoxy, and $R^{12}$ is methoxy. In an exemplary H, embodiment, $R^{10}$ is H, $R^{11}$ is unsubstituted C$_4$-C$_6$ alkoxy, and $R^{12}$ is unsubstituted C$_1$-C$_6$ alkoxy. In an exemplary embodiment, $R^{10}$ is H, $R^{11}$ is methoxy, and $R^{12}$ is unsubstituted C$_4$-C$_6$ alkoxy. In an exemplary embodiment, $R^{10}$ is H, $R^{11}$ is butoxy, and $R^{12}$ is methoxy. In an exemplary embodiment, $R^{10}$ is $R^{11}$ is butoxy, and $R^{12}$ is methoxy. In an exemplary embodiment, $R^{10}$ is $R^{11}$ is halogen, and $R^{12}$ is H, unsubstituted C$_1$-C$_6$ alkoxy. In an exemplary embodiment, $R^{10}$ is H, $R^{11}$ is unsubstituted C$_1$-C$_6$ alkoxy, and $R^{12}$ is halogen. In an exemplary embodiment, $R^{10}$ is H, is methoxy, and $R^{12}$ is halogen. In an exemplary embodiment, $R^{10}$ is H, $R^{11}$ is halogen, and $R^{12}$ is methoxy. In an exemplary embodiment, $R^{10}$ is H, $R^{11}$ is F, and $R^{12}$ is unsubstituted C$_1$-C$_6$ alkoxy. In an exemplary embodiment, $R^{10}$ is H, $R^{11}$ is unsubstituted C$_1$-C$_6$ alkoxy, and $R^{12}$ is F. In an exemplary embodiment, $R^{10}$ is unsubstituted C$_1$-C$_6$ alkyl, is unsubstituted C$_1$-C$_6$ alkoxy, and $R^{12}$ is unsubstituted C$_1$-C$_6$ alkoxy. In an exemplary embodiment, $R^{10}$ is unsubstituted C$_1$-C$_3$ alkyl, is unsubstituted C$_1$-C$_3$ alkoxy, and $R^{12}$ is unsubstituted C$_1$-C$_3$ alkoxy. In an exemplary embodiment, $R^{10}$ is methyl, is unsubstituted C$_1$-C$_6$ alkoxy, and $R^{12}$ is unsubstituted C$_1$-C$_6$ alkoxy. In an exemplary embodiment, $R^{10}$ is unsubstituted C$_1$-C$_6$ alkyl, $R^{11}$ is unsubstituted C$_3$-C$_6$ alkoxy, and $R^{12}$ is unsubstituted C$_1$-C$_3$ alkoxy.

In an exemplary embodiment, $R^{10}$ is unsubstituted C$_1$-C$_6$ alkyl, $R^{11}$ is butoxy, and $R^{12}$ is unsubstituted C$_1$-C$_3$ alkoxy. In an exemplary embodiment, $R^{10}$ is unsubstituted C$_1$-C$_6$ alkyl, $R^{11}$ is unsubstituted C$_1$-C$_6$ alkoxy, and $R^{12}$ is methoxy. In an exemplary embodiment, $R^{10}$ is methyl, is unsubstituted C$_1$-C$_6$ alkoxy, and $R^{12}$ is methoxy. In an exemplary embodiment, $R^{10}$ is methyl, $R^{11}$ is butoxy, and $R^{12}$ is methoxy. In an exemplary embodiment, $R^{10}$ is $R^{11}$ is unsubstituted C$_1$-C$_6$ alkoxy, and $R^{12}$ is H, unsubstituted C$_1$-C$_6$ alkoxy. In an exemplary embodiment, $R^{10}$ is H, $R^{11}$ is unsubstituted C$_1$-C$_3$ alkoxy, and $R^{12}$ is unsubstituted C$_1$-C$_3$ alkoxy. In an exemplary embodiment, $R^{10}$ is H, $R^{11}$ is unsubstituted C$_1$-C$_3$ alkoxy, and $R^{12}$ is methoxy. In an exemplary embodiment, $R^{10}$ is H, $R^{11}$ is methoxy, and $R^{12}$ is unsubstituted C$_1$-C$_3$ alkoxy. In an exemplary embodiment, $R^{10}$ is H, $R^{11}$ is methoxy, and $R^{12}$ is methoxy.

In an exemplary embodiment, $R^1$, $R^2$ and $R^3$ are as described herein, and A is

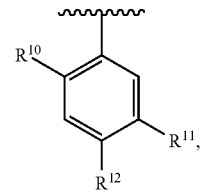

wherein $R^{10}$ is NR$^{20}$R$^{21}$, wherein $R^{20}$ and $R^{21}$ are each independently selected from H or unsubstituted alkyl, and wherein $R^{11}$ and $R^{12}$ are each independently selected from H or halogen or unsubstituted alkyl or halogen-substituted alkyl or unsubstituted alkoxy or phenyl-substituted alkoxy. In an exemplary embodiment, $R^{10}$ is N(CH$_3$)$_2$, wherein $R^{20}$ and $R^{21}$ are each independently selected from H or unsubstituted alkyl, and wherein $R^{11}$ and $R^{12}$ are each independently selected from H or halogen or unsubstituted alkyl or halogen-substituted alkyl or unsubstituted alkoxy or phenyl-substituted alkoxy. In an exemplary embodiment, $R^{10}$ is $NH_2$, wherein $R^{20}$ and $R^{21}$ are each independently selected from H or unsubstituted alkyl, and wherein $R^{11}$ and $R^{12}$ are each independently selected from H or halogen or unsubstituted alkyl or halogen-substituted alkyl or unsubstituted alkoxy or phenyl-substituted alkoxy.

In an exemplary embodiment, $R^1$, $R^2$ and $R^3$ are as described herein, and A is

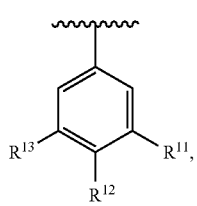

wherein each $R^{11}$, $R^{12}$, and $R^{13}$ is independently selected from H or halogen or unsubstituted alkyl or halogen-substituted alkyl or unsubstituted alkoxy or phenyl-substituted alkoxy, wherein at least one of said $R^{11}$ or $R^{12}$ or $R^{13}$ is unsubstituted alkoxy. In an exemplary embodiment, $R^{11}$ and $R^{12}$ are as described herein, and $R^{13}$ is —$CH_3$. In an exemplary embodiment, $R^{11}$ and $R^{12}$ are as described herein, and $R^{13}$ is —$CH_2CH_3$. In an exemplary embodiment, $R^{11}$ and $R^{12}$ are as described herein, and $R^{13}$ is —$OCH_3$. In an exemplary embodiment, $R^{11}$ and $R^{12}$ are as described herein, and $R^{13}$ is —$OCH_2CH_3$. In an exemplary embodiment, $R^{11}$ is unsubstituted $C_1$-$C_6$ alkoxy, $R^{12}$ is unsubstituted $C_1$-$C_6$ alkoxy, and $R^{13}$ is unsubstituted $C_1$-$C_6$ alkoxy. In an exemplary embodiment, $R^{11}$ is methoxy, $R^{12}$ is unsubstituted $C_1$-$C_6$ alkoxy, and $R^{13}$ is unsubstituted $C_1$-$C_6$ alkoxy. In an exemplary embodiment, $R^{11}$ is unsubstituted $C_1$-$C_3$ alkoxy, $R^{12}$ is methoxy, and $R^{13}$ is unsubstituted $C_1$-$C_3$ alkoxy. In an exemplary embodiment, $R^{11}$ is unsubstituted $C_1$-$C_3$ alkoxy, $R^{12}$ is unsubstituted $C_1$-$C_3$ alkoxy, and $R^{13}$ is unsubstituted $C_1$-$C_3$ alkoxy.

In an exemplary embodiment, $R^1$, $R^2$ and $R^3$ are as described herein, and A is

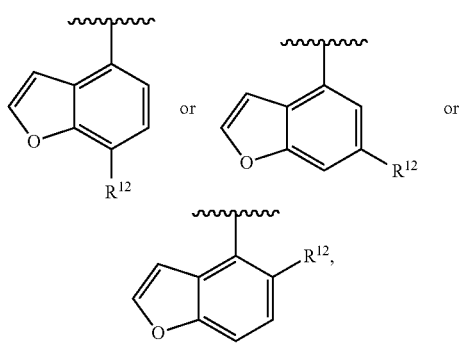

wherein $R^{12}$ is H or halogen or unsubstituted alkyl or halogen-substituted alkyl or unsubstituted alkoxy or phenyl-substituted alkoxy. In an exemplary embodiment, $R^1$, $R^2$ and $R^3$ are as described herein, and A is

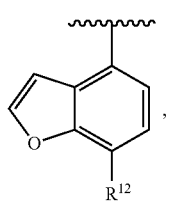

wherein $R^{12}$ is H or halogen or unsubstituted alkyl or halogen-substituted alkyl or unsubstituted alkoxy or phenyl-substituted alkoxy. In an exemplary embodiment, $R^1$, $R^2$ and $R^3$ are as described herein, and A is

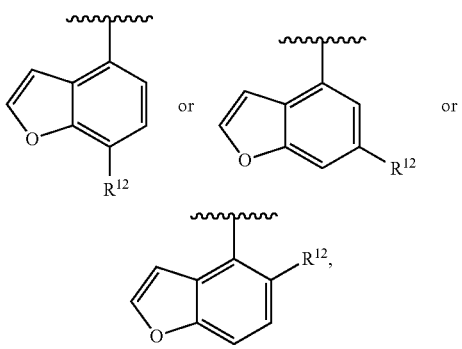

wherein $R^{12}$ is $C_1$-$C_6$ alkoxy. In an exemplary embodiment, $R^1$, $R^2$ and $R^3$ are as described herein, and A is

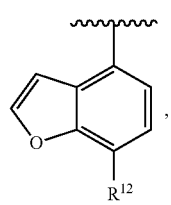

wherein $R^{12}$ is $C_1$-$C_6$ alkoxy.

In an exemplary embodiment, $R^1$, $R^2$ and $R^3$ are as described herein, and A is

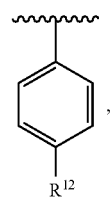

wherein $R^{12}$ is unsubstituted $C_1$-$C_6$ alkoxy. In an exemplary embodiment, $R^1$, $R^2$ and $R^3$ are as described herein, and A is

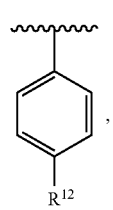

wherein $R^{12}$ is unsubstituted $C_1$-$C_3$ alkoxy. In an exemplary embodiment, $R^1$, $R^2$ and $R^3$ are as described herein, and A is

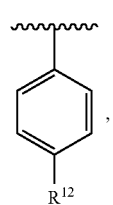

wherein $R^{12}$ is methoxy.

In an exemplary embodiment, $R^1$, $R^2$ and $R^3$ are as described herein, and A is

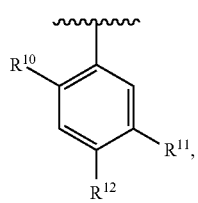

wherein $R^{10}$ is H or halogen or unsubstituted alkyl or halogen-substituted alkyl or unsubstituted alkoxy or phenyl-substituted alkoxy, $R^{11}$ is unsubstituted $C_1$-$C_6$ alkoxy and $R^{12}$ is H or halogen or unsubstituted alkyl or halogen-substituted alkyl or unsubstituted alkoxy or phenyl-substituted alkoxy. In an exemplary embodiment, $R^{10}$ is H or halogen or unsubstituted alkyl or halogen-substituted alkyl or unsubstituted alkoxy or phenyl-substituted alkoxy, $R^{11}$ is unsubstituted ethoxy or propoxy or isopropoxy or butoxy or isobutoxy or t-butoxy and $R^{12}$ is H or halogen or unsubstituted alkyl or halogen-substituted alkyl or unsubstituted alkoxy or phenyl-substituted alkoxy. In an exemplary embodiment, $R^{10}$ is H or halogen or unsubstituted alkyl or halogen-substituted alkyl or unsubstituted alkoxy or phenyl-substituted alkoxy, is unsubstituted methoxy and $R^{12}$ is H or halogen or unsubstituted alkyl or halogen-substituted alkyl or unsubstituted alkoxy or phenyl-substituted alkoxy. In an exemplary embodiment, $R^{10}$ is $C_1$-$C_6$ unsubstituted alkoxy, $R^{11}$ is $C_1$-$C_6$ unsubstituted alkoxy and $R^{12}$ is $C_1$-$C_6$ unsubstituted alkoxy. In an exemplary embodiment, $R^{10}$ is $C_1$-$C_3$ unsubstituted alkoxy, $R^{11}$ is $C_1$-$C_3$ unsubstituted alkoxy and $R^{12}$ is $C_1$-$C_3$ unsubstituted alkoxy. In an exemplary embodiment, $R^{10}$ is H or halogen or unsubstituted alkyl or halogen-substituted alkyl or unsubstituted alkoxy or phenyl-substituted alkoxy, $R^{11}$ is methoxy and $R^{12}$ is methoxy. In an exemplary embodiment, $R^{10}$ is $C_1$-$C_6$ unsubstituted alkoxy, is methoxy and $R^{12}$ is methoxy. In an exemplary embodiment, $R^{10}$ is $C_1$-$C_3$ unsubstituted alkoxy, $R^{11}$ is methoxy and $R^{12}$ is methoxy.

In an exemplary embodiment, $R^1$, $R^2$ and $R^3$ are as described herein, and A is

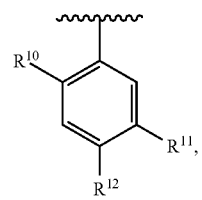

wherein $R^{10}$ is H or halogen or unsubstituted alkyl or halogen-substituted alkyl or unsubstituted alkoxy or phenyl-substituted alkoxy, $R^{12}$ is unsubstituted $C_1$-$C_6$ alkoxy and $R^{11}$ is H or halogen or unsubstituted alkyl or halogen-substituted alkyl or unsubstituted alkoxy or phenyl-substituted alkoxy. In an exemplary embodiment, $R^{10}$ is H or halogen or unsubstituted alkyl or halogen-substituted alkyl or unsubstituted alkoxy or phenyl-substituted alkoxy, $R^{12}$ is unsubstituted ethoxy or propoxy or isopropoxy or butoxy or isobutoxy or t-butoxy and $R^{11}$ is H or halogen or unsubstituted alkyl or halogen-substituted alkyl or unsubstituted alkoxy or phenyl-substituted alkoxy. In an exemplary embodiment, $R^{10}$ is H or halogen or unsubstituted alkyl or halogen-substituted alkyl or unsubstituted alkoxy or phenyl-substituted alkoxy, $R^{12}$ is unsubstituted methoxy and $R^{11}$ is H or halogen or unsubstituted alkyl or halogen-substituted alkyl or unsubstituted alkoxy or phenyl-substituted alkoxy.

In an exemplary embodiment, $R^1$, $R^2$ and $R^3$ are as described herein, and A is wherein $R^{10}$ is H or halogen or unsubstituted alkyl or halogen-substituted alkyl or unsubstituted alkoxy or phenyl-substituted alkoxy.

In an exemplary embodiment, $R^1$, $R^2$ and $R^3$ are as described herein, and A is wherein $R^{10}$ is H or halogen or unsubstituted alkyl or halogen-substituted alkyl or unsubstituted alkoxy or phenyl-substituted alkoxy.

In an exemplary embodiment, $R^1$, $R^2$ and $R^3$ are as described herein, and A is

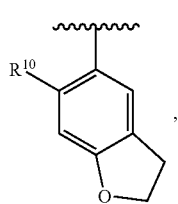

wherein R¹⁰ is H or halogen or unsubstituted alkyl or halogen-substituted alkyl or unsubstituted alkoxy or phenyl-substituted alkoxy. In an exemplary embodiment, R¹, R² and R³ are as described herein, and A is

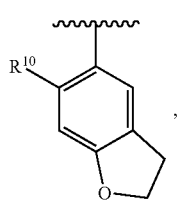

wherein R¹⁰ is unsubstituted $C_1$-$C_6$ alkyl or unsubstituted $C_1$-$C_6$ alkoxy. In an exemplary embodiment, R¹, R² and R³ are as described herein, and A is

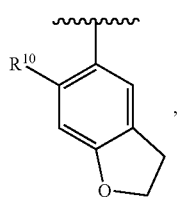

wherein R¹⁰ is unsubstituted $C_1$-$C_3$ alkyl or unsubstituted $C_1$-$C_3$ alkoxy. In an exemplary embodiment, R¹, R² and R³ are as described herein, and A is

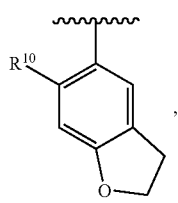

wherein R¹⁰ is methyl or methoxy.

In an exemplary embodiment, R¹, R² and R³ are as described herein, and A is

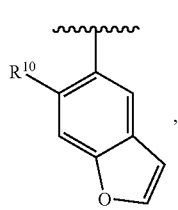

wherein R¹⁰ is H or halogen or unsubstituted alkyl or halogen-substituted alkyl or unsubstituted alkoxy or phenyl-substituted alkoxy.

In an exemplary embodiment, R¹, R² and R³ are as described herein, and A is

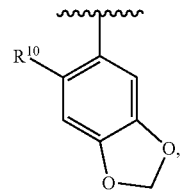

wherein R¹⁰ is H or halogen or unsubstituted alkyl or halogen-substituted alkyl or unsubstituted alkoxy or phenyl-substituted alkoxy. In an exemplary embodiment, R¹, R² and R³ are as described herein, and A is

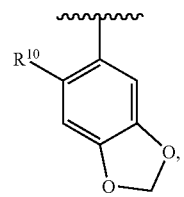

wherein R¹⁰ is halogen or unsubstituted alkyl or halogen-substituted alkyl or unsubstituted alkoxy or phenyl-substituted alkoxy. In an exemplary embodiment, R¹, R² and R³ are as described herein, and A is

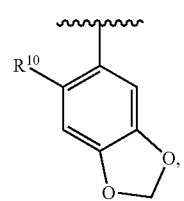

wherein R¹⁰ is $C_1$-$C_3$ unsubstituted alkyl.

In an exemplary embodiment, R¹, R² and R³ are as described herein, and A is

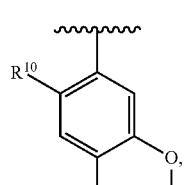

wherein R¹⁰ is H or halogen or unsubstituted alkyl or halogen-substituted alkyl or unsubstituted alkoxy or phenyl-substituted alkoxy.

In an exemplary embodiment, R¹, R² and R³ are as described herein, and A is

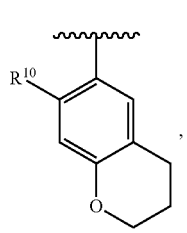

wherein $R^{10}$ is H or halogen or unsubstituted alkyl or halogen-substituted alkyl or unsubstituted alkoxy or phenyl-substituted alkoxy. In an exemplary embodiment, $R^1$, $R^2$ and $R^3$ are as described herein, and A is

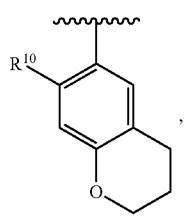

wherein $R^{10}$ is unsubstituted $C_1$-$C_6$ alkyl or unsubstituted $C_1$-$C_6$ alkoxy. In an exemplary embodiment, $R^1$, $R^2$ and $R^3$ are as described herein, and A is

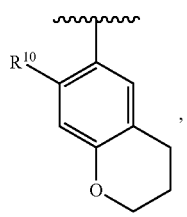

wherein $R^{10}$ is unsubstituted $C_1$-$C_3$ alkyl. In an exemplary embodiment, $R^1$, $R^2$ and $R^3$ are as described herein, and A is

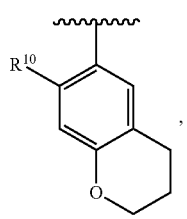

wherein $R^{10}$ is methyl or methoxy. In an exemplary embodiment, $R^1$, $R^2$ and $R^3$ are as described herein, and A is

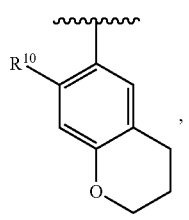

wherein $R^{10}$ is unsubstituted $C_1$-$C_3$ alkoxy.

In an exemplary embodiment, $R^1$, $R^2$ and $R^3$ are as described herein, and A is

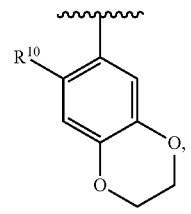

wherein $R^{10}$ is H or halogen or unsubstituted alkyl or halogen-substituted alkyl or unsubstituted alkoxy or phenyl-substituted alkoxy. In an exemplary embodiment, $R^1$, $R^2$ and $R^3$ are as described herein, and A is

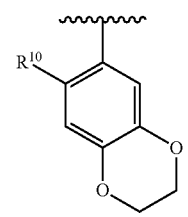

wherein $R^{10}$ is halogen or unsubstituted alkyl or halogen-substituted alkyl or unsubstituted alkoxy or phenyl-substituted alkoxy. In an exemplary embodiment, $R^1$, $R^2$ and $R^3$ are as described herein, and A is

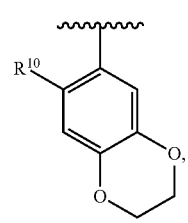

wherein $R^{10}$ is $C_1$-$C_3$ unsubstituted alkyl. In an exemplary embodiment, $R^1$, $R^2$ and $R^3$ are as described herein, and A is

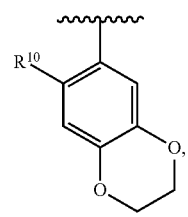

wherein $R^{10}$ is unsubstituted $C_1$-$C_6$ alkyl or unsubstituted $C_1$-$C_6$ alkoxy. In an exemplary embodiment, $R^1$, $R^2$ and $R^3$ are as described herein, and A is

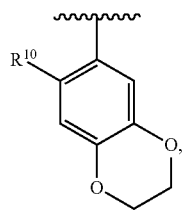

wherein $R^{10}$ is unsubstituted $C_1$-$C_3$ alkyl. In an exemplary embodiment, $R^1$, $R^2$ and $R^3$ are as described herein, and A is

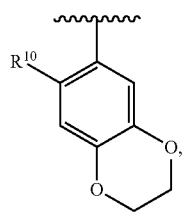

wherein $R^{10}$ is methyl or methoxy. In an exemplary embodiment, $R^1$, $R^2$ and $R^3$ are as described herein, and A is

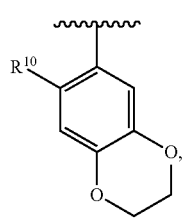

wherein $R^{10}$ is unsubstituted $C_1$-$C_3$ alkoxy. In an exemplary embodiment, $R^1$, $R^2$ and $R^3$ are as described herein, and A is

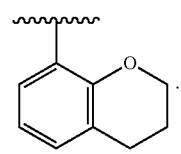 [SMILES: *c1cccc2c1OCCC2]

In an exemplary embodiment, $R^1$, $R^2$ and $R^3$ are as described herein, and A is

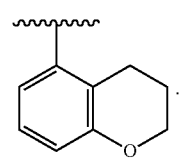 [SMILES: *c1cccc2c1CCCO2]

In an exemplary embodiment, $R^1$, $R^2$ and $R^3$ are as described herein, and A is

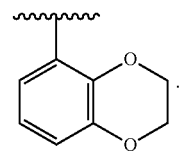 [SMILES: *c1cccc2c1OCCO2]

In an exemplary embodiment, $R^1$, $R^2$ and $R^3$ are as described herein, and A is

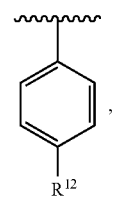

wherein $R^{12}$ is substituted or unsubstituted aryl or substituted or unsubstituted heteroaryl. In an exemplary embodiment, $R^1$, $R^2$ and $R^3$ are as described herein, and A is

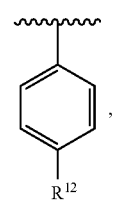

wherein $R^{12}$ is substituted or unsubstituted aryl or substituted or unsubstituted heteroaryl. In an exemplary embodiment, $R^1$, $R^2$ and $R^3$ are as described herein, and A is

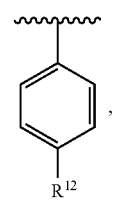

wherein $R^{12}$ is a substituted or unsubstituted nitrogen-containing 4-8 membered ring. In an exemplary embodiment, $R^1$, $R^2$ and $R^3$ are as described herein, and A is

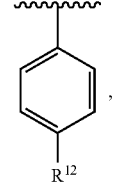

wherein $R^{12}$ is a substituted or unsubstituted nitrogen-containing 5-6 membered ring. In an exemplary embodiment, $R^1$, $R^2$ and $R^3$ are as described herein, and A is

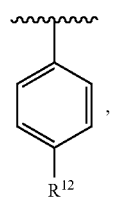

wherein $R^{12}$ is substituted or unsubstituted pyridinyl. In an exemplary embodiment, $R^1$, $R^2$ and $R^3$ are as described herein, and A is

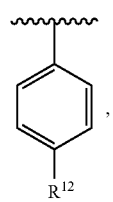

wherein $R^{12}$ is substituted or unsubstituted pyridin-4-yl. In an exemplary embodiment, $R^1$, $R^2$ and $R^3$ are as described herein, and A is

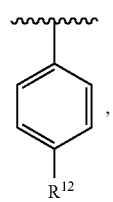

wherein $R^{12}$ is substituted or unsubstituted pyridin-3-yl. In an exemplary embodiment, $R^1$, $R^2$ and $R^3$ are as described herein, and A is

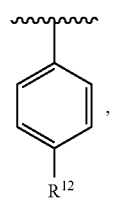

wherein $R^{12}$ is substituted or unsubstituted pyridin-2-yl. In an exemplary embodiment, $R^1$, $R^2$ and $R^3$ are as described herein, and A is

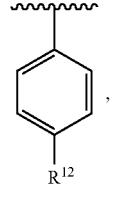

wherein $R^{12}$ is unsubstituted pyridinyl.

In an exemplary embodiment, $R^1$, $R^2$ and $R^3$ are as described herein, and A is

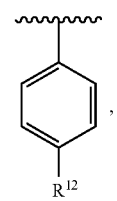

wherein $R^{12}$ is substituted or unsubstituted pyrimidinyl. In an exemplary embodiment, $R^1$, $R^2$ and $R^3$ are as described herein, and A is

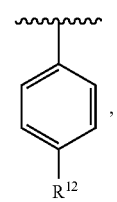

wherein $R^{12}$ is substituted or unsubstituted pyrimidin-5-yl. In an exemplary embodiment, $R^1$, $R^2$ and $R^3$ are as described herein, and A is

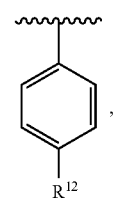

wherein $R^{12}$ is substituted or unsubstituted pyrimidin-2-yl. In an exemplary embodiment, $R^1$, $R^2$ and $R^3$ are as described herein, and A is

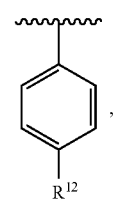

wherein $R^{12}$ is substituted or unsubstituted pyrimidin-4-yl. In an exemplary embodiment, $R^1$, $R^2$ and $R^3$ are as described herein, and A is wherein $R^{12}$ is unsubstituted pyrimidin-5-yl. In an exemplary embodiment, $R^1$, $R^2$ and $R^3$ are as described herein, and A is

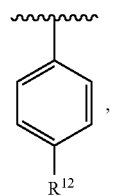

wherein $R^{12}$ is unsubstituted pyrimidin-2-yl. In an exemplary embodiment, $R^1$, $R^2$ and $R^3$ are as described herein, and A is

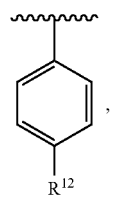

wherein $R^{12}$ is unsubstituted pyrimidin-4-yl.

In an exemplary embodiment, $R^1$, $R^2$ and $R^3$ are as described herein, and A is

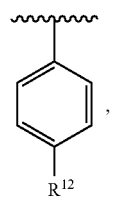

wherein $R^{12}$ is substituted or unsubstituted imidazolyl. In an exemplary embodiment, $R^1$, $R^2$ and $R^3$ are as described herein, and A is


wherein $R^{12}$ is substituted or unsubstituted imidazol-1-yl.

In an exemplary embodiment, $R^1$, $R^2$ and $R^3$ are as described herein, and A is

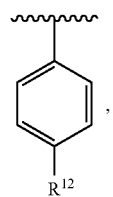

wherein $R^{12}$ is substituted or unsubstituted indolyl. In an exemplary embodiment, $R^1$, $R^2$ and $R^3$ are as described herein, and A is

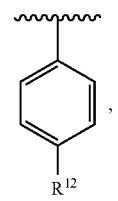

wherein $R^{12}$ is indolyl substituted with —C(O)O$R^{22}$, wherein $R^{22}$ is $C_1$-$C_6$ alkyl. In an exemplary embodiment, $R^1$, $R^2$ and $R^3$ are as described herein, and A is

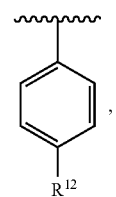

wherein $R^{12}$ is indolyl substituted with —C(O)O$R^{22}$, wherein $R^{22}$ is t-butyl. In an exemplary embodiment, $R^1$, $R^2$ and $R^3$ are as described herein, and A is

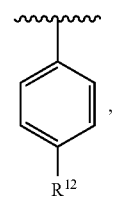

wherein $R^{12}$ is indolyl substituted with $C_1$-$C_6$ alkyl. In an exemplary embodiment, $R^1$, $R^2$ and $R^3$ are as described herein, and A is

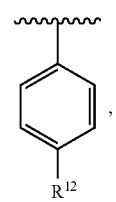

wherein $R^{12}$ is indolyl substituted with methyl. In an exemplary embodiment, $R^1$, $R^2$ and $R^3$ are as described herein, and A is

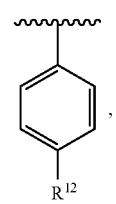

wherein $R^{12}$ is substituted or unsubstituted indol-3-yl. In an exemplary embodiment, $R^1$, $R^2$ and $R^3$ are as described herein, and A is

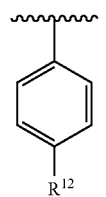, wherein R[12] is indol-3-yl substituted with $C_1$-$C_6$ alkyl. In an exemplary embodiment, R[1], R[2] and R[3] are as described herein, and A is

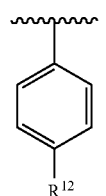, wherein R[12] is indol-3-yl substituted with methyl. In an exemplary embodiment, R[1], R[2] and R[3] are as described herein, and A is

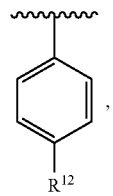, wherein R[12] is indol-3-yl substituted with —C(O)OR[22], wherein R[22] is $C_1$-$C_6$ alkyl. In an exemplary embodiment, R[1], R[2] and R[3] are as described herein, and A is

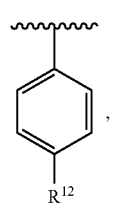, wherein R[12] is indol-3-yl substituted with —C(O)OR[22], wherein R[22] is t-butyl.

In an exemplary embodiment, R[1], R[2] and R[3] are as described herein, and A is

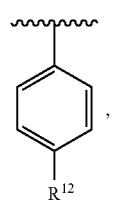, wherein R[12] is substituted or unsubstituted pyrrolopyridinyl. In an exemplary embodiment, R[1], R[2] and R[3] are as described herein, and A is

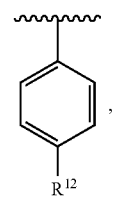, wherein R[12] is pyrrolopyridinyl substituted with $C_1$-$C_6$ alkyl. In an exemplary embodiment, R[1], R[2] and R[3] are as described herein, and A is

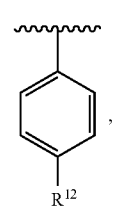, wherein R[12] is pyrrolopyridinyl substituted methyl. In an exemplary embodiment, R[1], R[2] and R[3] are as described herein, and A is

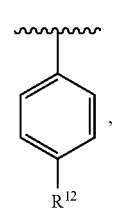, wherein R[12] is pyrrolopyridinyl substituted with —C(O)OR[22], wherein R[22] is $C_1$-$C_6$ alkyl. In an exemplary embodiment, R[1], R[2] and R[3] are as described herein, and A is

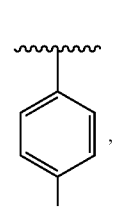, wherein R[12] is pyrrolopyridinyl substituted with —C(O)OR[22], wherein R[22] is t-butyl. In an exemplary embodiment, R[1], R[2] and R[3] are as described herein, and A is

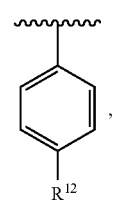, wherein R[12] is substituted or unsubstituted pyrrolopyridin-3-yl. In an exemplary embodiment, R[1], R[2] and R[3] are as described herein, and A is

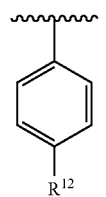

wherein $R^{12}$ is pyrrolopyridin-3-yl substituted with $C_1$-$C_6$ alkyl. In an exemplary embodiment, $R^1$, $R^2$ and $R^3$ are as described herein, and A is

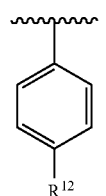

wherein $R^{12}$ is pyrrolopyridin-3-yl substituted with methyl. In an exemplary embodiment, $R^1$, $R^2$ and $R^3$ are as described herein, and A is

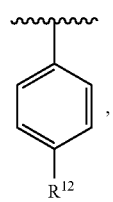

wherein $R^{12}$ is pyrrolopyridin-3-yl substituted with —C(O)OR$^{22}$, wherein $R^{22}$ is $C_1$-$C_6$ alkyl. In an exemplary embodiment, $R^1$, $R^2$ and $R^3$ are as described herein, and A is

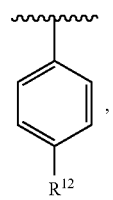

wherein $R^{12}$ is pyrrolopyridin-3-yl substituted with —C(O)OR$^{22}$, wherein $R^{22}$ is t-butyl.

In an exemplary embodiment, $R^1$, $R^2$ and $R^3$ are as described herein, and A is

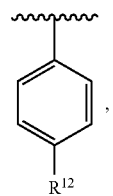

wherein $R^{12}$ is substituted or unsubstituted triazolyl. In an exemplary embodiment, $R^1$, $R^2$ and $R^3$ are as described herein, and A is

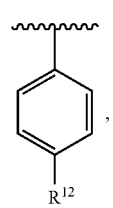

wherein $R^{12}$ is triazol-1-yl.

In an exemplary embodiment, $R^1$, $R^2$ and $R^3$ are as described herein, and A is

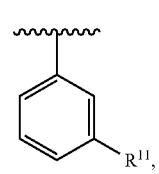

wherein $R^{11}$ is substituted or unsubstituted aryl or substituted or unsubstituted heteroaryl. In an exemplary embodiment, $R^1$, $R^2$ and $R^3$ are as described herein, and A is

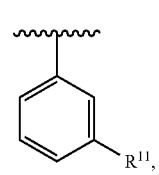

wherein $R^{11}$ is substituted or unsubstituted aryl or substituted or unsubstituted heteroaryl. In an exemplary embodiment, $R^1$, $R^2$ and $R^3$ are as described herein, and A is

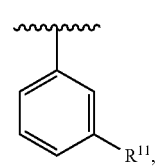

wherein $R^{11}$ is a substituted or unsubstituted nitrogen-containing 4-8 membered ring. In an exemplary embodiment, $R^1$, $R^2$ and $R^3$ are as described herein, and A

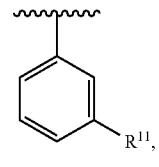

is wherein is a substituted or unsubstituted nitrogen-containing 5-6 membered ring. In an exemplary embodiment, $R^1$, $R^2$ and $R^3$ are as described herein, and A is

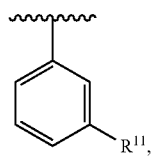

wherein $R^{11}$ is substituted or unsubstituted pyridinyl. In an exemplary embodiment, $R^1$, $R^2$ and $R^3$ are as described herein, and A is

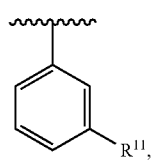

wherein $R^{11}$ is substituted or unsubstituted pyridin-4-yl. In an exemplary embodiment, $R^1$, $R^2$ and $R^3$ are as described herein, and A is

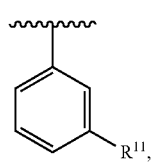

wherein $R^{11}$ is substituted or unsubstituted pyridin-3-yl. In an exemplary embodiment, $R^1$, $R^2$ and $R^3$ are as described herein, and A is

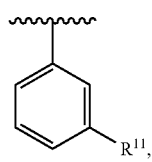

wherein $R^{11}$ is substituted or unsubstituted pyridin-2-yl. In an exemplary embodiment, $R^1$, $R^2$ and $R^3$ are as described herein, and A is

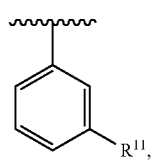

wherein $R^{11}$ is unsubstituted pyridinyl.

In an exemplary embodiment, $R^1$, $R^2$ and $R^3$ are as described herein, and A is

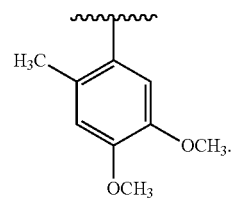

In an exemplary embodiment, $R^1$, $R^2$ and $R^3$ are as described herein, and A is

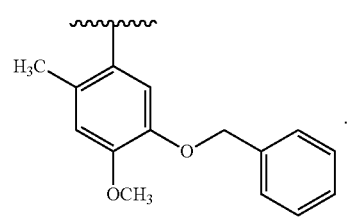 [SMILES: *c1cc(OCc2ccccc2)c(OC)cc1C]

In an exemplary embodiment, $R^1$, $R^2$ and $R^3$ are as described herein, and A is

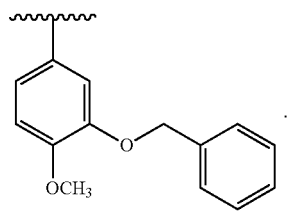 [SMILES: *c1ccc(OC)c(OCc2ccccc2)c1]

In an exemplary embodiment, $R^1$, $R^2$ and $R^3$ are as described herein, and A is

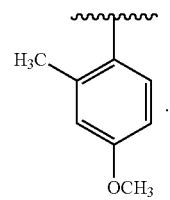

In an exemplary embodiment, $R^1$, $R^2$ and $R^3$ are as described herein, and A is

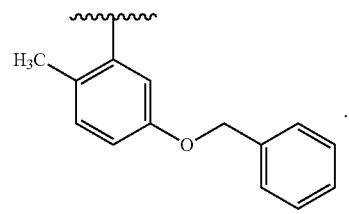 [SMILES: *c1cc(OCc2ccccc2)ccc1C]

In an exemplary embodiment, $R^1$, $R^2$ and $R^3$ are as described herein, and A is

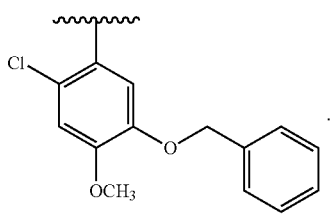 [SMILES: *c1cc(OCc2ccccc2)c(OC)cc1Cl]

In an exemplary embodiment, $R^1$, $R^2$ and $R^3$ are as described herein, and A is

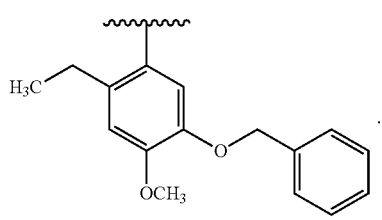 [SMILES: *c1cc(OCc2ccccc2)c(OC)cc1CC]

In an exemplary embodiment, $R^1$, $R^2$ and $R^3$ are as described herein, and A is

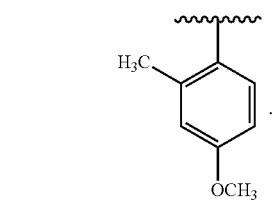 [SMILES: *c1ccc(OC)cc1C(F)(F)F]

In an exemplary embodiment, $R^1$, $R^2$ and $R^3$ are as described herein, and A is

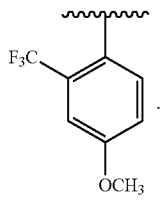

In an exemplary embodiment, $R^1$, $R^2$ and $R^3$ are as described herein, and A is

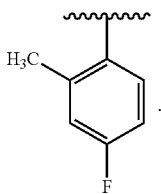

In an exemplary embodiment, $R^1$, $R^2$ and $R^3$ are as described herein, and A is

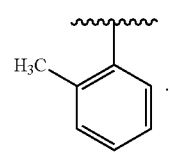

In an exemplary embodiment, $R^1$, $R^2$ and $R^3$ are as described herein, and A is

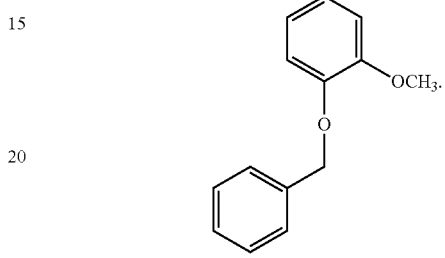

In an exemplary embodiment, $R^1$, $R^2$ and $R^3$ are as described herein, and A is unsubstituted pyrazolyl. In an exemplary embodiment, $R^1$, $R^2$ and $R^3$ are as described herein, and A is substituted pyrazolyl. In an exemplary embodiment, $R^1$, $R^2$ and $R^3$ are as described herein, and A is pyrazolyl substituted with $C_1$-$C_3$ alkyl. In an exemplary embodiment, $R^1$, $R^2$ and $R^3$ are as described herein, and A is pyrazolyl substituted with methyl. In an exemplary embodiment, $R^1$, $R^2$ and $R^3$ are as described herein, and A is

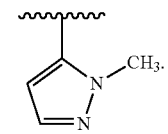 [SMILES: *c1ccnn1C]

In an exemplary embodiment, $R^1$, $R^2$ and $R^3$ are as described herein, and A is unsubstituted pyridinyl. In an exemplary embodiment, $R^1$, $R^2$ and $R^3$ are as described herein, and A is unsubstituted pyridin-3-yl. In an exemplary embodiment, $R^1$, $R^2$ and $R^3$ are as described herein, and A is unsubstituted pyridin-4-yl. In an exemplary embodiment, $R^1$, $R^2$ and $R^3$ are as described herein, and A is substituted pyridinyl. In an exemplary embodiment, $R^1$, $R^2$ and $R^3$ are as described herein, and A is substituted pyridin-4-yl. In an exemplary embodiment, $R^1$, $R^2$ and $R^3$ are as described herein, and A is substituted pyridin-3-yl. In an exemplary embodiment, $R^1$, $R^2$ and $R^3$ are as described herein, and A is pyridinyl substituted with $C_1$-$C_3$ alkyloxy. In an exemplary embodiment, $R^1$, $R^2$ and $R^3$ are as described herein, and A is pyridinyl substituted with two $C_1$-$C_3$ alkyloxy. In an exemplary embodiment, $R^1$, $R^2$ and $R^3$ are as described herein, and A is pyridinyl substituted with methoxy. In an exemplary embodiment, $R^1$, $R^2$ and $R^3$ are as described herein, and A is pyridin-3-yl substituted with methoxy. In an exemplary embodiment, $R^1$, $R^2$ and $R^3$ are as described herein, and A is pyridin-4-yl substituted with methoxy. In an exemplary embodiment, $R^1$, $R^2$ and $R^3$ are as described herein, and A is pyridin-3-yl substituted with two methoxy. In an exemplary embodiment, $R^1$, $R^2$ and $R^3$ are as described herein, and A is pyridin-4-yl substituted with two methoxy. In an exemplary embodiment, $R^1$, $R^2$ and $R^3$ are as described herein, and A is

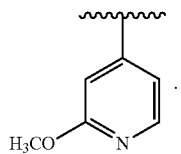

In an exemplary embodiment, $R^1$, $R^2$ and $R^3$ are as described herein, and A is

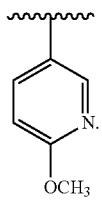

In an exemplary embodiment, $R^1$, $R^2$ and $R^3$ are as described herein, and A is

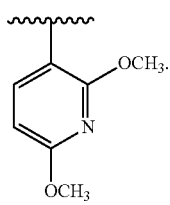 [SMILES: *c1ccc(OC)nc1OC]

In an exemplary embodiment, $R^1$, $R^2$ and $R^3$ are as described herein, and A is pyridinyl substituted with $NR^{10}R^{11}$, wherein $R^{10}$ and $R^{11}$ are each independently selected from H or unsubstituted $C_1$-$C_3$ alkyl. In an exemplary embodiment, $R^1$, $R^2$ and $R^3$ are as described herein, and A is pyridinyl substituted with two $NR^{10}R^{11}$, wherein $R^{10}$ and $R^{11}$ are each independently selected from H or unsubstituted $C_1$-$C_3$ alkyl. In an exemplary embodiment, $R^1$, $R^2$ and $R^3$ are as described herein, and A is pyridinyl substituted with $N(CH_3)_2$. In an exemplary embodiment, $R^1$, $R^2$ and $R^3$ are as described herein, and A is pyridinyl substituted with $NH_2$. In an exemplary embodiment, $R^1$, $R^2$ and $R^3$ are as described herein, and A is pyridin-3-yl substituted with $N(CH_3)_2$. In an exemplary embodiment, $R^1$, $R^2$ and $R^3$ are as described herein, and A is pyridin-4-yl substituted with $N(CH_3)_2$. In an exemplary embodiment, $R^1$, $R^2$ and $R^3$ are as described herein, and A is pyridin-3-yl substituted with $NH_2$. In an exemplary embodiment, $R^1$, $R^2$ and $R^3$ are as described herein, and A is pyridin-4-yl substituted with $NH_2$. In an exemplary embodiment, $R^1$, $R^2$ and $R^3$ are as described herein, and A is

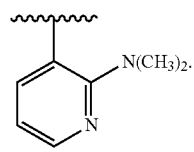 [SMILES: *c1cccnc1N(C)C]

In an exemplary embodiment, $R^1$, $R^2$ and $R^3$ are as described herein, and A is unsubstituted pyrimidinyl. In an exemplary embodiment, $R^1$, $R^2$ and $R^3$ are as described herein, and A is unsubstituted pyrimidin-5-yl. In an exemplary embodiment, $R^1$, $R^2$ and $R^3$ are as described herein, and A is unsubstituted pyrimidin-4-yl. In an exemplary embodiment, $R^1$, $R^2$ and $R^3$ are as described herein, and A is substituted pyrimidinyl. In an exemplary embodiment, $R^1$, $R^2$ and $R^3$ are as described herein, and A is substituted pyrimidin-5-yl. In an exemplary embodiment, $R^1$, $R^2$ and $R^3$ are as described herein, and A is substituted pyrimidin-4-yl. In an exemplary embodiment, $R^1$, $R^2$ and $R^3$ are as described herein, and A is pyrimidinyl substituted with $C_1$-$C_3$ alkyloxy. In an exemplary embodiment, $R^1$, $R^2$ and $R^3$ are as described herein, and A is pyrimidinyl substituted with two $C_1$-$C_3$ alkyloxy. In an exemplary embodiment, $R^1$, $R^2$ and $R^3$ are as described herein, and A is pyrimidinyl substituted with methoxy. In an exemplary embodiment, $R^1$, $R^2$ and $R^3$ are as described herein, and A is pyrimidin-5-yl substituted with methoxy. In an exemplary embodiment, $R^1$, $R^2$ and $R^3$ are as described herein, and A is pyrimidin-4-yl substituted with methoxy. In an exemplary embodiment, $R^1$, $R^2$ and $R^3$ are as described herein, and A is

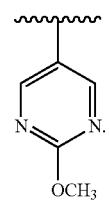 [SMILES: *c1cnc(OC)nc1]

In an exemplary embodiment, $R^1$, $R^2$ and $R^3$ are as described herein, and A is pyrimidinyl substituted with substituted phenyl. In an exemplary embodiment, $R^1$, $R^2$ and $R^3$ are as described herein, and A is pyrimidinyl substituted with unsubstituted phenyl. In an exemplary embodiment, $R^1$, $R^2$ and $R^3$ are as described herein, and A is pyrimidinyl substituted with unsubstituted phenyl substituted with $C_1$-$C_3$ alkyloxy. In an exemplary embodiment, $R^1$, $R^2$ and $R^3$ are as described herein, and A is pyrimidinyl substituted with unsubstituted phenyl substituted with methoxy. In an exemplary embodiment, $R^1$, $R^2$ and $R^3$ are as described herein, and A is

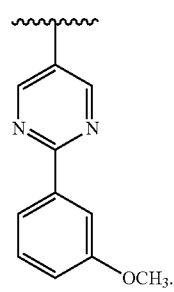 [SMILES: *c1cnc(-c2cccc(OC)c2)nc1]

In an exemplary embodiment, $R^1$, $R^2$ and $R^3$ are as described herein, and A is unsubstituted thienyl. In an exemplary embodiment, $R^1$, $R^2$ and $R^3$ are as described herein, and A is unsubstituted thien-2-yl. In an exemplary embodiment, $R^1$, $R^2$ and $R^3$ are as described herein, and A is unsubstituted thien-3-yl. In an exemplary embodiment, $R^1$, $R^2$ and $R^3$ are as described herein, and A is thienyl substituted with $C_1$-$C_3$ alkyl. In an exemplary embodiment, $R^1$, $R^2$ and $R^3$ are as described herein, and A is thien-2-yl substituted with $C_1$-$C_3$ alkyl. In an exemplary embodiment, $R^1$, $R^2$ and $R^3$ are as described herein, and A is thien-3-yl substituted with $C_1$-$C_3$ alkyl.

In an exemplary embodiment, $R^1$, $R^2$ and $R^3$ are as described herein, and A is unsubstituted thiazolyl. In an exemplary embodiment, $R^1$, $R^2$ and $R^3$ are as described herein, and A is unsubstituted thiazol-4-yl. In an exemplary embodiment, $R^1$, $R^2$ and $R^3$ are as described herein, and A is unsubstituted thiazol-5-yl. In an exemplary embodiment, $R^1$, $R^2$ and $R^3$ are as described herein, and A is unsubstituted thiazol-2-yl. In an exemplary embodiment, $R^1$, $R^2$ and $R^3$ are as described herein, and A is thiazolyl substituted with $C_1$-$C_3$ alkyl. In an exemplary embodiment, $R^1$, $R^2$ and $R^3$ are as described herein, and A is thiazol-4-yl substituted with $C_1$-$C_3$ alkyl. In an exemplary embodiment, $R^1$, $R^2$ and $R^3$ are as described herein, and A is thiazol-5-yl substituted with $C_1$-$C_3$ alkyl. In an exemplary embodiment, $R^1$, $R^2$ and $R^3$ are as described herein, and A is thiazol-2-yl substituted with $C_1$-$C_3$ alkyl.

In an exemplary embodiment, the compound has the formula which is:

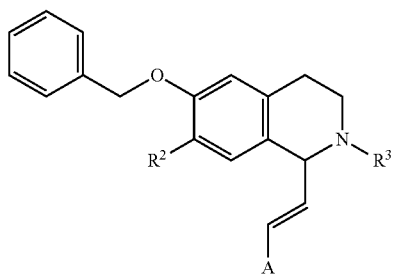

wherein $R^2$, $R^3$ and A are as described herein, or a hydrate, solvate, or salt thereof.

In an exemplary embodiment, the compound has the formula which is:

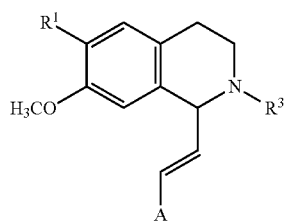

wherein $R^1$, $R^3$ and A are as described herein, or a hydrate, solvate, or salt thereof.

In an exemplary embodiment, the compound has the formula which is:

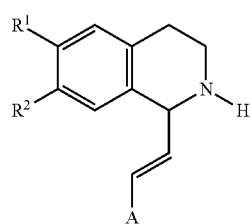

wherein $R^1$, $R^2$ and A are as described herein, or a hydrate, solvate, or salt thereof.

In an exemplary embodiment, the compound has the formula which is:

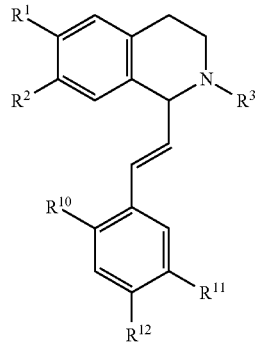

wherein $R^1$, $R^2$, $R^3$, $R^{10}$, and $R^{12}$ are as described herein, or a hydrate, solvate, or salt thereof.

In an exemplary embodiment, the compound has the formula which is:

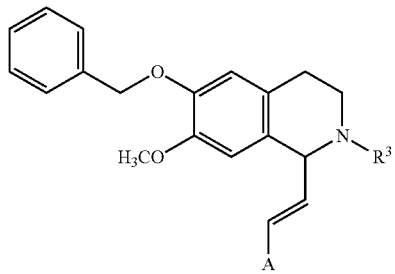

wherein $R^3$ and A are as described herein, or a hydrate, solvate, or salt thereof.

In an exemplary embodiment, the compound has the formula which is:

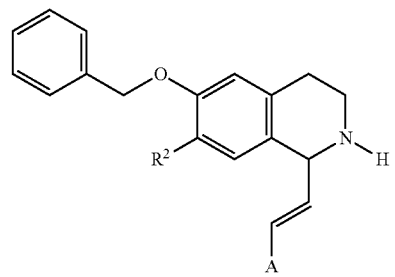

wherein $R^2$ and A are as described herein, or a hydrate, solvate, or salt thereof.

In an exemplary embodiment, the compound has the formula which is:

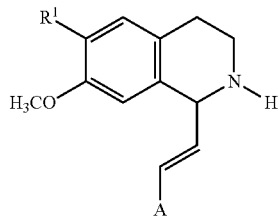

wherein $R^1$ and A are as described herein, or a hydrate, solvate, or salt thereof.

In an exemplary embodiment, the compound has the formula which is:

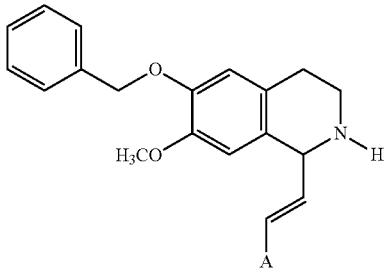

wherein A is as described herein, or a hydrate, solvate, or salt thereof.

In an exemplary embodiment, the compound has the formula which is:

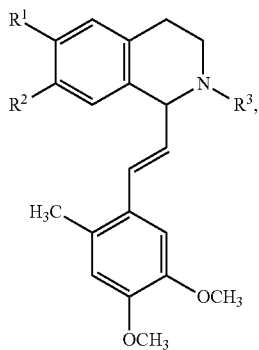

or a hydrate, solvate, or salt thereof.

In an exemplary embodiment, the compound has the formula which is:

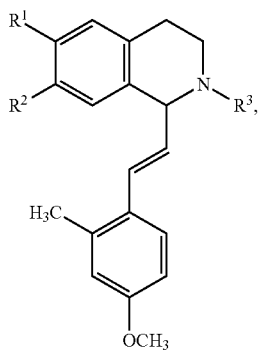

or a hydrate, solvate, or salt thereof.

In an exemplary embodiment, the compound has the formula which is:

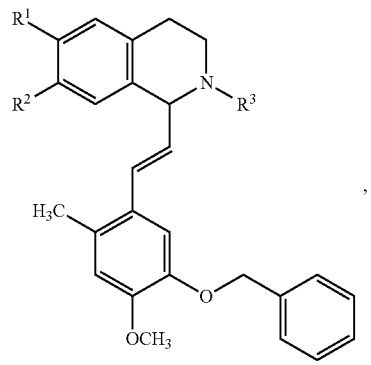

or a hydrate, solvate, or salt thereof.

In an exemplary embodiment, the invention provides a compound described herein, or a salt, hydrate or solvate thereof, or a combination thereof. In an exemplary embodiment, the invention provides a compound described in a FIGURE provided herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III.b) Preparation of Compounds

Compounds of use in the invention can be prepared using commercially available starting materials, known intermediates, or by using the synthetic methods described herein, or published in references described and incorporated by reference herein.

A general procedure to make compounds of the invention
General Procedure for the Synthesis of Substituted Phenethyl Amines$^a$

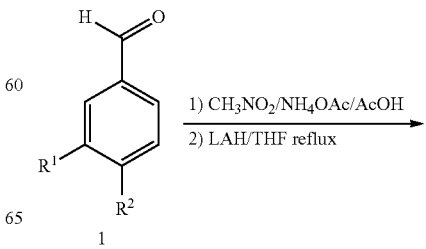

-continued

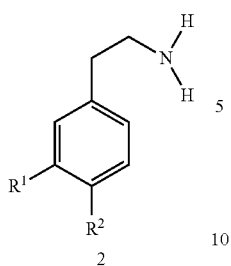

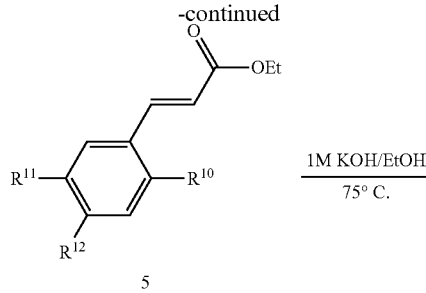

A solution of the Benzaldehyde 1 (0.1 mol), Nitromethane (50 ml, 0.93 mmol) and Ammonium acetate (0.26 mol) in Acetic acid (200 ml) was refluxed for 1 h. Upon cooling the product crystallized out of solution. The crystals were filtered out and washed with a small amount of ether to give a bright yellow nitrostyrene.

To a stirred solution of Lithium aluminum hydride (0.21 mol) in Tetrahydrofuran (270 ml) was added dropwise a solution of the above nitrostyrene (0.11 mol) in Tetrahydrofuran (200 ml). Upon completion the reaction mixture was refluxed with stirring for 16 h, cooled to room temperature and the excess hydride decomposed by the addition of aq. sat. $Na_2SO_4$. The mixture was filtered and the filtrate rotary evaporated to an amber-brown oil (the title compound) 2 which was used without further purification.

General Procedure for the Synthesis of Substituted Cinammic Acids[b]

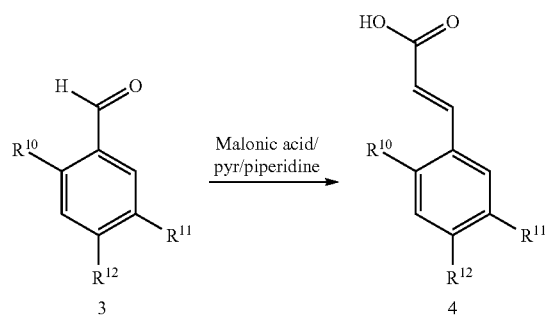

A mixture of the Benzaldehyde 3 (30 mmol), Malonic acid (60 mmol), Pyridine (20 mL) and Piperidine (5 mmol) was stirred at 80° C. for 1 h followed by refluxing at 110-115° C. for an additional 3 h. The cooled reaction mixture was poured into water (250 mL) and acidified with conc. HCl. The resulting precipitate was filtered off and washed several times with water. It was redissolved in 2M NaOH, diluted with water, acidified with conc. HCl. The solid precipitate was filtered washed several times with water, dried under high vacuum over $P_2O_5$ to afford the titled compound 4.

Alternate Synthesis of Cinnamic Acids

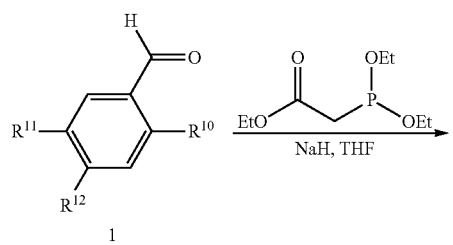

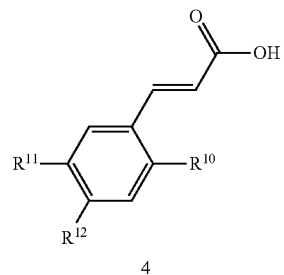

The ethyl-2-(diethoxyphosphino)acetate was dissolved in THF and cooled to 0° C. To this mixture was added 1 equivalent of NaH (60% in mineral oil) in portions. The mixture immediately evolved of $H_2$ gas. After the addition was complete, the mixture was stirred at room temperature for 1 hour. To this mixture at 0° C. was added one equivalent of the benzaldehyde. The mixture was stirred at 0° C. for 1 hour, then allowed to warm up to room temperature overnight. The mixture was pored over ice water and extracted with EtOAc. The combined organic layers were dried over $MgSO_4$, filtered and evaporated to give a residue, which was purified by flash chromatography. The correct product was confirmed by LC-MS.

The resulting cinnamoyl ester was dissolved in a 1/1 mixture of EtOH and 1M KOH solution and heated at 75° C. overnight. When all of the starting material was consumed, the reaction was allowed to cool to room temperature and the EtOH was removed by evaporation. The resulting residue was acidified with 2N $H_3PO_4$ and the product was either filtered off to dry under vacuum or extracted with EtOAc, followed by drying over $MgSO_4$, filtration and evaporation. The correct product was confirmed by LC-MS.

General Procedure for the Synthesis of Substituted Cinnamides'

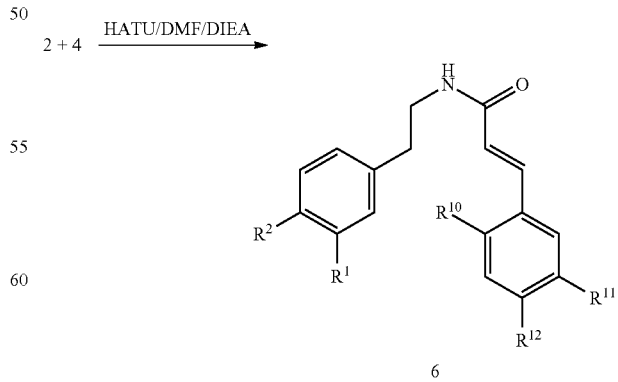

To a stirred mixture of the substituted Phenethylamine 2 (0.48 mmol), substituted Cinnamic acid 4 (0.72 mmol), DIEA [420 uL (2.4 mmol)] & 10 ml of DMF was added HATU (1 mmol). The reaction was stirred at rt for 1 h and then diluted with 20 ml of EtOAc and washed 2× with sat NaCl. The EtOAc layer was dried ($Na_2SO_4$) and the solvent removed yielding the title compound 6.

General Procedure for the Cyclization and Reduction of the Substituted Cinnamides: Synthesis of Substituted Tetrahydroisoquinolines[d]

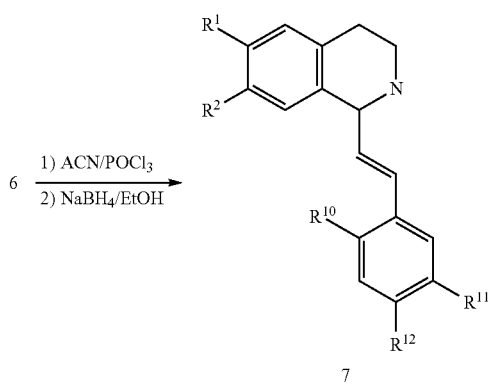

To the substituted Cinnamide 6 (0.563 mmol) in ACN (13 ml) was added, under reflux, $POCl_3$ (3.9 mmol). The reaction was stirred at reflux for 30 min and then rotary evaporated to dryness. The residue was taken up into 10 ml of chloroform and was then treated with 20 ml of 2N KOH and 50 mL of $Et_2O$. This mixture was rapidly stirred for 30 min at room temperature and the upper organic layer removed, washed with water, dried ($Na_2SO_4$) and the solvent removed. The resulting dark oil (Substituted Dihydroisoquinoline) was then dissolved into 8 ml of dry EtOH and then treated with $NaBH_4$ (0.395 mmol). The mixture was stirred for 1 h at room temperature and the resulting solid was carefully filtered off and dried. The solid was triturated with 50/50 ACN/water, filtered and vacuum dried yielding the title compound 7.

General Synthesis of Dihydroisoquinolines[e]

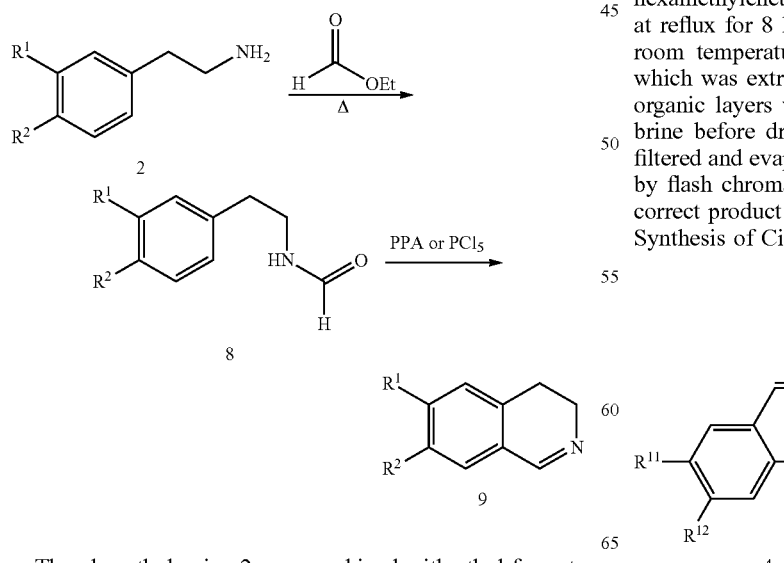

The phenethylamine 2 was combined with ethyl formate (20 mL) and heated at reflux overnight. The reaction was checked by TLC and LC-MS for the consumption of starting material. The reaction was allowed to cool to room temperature and the organic solvents were evaporated to five a residue, which solidified on standing at room temperature. The correct product 8 was confirmed by LC-MS and was used in the next step without purification.

The formamide was cyclized to the dihydroisoquinoline 9 by either of two methods:

a. The phenethylformamide was combined with polyphosphoric acid (PPA) and heated at 160° C. for 12 hours. The mixture was allowed to cool to room temperature and poured over ice. The mixture was made basic with NaOH solution and extracted with EtOAc. The combined organic layers were dried over $MgSO_4$, filtered and evaporated to give a residue. The residue was purified by flash chromatography. The correct product 9 was confirmed by LC-MS.

b. To a solution of the phenethylformamide in $CH_2Cl_2$ cooled to 0° C. was added 1 equivalent of $POCl_3$ dropwise. After the addition, the reaction was stirred from 2 hrs to 18 hrs. The reaction mixture was evaporated to dryness and the pH was adjusted to 10 with $NH_4OH$ solution. The mixture was extracted with EtOAc and the combined organic layers were dried over $MgSO_4$, filtered and evaporated. The residue was either recrystallized or purified by flash chromatography. The correct product 9 was confirmed by LC-MS.

Alternate Synthesis of Dihydoisoquinolines[f]

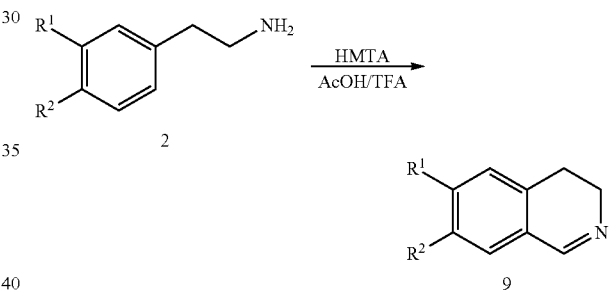

Acetic acid/trifluoroacetic acid (4/1) was added to a mixture of the phenylethylamine 2 and 2 equivalents of hexamethylenetetramine. The resulting solution was heated at reflux for 8 hours. The reaction was allowed to cool to room temperature and water was added to the solution, which was extracted with dichloromethane. The combined organic layers were washed with saturated $NaHCO_3$, and brine before drying over $MgSO_4$. The organic layer was filtered and evaporated to dryness. The residue was purified by flash chromatography to give the desired product. The correct product 9 was confirmed by LC-MS.

Synthesis of Cinnamoyl Bromide[g]

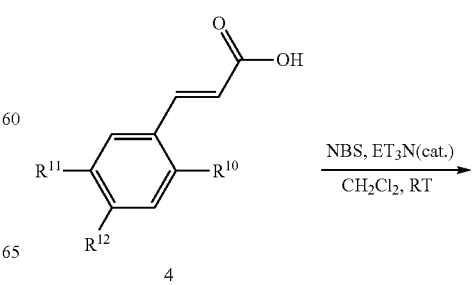

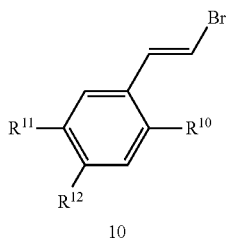

A catalytic amount of triethylamine (5 mol %) was added to a solution of the acrylic acid in $CH_2Cl_2$. The mixture was stirred for 5 minutes before NBS (120 mol %) was added in portions. Within 5 minutes of the first addition, $CO_2$ gas evolved. After all of the NBS was added, the mixture was allowed to stir overnight at room temperature. The organic solvent was evaporated and the residue was purified by flash chromatography to give very good yields of the desired cinnamoyl bromide.

General Method for Synthesis of Styrl-Tetrahydroisoquinoline Derivatives[h]

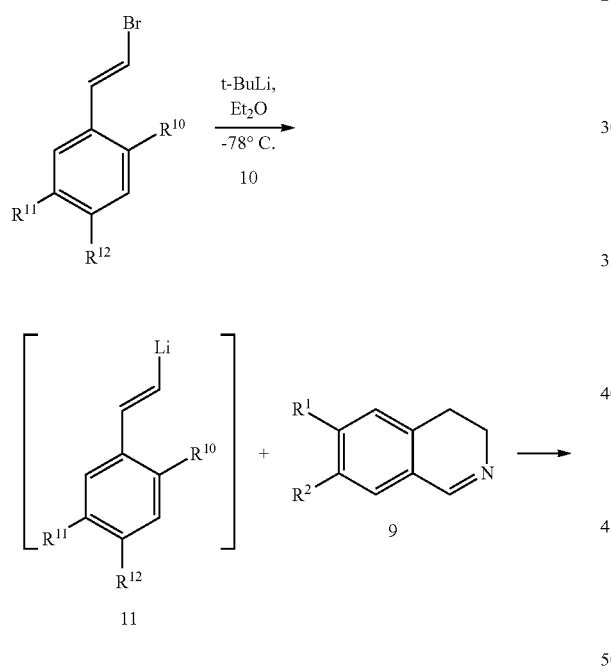

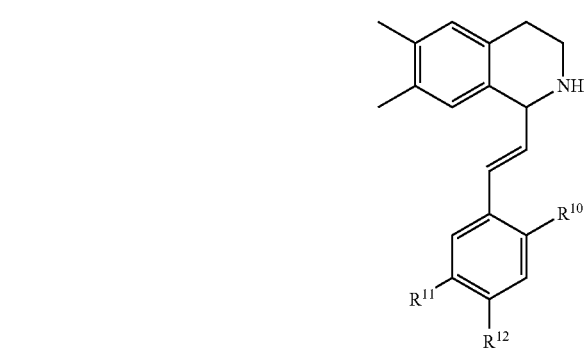

The bromovinylbenzene was dissolved in $Et_2O$ and cooled to −78° C. under argon. To this mixture was added 2.2 equivalents of t-BuLi dropwise. The resulting solution was stirred for 1 hour at −78° C. To this mixture was added a solution of 1 equivalent of the dihydroisoquinoline in THF. At the end of the addition, the mixture was allowed to stir at −78° C. for 1 to 2 hours. The mixture was quenched by the direct addition of a saturated solution of $NH_4Cl$. The mixture was extracted with EtOAc and the combined organic layers were dried over $MgSO_4$, filtered and evaporated to dryness. The residue was purified by flash chromatography (and Prep HPLC). The correct product was confirmed by LC-MS and/or $H^1$ NMR.

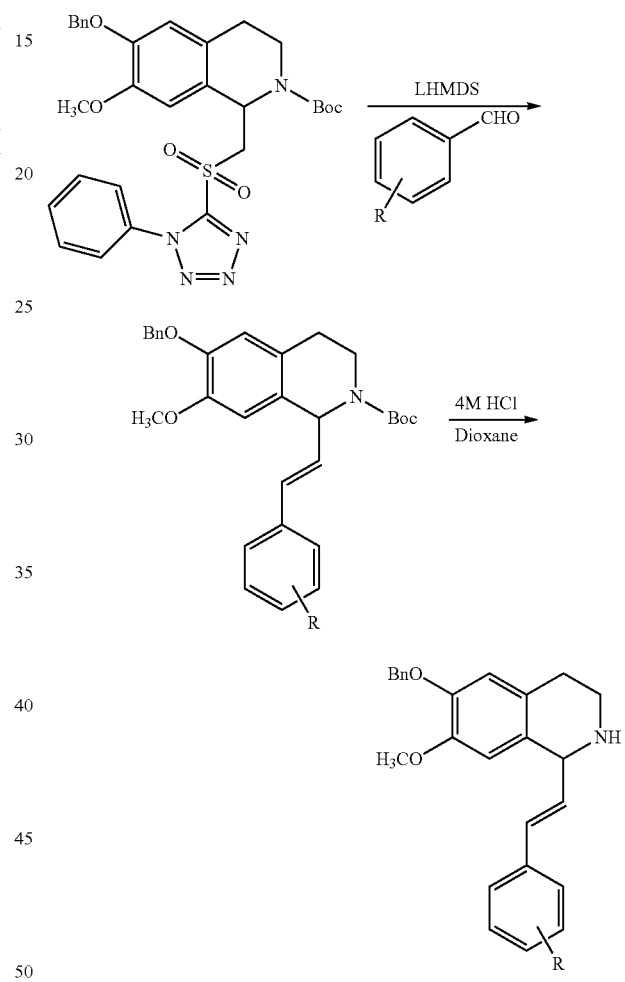

Typical Julia-Kocienski Reaction Conditions:

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and the aldehyde (0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography.

Synthesis of Key Intermediate tert-butyl 6-benzyloxy-7-methoxy-1-[(1-phenyltetrazol-5-yl)sulfonylmethyl]-3,4-dihydro-1H-isoquinoline-2-carboxylate[i]

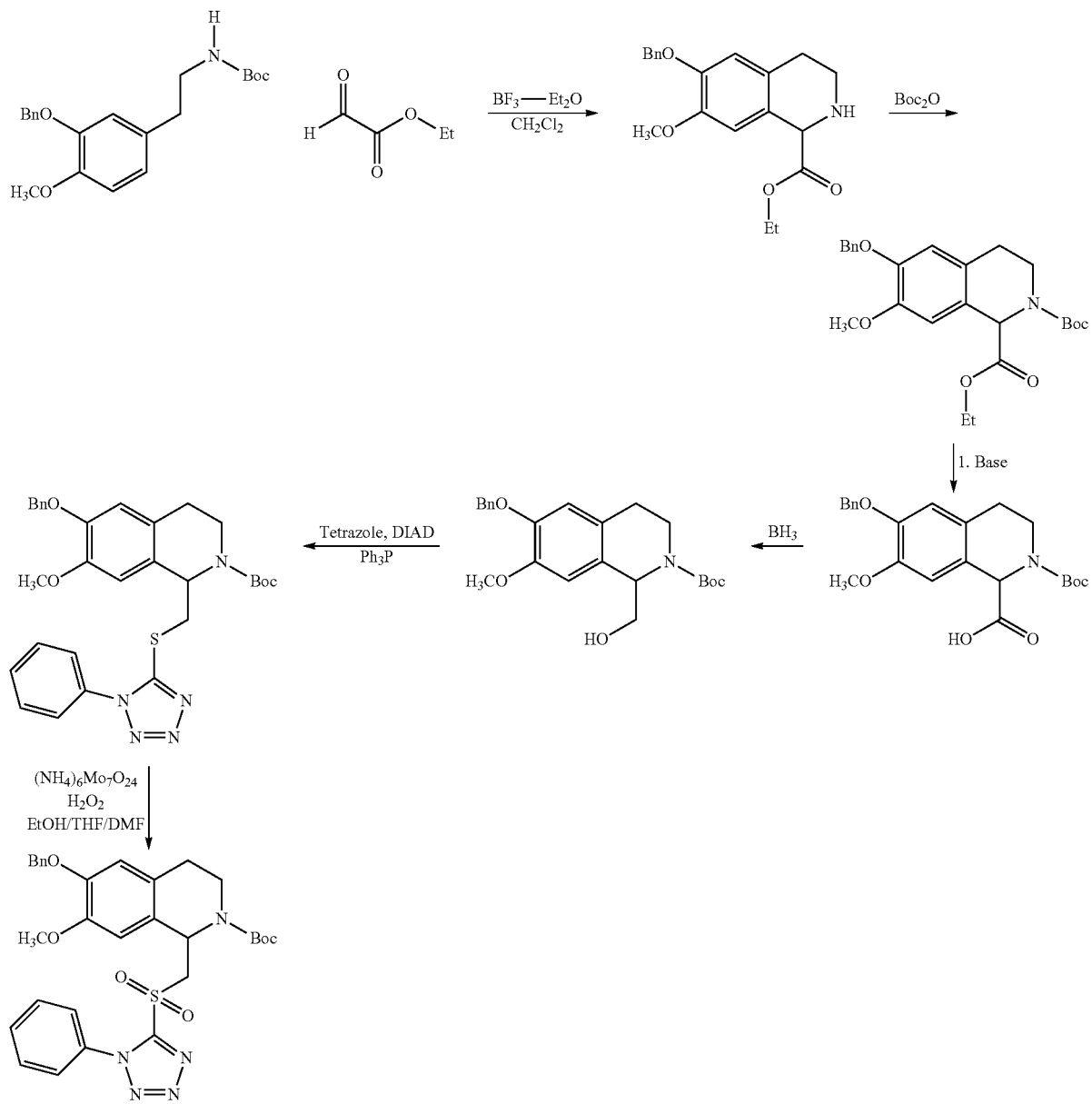

a. Ethyl 6-benzyloxy-7-methoxy-1,2,3,4-tetrahydroisoquinoline-1-carboxylate[f]

tert-ButylN-[2-(3-benzyloxy-4-methoxy-phenyl)ethyl] carbamate (8.9 g, 24.89 mmol) was dissolved in $CH_2Cl_2$ (250 mL) and cooled to 0° C. with stirring under argon. To this solution was added ethyl 2-oxoacetate (9.86 mL, 49.84 mmol, 50% in Toluene), followed by the dropwise addition of $BF_3 \cdot Et_2O$ (7.7 mL, 62.21 mmol) over 30 minutes. The mixture was stirred for 1 hour at 0° C., then allowed to warm to room temperature overnight. The organic layer was evaporated to give a residue, which was purified by flash chromatography. The correct product was confirmed by LC-MS; M+1=342.

b. O2-tert-Butyl O1-ethyl 6-benzyloxy-7-methoxy-3,4-dihydro-1H-isoquinoline-1,2-dicarboxylate Ethyl 6-benzyloxy-7-methoxy-1,2,3,4-tetrahydroisoquinoline-1-carboxylate (9.0 g, 26.63 mmol) was dissolved in $CH_2Cl_2$ (200 mL), followed by $Et_3N$ (4.0 mL, 28.8 mmol) and $Boc_2O$ (6.3 g, 28.8 mmol). The mixture was stirred overnight at room temperature. The mixture was washed with 1M $H_3PO_4$ and brine. The organic layer was dried over MgSO4, filtered and evaporated to give the crude product, which was used without further purification. LC-MS; M+1=442.

c. 6-Benzyloxy-2-tert-butoxycarbonyl-7-methoxy-3,4-dihydro-1H-isoquinoline-1-carboxylic acid O2-tert-Butyl O1-ethyl 6-benzyloxy-7-methoxy-3,4-dihydro-1H-isoquinoline-1,2-dicarboxylate (11.0 g, 24.9 mmol) was dissolved in THF (50 mL), EtOH (50 mL) and $H_2O$ (50 mL). To this solution was added solid KOH (3.8 g, 67.8 mmol) and the mixture was stirred at room temperature for 24 hours. The organic solvents were evaporated and the resulting residue was cooled in an ice bath and acidified with 2M $H_3PO_4$. The mixture was extracted with EtOAc and the combined organic layers were dried over $MgSO_4$, filtered and evaporated to give the crude product, which was used without further purification. LC-MS; M+1=414.

d. tert-Butyl 6-benzyloxy-1-(hydroxymethyl)-7-methoxy-3,4-dihydro-1H-isoquinoline-2-carboxylate To a solution of 6-benzyloxy-2-tert-butoxycarbonyl-7-methoxy-3,4-dihydro-1H-isoquinoline-1-carboxylic acid (4.0 g, 9.67 mmol) in THF (10 mL) at 0° C. was added Borane-THF complex (19.2 mL, 19.2 mmol, 1M). The reaction mixture was stirred at rt for 4 h. The reaction was quenched with water, extracted with EtOAc. The combined organic layer was washed with brine, dried ($MgSO_4$), and concentrated. The crude product was obtained as colorless oil and used in the next step without further purification. LC-MS; M+1=400.

e. tert-Butyl 6-benzyloxy-7-methoxy-1-[(1-phenyltetrazol-5-yl)sulfanylmethyl]-3,4-dihydro-1H-isoquinoline-2-carboxylate[g]

To a stirred solution of tert-butyl 6-benzyloxy-1-(hydroxymethyl)-7-methoxy-3,4-dihydro-1H-isoquinoline-2-carboxylate (3.0 g, 7.5 mmol), phenyl-1H-tetrazole-5-thiol (1.6 g, 9.0 mmol), and triphenylphosphine (2.36 g, 9.0 mmol) in THF (30 mL) was added diisopropyl azodicarboxylate (1.7 mL, 9.0 mol, 2.2 M solution in hexane) dropwise at 0° C. The solution was allowed to stir at 0° C. for an additional 30 min and allowed to warm to room temperature overnight. The reaction mixture was concentrated in vacuo to give a residue which was purified by flash column chromatography (20%-30% EtOAc in hexane) to give the correct product. LC-MS; M+1=560.

f. tert-Butyl 6-benzyloxy-7-methoxy-1-[(1-phenyltetrazol-5-yl)sulfonylmethyl]-3,4-dihydro-1H-isoquinoline-2-carboxylate tert-Butyl 6-benzyloxy-7-methoxy-1-[(1-phenyltetrazol-5-yl)sulfanylmethyl]-3,4-dihydro-1H-isoquinoline-2-carboxylate (14.0 g, 25.03 mmol) was dissolved in a mixture of THF (50 mL), EtOH (100 mL) and DMF (50 mL) and cooled to 0° C. A solution of ammonium paramolybdate tetrahydrate (12.6 g, 10.2 mmol) and 30% hydrogen peroxide (28 mL, 302.4 mmol) at 0° C. was added dropwise over 30 minutes. The reaction mixture was allowed to warm to room temperature overnight, poured into saturated aqueous sodium thiosulfate, and extracted with ethyl acetate three times. The combined organic layers were washed with water and brine and dried over $MgSO_4$. The solvent was removed in vacuo and the residual product was purified by flash chromatography (30% EtOAc in hexane) to give the correct product. LC-MS; M+1=592.

REFERENCES

[a] Cava, M. P.; Buck, K. T. *Tetrahedron* 1969, 25, 2795-2805

[b] Nag, Ahindra et al *Journal of Molecular Catalysis B: Enzymatic* 2012, 82, 92-95; Heo, J. N., et al., *Bull. Korean Chem. Soc.,* 32 (12), 4431, 2011; Srikrishna, A. et al, *Synthetic Communications,* 37(6), 965-976; 2007.

[c] Patent reference: WO2010001169, Astrazeneca.

[d] Herbert, Richard B. et al *Tetrahedron* 1990, 46, 7119-7138.

[e] Chen, T., et al., *Bioorganic and Medicinal Chemistry,* 17, 2351, 2009; Elliott, M. C., et al., Org. Biomol. Chem., 1, 3038, 2003; Bohme, T., et al. *J. Med Chem.,* 45, 3094, 2002.

[f] Miyazaki, M., et al, *Journal of Organic Chemistry,* 76(2), 534-542; 2011.

[g] Muller, D, et al., *Chem. Eur. J.,* 19. 15226, 2013.

[h] Curtin, D. Y., et. al., JACS, 73, 2716, 1951; Chrzanowska, M., et al., *Tetrahedron: Asymmetry,* 12, 1435, 2001; Kawate, T. et al., *Chem. Pharm. Bull.* 41, (2), 287, 1993; Nakagawa, M., *J. Chem. Soc., Chem Commun.,* 991, 1990.

[i] Reddy, R. J. et al., *J Org. Chem.,* 2012, 77, 11101.

IV. Methods of Inhibiting the Replication of a Virus

The compounds of the invention exhibit potency against viruses, and therefore have the potential to inhibit the replication of viruses.

In a further aspect, the invention provides a method of inhibiting the replication of a virus in an animal, comprising administering a compound or a pharmaceutical formulation described herein to the animal, wherein the animal is in need of treatment thereof, thereby inhibiting the replication of the virus in an animal. In an exemplary embodiment, the virus is a member of the retroviridae family. In an exemplary embodiment, the virus is a member of the orthoretroviridae subfamily. In an exemplary embodiment, the virus is a lentivirus. In an exemplary embodiment, the virus is human immunodeficiency virus (HIV). In an exemplary embodiment, the virus is HIV-1. In an exemplary embodiment, the virus is HIV-2. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the viral replication is inhibited through oral administration of the compound of the invention. In an exemplary embodiment, the viral replication is inhibited through intravenous administration of the compound of the invention. In an exemplary embodiment, the viral replication is inhibited through topical administration of the compound of the invention. In an exemplary embodiment, the viral replication is inhibited through intraperitoneal administration of the compound of the invention. In an exemplary embodiment, the compound is administered in a topically effective amount. In an exemplary embodiment, the pharmaceutical formulation is administered in an orally effective amount.

V. Methods of Treating and/or Preventing Disease

The compounds of the invention exhibit potency against a virus, and therefore have the potential to achieve therapeutic efficacy in the animals described herein.

In another aspect, the invention provides a method of treating a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment of viral-associated disease. In an exemplary embodiment, the compound of the invention can be used in human or veterinary medical therapy, particularly in the treatment or prophylaxis of lentivirus-associated disease. In an exemplary embodiment, the disease is associated with a human immunodeficiency virus. In an exemplary embodiment, the disease is associated with HIV-1. In an exemplary embodiment, the disease is associated with HIV-2. In an exemplary embodiment, the disease is AIDS. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the animal is a human. In another exemplary embodiment, the animal is cattle. In another exemplary embodiment, the animal is a cow. In another exemplary embodiment, the animal is a bull.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the pharmaceutical formulation is administered in an orally effective amount.

In an exemplary embodiment, the invention provides a method of treating AIDS by administering a therapeutically effective amount of a compound of the invention.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered intramuscularly. In an exemplary embodiment, the pharmaceutical formulation is administered subcutaneously. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be added as a food or drink supplement for humans.

Dosage levels of the order of from about 1 mg to about 250 mg per kilogram of body weight per day and more preferably from about 5 mg to about 150 mg per kilogram of body weight per day, and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 5000 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular animal (such as a human) will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 7000 mg of a compound of the invention. In an exemplary embodiment, the unit dosage form contains from about 1 mg to about 5000 mg of an active ingredient. In an exemplary embodiment, the unit dosage form contains from about 100 mg to about 2000 mg of a compound of the invention. In an exemplary embodiment, the unit dosage form contains from about 200 mg to about 1000 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the animal (such as a human) and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosages for use in humans or animals. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the human's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein.

For example, a dose can be formulated in animal models to achieve a circulating concentration range that includes the $EC_{50}$ (effective dose for 50% increase) as determined in cell culture, i.e., the concentration of the test compound which achieves a half-maximal inhibition of viral cell growth. Such information can be used to more accurately determine useful doses in humans or animals.

In general, the compounds prepared by the methods, and from the intermediates, described herein will be administered in a therapeutically effective amount by any of the accepted modes of administration for agents that serve similar utilities. It will be understood, however, that the specific dose level for any particular animal (such as a human) will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain viral growth inhibitory effects. Usual animal (such as a human) dosages for systemic administration range from 0.1 to 1000 mg/day, preferably, 1-500 mg/day, more preferably 10-200 mg/day, even more preferably 100-200 mg/day. Stated in terms of animal (such as a human) body surface areas, usual dosages range from 50-91 $mg/m^2/day$.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a pharmaceutical formulation comprising: a) the compound according to any of the above paragraphs, or a pharmaceutically acceptable salt thereof; and b) a pharmaceutically acceptable excipient.

In an exemplary embodiment, the invention provides a method of inhibiting the replication of a virus in an animal, comprising: administering a compound or a pharmaceutical formulation of a preceding claim to the animal, wherein the animal is in need of treatment thereof, thereby inhibiting the replication of the virus in an animal.

In an exemplary embodiment, according to any of the above paragraphs, wherein the virus is a member of the Orthoretroviridae family.

In an exemplary embodiment, according to any of the above paragraphs, wherein the virus is HIV.

In an exemplary embodiment, the invention provides a method of treating a disease in an animal, comprising: a)

administering a compound or a pharmaceutical formulation described herein to the animal, wherein the animal is in need of treatment thereof, thereby treating the disease in the animal.

In an exemplary embodiment, according to any of the above paragraphs, the disease is AIDS.

In an exemplary embodiment, according to any of the above paragraphs, the animal is a human.

In an exemplary embodiment, according to any of the above paragraphs, the invention is a use of a compound of the invention or a pharmaceutical formulation of the invention in the manufacture of a medicament for the treatment of a viral infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1$H NMR) spectra were recorded on a Varian INOVA NMR spectrometer [400 MHz (H) or 500 MHz ($^1$H)] or Varian 400-MR [400 MHz (1H)]. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer or Agilent 1200 series with a 6140 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

EXAMPLES

Example A: 1-[2-(3,4-Dimethoxyphenyl)ethyl]-6,7-dimethoxy-1,2,3,4-tetrahydroisoquinoline

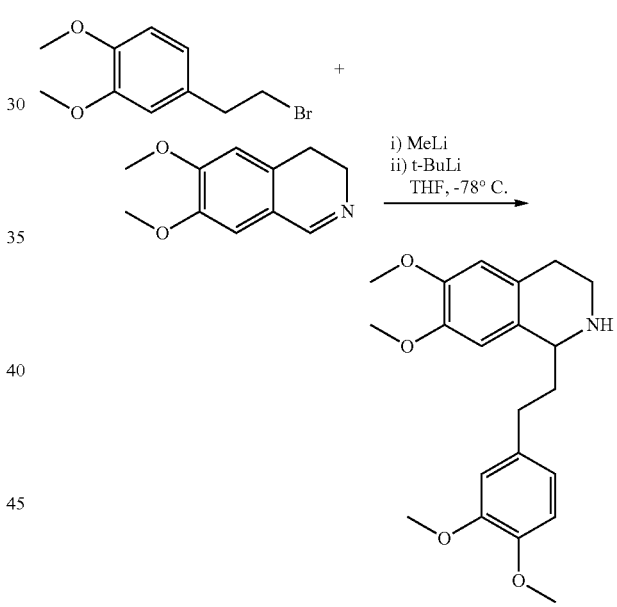

To the solution of 3,4-dimethoxyphenethyl bromide (1.78 g, 7.28 mmol) in anhydrous THF (30 mL), under argon, at −78° C. was added MeLi (6 mL, 1.6M in diethyl ether, 9.6 mmol), the resulting mixture was stirred for 1 hr. A solution of t-BuLi (9 mL, 1.7M in pentane, 15.30 mmol), stirred at −78° C. for another 1 hr, then the solution of commercially available 6,7-dimethoxy-3,4-dihydroisoquinoline (1.67 g, 8.73 mmol) in THF (20 mL) was added with the aid of a syringe. After all the addition, the resulting mixture was stirred at −78° C. for 3 hrs, quenched with satd. aqueous $NH_4Cl$ solution and gradually allowed to warm to room temperature and extracted with EtOAc. The organic layer was washed with brine, dried ($Na_2SO_4$), filtered, concentrated and purified with flash chromatography using MeOH ($NH_3$)/$CHCl_3$ gradient to afford the titled compound. M+H=358.

Example B: [6-Benzyloxy-1-[(E)-2-(3-benzyloxy-4-methoxy-phenyl)vinyl]-7-methoxy-3,4-dihydro-1H-isoquinolin-2-yl]-pyrazin-2-yl-methanone

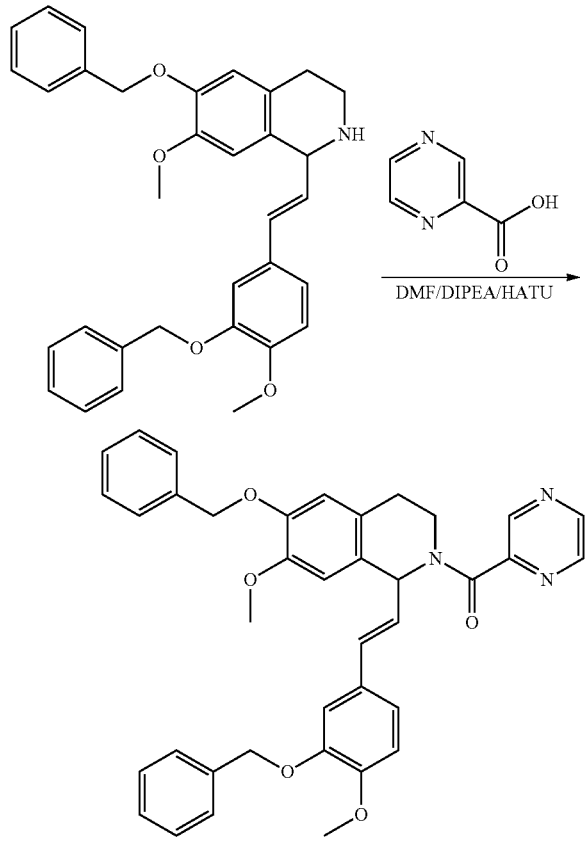

To the solution of (E)-6-(benzyloxy)-1-(3-(benzyloxy)-4-methoxystyryl)-7-methoxy-1,2,3,4-tetrahydroisoquinoline (81.4 mg, 0.13 mmol) in anhydrous DMF (2 mL), was added pyrazine-2-carboxylic acid (81 mg, 0.65 mmol), HATU (250 mg, 0.66 mmol) and DIPEA (1 mL). The resulting solution was stirred at room temperature overnight. After the usual workup, the crude obtained was purified on the Shimadzu HPLC system to afford the TFA salt. M+H (Neutral)=614.

Example C: 1-[(E)-2-(5-Benzyloxy-4-methoxy-2-methyl-phenyl)vinyl]-6,7-dimethoxy-1,2,3,4-tetrahydroisoquinoline

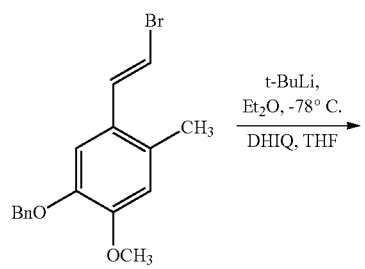

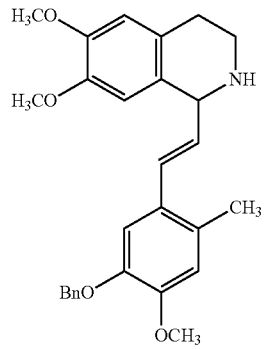

(E)-1-(Benzyloxy)-5-(2-bromovinyl)-2-methoxy-4-methylbenzene (334 mg, 1.0 mmol) was dissolved in dry Et$_2$O (15 mL) and cooled to −78° C. A solution of t-BuLi (1.3 mL mL, 2.2 mmol, 1.7M in pentane) was added dropwise and the resulting solution was stirred at −78° C. for 1 hour before a solution of 6,7-dimethoxy-3,4-dihydroisoquinoline (191 mg, 1.0 mmol), in THF (3 mL) was added dropwise. The resulting mixture was stirred for 2 hours at −78° C. and then quenched with sat. aqueous NH$_4$Cl solution. The mixture was extracted with EtOAc and the combined organic layers were dried over MgSO$_4$, filtered and evaporated to dryness. The residue obtained was purified by flash silica gel chromatography to afford the titled compound. LCMS: M+1=425.6.

Example D: 7-Benzyloxy-1-[(E)-2-(4-benzyloxy-3-methoxy-phenyl)vinyl]-2-butyl-6-methoxy-3,4-dihydro-1H-isoquinoline

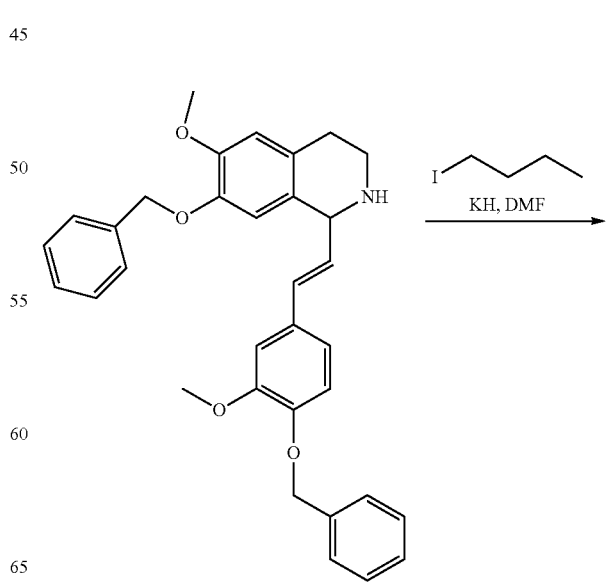

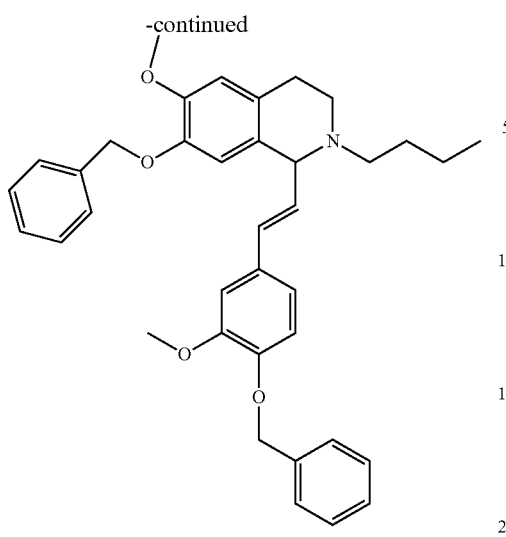

To the solution of (E)-7-(benzyloxy)-1-(4-(benzyloxy)-3-methoxystyryl)-6-methoxy-1,2,3,4-tetrahydroisoquinoline (86 mg, 0.17 mmol) in DMF (3 mL) was added KH (15 mg, 0.37 mmol), followed by 1-iodobutane (0.100 mL, 0.88 mmol). The resulting solution was stirred at room temperature overnight. The reaction mixture was diluted with EtOAc, washed with brine, dried (Na$_2$SO$_4$), filtered, concentrated and purified with flash chromatography using hexanes/EtOAc gradient to afford the titled compound. M+H=564.

Example E: 6-Benzyloxy-1-[(E)-2-(5-benzyloxy-4-methoxy-2-methyl-phenyl)vinyl]-7-methoxy-2-methyl-3,4-dihydro-1H-isoquinoline

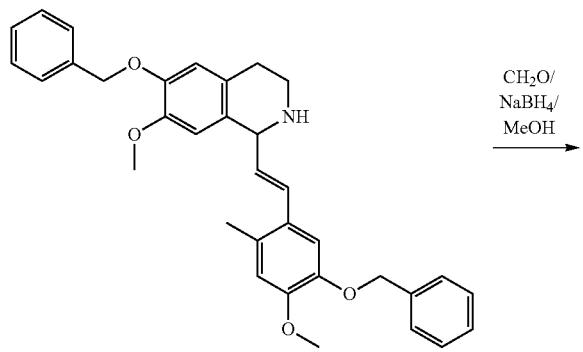

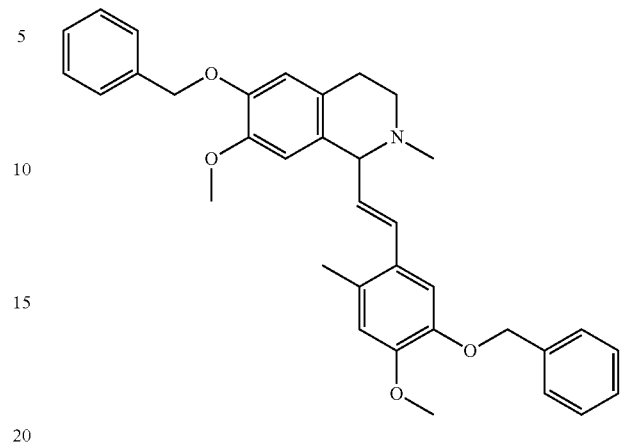

A mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.1 mmol)] and 50 µl of 38% formalin with 500 µl of MeOH was stirred at room temperature for 1 h then treated with 40 mg of NaBH$_4$. After stirring 12 h at room temperature the mixture was diluted with 10 mL of DCM and washed with water. The DCM layer was dried (Na$_2$SO$_4$) then filtered and the filtrate rotary evaporated to dryness. Yield=13.4 mg (25% yield) via prep chrom. MS (m/z): 536 [M+H]

Example F: (6-Amino-2-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone

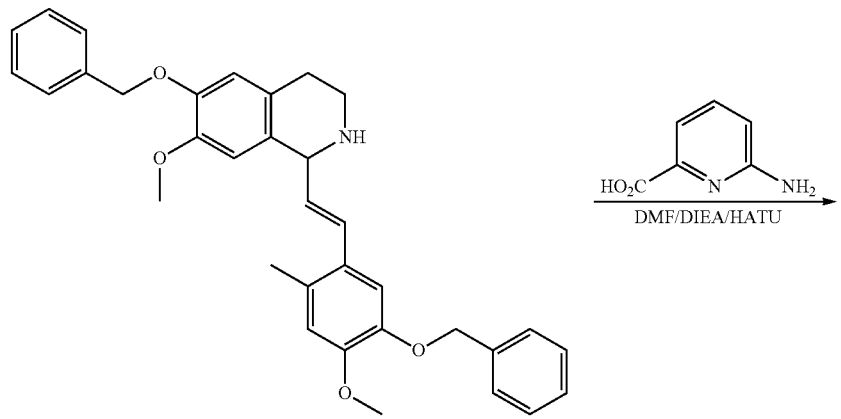

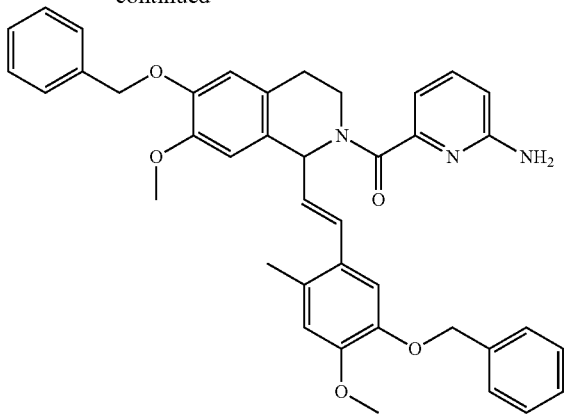

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], 6-aminopyridine-2-carboxylic acid [13.8 mg (0.1 mmol)], DIEA [50 uL (0.3 mmol)] and 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried ($Na_2SO_4$) and the solvent removed. Yield=35 mg (57%) via prep. chrom. MS (m/z): 642 [M+H]

Example G: 6-Benzyloxy-1-[(E)-2-(3-benzyloxy-4-methoxy-phenyl)vinyl]-2-butyl-7-methoxy-3,4-dihydro-1H-isoquinoline

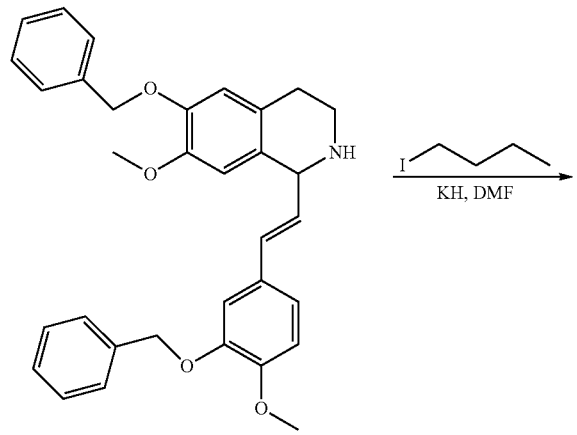

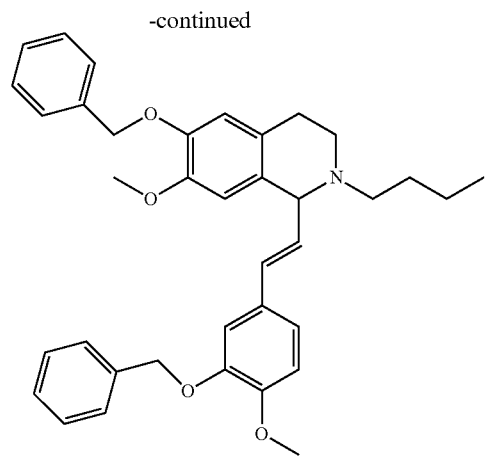

To the solution of (E)-6-(benzyloxy)-1-(3-(benzyloxy)-4-methoxystyryl)-7-methoxy-1,2,3,4-tetrahydroisoquinoline (0.2841 g, 0.56 mmol), in DMF (5 mL) was added KH (25 mg, 0.62 mmol), followed by 1-iodobutane (0.32 mL, 2.81 mmol). The resulting mixture was stirred at room temperature overnight, After workup, the crude obtained was purified on the Shimadzu HPLC system to afford the TFA salt. M+H (Neutral)=564.

Example H: [6-Benzyloxy-1-[(E)-2-(5-benzyloxy-4-methoxy-2-methyl-phenyl)vinyl]-7-methoxy-3,4-dihydro-1H-isoquinolin-2-yl]-pyrazin-2-yl-methanone

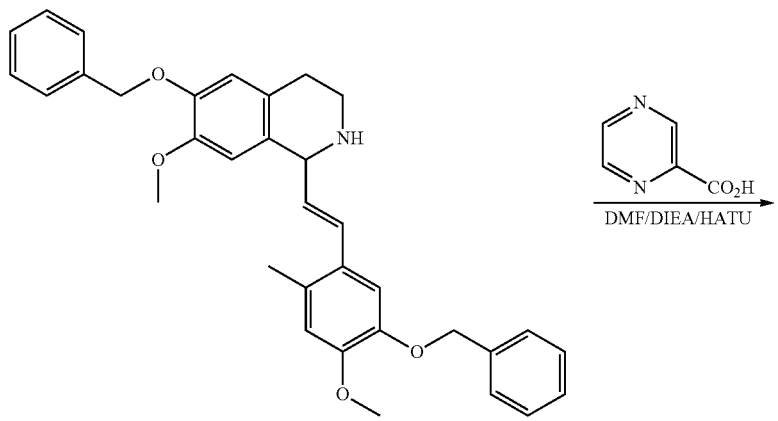

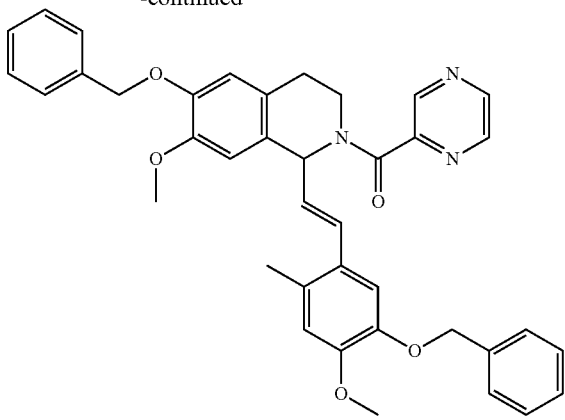

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], Pyrazine carboxylic acid [12.4 mg (0.1 mmol)], DIEA [50 ul (0.3 mmol)] and 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried (Na$_2$SO$_4$) and the solvent removed. Yield=51.2 mg (84%) via prep chrom. MS (m/z): 628 [M+H]

Example I: Methyl 6-benzyloxy-1-[(E)-2-(4,5-dimethoxy-2-methyl-phenyl)vinyl]-7-methoxy-3,4-dihydro-1H-isoquinoline-2-carboxylate

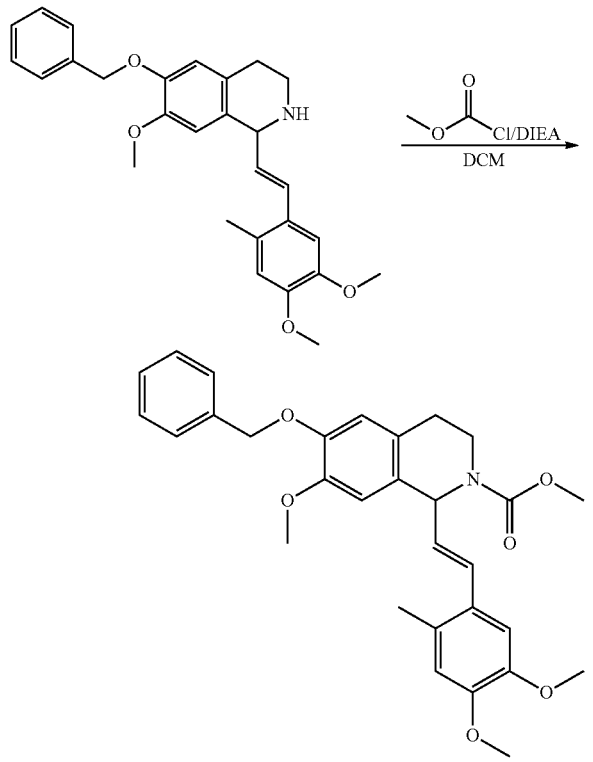

A mixture of 6-benzyloxy-1-[(E)-2-(4,5-dimethoxy-2-methyl-phenyl)vinyl]-7-methoxy-1,2,3,4-tetrahydroisoquinoline [44.5 mg (0.1 mmol)] and 2 mL of DCM with DIEA [26 uL (0.15 mmol)] was treated with Methyl chloroformate [14 ul (0.12 mmol)] and stirred at room temperature for 1 h. The mixture was diluted with 10 mL of DCM and washed with water. The DCM layer was dried (Na$_2$SO$_4$) then filtered and the filtrate rotary evaporated to dryness. Yield=50 mg (99% yield) MS (m/z): 504 [M+H]

Example J: 6-Benzyloxy-1-[(E)-2-(5-benzyloxy-2-tert-butyl-4-methoxy-phenyl)vinyl]-7-methoxy-1,2,3,4-tetrahydroisoquinoline

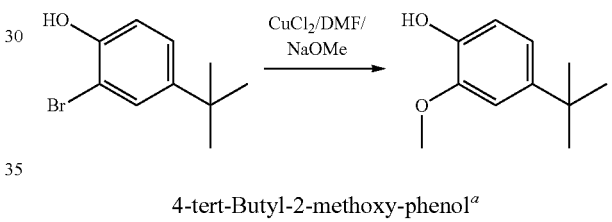

4-tert-Butyl-2-methoxy-phenol[a]

A mixture of 4-t-butyl-2-bromophenol [5. g (0.0218 mol)], Copper(II) chloride [1.5 g (0.0112 mol)], NaOMe [12 g (0.218 mol) in 150 mL of DMF was refluxed for 4.5 h, filtered and the solvent removed via rotary evaporation. The residue was diluted with water and treated with conc. HCl until neutral. The mixture was then extracted with DCM, dried (Na$_2$SO$_4$) and the solvent removed affording the desired 4-tert-butyl-2-methoxy-phenol. Yield=3.1 g (79% after flash chromatography with DCM) MS (m/z): 181 [M+H]

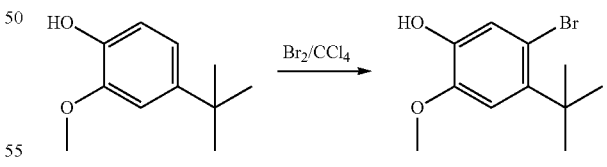

Synthesis of 5-bromo-4-tert-butyl-2-methoxy-phenol[b]

To a solution of 4-tert-butyl-2-methoxy-phenol [3.1 g (0.0172 mol)] in CCl$_4$ (62 mL) was added drop wise a solution of Br$_2$ [0.9 mL (0.0174 mol)] in CCl$_4$ (31 mL) at 100° C. Upon completion the reaction was washed with water, dried (Na$_2$SO$_4$) and the solvent removed affording 5-bromo-4-tert-butyl-2-methoxy-phenol. Yield=4 g (90% used without further purification) MS (m/z): 259 [M+H].

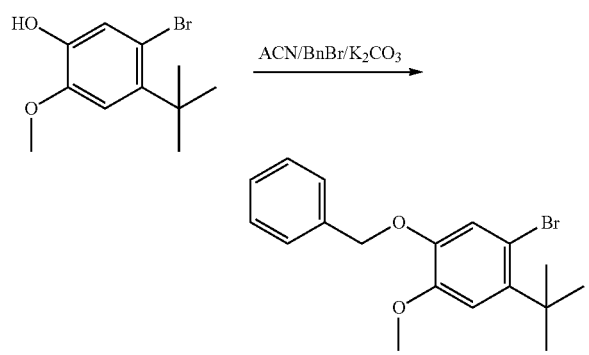

1-Benzyloxy-5-bromo-4-tert-butyl-2-methoxy-benzene[c]

A mixture of 5-bromo-4-tert-butyl-2-methoxy-phenol [4 g (0.01555 mol)], Benzyl bromide [5.3 g (0.031 mol)], K$_2$CO$_3$ [4.28 g (0.031 mol) in ACN (31 mL) was refluxed for 18 h, cooled and the solvent removed via rotary evaporation. The residue was diluted with water and extracted with EtOAc. The extract was then dried (MgSO$_4$) and the solvent removed affording the desired 1-benzyloxy-5-bromo-4-tert-butyl-2-methoxy-benzene. Yield=4.5 g (83% after flash chromatography with 10% EtOAc/Hexane) MS (m/z): 349 [M+H]

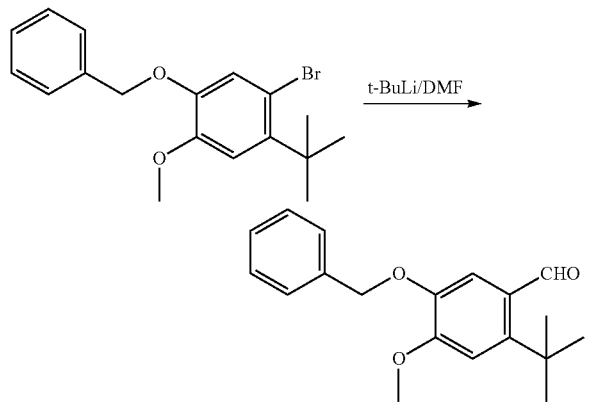

5-(Benzyloxy)-2-tert-butyl-4-methoxybenzaldehyde

To a solution of 1-benzyloxy-5-bromo-4-tert-butyl-2-methoxy-benzene [4.5 g (0.0129 mol)] in THF (15 mL) was added, at −78° C., 1.7M t-Butyl lithium [8.8 mL (0.014 mol)]. The reaction mixture was then stirred at −780 C for 40 min and then treated with DMF [5 mL (0.0645 mol)]. The mixture was then allowed to slowly come to room temperature overnight and was then quenched with sat NH$_4$Cl, extracted with Et$_2$O. The extract was dried (MgSO$_4$) and the solvent removed affording 5-benzyloxy-2-tert-butyl-4-methoxy-benzaldehyde. Yield=0.52 g (13% used without further purification) MS (m/z): 299 [M+H]

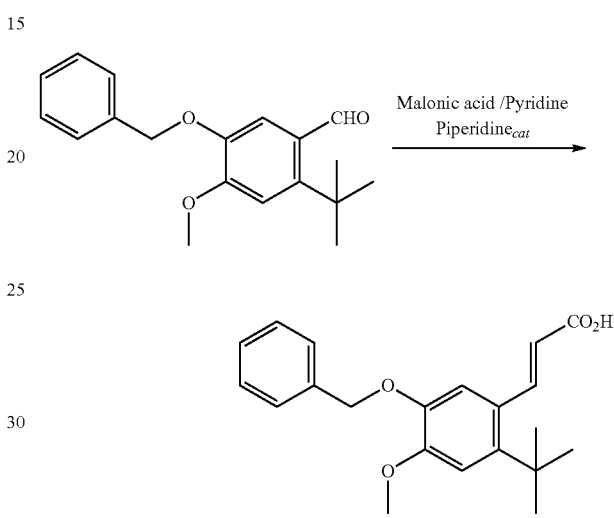

(E)-3-(5-Benzyloxy-2-tert-butyl-4-methoxy-phenyl)prop-2-enoic acid

A mixture of 5-benzyloxy-2-tert-butyl-4-methoxy-benzaldehyde [0.520 g (0.0017 mol)], malonic acid [0.354 g (0.0034 mol)], pyridine (3 mL) and piperidine (0.1 mL) was stirred at 80° C. for 1 h followed by stirring for 3 h at 115° C. The reaction was then poured into water (20 mL) and acidified with conc. HCl. The resulting white ppt. was filtered and vacuum dried affording the desired (E)-3-(5-benzyloxy-2-tert-butyl-4-methoxy-phenyl)prop-2-enoic acid. Yield=0.6 g (quant) MS (m/z): 341 [M+H]

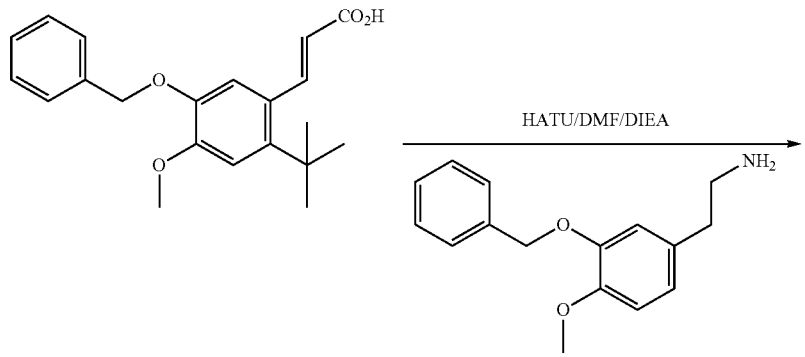

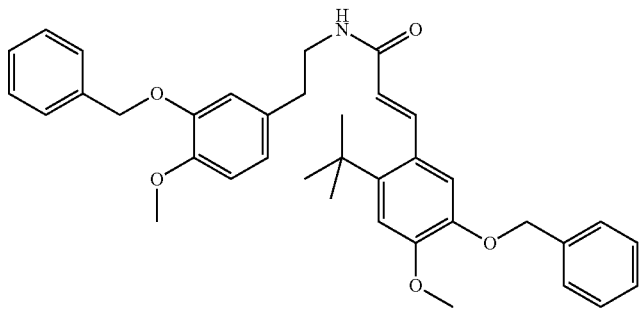

(E)-3-(5-Benzyloxy-2-tert-butyl-4-methoxy-phenyl)-N-[2-(3-benzyloxy-4-methoxy-phenyl)ethyl]prop-2-enamide To a mixture of (E)-3-(5-benzyloxy-2-tert-butyl-4-methoxy-phenyl)prop-2-enoic acid [163 mg (0.5 mmol)], 2-(3-benzyloxy-4-methoxy-phenyl)ethanamine [129 mg (0.5 mmol)], DMF (2 mL) and DIEA [0.250 mL (1.4 mmol)] was added HATU [238 mg (0.62 mmol)]. The reaction mix was stirred at room temperature 2 h then diluted with 20 mL of EtOAc and washed 2× with sat. NaCl aq. The EtOAc layer was dried (MgSO$_4$) and the solvent removed affording (E)-3-(5-benzyloxy-2-tert-butyl-4-methoxy-phenyl)-N-[2-(3-benzyloxy-4-methoxy-phenyl) ethyl] prop-2-enamide. Yield=225 mg (78% after flash with 10% MeOH/DCM) MS (m/z): 580 [M+H]

6-Benzyloxy-1-[(E)-2-(5-benzyloxy-2-tert-butyl-4-methoxy-phenyl)vinyl]-7-methoxy-3,4-dihydroisoquinoline To a solution of (E)-3-(5-benzyloxy-2-tert-butyl-4-methoxy-phenyl)-N-[2-(3-benzyloxy-4-methoxy-phenyl) ethyl]prop-2-enamide [225 mg (0.39 mmol)] in ACN (9 mL) was added, under reflux, POCl$_3$ [300 ul (3.21 mmol)]. The reaction was stirred at reflux for 10 min and then rotary evaporated to dryness. The residue was taken up into 10 mL of chloroform and was then treated with 20 mL of 2N KOH and 50 mL of Et$_2$O. This mixture was rapidly stirred for 30 min at room temperature and the upper organic layer removed, washed with water, dried (Na$_2$SO$_4$) and the solvent removed. Yield=205 mg crude: A 50 mg fraction was removed and purified via reverse phase preparatory chromatography affording 15 mg (23% yield) MS (m/z): 562 [M+H]

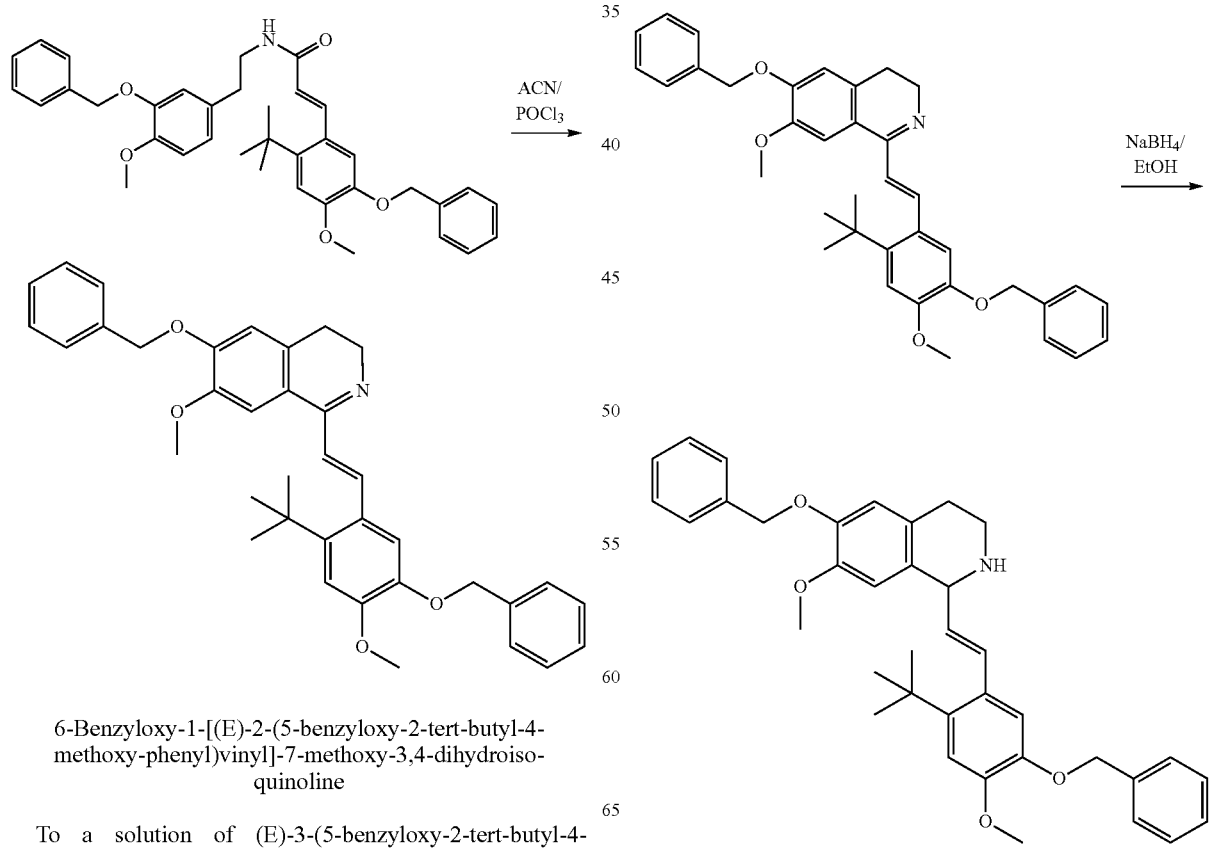

6-Benzyloxy-1-[(E)-2-(5-benzyloxy-2-tert-butyl-4-methoxy-phenyl)vinyl]-7-methoxy-1,2,3,4-tetrahydroisoquinoline The crude 6-benzyloxy-1-[(E)-2-(5-benzyloxy-2-tert-butyl-4-methoxy-phenyl)vinyl]-7-methoxy-3,4-dihydroisoquinoline from the previous reaction (155 mg) was the dissolved into 8 mL of dry EtOH and then treated with NaBH$_4$ [12 mg (0.32 mmol)]. The mixture was stirred for 1 h at room temperature and the resulting solid was carefully filtered off and dried. The solid was triturated with 50/50 ACN/water, filtered and vacuum dried. Yield=50 mg (11% overall) MS (m/z): 564 [M+H]

Example K: (2-Amino-3-pyridyl)-[6-benzyloxy-1-[(E)-2-(5-benzyloxy-4-methoxy-2-methyl-phenyl)vinyl]-7-methoxy-3,4-dihydro-1H-isoquinoline-2-yl] methanone

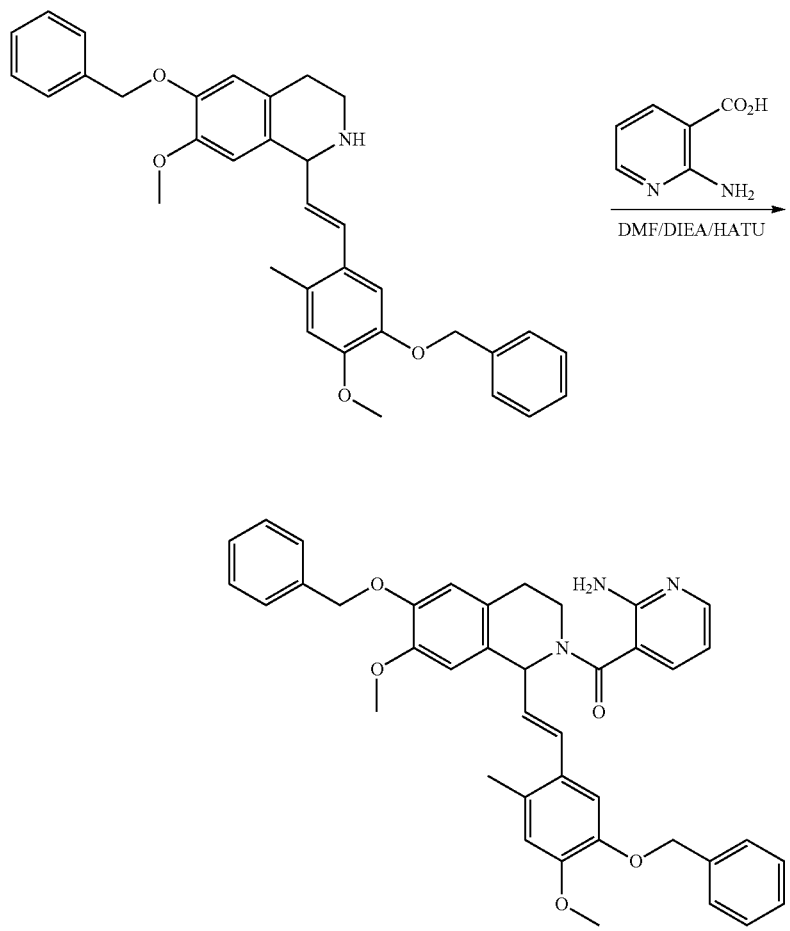 [SMILES: COc1cc(C)c(/C=C/C2NCCc3cc(OCc4ccccc4)c(OC)cc32)cc1OCc1ccccc1 ; Nc1ncccc1C(=O)O ; COc1cc(C)c(/C=C/C2c3cc(OC)c(OCc4ccccc4)cc3CCN2C(=O)c2cccnc2N)cc1OCc1ccccc1]

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], 2-aminopyridine-3-carboxylic acid [13.8 mg (0.1 mmol)], DIEA [50 ul (0.3 mmol)] and 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried (Na$_2$SO$_4$) and the solvent removed. Yield=24 mg (39%) via prep chrom MS (m/z): 642 [M+H]

Example L: Methyl 6-benzyloxy-1-[(E)-2-(3-benzyloxy-4-methoxy-phenyl)vinyl]-7-methoxy-3,4-dihydro-1H-isoquinoline-2-carboxylate

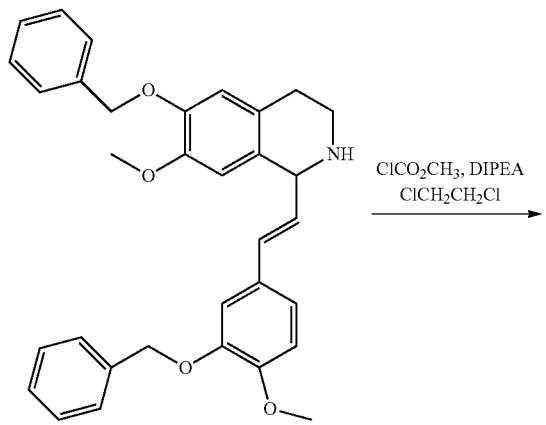

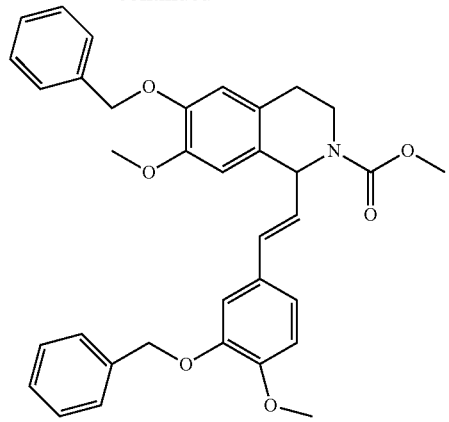

To the solution of (E)-6-(benzyloxy)-1-(3-(benzyloxy)-4-methoxystyryl)-7-methoxy-1,2,3,4-tetrahydroisoquinoline (51.4 mg, 0.083 mmol) in anhydrous 1,2-dichloroethane (3 mL) was added DIPEA (0.5 mL) followed by methyl chloroformate (33 micromL, 0.43 mmol). The resulting solution was stirred at room temperature overnight. It was concentrated to dryness and purified on the Shimadzu HPLC system to afford the TFA salt. M+H (Neutral)=566.

Example M: [6-benzyloxy-1-[(E)-2-(5-benzyloxy-4-methoxy-2-methyl-phenyl)vinyl]-7-methoxy-3,4-dihydro-1H-isoquinolin-2-yl]-(2-pyridyl)methanone

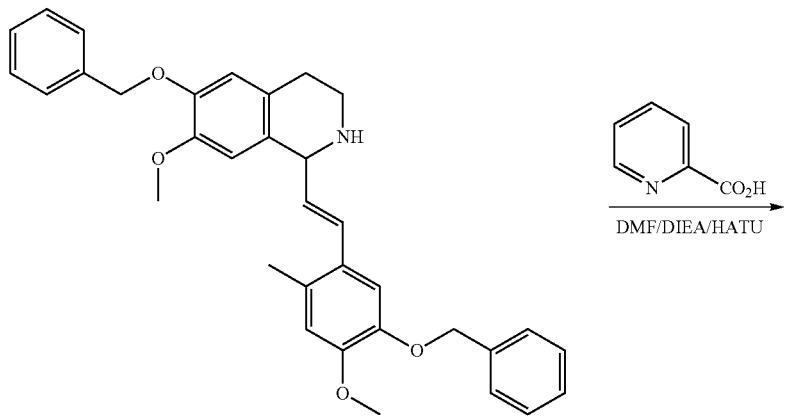

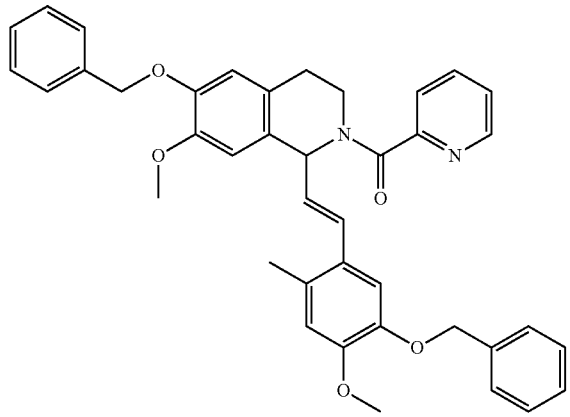

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], Picolinic acid [12.4 mg (0.1 mmol)], DIEA [50 ul (0.3 mmol)] & 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried ($Na_2SO_4$) and the solvent removed. Yield=42 mg (58%) via prep chrom. MS (m/z): 627 [M+H]

Example N: (2-amino-4-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone

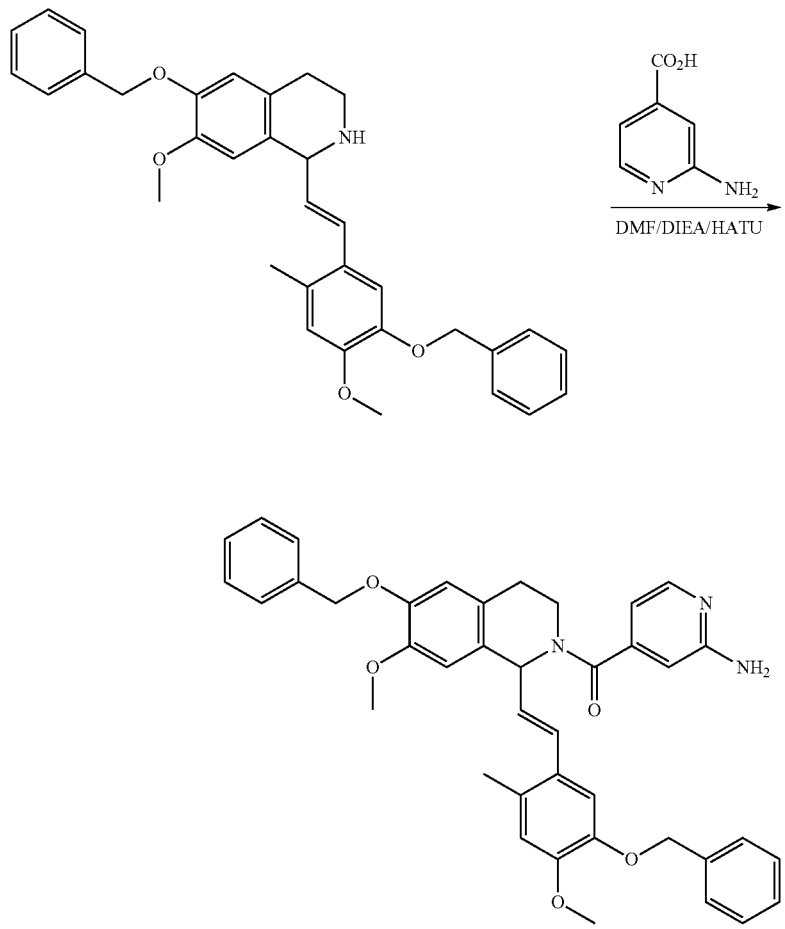 [SMILES: COc1cc(C)c(/C=C/C2NCCc3cc(OCc4ccccc4)c(OC)cc32)cc1OCc1ccccc1 ; Nc1cc(C(=O)O)ccn1 ; COc1cc(C)c(/C=C/C2c3cc(OC)c(OCc4ccccc4)cc3CCN2C(=O)c2ccnc(N)c2)cc1OCc1ccccc1]

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], 2-aminopyridine-4-carboxylic acid[13.8 mg (0.1 mmol)], DIEA [50 ul (0.3 mmol)] & 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried ($Na_2SO_4$) and the solvent removed. Yield=28 mg (46%) via prep chrom. MS (m/z): 642 [M+H]

Example O: 6-benzyloxy-1-[(E)-2-(5-benzyloxy-4-methoxy-2-methyl-phenyl)vinyl]-N-tert-butyl-7-methoxy-3,4-dihydro-1H-isoquinoline-2-carboxamide

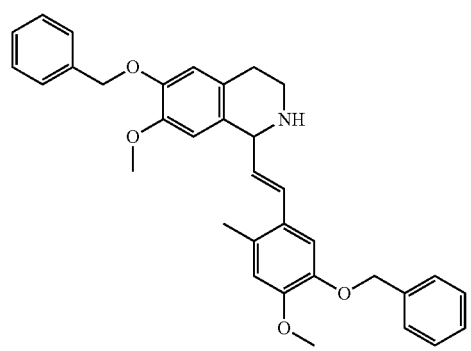

-continued

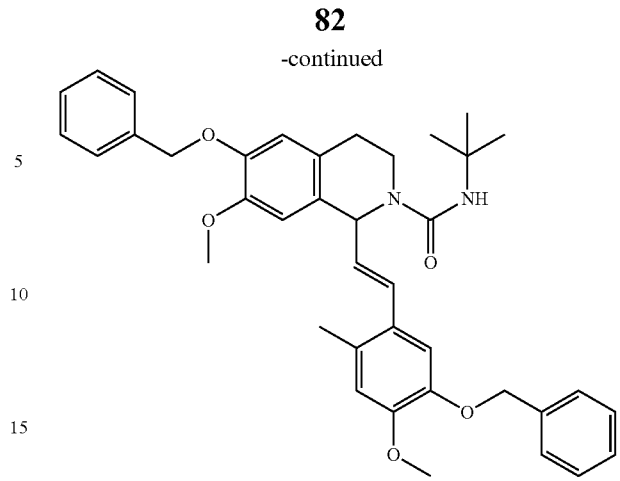

A mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.1 mmol)] and 2 mL of DCM was treated with t-Butylisocyanate [14 μl (0.12 mmol)] and stirred at room temperature for 1 h. The mixture was diluted with 10 mL of DCM and washed with water. The DCM layer was dried (Na$_2$SO$_4$) then filtered and the filtrate rotary evaporated to dryness. Yield=13 mg (21% yield) via prep chrom. MS (m/z): 621 [M+H]

Example P: (6-amino-3-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone

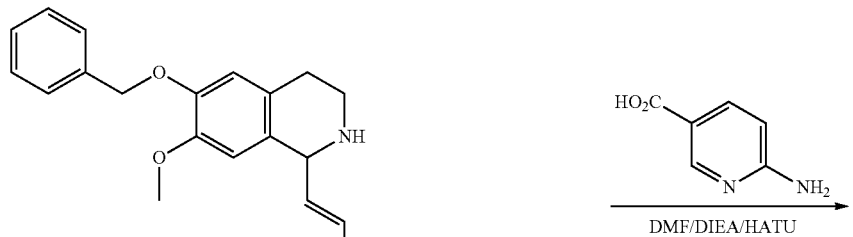

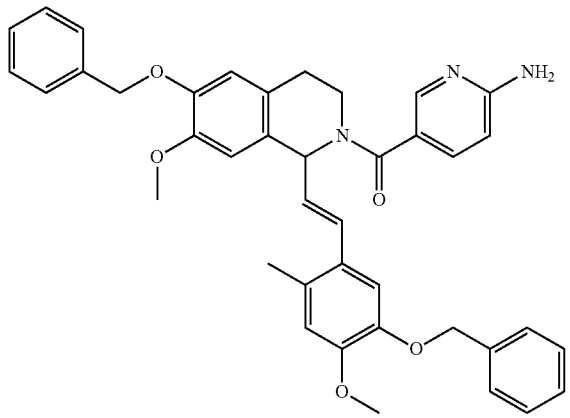

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], 6-aminopyridine-3-carboxylic acid [13.8 mg (0.1 mmol)], DIEA [50 ul (0.3 mmol)] and 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried (Na$_2$SO$_4$) and the solvent removed. Yield=30 mg (49%) via prep chrom. MS (m/z): 642 [M+H]

Example Q: 6-benzyloxy-1-[2-(5-benzyloxy-4-methoxy-2-methyl-phenyl)ethyl]-7-methoxy-1,2,3,4-tetrahydroisoquinoline Yield=44.6 mg (45% yield) via prep chrom. MS (m/z): 524 [M+H]

Example R: 6-benzyloxy-1-[(E)-2-(5-benzyloxy-4-methoxy-2-methyl-phenyl)vinyl]-7-methoxy-3,4-dihydro-1H-isoquinoline-2-carboxamide

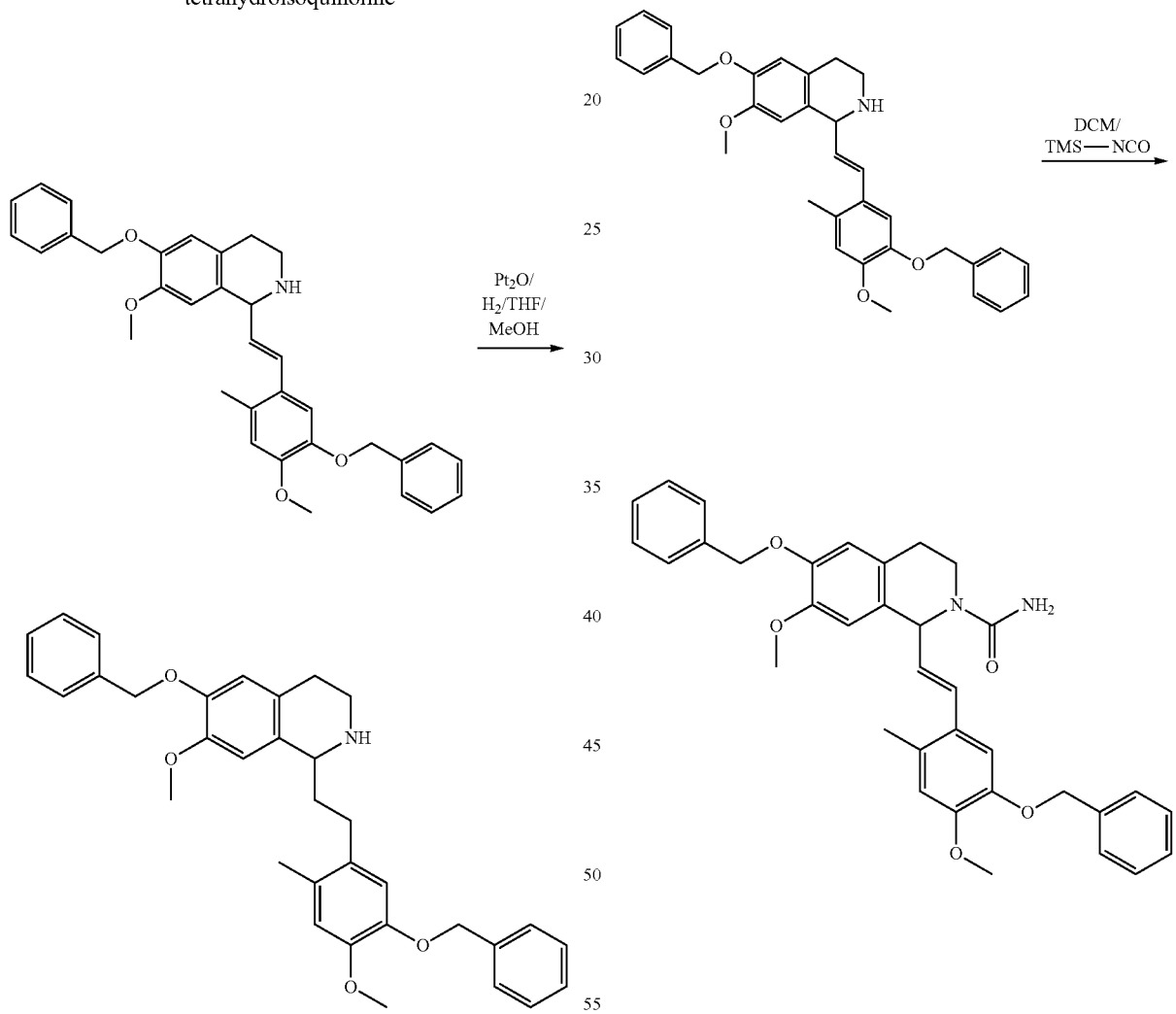

A mixture of 6-benzyloxy-1-[(E)-2-(3-benzyloxy-4-methoxy-2-methyl-phenyl)vinyl]-7-methoxy-1,2,3,4-tetrahydroisoquinoline [100 mg (0.1919 mmol)] and 10 mg of PtO$_2$ in 10 mL of 50/50 THF/EtOH was rapidly stirred, evacuated and filled with H$_2$ gas 3×. The reaction mix was then stirred under positive H$_2$ pressure using a balloon for 2 h, then filtered and the filtrate rotary evaporated to dryness.

A mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.1 mmol)] and 2 mL of DCM was treated with TMS-Isocyanate [13 mg (0.11 mmol)] and stirred at room temperature for 1 h. The mixture was diluted with 10 mL of DCM and washed with water. The DCM layer was dried (Na$_2$SO$_4$) then filtered and the filtrate rotary evaporated to dryness. Yield=38.1 mg (70% yield) Triturated from ACN/Water. MS (m/z): 565 [M+H]

Example S: 7-benzyloxy-1-[(E)-2-(4-benzyloxy-3-methoxy-phenyl)vinyl]-6-methoxy-1,2,3,4-tetrahydroisoquinoline of the 4-benzyloxy-3-methoxy-beta-nitrostyrene (11.51 g, 40.34 mmol) in THF (80 mL) over 1 hr. After the addition, the resulting mixture was stirred and heated to reflux for 16

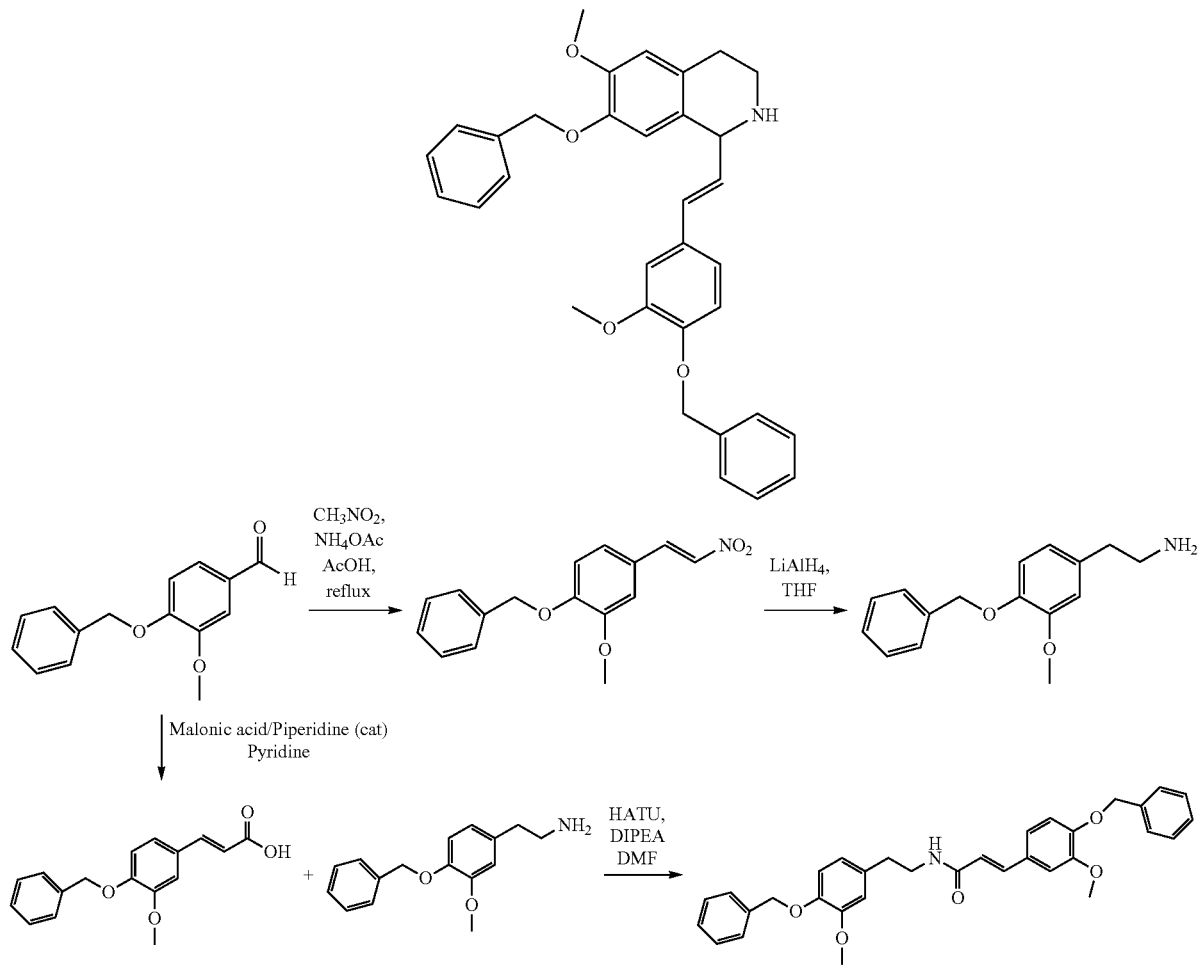

(E)-1-(Benzyloxy)-2-methoxy-4-(2-nitrovinyl)benzene

4-Benzyloxy-3-methoxyphenethylamine was prepared according to Schrittweieser. J. H, et, J.O.C. 2011, 76, 6703-6714. A solution of 4-(benzyloxy)-3-methoxybenzaldehyde (25 g, 103.2 mmol), nitromethane (18 mL, 333.2 mmol) and $NH_4OAc$ (20.23 g, 262.5 mmol) in AcOH (220 mL) was refluxed for 5 hr. After cooling it was poured into ice-water (300 mL), followed by addition $CH_2Cl_2$ (200 mL) stirred at room temperature until the phases were separated. The aqueous phase was extracted with the $CH_2Cl_2$ (3×100 mL). The combined organics were washed with water (200 mL), saturated $NaHCO_3$ (200 mL), brine (200 mL), dried ($Na_2SO_4$), filtered and concentrated to afford a brownish solid which was recrystallized from ethanol to afford the desired compound in 68% yield.

2-(4-(Benzyloxy)-3-methoxyphenyl)ethanamine

To a suspension of $LiAlH_4$ (8 g, 210 mmol) in anhydrous THF (120 mL) under argon was added dropwise a solution hr, then diluted with THF (100 mL), cooled (0° C.) ice-bath. To the vigorously stirred mixture was added water (8 mL), 15% NaOH (8 mL) and water (24 mL). The ice-bath was removed, the stirring was continued for 1 hr at room temperature. The resulting suspension was filtered through a celite pad washed with THF. The combined washings and filtrate were concentrated to dryness. The residue obtained was dissolved in 10% HCl (20 mL) washed with ether, basified and extracted with EtOAc (3×100 mL). The combined organics were washed with water, brine, dried ($K_2CO_3$), filtered and concentrated to dryness to afford 8 g of 4-benzyloxy-3-methoxyphenethylamine as a yellowish oil. M+H=258.

(E)-3-(4-(Benzyloxy)-3-methoxyphenyl)acrylic acid

The (E)-3-(4-(benzyloxy)-3-methoxyphenyl)acrylic acid was prepared by the Knoevenagel condensation reaction (Kaushik. M. et. al. J. of Molecular Catalysis B; Enzymatic 82 (2912) 92-95. A mixture of 4-(benzyloxy)-3-methoxybenzaldehyde (14.54 g, 60.02 mmol), malonic acid (12.5 g, 120 mmol), pyridine (40 mL) and piperidine (1 mL, 10.12 mmol) was stirred and heated to 85° C. for 1 hr and refluxed 115° C. for an additional 5 hr. The mixture was poured into water and acidified with conc HCl. The precipitate was collected washed with cold water. The white solid residue was dissolved in NaOH, diluted with water, acidified again, the white solid precipitate was collected washed several times with water, and dried over $P_2O_5$ under high vacuum overnight.

(E)-N-(4-(Benzyloxy)-3-methoxyphenethyl)-3-(4-(benzyloxy)-3-methoxyphenyl)acrylamide To the mixture of (E)-3-(4-benzyloxy)-3-methoxyphenyl) acrylic acid (5.16 g, 18.15 mmol), 2-(4-(benzyloxy-3-methoxyphenyl)ethanamine (5.6 g, 21.76 mmol), HATU (8.3 g, 21.83 mmol) in anhydrous DMF (100 mL) was added DIPEA (16 mL, 91.85 mmol). The resulting mixture was stirred at room temperature for 2 hr, diluted with EtOAc (500 mL), washed sequentially with water, brine, dried ($Na_2SO_4$), filtered, concentrated and purified by flash chromatography using MeOH/CHCl$_3$ gradient to afford the titled compound in 60% yield. M+H=524.

(E)-7-(Benzyloxy)-1-(4-(benzyloxy)-3-methoxystyryl)-6-methoxy-1,2,3,4-tetrahydroisoquinoline The mixture of (E)-N-(benzyloxy)-3-methoxyphenethyl)-3-(4-(benzyloxy)-3-methoxyphenyl)acrylamide (1.7 g, 3.25 mmol) and anhydrous acetonitrile (60 mL) was stirred and heated to reflux, POCl$_3$ (2.2 mL, 23.60 mmol) was added dropwise. After the addition, the resulting reddish solution was stirred and heated to reflux for 1 hr, and concentrated to dryness. The residue was taken up EtOAc (100 mL), treated with 2M KOH solution (20 mL), stirred rapidly for 1 hr. The organic layer was washed with water, brine, dried over Na$_2$SO$_4$, filtered and concentrated to dryness. To the residue obtained was added NaBH$_4$ (100 mg, 2.63 mmol), EtOH (35 mL) and stirred at room temperature for 1 hr. The excess reagent was destroyed by dropwise addition of 2M HCl, basified with 2M KOH and evaporated to dryness to remove EtOH. The residue obtained was partitioned between water and CHCl$_3$, the organic layer was washed with brine, dried (K$_2$CO$_3$), filtered, concentrated and purified by flash chromatography using MeOH (NH$_3$)/CHCl$_3$ gradient to afford the titled compound. M+H=508.

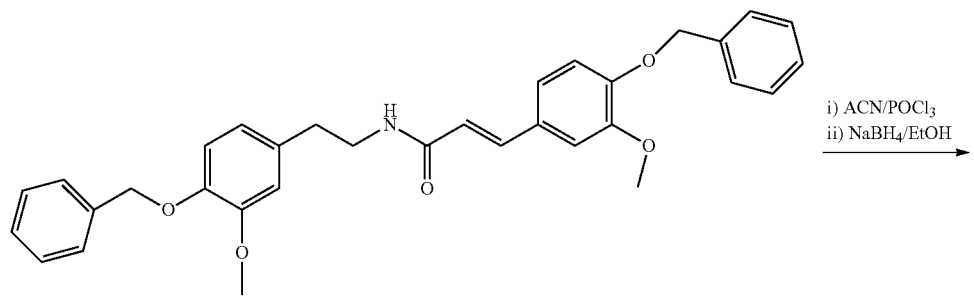

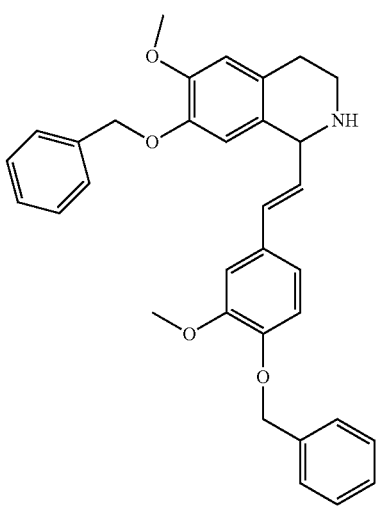

Example T: [6-benzyloxy-1-[(E)-2-(5-benzyloxy-4-methoxy-2-methyl-phenyl)vinyl]-7-methoxy-3,4-dihydro-1H-isoquinolin-2-yl]-(3-pyridyl)methanone

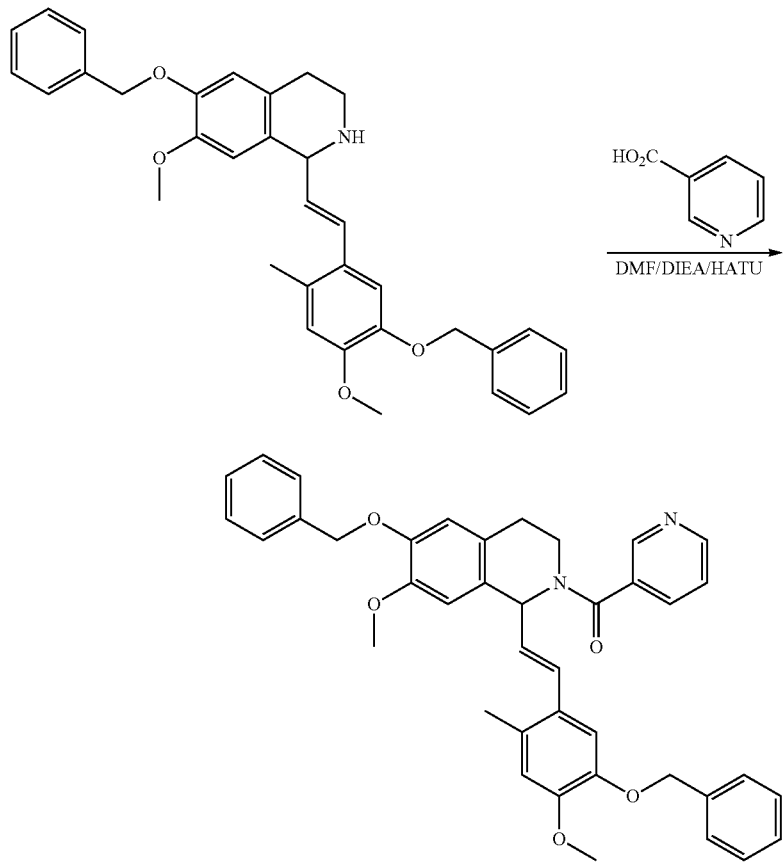 [SMILES: COc1cc(C)c(/C=C/C2NCCc3cc(OCc4ccccc4)c(OC)cc32)cc1OCc1ccccc1 ; O=C(O)c1cccnc1 ; COc1cc(C)c(/C=C/C2c3cc(OC)c(OCc4ccccc4)cc3CCN2C(=O)c2cccnc2)cc1OCc1ccccc1]

To a mixture of 6-benzyloxy-1-[(E)-2-(5-benzyloxy-4-methoxy-2-methyl-phenyl)vinyl]-7-methoxy-1,2,3,4-tetrahydroisoquinoline [50 mg (0.097 mmol)], Nicotinic acid [12.4 mg (0.1 mmol)], DIEA [50 ul (0.3 mmol)] & 1 mL of DMF was added HATU [47.5 mg (0.125 mmol)]. The reaction was stirred at rt for 1 h and then diluted with 20 mL of EtOAc and washed 2× with sat NaCl. The EtOAc layer was dried ($Na_2SO_4$) and the solvent removed. Yield=62 mg (86%) via prep chrom. MS (m/z): 627 [M+H]

Example U: [6-benzyloxy-1-[(E)-2-(5-benzyloxy-4-methoxy-2-methyl-phenyl)vinyl]-7-methoxy-3,4-dihydro-1H-isoquinolin-2-yl]-(4-pyridyl)methanone

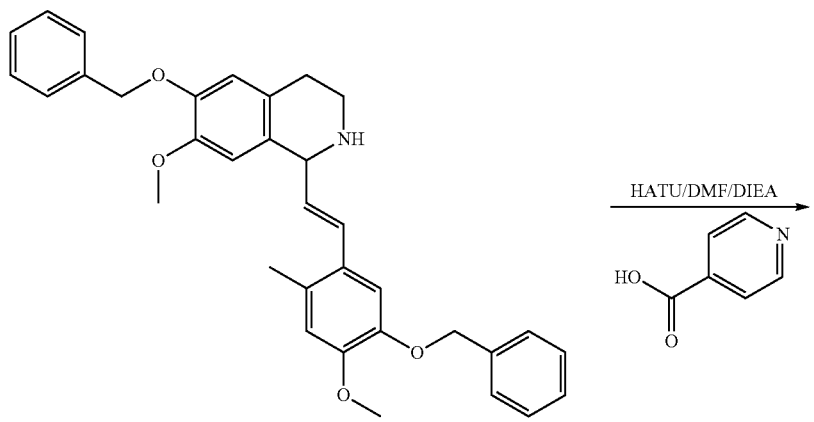

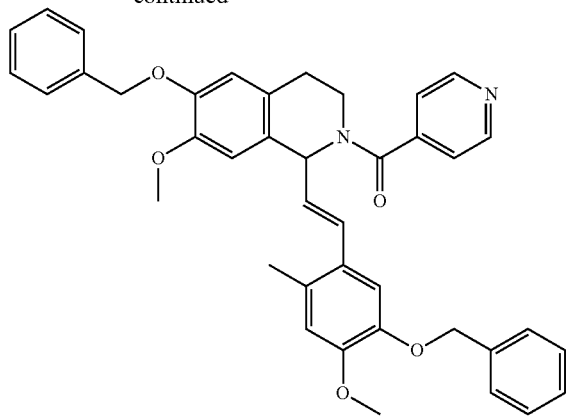

To a mixture of 6-benzyloxy-1-[(E)-2-(5-benzyloxy-4-methoxy-2-methyl-phenyl)vinyl]-7-methoxy-1,2,3,4-tetrahydroisoquinoline) [25 mg (0.048 mmol)], Isonicotinic acid [9 mg (0.072 mmol)], DIEA [42 ul (0.24 mmol)] & 1 mL of DMF was added HATU [38 mg (0.1 mmol)]. The reaction was stirred at rt for 1 h and then diluted with 20 mL of EtOAc and washed 2× with sat NaCl. The EtOAc layer was dried (Na$_2$SO$_4$) and the solvent removed. Yield=11.5 mg (38%) via prep chrom. MS (m/z): 627 [M+H]

Example V: 6-benzyloxy-1-[(E)-2-(3-benzyloxy-4-methoxy-phenyl)vinyl]-7-methoxy-2-methyl-3,4-dihydro-1H-isoquinoline A mixture of (E)-6-(benzyloxy)-1-(3-(benzyloxy)-4-methoxystyryl)-7-methoxy-1,2,3,4-tetrahydroisoquinoline (0.4697 g, 0.93 mmol) and (0.4844 mL) of 38% formalin with EtOH (10 mL) was stirred at room temperature for 1 hr then treated with NaBH$_4$ (0.372 g, 9.83 mmol) and stirred overnight. The mixture was diluted with DCM (50 mL), washed with brine, dried (Na$_2$SO$_4$), filtered, concentrated and purified on the Shimadzu HPLC system to afford the TFA salt. M+H (Neutral)=522.

Example W: 6-benzyloxy-7-methoxy-1-[(E)-2-(o-tolyl)vinyl]-1,2,3,4-tetrahydroisoquinoline

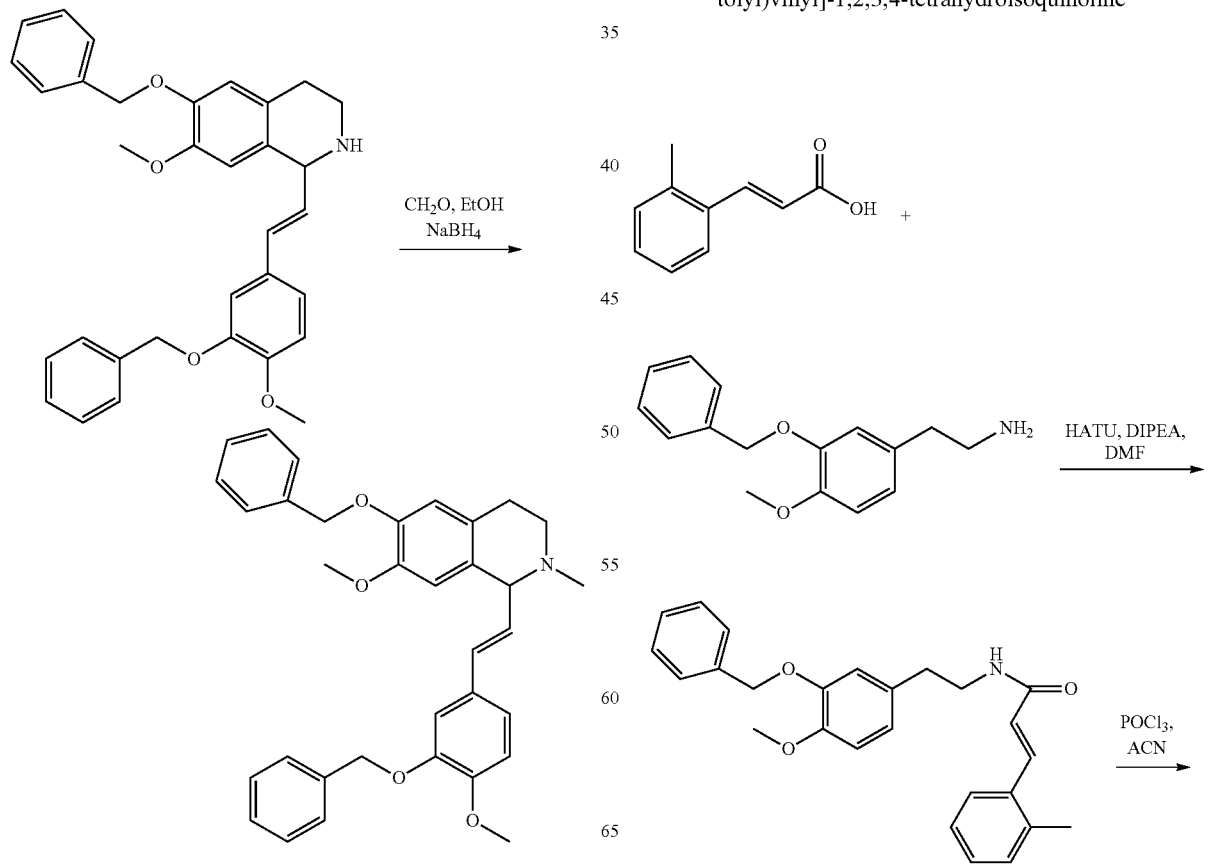

93

-continued

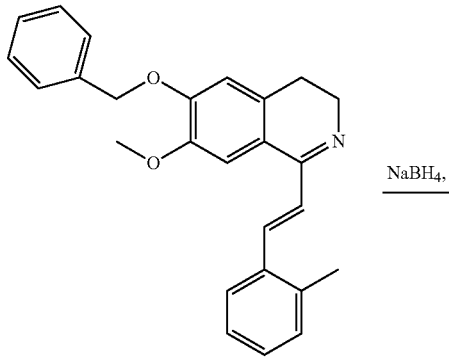

(E)-6-(Benzyloxy)-7-methoxy-1-(2-methylstyryl)-1,2,3,4-tetrahydroisoquinoline

Title compound was prepared analogously as Example X using (E)-3-o-tolylacrylic acid (0.4235 g, 2.61 mmol) and 2-(3-(benzyloxy)-4-methoxyphenyl)ethanamine (0.7392 g, 2.87 mmol) via the HATU coupling, the imine formation, and NaBH₄ reduction in EtOH/DCM mixture. M+H=386.

Example X: 6-benzyloxy-1-[(E)-2-(4-fluoro-2-methyl-phenyl)vinyl]-7-methoxy-1,2,3,4-tetrahydroisoquinoline

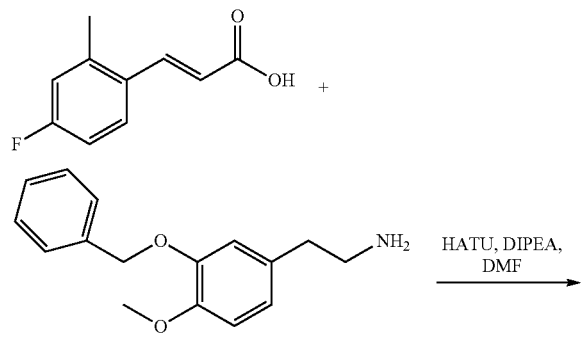

94

-continued (E)-N-(3-(Benzyloxy)-4-methoxyphenethyl)-3-(4-fluoro-2-methylphenyl)acrylamide The amide was formed from the (E)-3-(4-fluoro-2-methylphenyl)acrylic acid (0.8 g, 4.88 mmol) and the amine (1.63 g, 6.33 mmol) by the HATU coupling procedure.

(E)-6-(Benzyloxy)-1-(4-fluoro-2-methylstyryl)-7-methoxy-3,4-dihydroisoquinoline

The mixture of the amide (1.04 g, 2.48 mmol) in acetonitrile (30 mL) was stirred and heated to reflux, POCl₃ (1.6 mL, 17.17 mmol) was added dropwise, stirred for 1 hr and worked up as usual.

(E)-6-(Benzyloxy)-1-(4-fluoro-2-methylstyryl)-7-methoxy-1,2,3,4-tetrahydroisoquinoline The crude imine obtained was treated with NaBH₄ (60 mg, 1.59 mmol) in EtOH (5 mL)/DCM 2 (mL), stirred at room temperature for 1 hr, the solid precipitate was filtered off washed with 50/50 ACN/water and dried under high vacuum to afford the titled compound. M+H=404.

Example Y: tert-butyl 6-benzyloxy-1-[(E)-2-(5-benzyloxy-4-methoxy-2-methyl-phenyl)vinyl]-7-methoxy-3,4-dihydro-1H-isoquinoline-2-carboxylate

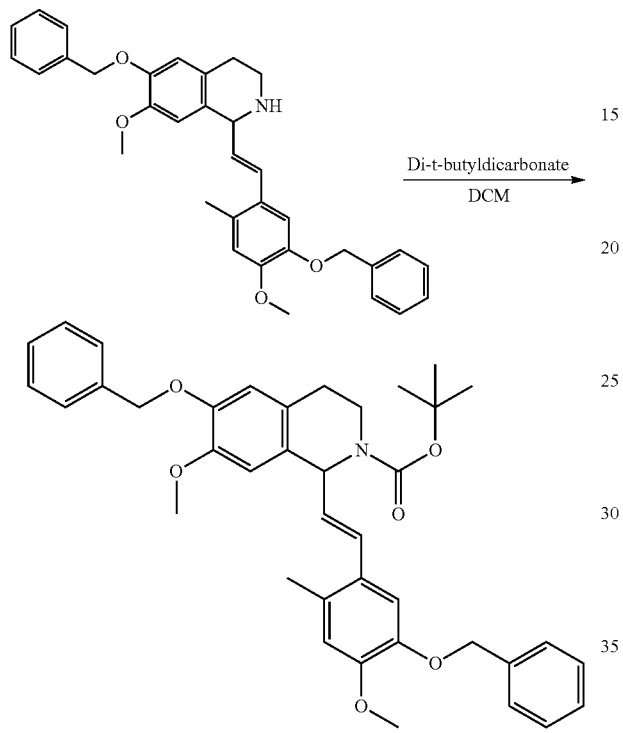

To a mixture of 6-benzyloxy-1-[(E)-2-(5-benzyloxy-4-methoxy-2-methyl-phenyl)vinyl]-7-methoxy-1,2,3,4-tetrahydroisoquinoline [100 mg (0.1919 mmol)] and Di-t-butyl dicarbonate [42 mg (0.1919 mmol)] in 5 mL of DCM was stirred at room temperature for 1 h then rotary evaporated to dryness. Yield=25 mg (21% yield) via prep chrom. MS (m/z): 622 [M+H].

Example Z: 6-benzyloxy-7-methoxy-1-[(E)-2-[4-methoxy-2-(trifluoromethyl)phenyl]vinyl]-1,2,3,4-tetrahydroisoquinoline

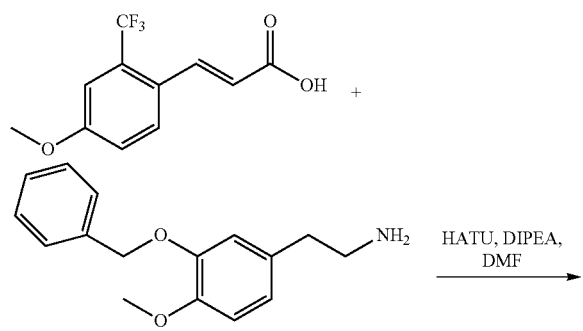

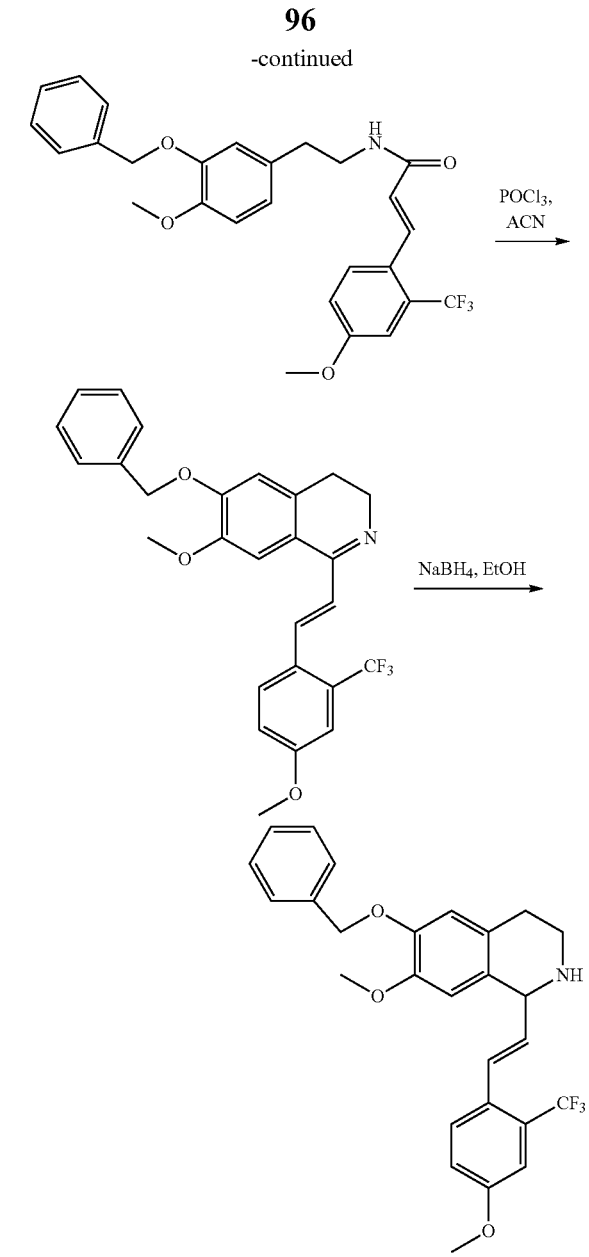

(E)-6-(Benzyloxy)-7-methoxy-1-(4-methoxy-2-(trifluoromethyl)styryl)-3,4-dihydroisoquinoline To the mixture of (E)-3-(4-methoxy-2-(trifluoromethyl)phenyl)acrylic acid (1.36 g, 5.52 mmol) prepared from the aldehyde by the usual Knoevenagel condensation reaction (1.56 g, 6.06 mmol), HATU (2.30 g, 6.06 mmol) in DMF (25 mL) was added DIPEA (4.8 mL, 27.56 mmol) and stirred at room temperature for 2 hr. After workup, the crude was purified with flash chromatography using EtOAc/Hexanes gradient to afford the amide. The mixture of the amide (1.04 g, 2.14 mmol) and acetonitrile (25 mL) was stirred and heated to reflux, POCl₃ (1.4 mL, 15.02 mmol) was added dropwise, stirred and heated to reflux for 1 hr. After the usual workup, ca 200 mg of the desired product was purified on the Shimadzu HPLC to afford the TFA salt.

(E)-6-(Benzyloxy)-7-methoxy-1-(4-methoxy-2-(trifluoromethyl)styryl)-1,2,3,4-tetrahydroisoquinoline The remaining crude was treated with NaBH₄ (51 mg, 1.35 mmol) in EtOH (25 mL) for 1 hr. After the usual workup it was purified with flash chromatography using MeOH (NH₃)/CHCl₃ gradient to afford the titled compound. M+H=470.

Example AA: 6-benzyloxy-1-[(E)-2-(5-benzyloxy-2-ethyl-4-methoxy-phenyl)vinyl]-7-methoxy-1,2,3,4-tetrahydroisoquinoline

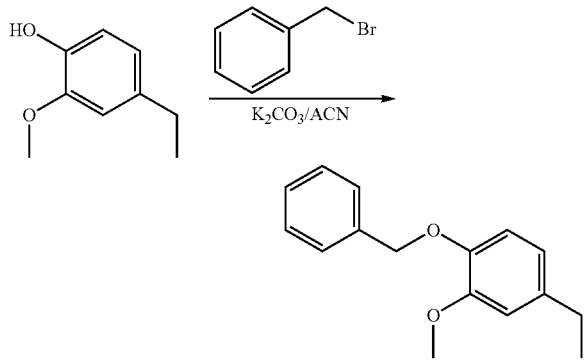

1-Benzyloxy-4-ethyl-2-methoxy-benzene

A mixture of 4-ethyl-2-methoxy-phenol [5.5 g (0.036 mol)], Benzyl bromide [12.3 g (0.072 mol)], K₂CO₃ [10 g (0.072 mol) in 73 mL of ACN was refluxed overnight. The reaction mixture was then rotary evaporated and the residue treated with water then extracted with EtOAc. The extract was washed with sat. NaCl, dried (MgSO₄) and the solvent removed. Yield=8.7 g (quant) MS (m/z): 243 [M+H]

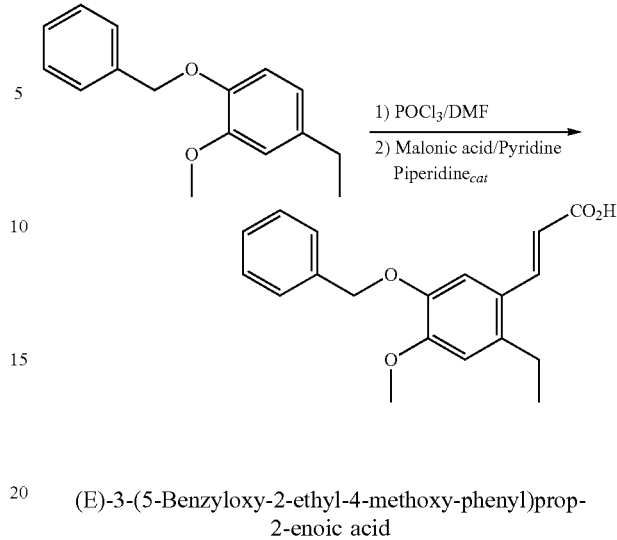

(E)-3-(5-Benzyloxy-2-ethyl-4-methoxy-phenyl)prop-2-enoic acid

The compound 1-benzyloxy-4-ethyl-2-methoxy-benzene [8.7 g (0.036 mol)] was added to a mixture of POCl₃ [20 mL (0.21 mol)] and DMF [17 g (0.22 mol)] with stirring at 0° C. The viscous mixture was then heated to 80° C. and stirred there for 4 h. The reaction mix was then poured onto ice and then extracted with Et₂O. The extract was dried (MgSO₄) and the solvent removed. Flash chrom. with 10% EtOAc/Hexane afforded the desired aldehyde [3 g (0.011 mol)] 31% yield.

A mixture of the above aldehyde [3 g (0.011 mol)], malonic acid [2.2 g (0.022 mol)], pyridine (7 mL) and piperidine (0.2 mL) was stirred at 80° C. for 1 h followed by stirring for 3 h at 115° C. The reaction was then poured into water (200 mL) and acidified with conc. HCl. The resulting white ppt. was filtered and vacuum dried. Yield=3.2 g (29% overall) MS (m/z): 313 [M+H]

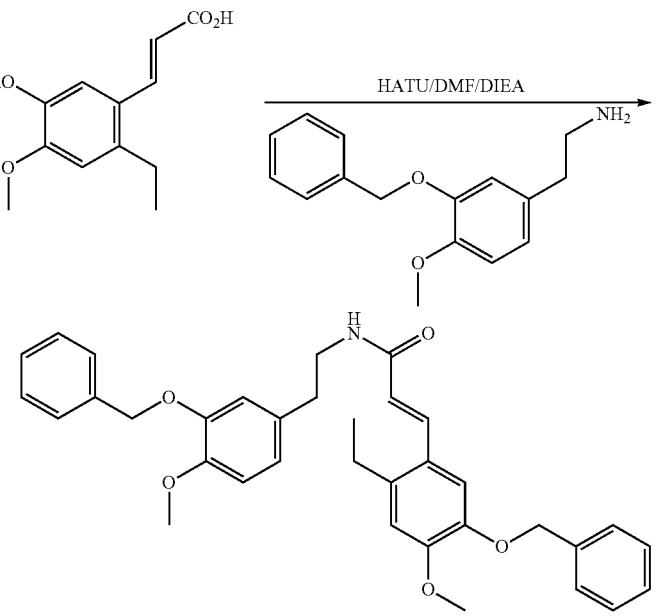

(E)-3-(5-Benzyloxy-2-ethyl-4-methoxy-phenyl)-N-[2-(3-benzyloxy-4-methoxy-phenyl)ethyl]prop-2-enamide To a mixture of (E)-3-(4,5-dimethoxy-2-ethyl-phenyl) prop-2-enoic acid [393 mg (1.7 mmol)], 2-(3-benzyloxy-4-methoxy-phenyl)ethanamine[257 mg (1 mmol)], DMF (10 mL) and DIEA (1 mL (6 mmol) was added HATU [950 mg (2.5 mmol)]. The reaction mix was stirred at room temperature 2 h then diluted with 50 mL of EtOAc and washed 2× with sat. NaCl aq. The EtOAc layer was dried (MgSO$_4$) and the solvent removed. Yield=310 mg (54% after flash with 10% MeOH/DCM) MS (m/z): 552 [M+H]

2-enamide [310 mg (0.563 mmol)] in ACN (13 mL) was added, under reflux, POCl$_3$ [361 ul (3.9 mmol)]. The reaction was stirred at reflux for 10 min and then rotary evaporated to dryness. The residue was taken up into 10 mL of chloroform and was then treated with 20 mL of 2N KOH and 50 mL of Et$_2$O. This mixture was rapidly stirred for 30 min at room temperature and the upper organic layer removed, washed with water, dried (Na$_2$SO$_4$) and the solvent removed. The dark oil was the dissolved into 8 mL of dry EtOH and then treated with NaBH$_4$ [15 mg (0.395 mmol)]. The mixture was stirred for 1 h at room temperature and the resulting solid was carefully filtered off and dried. The solid was triturated with 50/50 ACN/water, filtered and vacuum dried. Yield=150 mg (50% overall) MS (m/z): 536 [M+H]

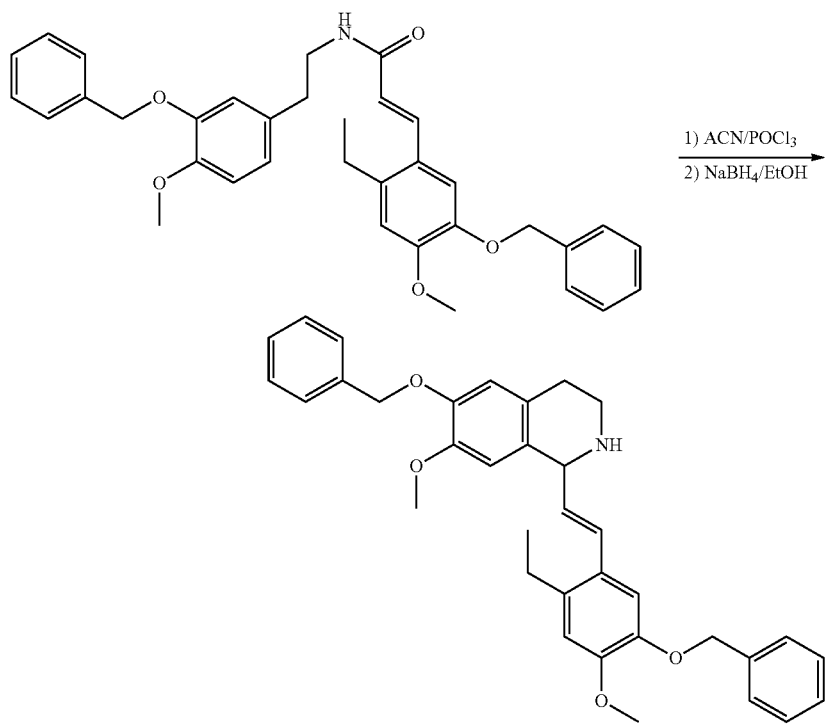

1) ACN/POCl$_3$
2) NaBH$_4$/EtOH

6-Benzyloxy-1-[(E)-2-(5-benzyloxy-2-ethyl-4-methoxy-phenyl)vinyl]-7-methoxy-1,2,3,4-tetrahydroisoquinoline To a solution of (E)-3-(5-benzyloxy-2-ethyl-4-methoxy-phenyl)-N-[2-(3-benzyloxy-4-methoxy-phenyl)ethyl]prop-

Example AB: 6-benzyloxy-1-[(E)-2-(3-benzyloxy-4-methoxy-phenyl)vinyl]-7-methoxy-1,2,3,4-tetrahydroisoquinoline

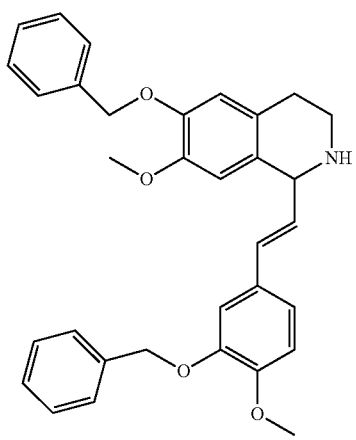

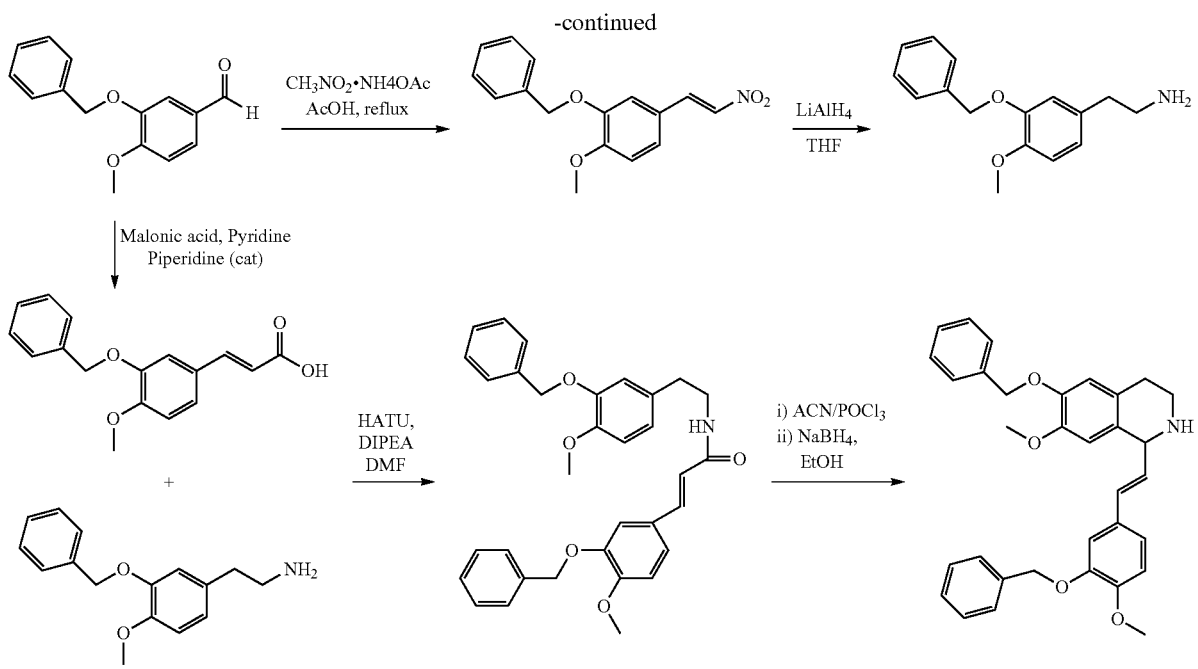

2-(3-(Benzyloxy)-4-methoxyphenyl)ethanamine: were prepared as described in detail above.

(E)-3-(3-(Benzyloxy)-4-methoxyphenyl)acrylic acid: were prepared as described in detail above.

(E)-N-(3-(Benzyloxy)-4-methoxyphenethyl)-3-(3-(benzyloxy)-4-methoxyphenyl)acrylamide To the mixture of (E)-3-(3-(benzyloxy)-4-methoxyphenyl)acrylic acid (3.3 g, 11.61 mmol), 2-(3-(benzyloxy)-4-methoxyphenyl)ethanamine (4.45 g, 17.30 mmol) and HATU (6.58 g, 17.31 mmol) in DMF (100 mL) was added DIPEA (10 mL, 57.41 mmol). The resulting solution was stirred at room temperature for 2 hrs, diluted with EtOAc (300 mL), washed with brine, dried (Na$_2$SO$_4$), filtered, concentrated and purified by flash chromatography using MeOH (NH$_3$)/CHCl$_3$ gradient to afford 10 in 50% yield. M+H=524.

(E)-6-(Benzyloxy)-1-(3-(benzyloxy)-4-methoxystyryl)-7-methoxy-1,2,3,4-tetrahydroisoquinoline The mixture of (E)-N-(3-(benzyloxy)-4-methoxyphenethyl)-3-(3-(benzyloxy)-4-methoxyphenyl)acrylamide (2.5 g, 4.77 mmol) and acetonitrile (90 mL) was stirred and heated to reflux, POCl3 (3.3 mL, 35.40 mmol) was added dropwise. The resulting reddish mixture was stirred and heated to reflux for 1 hr and treated as described in detail for (E)-7-(benzyloxy)-1-(4-(benzyloxy)-3-methoxystyryl)-6-methoxy-1,2,3,4-tetrahydroisoquinoline. The crude obtained was purified on the Shimadzu HPLC system to afford the titled compound as the TFA salt. M+H (Neutral) =508.

Example AC: 6-benzyloxy-1-[(E)-2-(5-benzyloxy-2-chloro-4-methoxy-phenyl)vinyl]-7-methoxy-1,2,3,4-tetrahydroisoquinoline

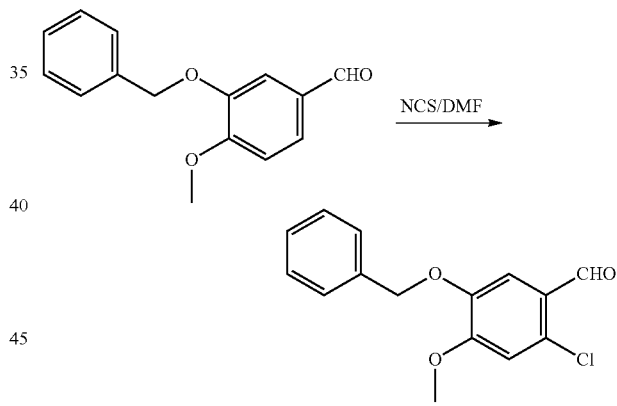

5-Benzyloxy-2-chloro-4-methoxy-benzaldehyde

A mixture of 3-benzyloxy-4-methoxy-benzaldehyde [5 g (0.021 mol)] and NCS [3.4 g (0.0252 mol)] in 50 mL of DMF was heated to 70° C. and stirred there for 3 h. After cooling water was added and the resulting ppt. was filtered off and dried under high vacuum. Yield=2 g (34%) after flash chrom with DCM/Hexane MS (m/z): 277 [M+H]

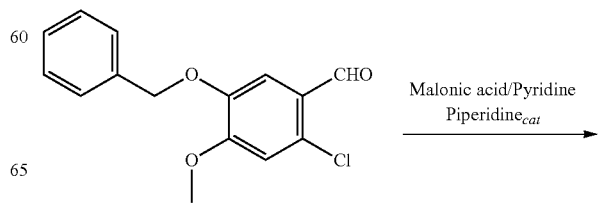

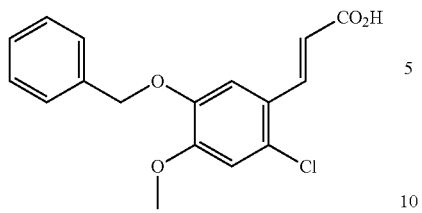

(E)-3-(5-Benzyloxy-2-chloro-4-methoxy-phenyl)prop-2-enoic acid

A mixture of 5-benzyloxy-2-chloro-4-methoxy-benzaldehyde [2 g (0.072 mol)], malonic acid [1.5 g (0.014 mol)], pyridine (4 mL) and piperidine (0.150 mL) was stirred at 80° C. for 1 h followed by stirring for 3 h at 115° C. The reaction was then poured into water (200 mL) and acidified with conc. HCl. The resulting white ppt., product, was filtered and vacuum dried. Yield=2.2 g (96%) MS (m/z): 319 [M+H]

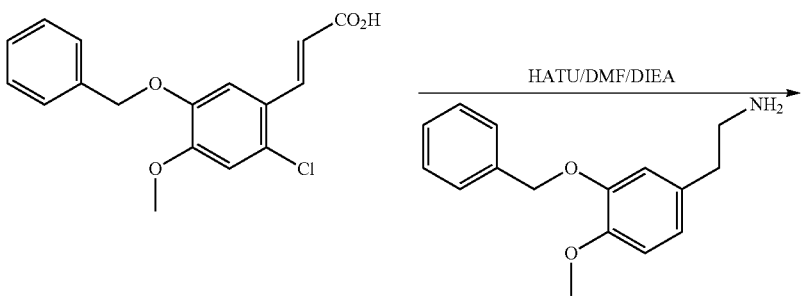

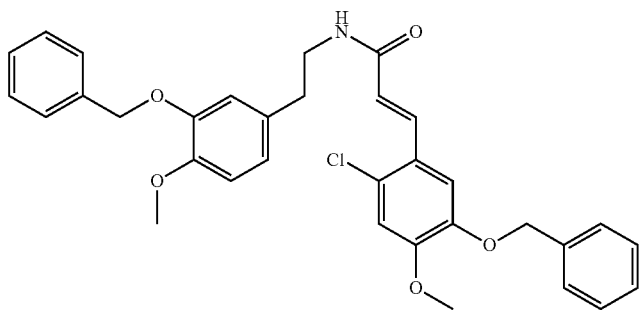

(E)-3-(5-Benzyloxy-2-chloro-4-methoxy-phenyl)-N-[2-(3-benzyloxy-4-methoxy-phenyl)ethyl]prop-2-enamide To a mixture of (E)-3-(5-benzyloxy-2-chloro-4-methoxy-phenyl)prop-2-enoic acid [318 mg (1 mmol)], 2-(3-benzyloxy-4-methoxy-phenyl)ethanamine 150 mg (0.6 mmol)], DMF (5 mL) and DIEA [0.5 mL (3 mmol)] was added HATU [475 mg (1.25 mmol)]. The reaction mix was stirred at room temperature 2 h then diluted with 50 mL of EtOAc and washed 2× with sat. NaCl aq. The EtOAc layer was dried (MgSO₄) and the solvent removed. Yield=256 mg (74% after flash with 10% MeOH/DCM) MS (m/z): 558 [M+H]

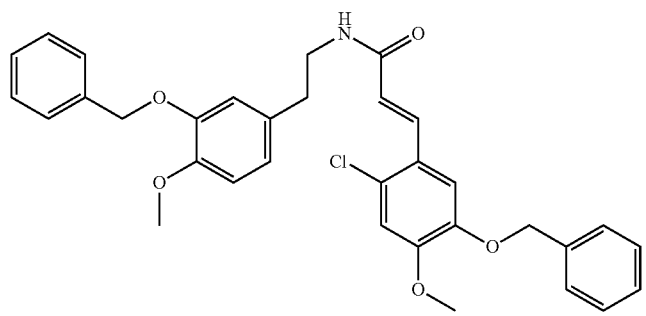

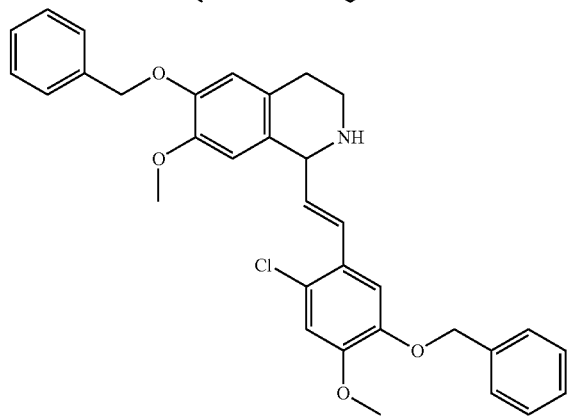

6-Benzyloxy-1-[(E)-2-(5-benzyloxy-2-chloro-4-methoxy-phenyl)vinyl]-7-methoxy-1,2,3,4-tetrahydroisoquinoline To a solution of (E)-3-(5-benzyloxy-2-chloro-4-methoxy-phenyl)-N-[2-(3-benzyloxy-4-methoxy-phenyl)ethyl]prop-2-enamide [256 mg (0.46 mmol)] in ACN (9 mL) was added, under reflux, POCl$_3$ [300 ul (3.21 mmol)]. The reaction was stirred at reflux for 10 min and then rotary evaporated to dryness. The residue was taken up into 10 mL of chloroform and was then treated with 20 mL of 2N KOH and 50 mL of Et$_2$O. This mixture was rapidly stirred for 30 min at room temperature and the upper organic layer removed, washed with water, dried (Na$_2$SO$_4$) and the solvent removed. The dark oil was the dissolved in 8 mL of dry EtOH and then treated with NaBH$_4$ [12 mg (0.32 mmol)]. The mixture was stirred for 1 h at room temperature and the resulting solid was carefully filtered off and dried. The solid was triturated with 50/50 ACN/water, filtered and vacuum dried. Yield=126 mg (51% overall) MS (m/z): 542 [M+H]

Example AD: 6-benzyloxy-1-[(E)-2-(5-benzyloxy-2-methyl-phenyl)vinyl]-7-methoxy-1,2,3,4-tetrahydroisoquinoline

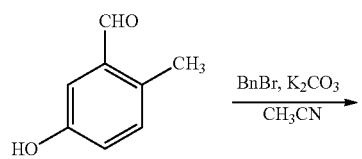

-continued

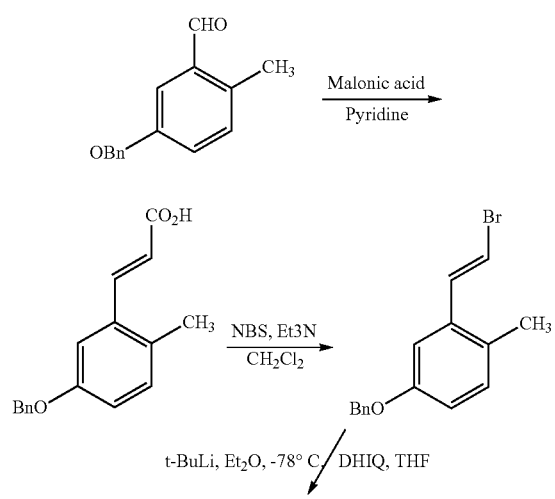

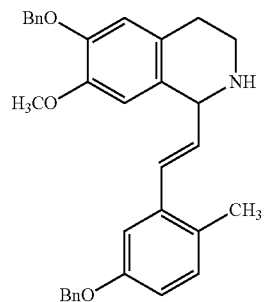

5-(Benzyloxy)-2-methylbenzaldehyde

5-Hydroxy-2-methylbenzaldehyde (2.07 g, 15.20 mmol) was combined with benzylbromide (2.71 mL, 22.8 mmol) and $Cs_2CO_3$ (9.91 g, 30.4 mmol) in DMF (100 mL). The resulting mixture was stirred at 80° C. overnight. Upon consumption of the starting material by TLC analysis, the reaction was allowed to cool to room temperature. The organic solvent was removed under reduced pressure. The residue obtained was purified by flash chromatography to afford the titled compound LCMS: M+1=227.3.

(E)-3-(5-(Benzyloxy)-2-methylphenyl)acrylic acid 5-(Benzyloxy)-2-methylbenzaldehyde (3.00 g, 13.26 mmol) was dissolved in pyridine (50 mL) along with malonic acid (2.78 g, 26.52 mmol) and a catalytic amount of piperidine (0.35 mL). The resulting mixture was heated at reflux for 18 hours, then the reaction mixture was allowed to cool to room temperature. The reaction was poured into ice cold 1M $H_3PO_4$ (100 mL) and the resulting mixture was stirred for 10 minutes, the solid precipitate was filtered, washed with water and dried over $P_2O_5$ overnight. LCMS: M+1=269.3.

(E)-4-(Benzyloxy)-2-(2-bromovinyl)-1-methylbenzene

The solution of (E)-3-(5-(benzyloxy)-2-methylphenyl) acrylic acid (1.00 g, 3.73 mmol) in $CH_2Cl_2$ (20 mL) with $Et_3N$ (0.025 mL, 0.184 mmol) was stirred for 5 minutes. To this solution was added NBS (809 mg, 4.42 mmol) portionwise, as the reaction gave off $CO_2$ gas. After all the additions the reaction mixture was stirred overnight. Additional NBS (809 mg, 4.42 mmol) was added and the mixture stirred for another 18 hours. Upon complete reaction by TLC indication, it was purified by flash silica gel chromatography to furnish the titled compound.

(E)-6-(Benzyloxy)-1-(5-(benzyloxy)-2-methyl-styryl)-7-methoxy-1,2,3,4-tetrahydroisoquinoline A solution of (E)-4-(benzyloxy)-2-(2-bromovinyl)-1-methylbenzene (303 mg, 1 mmol) was dissolved in dry $Et_2O$ (15 mL) and cooled to −78° C. A solution of t-BuLi (1.3 mL, 2.2 mmol, 1.7M in pentane) was added dropwise and the resulting solution was stirred at −78° C. for 1 hour before a solution of 6-(benzyloxy)-7-methoxy-3,4-dihydroisoquinoline (134 mg, 0.5 mmol) in THF (3 mL) was added dropwise. The resulting mixture was stirred for 2 hours at −78° C. and then quenched with sat. aqueous $NH_4Cl$ solution. The mixture was extracted with EtOAc and the combined organic layers were dried over $MgSO_4$, filtered and evaporated to dryness. The residue obtained was purified by flash silica gel chromatography to afford the tiled compound. LCMS: M+1=492.6.

Examples AE/AF: 6-benzyloxy-1-[(E)-2-(5-benzyloxy-4-methoxy-2-methyl-phenyl)vinyl]-7-methoxy-3,4-dihydroisoquinoline and 6-benzyloxy-1-[(E)-2-(5-benzyloxy-4-methoxy-2-methyl-phenyl)vinyl]-7-methoxy-1,2,3,4-tetrahydroisoquinoline

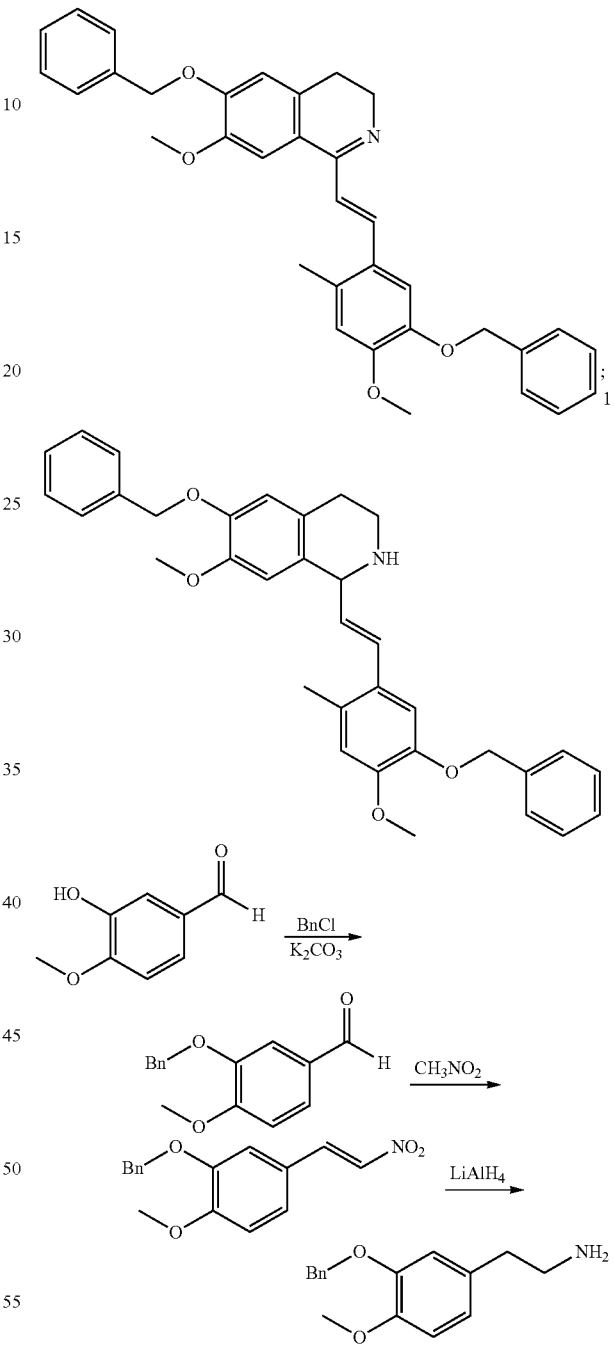

O-Benzylisovanillin:

A mixture of isovanillin (10.0 g, 66 mmol), benzyl chloride (16.7 g, 15.2 mL, 131 mmol), and anhydrous $K_2CO_3$ (6.4 g, 46 mmol) in EtOH (100 mL) was refluxed for 5 h. After being stirred, the reaction mixture was concentrated to dryness and redissolved in 100 mL of $CH_2Cl_2$, and then 5% aqueous NaOH (3×50 mL) was added. The organic layer was washed with brine (2×50 mL) and $H_2O$ (2×50 mL), dried with anhydrous $Na_2SO_4$, and evaporated to dryness. Needles were obtained after crystallization from MeOH/CH₂Cl₂ corresponding to O-benzylisovanillin (3-benzyloxy-4-methoxybenzaldehyde, 15 g, 94%).

3-Benzyloxy-4-methoxy-β-nitrostyrene

A mixture of O-benzylisovanillin (15.0 g, 61.9 mmol), nitromethane (11.34 g, 10.0 mL, 186 mmol), and NH₄OAc (11.9 g, 155 mmol) in AcOH (100 mL) was refluxed for 4 h. After cooling, the mixture was diluted with H₂O (100 mL) and extracted with CH₂Cl₂ (3×30 mL). The organic solution was washed with brine (2×50 mL) and H₂O (2×30 mL), dried with anhydrous Na₂SO₄ and evaporated to dryness. Yellow needles were obtained after recrystallization from EtOH affording the 3-benzyloxy-4-methoxy-â-nitrostyrene (15.4 g, 87%).

β-(3-Benzyloxy-4-methoxyphenyl)ethylamine

A solution of 3-benzyloxy-4-methoxy-β-nitrostyrene (11.1 g, 39 mmol) in 150 mL of anhydrous THF was added dropwise to a vigorously stirred suspension of LiAlH₄ (5.9 g, 156 mmol) in 120 mL of anhydrous Et₂O under nitrogen atmosphere and was refluxed for 16 h. After the solution was cooled, the excess reagent was destroyed by dropwise addition of H₂O and 15% aqueous NaOH. After partial evaporation of the filtered portion, the aqueous solution was extracted with CH₂Cl₂ (3×50 mL) and the organic layers were treated with 5% aqueous HCl. The resulting aqueous acid layer was made basic (5% aqueous NH₄OH, pH 9) and extracted with CH₂Cl₂. The organic solution was washed with brine (2×50 mL) and H₂O (2×50 mL), dried with anhydrous K₂CO₃, and evaporated to dryness, to afford β-(3-benzyloxy-4-methoxyphenyl) ethylamine (6.8 g, 69%) as an oil.

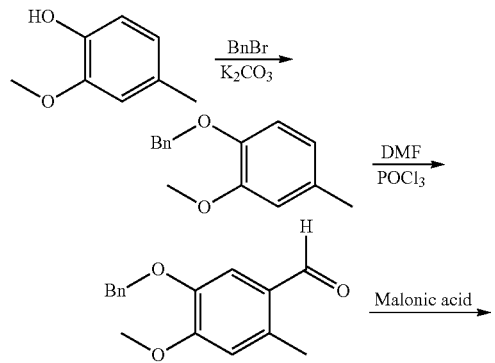

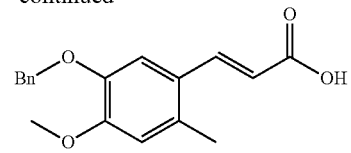

1-(Benzyloxy)-2-methoxy-4-methylbenzene

To a solution of 2-methoxy-4-methylphenol (10.0 g, 72.4 mmol) in 145 mL of CH₃CN was added K₂CO₃ (20.0 g, 145 mmol) and benzyl bromide (24.8 g, 145 mmol). The resulting mixture was refluxed for 18 h and the solvent was removed with a rotary evaporator. The residue was treated with H₂O and extracted with EtOAc (3×50 mL). The combined organic extracts were washed with brine, dried over MgSO4, and concentrated in vacuo. The residue was purified by silica gel flash column chromatography (10% EtOAc/hexanes) to yield 1-(benzyloxy)-2-methoxy-4-methylbenzene (16.2 g, 98%).

5-Benzyloxy-4-methoxy-2-methylbenzaldehyde

To a mixture of POCl₃ (60.9 g, 397 mmol) and DMF (29.0 g, 397 mmol) at 0° C. was added 1-(benzyloxy)-2-methoxy-4-methylbenzene (15.1 g, 66 mmol). The resulting solution was heated to 80° C. and stirred for 4 h. After being cooled to room temperature, the reaction mixture was poured into ice and extracted with ether. The combined extracts were concentrated in vacuo and purified by silica gel flash column chromatography (10% EtOAc/hexanes) to afford benzaldehyde 10 (12.0 g, 71%) as a white solid.

2-Methyl-4-methoxy-5-benzyloxycinnamic acid

5-Benzyloxy-4-methoxy-2-methylbenzaldehyde (13.5 g, 52.7 mM), malonic acid (11.0 g, 105.4 mM), pyridine (30 mL), and piperidine (0.9 g, 1.0 mL, 11 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over P₂O₅ and used without further purifications.

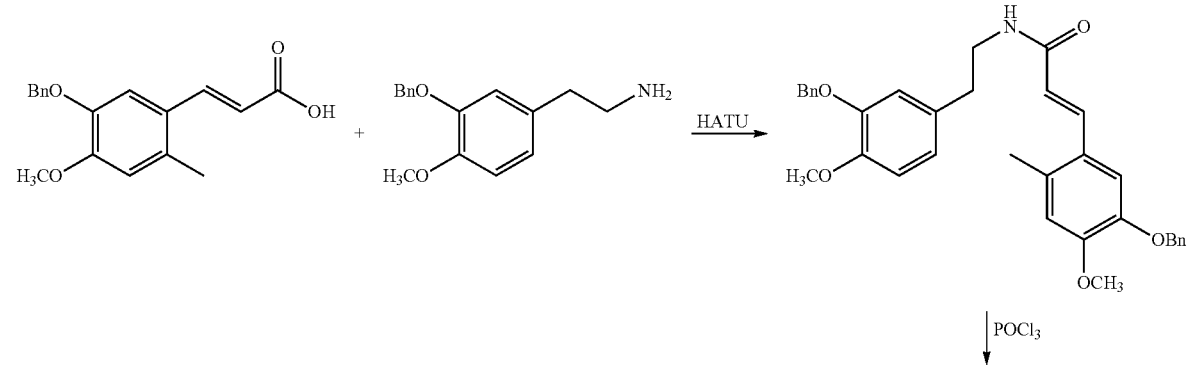

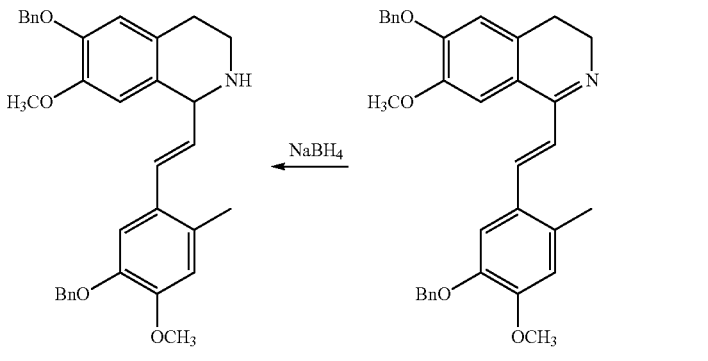

(E)-3-(5-(Benzyloxy)-4-methoxy-2-methylphenyl)-N-(3-(benzyloxy)-4-methoxyphenethyl)acrylamide To the stirred solution of the 2-methyl-4-methoxy-5-benzyloxycinnamic acid (3.0 g, 10.0 mmol) and β-(3-benzyloxy-4-methoxyphenyl)ethylamine (2.6 g, 10.0 mmol) in DMF (40 mL) was added HATU (5.7 g, 15 mmol) followed by diisopropylethylamine (1.95 g, 2.6 mL, 15.0 mmol). The reaction mixture was stirred at room temperature for 1 h. The solution was diluted with EtOAc (50 mL), washed with 10% citric acid, saturated aqueous solution of $NaHCO_3$, dried ($Na_2SO_4$), filtered and was purified by flash chromatography Yield 3.5 g (65%).

(E)-6-(benzyloxy)-1-(5-(benzyloxy)-4-methoxy-2-methylstyryl)-7-methoxy-3,4-dihydroisoquinoline and (E)-6-(Benzyloxy)-1-(5-(benzyloxy)-4-methoxy-2-methylstyryl)-7-methoxy-1,2,3,4-tetrahydroisoquinoline The amide (200 mg, 0.37 mmol) was suspended in dry acetonitrile (10 mL). The stirred mixture was heated to reflux. Then phosphorus oxychloride (400 mg, 0.24 mL, 2.6 mmol) was added drop wise. The reflux was continued for a further 1 h. The solution was evaporated thoroughly to dryness under high vacuum to remove the excess of $POCl_3$. The residue was dissolved in chloroform (10 mL), shaken with 2M KOH (10 mL) and ether (20 mL). The separated upper layer was washed with water (2×10 mL) and evaporated in vacuo to give an oil. A portion of the material was purified and isolated as Example AE. The remaining material was dissolved in ethanol (8 mL) sodium borohydride (9.8 mg, 0.26 mmol) was added. The mixture was stirred at room temperature for 30 min. The excess reagent was destroyed by dropwise addition of 2M HCl. The reaction mixture was basified with 2M NaOH. Most of the ethanol was removed in vacuo. The residue was partitioned between water (10 mL) and chloroform (10 mL). The organic layer was washed with water (2×10 mL). The solvent was removed in vacuo. The residue was purified by column chromatography to afford the titled isoquinoline (0.12 g, 62%).

Example AG: 6-benzyloxy-7-methoxy-1-[(E)-2-(4-methoxy-2-methyl-phenyl)vinyl]-1,2,3,4-tetrahydroisoquinoline

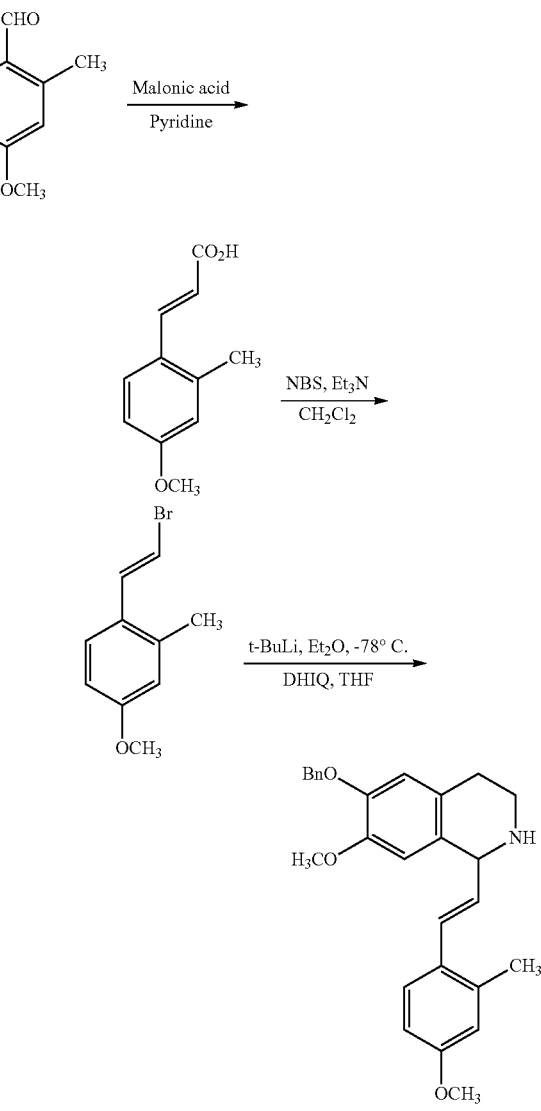

(E)-3-(4-Methoxy-2-methylphenyl)acrylic acid

4-Methoxy-2-methylbenzaldehyde (5.0 g, 33.3 mmol) was dissolved in pyridine (14 mL) along with malonic acid (6.93 g, 66.58 mmol) and a catalytic amount of piperidine (0.5 mL). The resulting mixture was heated at reflux for 18 hours. After the starting material was consumed, the reaction mixture was allowed to cool to room temperature. The reaction was poured into ice cold 1M $H_3PO_4$ (100 mL) and the resulting mixture was stirred for 10 minutes and the solid was filtered off. The solid was washed with water and dried over $P_2O_5$ overnight. LCMS: M+1=193.2

(E)-1-(2-Bromovinyl)-4-methoxy-2-methylbenzene

The (E)-3-(4-methoxy-2-methylphenyl)acrylic acid (1.93 g, 10.06 mmol) was stirred in $CH_2Cl_2$ (30 mL) along with $Et_3N$ (0.069 mL, 0.502 mmol) for 5 minutes. To this solution was added NBS (2.14 g, 12.04 mmol) in portions, as the reaction gave off $CO_2$ gas. The reaction mixture was allowed to stir overnight. After TLC analysis indicated complete reaction it was purified by flash silica gel chromatography to afford (1.95 g) of a solid.

(E)-6-(Benzyloxy)-7-methoxy-1-(4-methoxy-2-methylstyryl)-1,2,3,4-tetrahydroisoquinoline A solution of (E)-1-(2-bromovinyl)-4-methoxy-2-methylbenzene (228 mg, 1 mmol) was dissolved in dry $Et_2O$ (15 mL) and cooled to −78° C. A solution of t-BuLi (1.3 mL, 2.2 mmol, 1.7M in pentane) was added dropwise and the resulting solution was stirred at −78° C. for 1 hour before a solution of 6-(benzyloxy)-7-methoxy-3,4-dihydroisoquinoline (134 mg, 0.5 mmol) in THF (3 mL) was added dropwise. The resulting mixture was stirred for 2 hours at −78° C. and then quenched with sat. aqueous $NH_4Cl$ solution. The mixture was extracted with EtOAc and the combined organic layers were dried over $MgSO_4$, filtered and evaporated to dryness. The residue obtained was purified by flash silica gel chromatography to afford the titled compound. LCMS: M+1=416.6.

Example AH: 6-benzyloxy-1-[(E)-2-(4,5-dimethoxy-2-methyl-phenyl)vinyl]-7-methoxy-1,2,3,4-tetrahydroisoquinoline

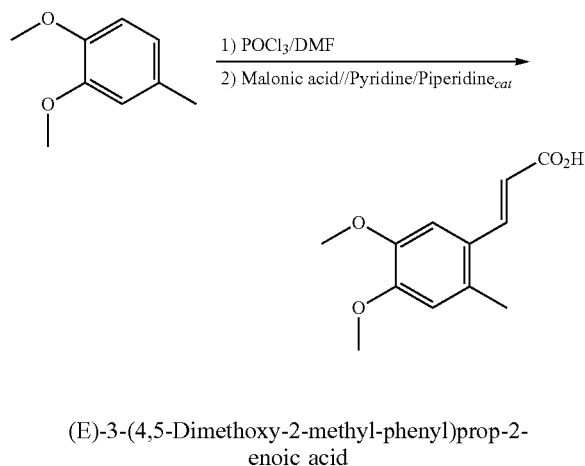

(E)-3-(4,5-Dimethoxy-2-methyl-phenyl)prop-2-enoic acid

The compound 1,2-dimethoxy-4-methyl-benzene [25 g (0.164 mol)] was added to a mixture of $POCl_3$ [151 g (0.987 mol)] and DMF [73 g (1 mol)] with stirring at 0° C. The viscous mixture was then heated to 80° C. and stirred there for 4 h. The reaction mix was then poured onto ice and then extracted with $Et_2O$. The extract was dried ($MgSO_4$) and the solvent removed. Flash chrom. with 10% EtOAc/Hexane afforded the desired aldehyde [26 g (0.144 mol)] 88% yield.

A mixture of the above aldehyde [5.4 g (0.03 mol)], malonic acid [6.24 g (0.06 mol)], pyridine (20 mL) and piperidine (0.5 mL) was stirred at 80° C. for 1 h followed by stirring for 3 h at 115° C. The reaction was then poured into water (200 mL) and acidified with conc. HCl. The resulting white ppt. was filtered and vacuum dried. Yield=4.8 g (63% overall) MS (m/z): 223 [M+H]

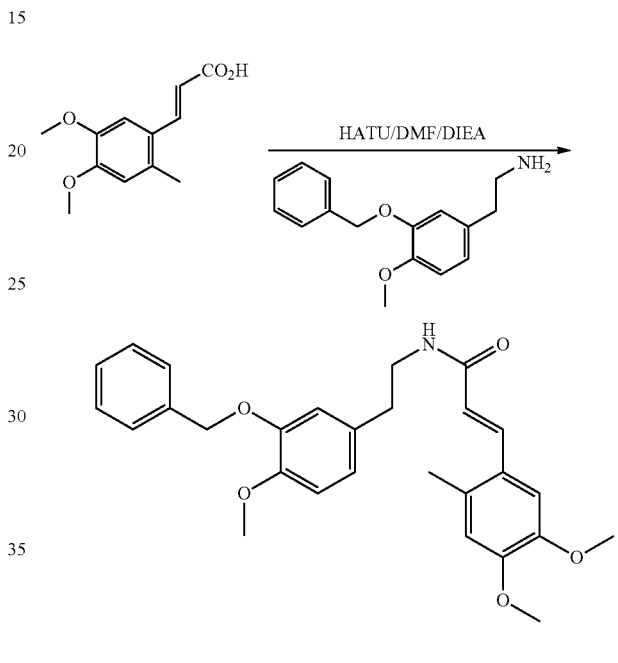

(E)-N-[2-(3-Benzyloxy-4-methoxy-phenyl)ethyl]-3-(4,5-dimethoxy-2-methyl-phenyl)prop-2-enamide To a mixture of (E)-3-(4,5-dimethoxy-2-methyl-phenyl)prop-2-enoic acid [444 mg (2 mmol)], 2-(3-benzyloxy-4-methoxy-phenyl)ethanamine [300 mg (1.2 mmol)], DMF (10 mL) and DIEA (1 mL (6 mmol)) was added HATU [950 mg (2.5 mmol)]. The reaction mix was stirred at room temperature 2 h then diluted with 50 mL of EtOAc and washed 2× with sat. NaCl aq. The EtOAc layer was dried ($MgSO_4$) and the solvent removed. Yield=300 mg (54% after flash with 10% MeOH/DCM) MS (m/z): 462 [M+H]

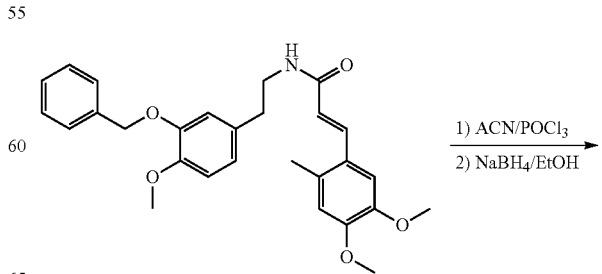

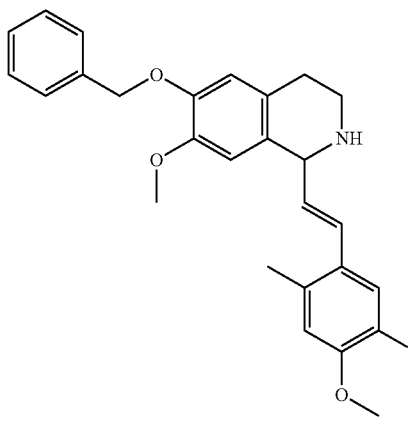

6-Benzyloxy-1-[(E)-2-(4,5-dimethoxy-2-methyl-phenyl)vinyl]-7-methoxy-1,2,3,4-tetrahydroisoquinoline To a solution of (E)-N-[2-(3-benzyloxy-4-methoxy-phenyl)ethyl]-3-(4,5-dimethoxy-2-methyl-phenyl)prop-2-enamide [300 mg (0.651 mmol)] in ACN (13 mL) was added, under reflux, POCl$_3$ [417 ul (4.5 mmol)]. The reaction was stirred at reflux for 10 min and then rotary evaporated to dryness. The residue was taken up into 10 mL of chloroform and was then treated with 20 mL of 2N KOH and 50 mL of Et$_2$O. This mixture was rapidly stirred for 30 min at room temperature and the upper organic layer removed, washed with water, dried (Na$_2$SO$_4$) and the solvent removed. The dark oil was the dissolved into 8 mL of dry EtOH and then treated with NaBH$_4$ [17 mg (0.447 mmol)]. The mixture was stirred for 1 h at room temperature and the resulting solid was carefully filtered off and dried. The solid was triturated with 50/50 ACN/water, filtered and vacuum dried. Yield=124 mg (44% overall) MS (m/z): 446 [M+H]

Example AI: (E)-6-(benzyloxy)-7-methoxy-1-(4-methoxy-2-(4-methoxybutoxy)styryl)-1,2,3,4-tetrahydroisoquinoline

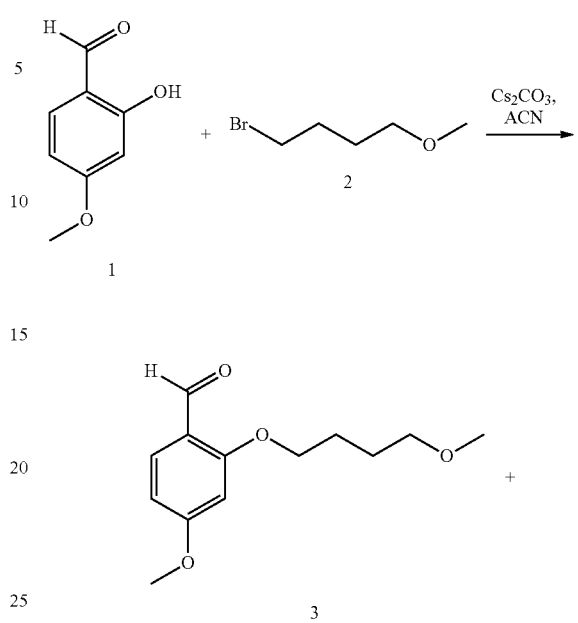

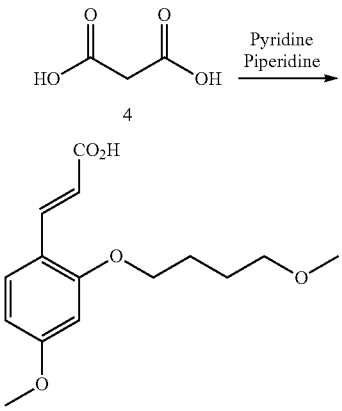

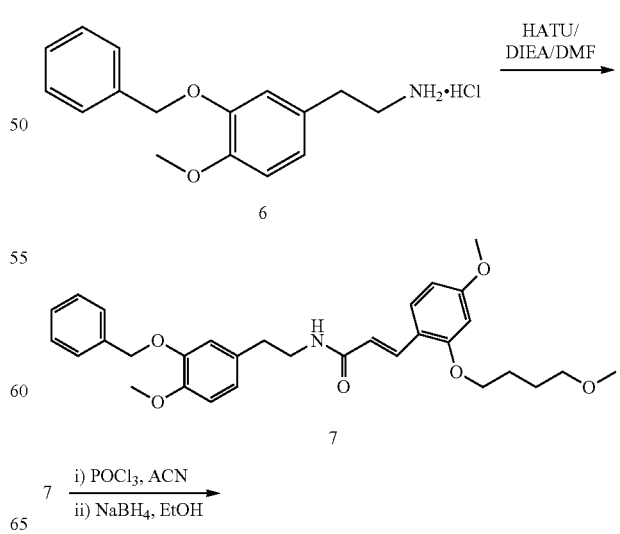

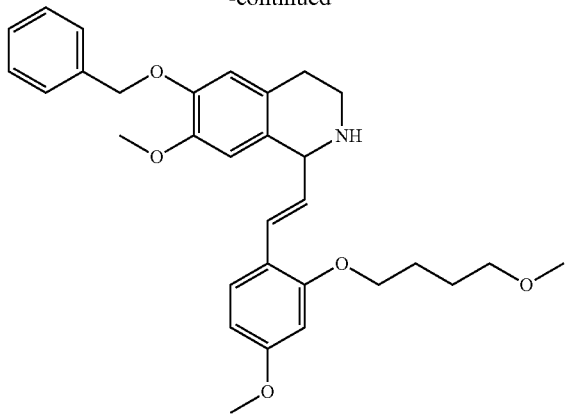

To the solution of 2-hydroxy-methoxybenzaldehyde 1 (1.0 g, 6.57 mmol) in anhydrous acetonitrile (20 ml) under argon was added Cs$_2$CO$_3$ (2.14 g, 6.58 mmol), the resulting mixture was stirred at room temperature for 30 mins, then 1-bromo-4-methoxybutane 2 (1.1 g, 6.58 mmol) was added. The resulting mixture was stirred at room temperature overnight. The volatiles were removed, partitioned between water and EtOAc. The organic layer was washed with brine, dried (Na$_2$SO$_4$), filtered, concentrated to dryness and purified on the ISCO using EtOAc/Hexanes gradient to afford 4-methoxy-2-(4-methoxybutoxy)benzaldehyde 3. The (E)-3-(4-methoxy-2-(4-methoxybutoxy)phenyl)acrylic acid 5 was prepared by the Knoevenagel condensation reaction as described in detail in the first patent writeup.

To the mixture of 5 (0.9542 g, 3.40 mmol), 2-(3-(benzyloxy)-4-methoxyphenyl)ethanamine hydrochloride 6 (1.2 g, 4.085 mmol), HATU (1.55 g, 4.085 mmol) in anhydrous DMF (25 ml) was added DIEA (5 ml, 28.70 mmol). The resulting mixture was stirred at room temperature for 2 hrs, diluted with EtOAc and washed with brine. The organic layer was dried (Na$_2$SO$_4$), filtered, concentrated and purified on the ISCO using EtOAc/Hexanes gradient to furnish the acrylamide 7. To the mixture of the acrylamide in anhydrous acetonitrile (60 ml) was added POCl$_3$ (5 ml, 53.64 mmol), stirred and heated to reflux monitored by LCMS. Ca 1 hr, the reaction was worked up as described in detail on the first patent writeup. NaBH$_4$ reduction of the imine in EtOH afforded the titled compound. M+H=504.

Example AJ: (E)-6-(benzyloxy)-7-methoxy-1-(2-methyl-4-(trifluoromethoxy)styryl)-1,2,3,4-tetrahydroisoquinoline

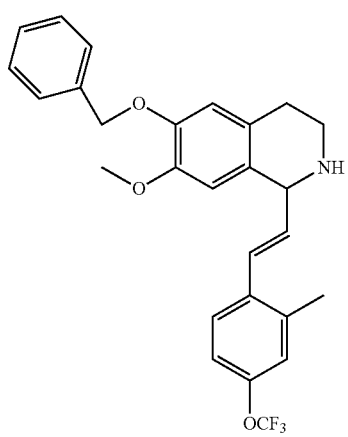

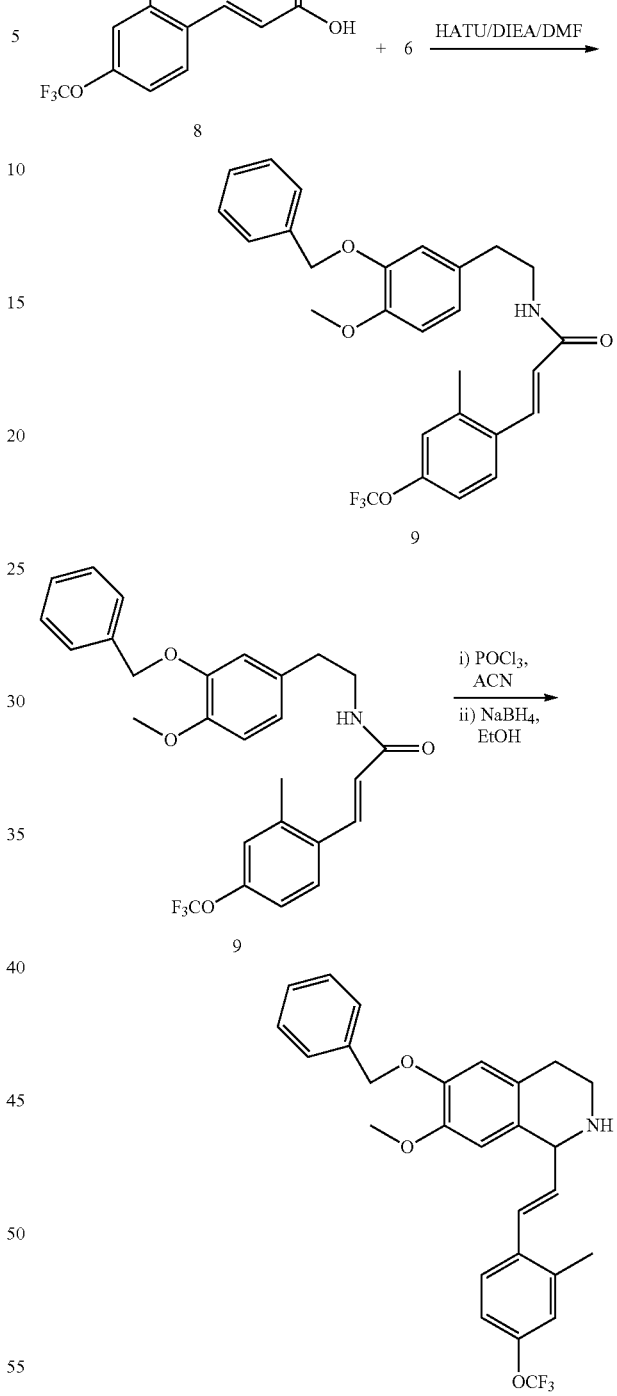

To the mixture of the acrylamide 9 (1.0 g, 2.06 mmol) obtained by the HATU coupling of 8 and 9 described in detail in Example AI, in anhydrous acetonitrile (25 ml), was stirred and heated to reflux, to the solution was added POCl$_3$ (2 ml). The reaction was carried out as described in details in the provisional writeup. The imine obtained was subjected to the NaBH$_4$ reduction in EtOH. After the usual workup, the crude obtained was purified by HPLC to afford the titled compound as the TFA salt. M+H=470, M+H+TFA=584.

Example AK: 6-benzyloxy-7-methoxy-1-[(E)-2-(2-methylpyrazol-3-yl)vinyl]-1,2,3,4-tetrahydroisoquinoline

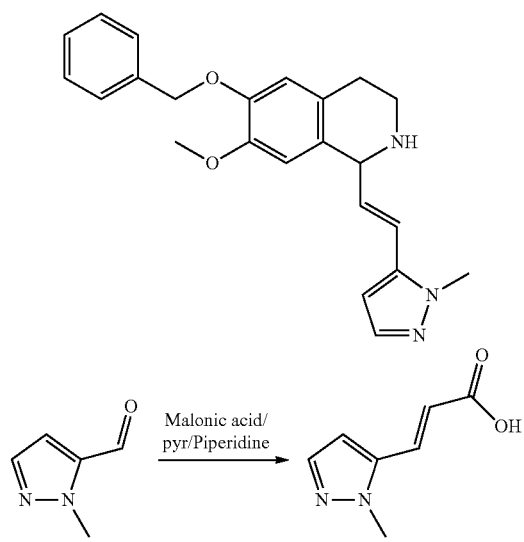

(E)-3-(2-Methylpyrazol-3-yl)prop-2-enoic acid: A mixture of 2-methylpyrazole-3-carbaldehyde [0.286 g (0.0026 mol)], malonic acid [0.53 g (0.0052 mol)], pyridine (5 mL) and piperidine (0.050 mL) was stirred at 80° C. for 1 h followed by stirring for 3 h at 115° C. The reaction was then poured into water (100 mL) and acidified with conc. HCl. The resulting white ppt., product, was filtered and vacuum dried. Yield=395 mg (99%) MS (m/z): 153 [M+H]

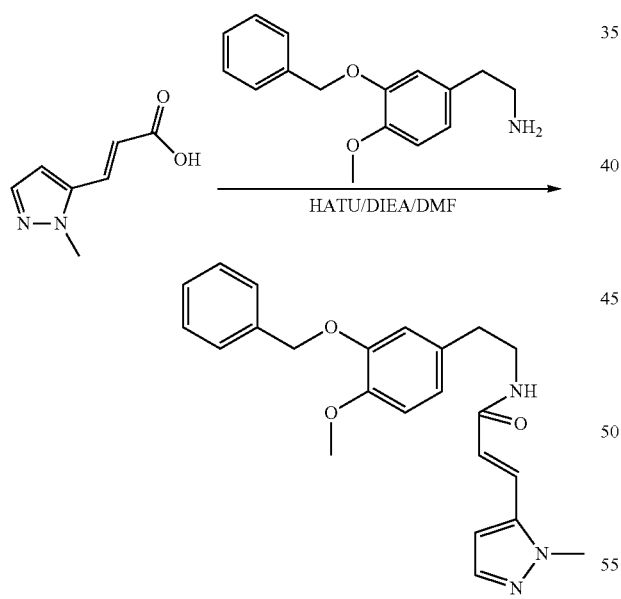

(E)-N-[2-(3-Benzyloxy-4-methoxy-phenyl)ethyl]-3-(2-methylpyrazol-3-yl)prop-2-enamide: To a mixture of (E)-3-(2-Methylpyrazol-3-yl)prop-2-enoic acid [304 mg (2 mmol)], 2-(3-benzyloxy-4-methoxy-phenyl)ethanamine [514 mg (2 mmol)], DMF (8 mL) and DIEA [1 mL (6 mmol)] was added HATU [950 mg (2.5 mmol)]. The reaction mix was stirred at room temperature 2 h then diluted with 50 mL of EtOAc and washed 2× with sat. NaCl aq. The EtOAc layer was dried (MgSO₄) and the solvent removed. Yield=800 mg (99% after flash with 10% MeOH/DCM) MS (m/z): 392 [M+H]

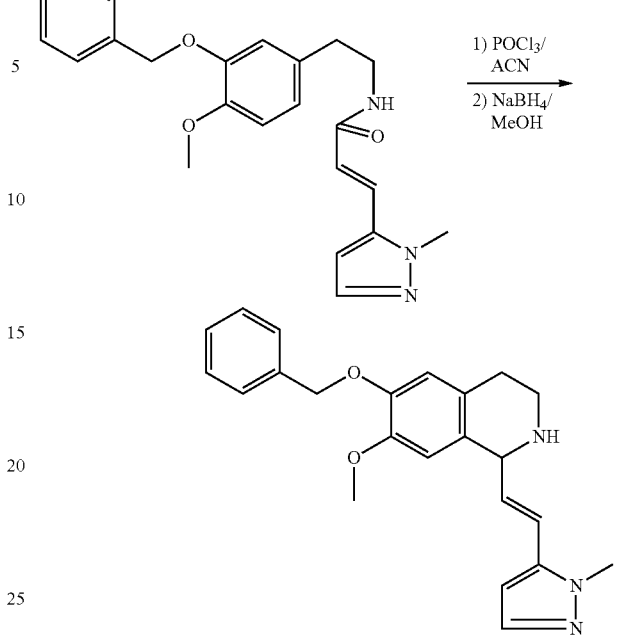

6-Benzyloxy-7-methoxy-1-[(E)-2-(2-methylpyrazol-3-yl)vinyl]-1,2,3,4-tetrahydroisoquinoline: To a solution of (E)-N-[2-(3-benzyloxy-4-methoxy-phenyl)ethyl]-3-(2-methylpyrazol-3-yl)prop-2-enamide [800 mg (2 mmol)] in ACN (30 ml) was added, under reflux, POCl₃ [1000 ul (11 mmol)]. The reaction was stirred at reflux for 10 min and then rotary evaporated to dryness. The residue was taken up into 10 ml of chloroform and was then treated with 20 ml of 2N KOH and 50 ml of Et₂O. This mixture was rapidly stirred for 30 min at room temperature and the upper organic layer removed, washed with water, dried (Na2SO4) and the solvent removed. The dark oil was the dissolved into 24 ml of dry MeOH and then treated with NaBH₄ [60 mg (1.65 mmol)]. The mixture was stirred for 1 h at room temperature. A light yellow solid ppt'd out of solution, was filtered off, triturated with 0.1% TFA and then dried in vacuo. Yield=500 mg (64%) as TFA salt. MS (m/z): 376 [M+H]

Example AL: 6-Benzyloxy-1-[(E)-2-(1-ethylpyrazol-4-yl)vinyl]-7-methoxy-1,2,3,4-tetrahydroisoquinoline

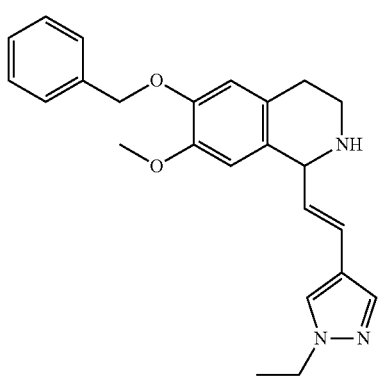

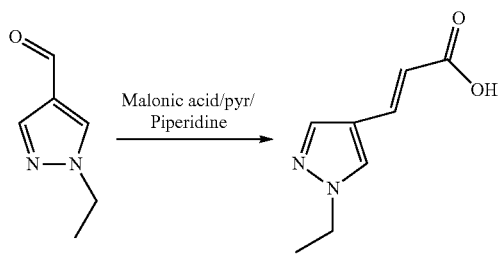

(E)-3-(1-Ethylpyrazol-4-yl)prop-2-enoic acid: A mixture of 1-ethylpyrazole-4-carbaldehyde [0.322 g (2.6 mmol)], malonic acid [0.530 g (5.2 mmol)], pyridine (5 mL) and piperidine (0.050 mL) was stirred at 80° C. for 1 h followed by stirring for 3 h at 115° C. The reaction was then poured into water (100 mL) and acidified with conc. HCl. The resulting white ppt., product, was filtered and vacuum dried. Yield=436 mg (99%) MS (m/z): 169 [M+H]

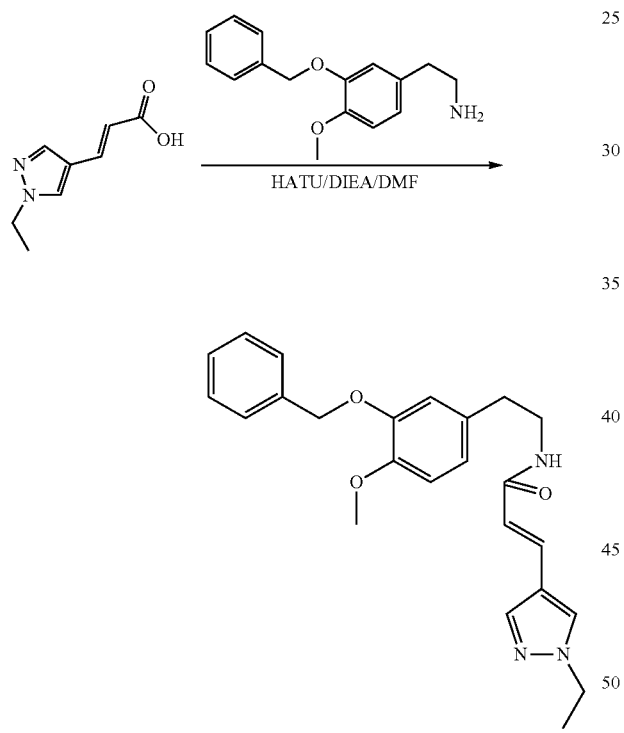

(E)-N-[2-(3-Benzyloxy-4-methoxy-phenyl)ethyl]-3-(1-ethylpyrazol-4-yl)prop-2-enamide: To a mixture of (E)-3-(1-Ethylpyrazol-4-yl)prop-2-enoic acid [370 mg (2.2 mmol)], 2-(3-benzyloxy-4-methoxy-phenyl)ethanamine [565 mg (2.2 mmol)], DMF (8 mL) and DIEA [1 mL (6 mmol)] was added HATU [950 mg (2.5 mmol)]. The reaction mix was stirred at room temperature 2 h then diluted with 50 mL of EtOAc and washed 2× with sat. NaCl aq. The EtOAc layer was dried (MgSO4) and the solvent removed. Yield=900 mg (99%) after flash with 10% MeOH/DCM) MS (m/z): 406 [M+H]

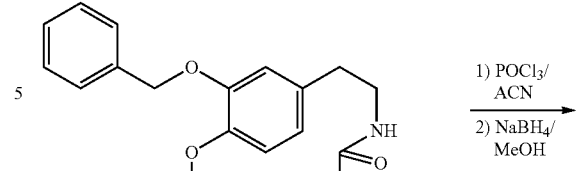

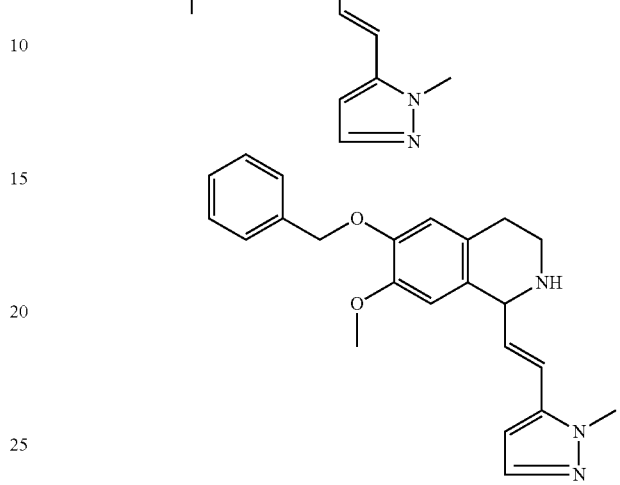

6-Benzyloxy-1-[(E)-2-(1-ethylpyrazol-4-yl)vinyl]-7-methoxy-1,2,3,4-tetrahydroisoquinoline: To a solution of (E)-N-[2-(3-benzyloxy-4-methoxy-phenyl)ethyl]-3-(1-ethylpyrazol-4-yl)prop-2-enamide [900 mg (2.2 mmol)] in ACN (30 ml) was added, under reflux, POCl$_3$ [1000 ul (11 mmol)]. The reaction was stirred at reflux for 10 min and then rotary evaporated to dryness. The residue was taken up into 10 ml of chloroform and was then treated with 20 ml of 2N KOH and 50 ml of Et$_2$O. This mixture was rapidly stirred for 30 min at room temperature and the upper organic layer removed, washed with water, dried (Na$_2$SO$_4$) and the solvent removed. The dark oil was the dissolved into 24 ml of dry MeOH and then treated with NaBH$_4$ [60 mg (1.65 mmol)]. The mixture was stirred for 1 h at room temperature. A light yellow solid ppt'd out of solution, was filtered off, triturated with 0.1% TFA and then dried in vacuo. Yield=600 mg (70%) as TFA salt. MS (m/z): 390 [M+H]

Example AM: 6-Benzyloxy-7-methoxy-1-[(E)-2-(3,4,5-trimethoxyphenyl)vinyl]-1,2,3,4-tetrahydroisoquinoline

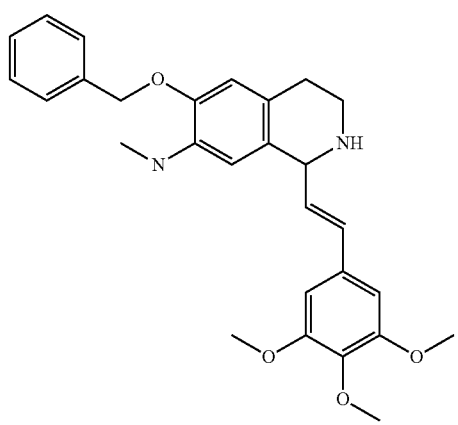

-continued

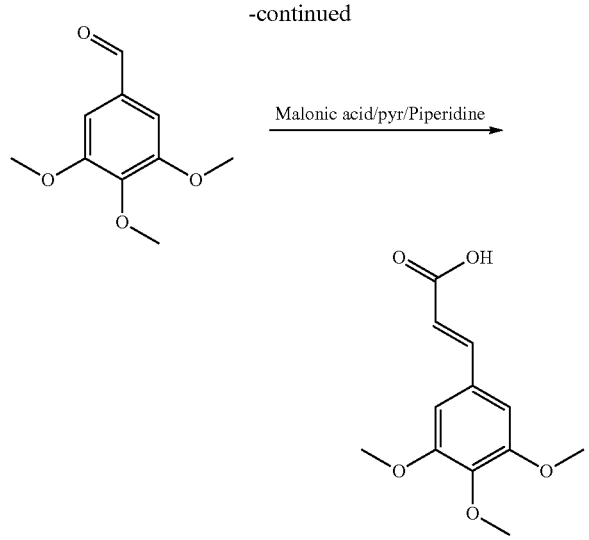

(E)-3-(3,4,5-Trimethoxyphenyl)prop-2-enoic acid: A mixture of 3,4,5-trimethoxybenzaldehyde [0.5 g (0.0026 mol)], malonic acid [0.53 g (0.0052 mol)], pyridine (5 mL) and piperidine (0.050 mL) was stirred at 80° C. for 1 h followed by stirring for 3 h at 115° C. The reaction was then poured into water (100 mL) and acidified with conc. HCl. The resulting white ppt., product, was filtered and vacuum dried. Yield=530 mg (86%) MS (m/z): 239 [M+H]

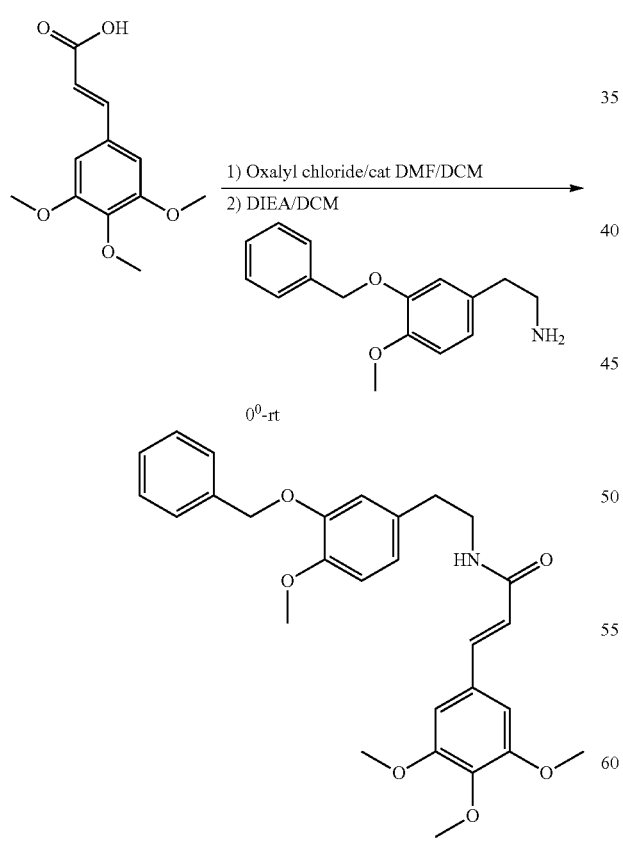

(E)-N-[2-(3-Benzyloxy-4-methoxy-phenyl)ethyl]-3-(3,4,5-trimethoxyphenyl)prop-2-enamide: To a suspension of (E)-3-(3,4,5-trimethoxyphenyl)prop-2-enoic acid [0.530 g (0.0022 mol)] in 20 ml of Dichloromethane was added 2 drops of DMF followed by oxalyl chloride [271 ul (3.2 mol)]. After 1 h stirring at room temperature the reaction was rotary evaporated to dryness and the resulting yellow residue was dried in vacuo. To a solution of 2-(3-benzyloxy-4-methoxy-phenyl)ethanamine [565 mg (2.2 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO4) and the solvent removed. Yield=1 g (99%) after flash with 10% MeOH/DCM) MS (m/z): 478 [M+H]

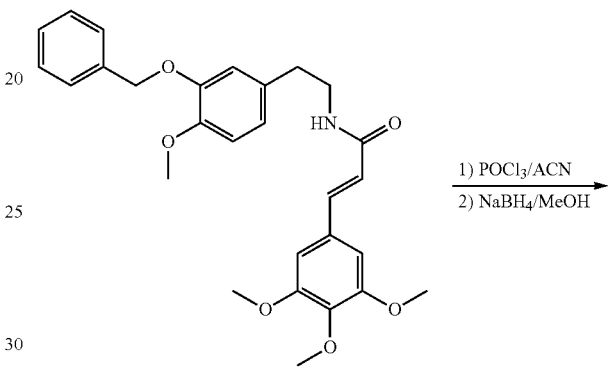

6-Benzyloxy-7-methoxy-1-[(E)-2-(3,4,5-trimethoxyphenyl)vinyl]-1,2,3,4-tetrahydroisoquinoline: To a solution of (E)-N-[2-(3-benzyloxy-4-methoxy-phenyl)ethyl]-3-(3,4,5-trimethoxyphenyl)prop-2-enamide [1000 mg (2.2 mmol)] in ACN (45 ml) was added, under reflux, POCl3 [1500 ul (16 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na2SO4) and the solvent removed. The dark oil was the dissolved into 24 ml of dry MeOH and then treated with NaBH4 [60 mg (1.65 mmol)] at 00. The mixture was stirred for 1 h at room temperature. An off white solid ppt'd out of solution, was filtered off, triturated with 0.1% TFA and then dried in vacuo. Yield=605 mg (60%) as TFA salt. MS (m/z): 462 [M+H]

Example AN: 6-Benzyloxy-7-methoxy-1-[(E)-2-(7-methoxybenzofuran-4-yl)vinyl]-1,2,3,4-tetrahydroisoquinoline

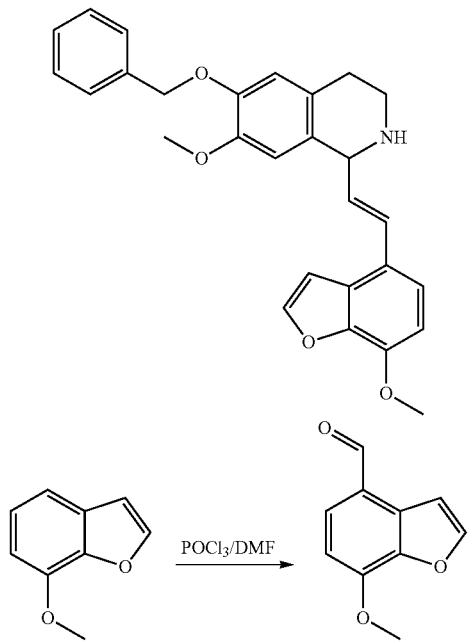

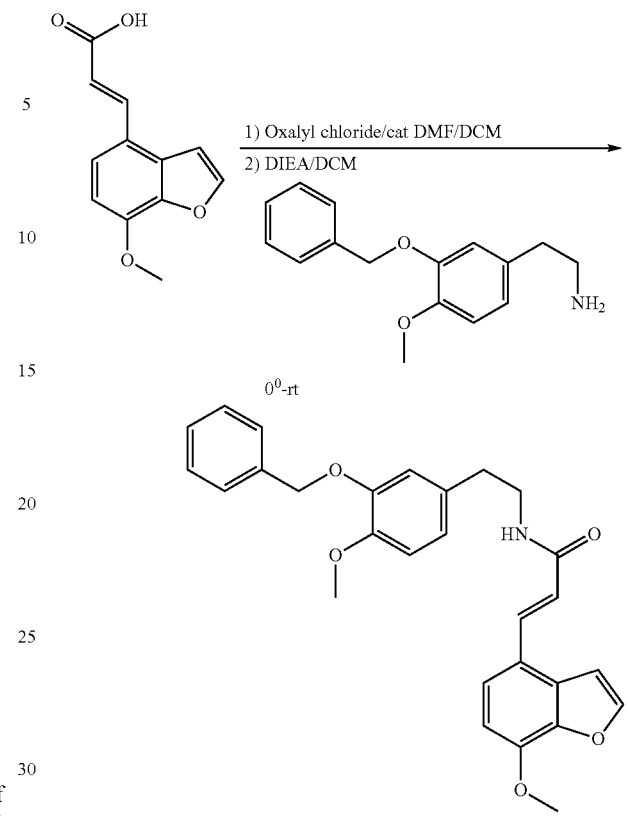

7-methoxybenzofuran-4-carbaldehyde: To a mixture of POCl3 (0.65 ml, 0.04 mol) and DMF (2.1 ml, 0.04 mol) at 0° C. was added 7-methoxybenzofuran (1 g, 0.0067 mol). The resulting solution was heated to 80° C. and stirred for 4 h. After being cooled to room temperature, the reaction mixture was poured into ice and extracted with ether. The combined extracts were concentrated in vacuo and purified by silica gel flash column chromatography (10% EtOAc/hexanes) to afford benzaldehyde (750 mg, 64%) as an off-white solid.

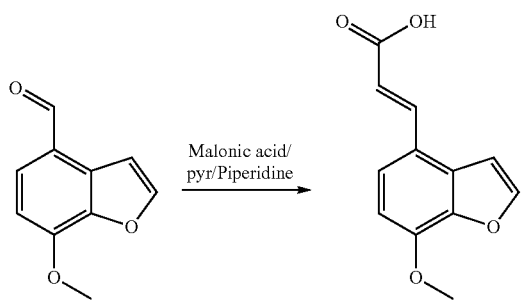 [SMILES: COc1ccc(C=O)c2ccoc12 ; COc1ccc(/C=C/C(=O)O)c2ccoc12]

(E)-3-(7-Methoxybenzofuran-4-yl)prop-2-enoic acid: 7-methoxybenzofuran-4-carbaldehyde (0.4 g, 0.0023 mol), malonic acid (0.53 g, 0.0052 mol), pyridine (5 mL), and piperidine (50 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=444 mg.

(E)-N-[2-(3-Benzyloxy-4-methoxy-phenyl)ethyl]-3-(7-methoxybenzofuran-4-yl)prop-2-enamide: To a suspension of (E)-3-(7-methoxybenzofuran-4-yl)prop-2-enoic acid [444 mg (0.002 mol)] in 20 ml of Dichloromethane was added 2 drops of DMF followed by oxalyl chloride [271 ul (3.2 mol)]. After 1 h stirring at room temperature the reaction was rotary evaporated to dryness and the resulting yellow residue was dried in vacuo. To a solution of 2-(3-benzyloxy-4-methoxy-phenyl)ethanamine [565 mg (2.2 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO4) and the solvent removed. Yield=0.850 g (93%) after flash chromatography with 10% MeOH/DCM).

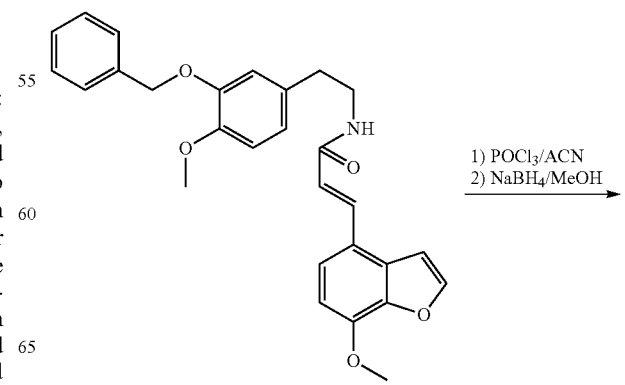

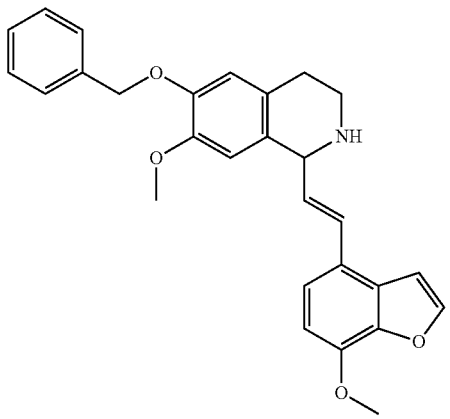

6-Benzyloxy-7-methoxy-1-[(E)-2-(7-methoxybenzofuran-4-yl)vinyl]-1,2,3,4-tetrahydroisoquinoline: To a solution of (E)-N-[2-(3-benzyloxy-4-methoxy-phenyl)ethyl]-3-(7-methoxybenzofuran-4-yl)prop-2-enamide [850 mg (1.85 mmol)] in ACN (30 ml) was added, under reflux, POCl₃ [1000 ul (11 mmol)]. The reaction was stirred at reflux for 10 min and then rotary evaporated to dryness. The residue was taken up into 10 ml of chloroform and was then treated with 20 ml of 2N KOH and 50 ml of Et₂O. This mixture was rapidly stirred for 30 min at room temperature and the upper organic layer removed, washed with water, dried (Na₂SO₄) and the solvent removed. The dark oil was the dissolved into 24 ml of dry MeOH and then treated with NaBH₄ [60 mg (1.65 mmol)]. The mixture was stirred for 1 h at room temperature. A light yellow solid ppt'd out of solution, was filtered off, triturated with 0.1% TFA and then dried in vacuo. Yield=700 mg (84%) as TFA salt. MS (m/z): 442 [M+H]

Example AO: 6-Benzyloxy-7-methoxy-1-[(E)-2-(4-methoxybenzofuran-7-yl)vinyl]-1,2,3,4-tetrahydroisoquinoline

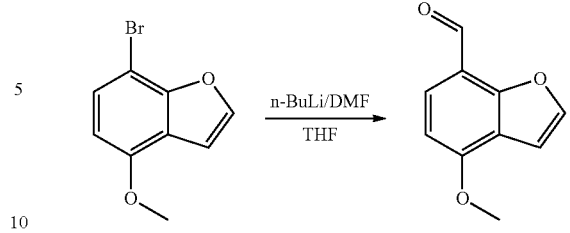

4-Methoxybenzofuran-7-carbaldehyde: To a solution of 7-bromo-4-methoxy-benzofuran (1.1 g (5 mmol) in THF (13 ml) at −78° C. was added 1.6M n-BuLi (3.4 ml, 5.5 mmol). The resulting solution was stirred at −75° C. for 40 min followed by the addition of DMF (0.401 ml, 5.5 mmol). The mixture was allowed to warm slowly to room temperature and stirred overnight. The reaction was quenched with NH₄Cl sat and extracted with Et₂O. The extracts were dried (Na₂SO₄) and the solvent removed. Yield=528 mg after trituration with hexane.

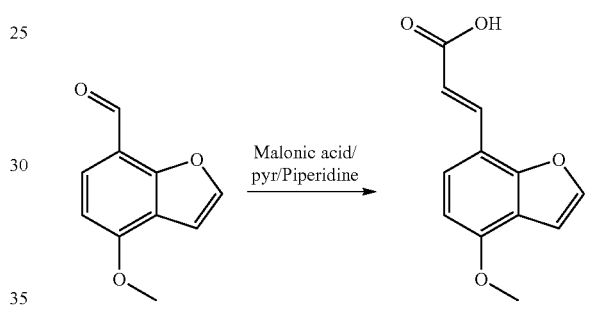

(E)-3-(4-methoxybenzofuran-7-yl)prop-2-enoic acid: 4-methoxybenzofuran-7-carbaldehyde (0.4 g, 0.0023 mol), malonic acid (0.53 g, 0.0052 mol), pyridine (5 mL), and piperidine (50 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over P₂O₅ and used without further purifications. Yield=444 mg.

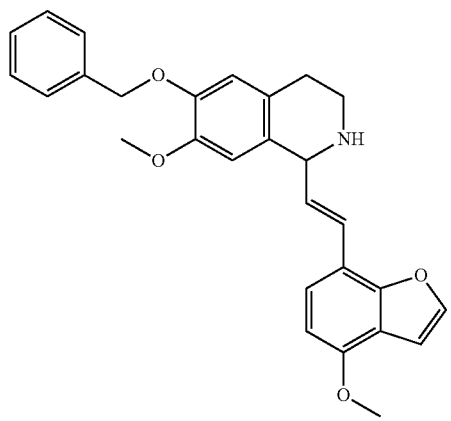

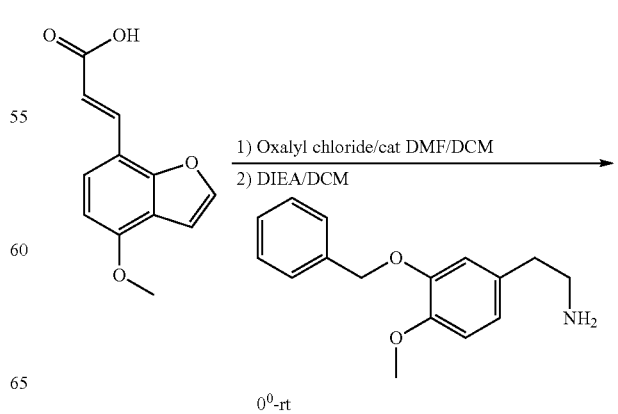

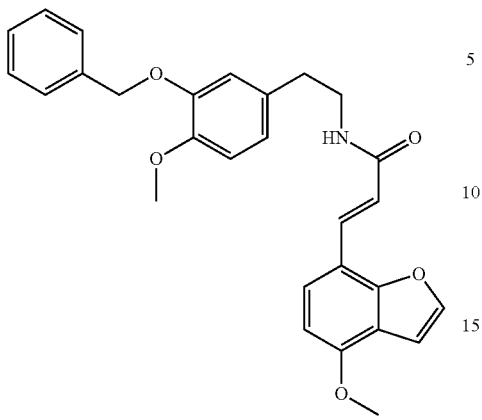

(E)-N-[2-(3-Benzyloxy-4-methoxy-phenyl)ethyl]-3-(7-methoxybenzofuran-4-yl)prop-2-enamide: To a suspension of (E)-3-(4-methoxybenzofuran-7-yl)prop-2-enoic acid [444 mg (0.002 mol)] in 20 ml of Dichloromethane was added 2 drops of DMF followed by oxalyl chloride [271 ul (3.2 mol)]. After 1 h stirring at room temperature the reaction was rotary evaporated to dryness and the resulting yellow residue was dried in vacuo. To a solution of 2-(3-benzyloxy-4-methoxy-phenyl)ethanamine [565 mg (2.2 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO$_4$) and the solvent removed. Yield=0.847 g (93%) after flash chromatography with 10% MeOH/DCM)

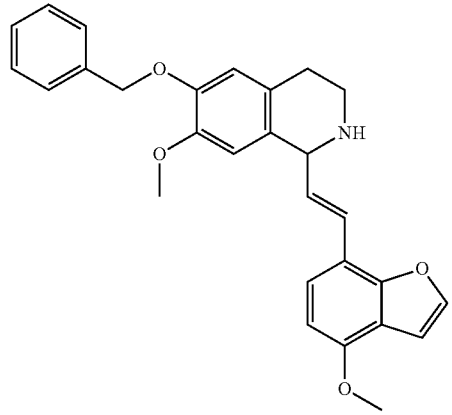

6-Benzyloxy-7-methoxy-1-[(E)-2-(4-methoxybenzofuran-7-yl)vinyl]-1,2,3,4-tetrahydroisoquinoline: To a solution of (E)-N-[2-(3-benzyloxy-4-methoxy-phenyl)ethyl]-3-(4-methoxybenzofuran-7-yl)prop-2-enamide [315 mg (0.69 mmol)] in ACN (13 ml) was added, under reflux, POCl$_3$ [400 ul (4.3 mmol)]. The reaction was stirred at reflux for 10 min and then rotary evaporated to dryness. The residue was taken up into 30 ml of chloroform and was then treated with 30 ml of 2N KOH and 100 ml of Et2O. This mixture was rapidly stirred for 30 min at room temperature and the upper organic layer removed, washed with water, dried (Na$_2$SO$_4$) and the solvent removed. The dark oil was the dissolved into 7 ml of dry MeOH (with 1 ml of DCM) and then treated with NaBH$_4$ [18 mg (0.47 mmol)]. The mixture was stirred for 1 h at room temperature. A light yellow solid ppt'd out of solution, was filtered off, triturated with 0.1% TFA and then dried in vacuo. Yield=300 mg (99%) as TFA salt. MS (m/z): 442 [M+H]

Example AP: 6-Benzyloxy-1-[(E)-2-(4-benzyloxy-3,5-dimethoxy-phenyl)vinyl]-7-methoxy-1,2,3,4-tetrahydroisoquinoline

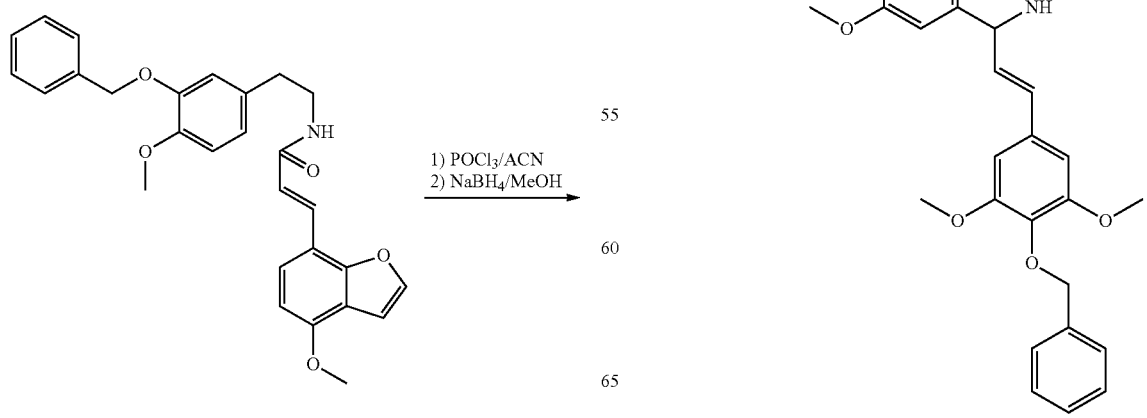

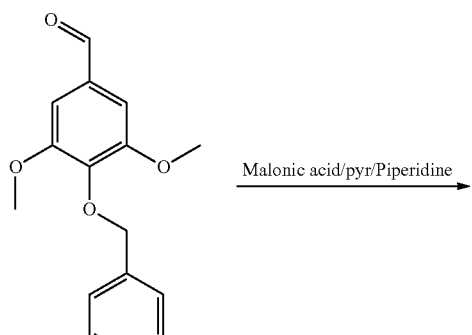

Malonic acid/pyr/Piperidine →

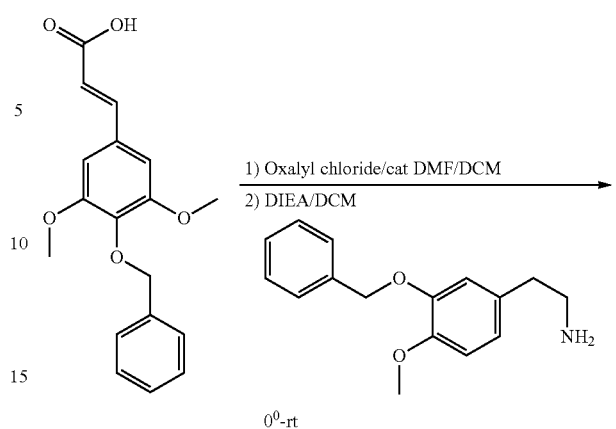

1) Oxalyl chloride/cat DMF/DCM
2) DIEA/DCM →
0°-rt

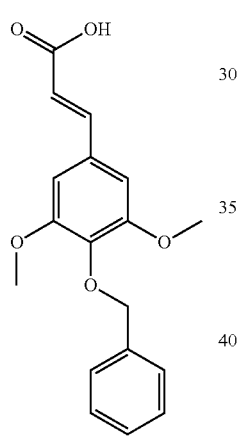

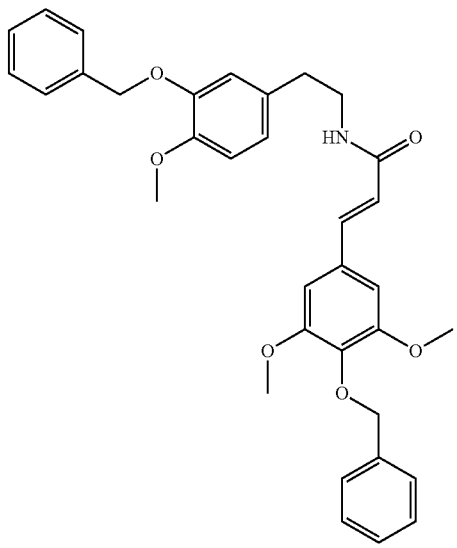

(E)-3-(4-Benzyloxy-3,5-dimethoxy-phenyl)prop-2-enoic acid: 4-benzyloxy-3,5-dimethoxy-benzaldehyde (0.71 g (0.0026 mmol)), malonic acid (0.53 g, 0.0052 mol), pyridine (5 mL), and piperidine (50 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=769 mg.

(E)-3-(4-Benzyloxy-3,5-dimethoxy-phenyl)-N-[2-(3-benzyloxy-4-methoxy-phenyl)ethyl]prop-2-enamide: To a suspension of (E)-3-(4-benzyloxy-3,5-dimethoxy-phenyl)proEp-2-enoic acid [628 mg (0.002 mol)] in 20 ml of Dichloromethane was added 2 drops of DMF followed by oxalyl chloride [271 ul (3.2 mol)]. After 1 h stirring at room temperature the reaction was rotary evaporated to dryness and the resulting yellow residue was dried in vacuo. To a solution of 2-(3-benzyloxy-4-methoxy-phenyl)ethanamine [565 mg (2.2 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried ($MgSO_4$) and the solvent removed. Yield=1.2 g (99%) after flash chromatography with 10% MeOH/DCM)

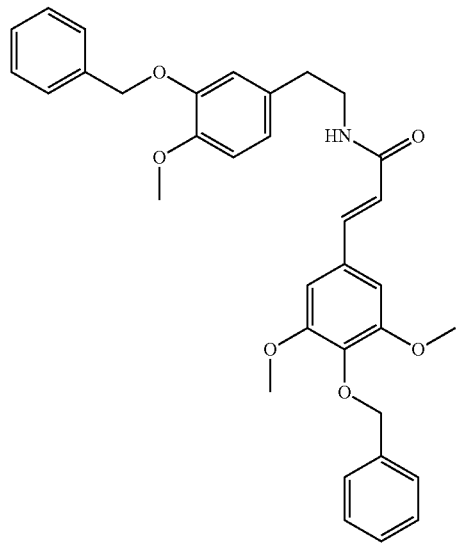
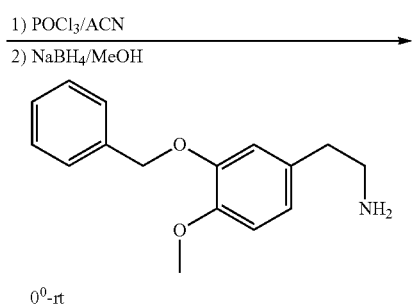
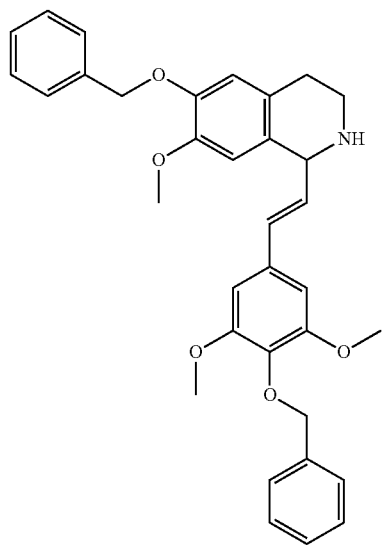

6-Benzyloxy-1-[(E)-2-(4-benzyloxy-3,5-dimethoxy-phenyl)vinyl]-7-methoxy-1,2,3,4-tetrahydroisoquinoline: To a solution of (E)-3-(4-benzyloxy-3,5-dimethoxy-phenyl)-N-[2-(3-benzyloxy-4-methoxy-phenyl)ethyl]prop-2-enamide [1200 mg (2.2 mmol)] in ACN (45 ml) was added, under reflux, POCl$_3$ [1500 ul (16 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na$_2$SO$_4$) and the solvent removed. The dark oil was the dissolved into 24 ml of dry MeOH and then treated with NaBH$_4$ [60 mg (1.65 mmol)] at 00. The mixture was stirred for 1 h at room temperature. A off white solid ppt'd out of solution, was filtered off, triturated with 0.1% TFA and then dried in vacuo. Yield=571 mg (48% overall) as TFA salt. MS (m/z): 538 [M+H]

Example AQ: 6-Benzyloxy-7-methoxy-1-[(E)-2-(2,4,5-trimethoxyphenyl)vinyl]-1,2,3,4-tetrahydroisoquinoline

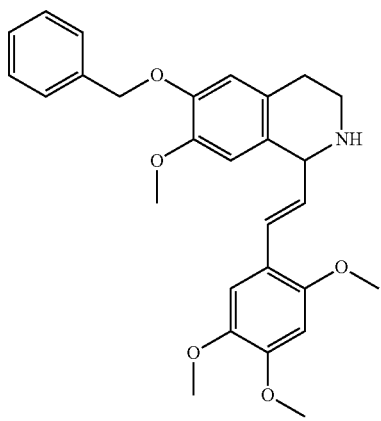

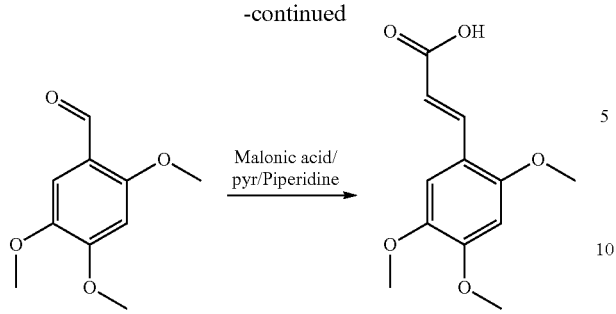

(E)-3-(2,4,5-Trimethoxyphenyl)prop-2-enoic acid: 2,4,5-trimethoxybenzaldehyde (0.5 g, 0.0026 mol), malonic acid (0.53 g, 0.0052 mol), pyridine (5 mL), and piperidine (50 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=594 mg.

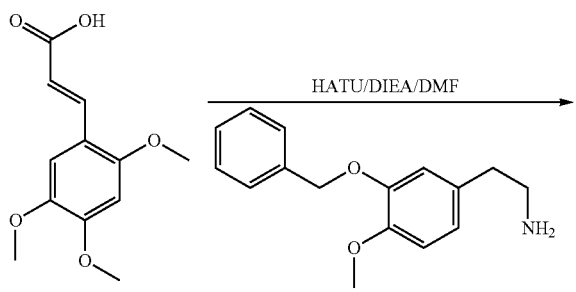

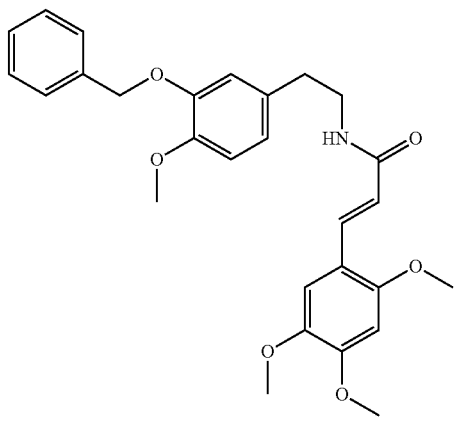

(E)-N-[2-(3-Benzyloxy-4-methoxy-phenyl)ethyl]-3-(2,4,5-trimethoxyphenyl)prop-2-enamide: To a solution of (E)-3-(2,4,5-trimethoxyphenyl)prop-2-enoic acid [594 mg (0.0025 mol)], 2-(3-benzyloxy-4-methoxy-phenyl)ethanamine [565 mg (2.2 mmol)] and DIEA [3 ml (0.0025 mol] in 9 ml of Dimethylforamide was added HATU [1.3 g (0.0034 mol)]. After 1 h stirring at room temperature the reaction mix was then diluted with 50 mL of EtOAc and washed 2× with sat. NaCl aq. The EtOAc layer was dried ($MgSO_4$) and the solvent removed. Yield=1.2 g (99%) after flash chromatography with 10% MeOH/DCM)

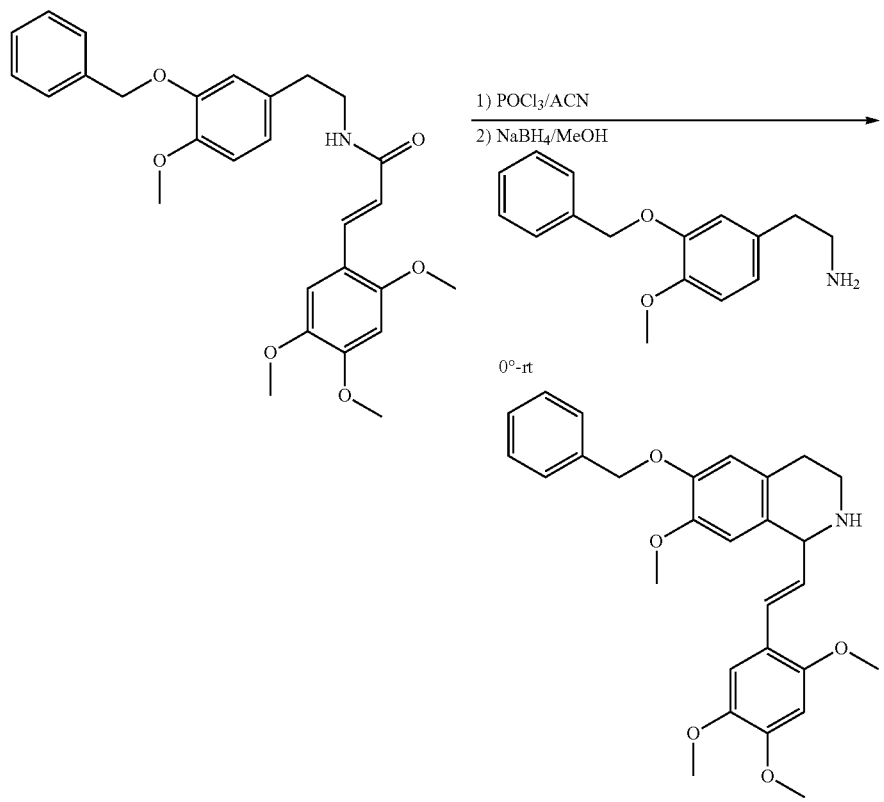

6-Benzyloxy-7-methoxy-1-[(E)-2-(2,4,5-trimethoxyphenyl)vinyl]-1,2,3,4-tetrahydroisoquinoline: To a solution of (E)-N-[2-(3-benzyloxy-4-methoxy-phenyl)ethyl]-3-(2,4,5-trimethoxyphenyl)prop-2-enamide [1190 mg (2.5 mmol)] in ACN (45 ml) was added, under reflux, POCl$_3$ [1500 ul (16 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na2SO4) and the solvent removed. The dark oil was the dissolved into 24 ml of dry MeOH and then treated with NaBH4 [60 mg (1.65 mmol)]. The mixture was stirred for 1 h at room temperature. A light yellow solid ppt'd out of solution, was filtered off, triturated with 0.1% TFA and then dried in vacuo. Yield=295 mg (26% overall) as TFA salt. MS (m/z): 462 [M+H]

Example AR: 6-Benzyloxy-1-[(E)-2-(3-bromo-4-methoxy-phenyl)vinyl]-7-methoxy-1,2,3,4-tetrahydroisoquinoline piperidine (88 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over P$_2$O$_5$ and used without further purifications. Yield=1.2 g.

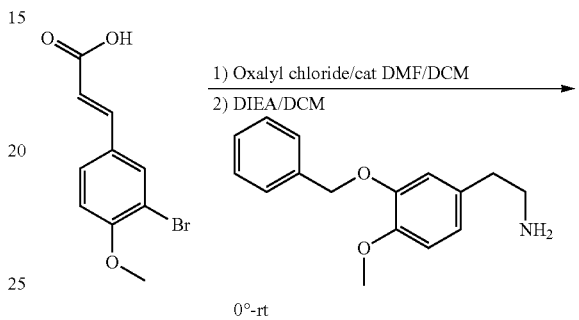

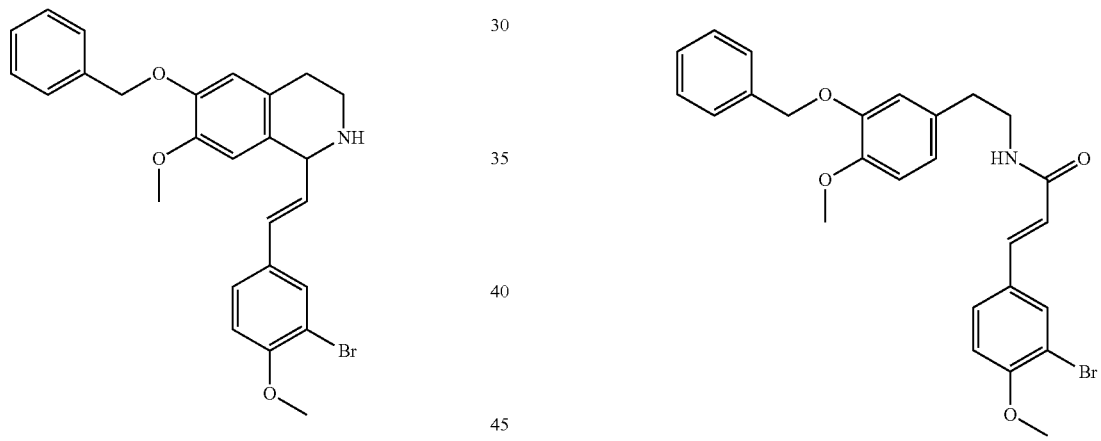

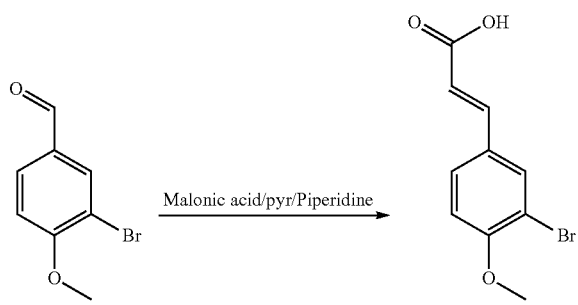

(E)-3-(3-Bromo-4-methoxy-phenyl)prop-2-enoic acid: 3-bromo-4-methoxy-benzaldehyde (1 g (0.0046 mmol)), malonic acid (0.93 g, 0.0092 mol), pyridine (9 mL), and (E)-N-[2-(3-Benzyloxy-4-methoxy-phenyl)ethyl]-3-(3-bromo-4-methoxy-phenyl)prop-2-enamide: To a suspension of (E)-3-(3-bromo-4-methoxy-phenyl)prop-2-enoic acid [1.2 g (0.0046 mol)] in 20 ml of Dichloromethane was added 5 drops of DMF followed by oxalyl chloride [613 ul (6.9 mol)]. After 1 h stirring at room temperature the reaction was rotary evaporated to dryness and the resulting yellow residue was dried in vacuo. To a solution of 2-(benzyloxy-4-methoxy-phenyl)ethanamine [1.2 g (4.6 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO$_4$) and the solvent removed. Yield=2.3 g (99%) after flash chromatography with 10% MeOH/DCM)

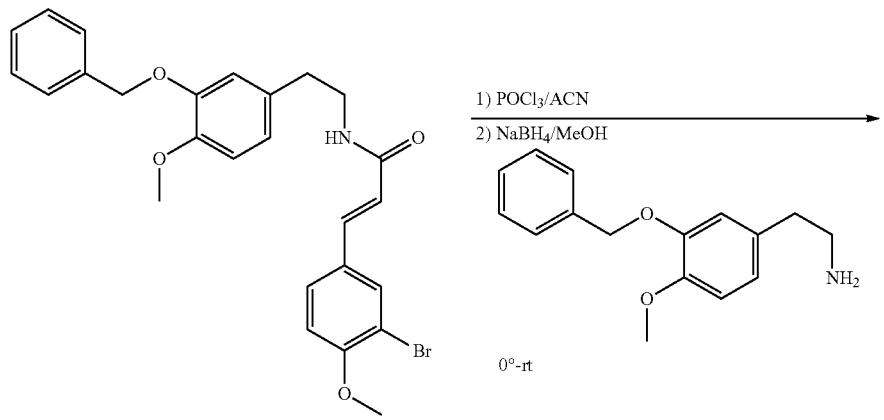

6-Benzyloxy-1-[(E)-2-(3-bromo-4-methoxy-phenyl)vinyl]-7-methoxy-1,2,3,4-tetrahydroisoquinoline: To a solution of (E)-N-[2-(3-benzyloxy-4-methoxy-phenyl)ethyl]-3-(3-bromo-4-methoxy-phenyl)prop-2-enamide [2.3 g (0.0046 mol)] in ACN (90 ml) was added, under reflux, POCl3 [3000 ul (33 mmol)]. The reaction was stirred at reflux for 10 min and then rotary evaporated to dryness. The residue was taken up into 30 ml of chloroform and was then treated with 30 ml of 2N KOH and 100 ml of Et2O. This mixture was rapidly stirred for 30 min at room temperature and the upper organic layer removed, washed with water, dried (Na2SO4) and the solvent removed. The dark oil was the dissolved into 40 ml of dry MeOH and then treated with NaBH4 [120 mg (3.3 mmol)]. The mixture was stirred for 1 h at room temperature. A light yellow solid ppt'd out of solution, was filtered off, triturated with 0.1% TFA and then dried in vacuo. Yield=2 g (91% overall) as TFA salt. MS (m/z): 480 [M+H]

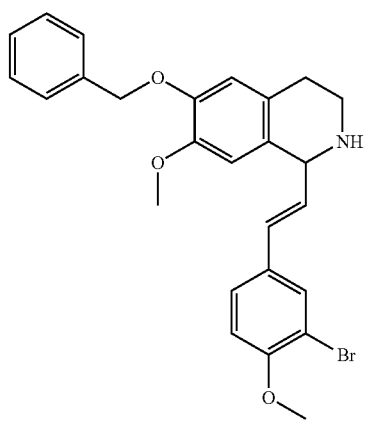

Example AS: 6-Benzyloxy-1-[(E)-2-(5-benzyloxy-2-tert-butyl-4-methoxy-phenyl)vinyl]-7-methoxy-1,2,3,4-tetrahydroisoquinoline

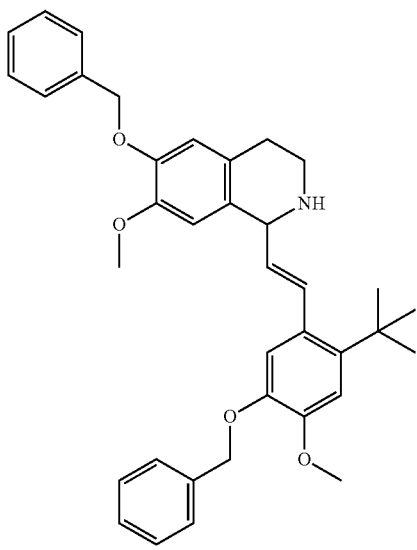

-continued

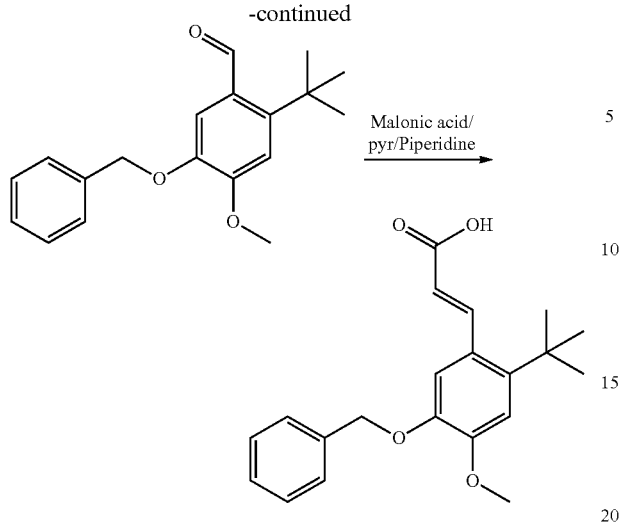

(E)-3-(5-Benzyloxy-2-tert-butyl-4-methoxy-phenyl) prop-2-enoic acid: 5-benzyloxy-2-tert-butyl-4-methoxy-benzaldehyde (0.116 g (0.39 mmol)), malonic acid (83 g, 0.8 mol), pyridine (5 mL), and piperidine (88 ul, 0.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=133 mg.

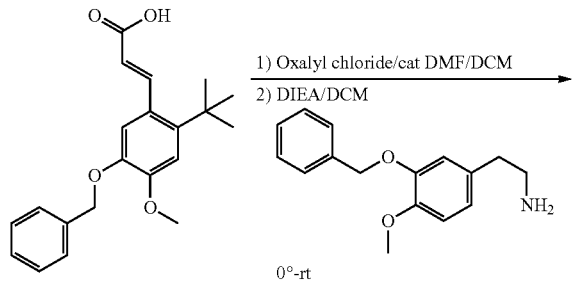

-continued

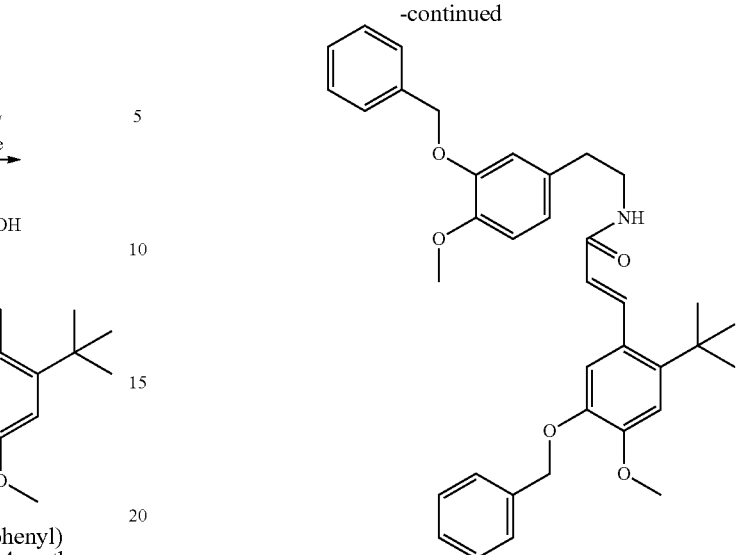

(E)-3-(5-Benzyloxy-2-tert-butyl-4-methoxy-phenyl)-N-[2-(3-benzyloxy-4-methoxy-phenyl)ethyl]prop-2-enamide:
To a suspension of (E)-3-(5-benzyloxy-2-tert-butyl-4-methoxy-phenyl)prop-2-enoic acid [113 mg (0.39 mmol)] in 10 ml of Dichloromethane was added 2 drops of DMF followed by oxalyl chloride [51 ul (0.6 mmol)]. After 1 h stirring at room temperature the reaction was rotary evaporated to dryness and the resulting yellow residue was dried in vacuo. To a solution of 2-(3-benzyloxy-4-methoxy-phenyl)ethanamine [103 mg (0.4 mmol)] and DIEA [100 uL (0.6 mmol)] in 10 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO$_4$) and the solvent removed. Yield=225 mg (99%) after flash chromatography with 10% MeOH/DCM)

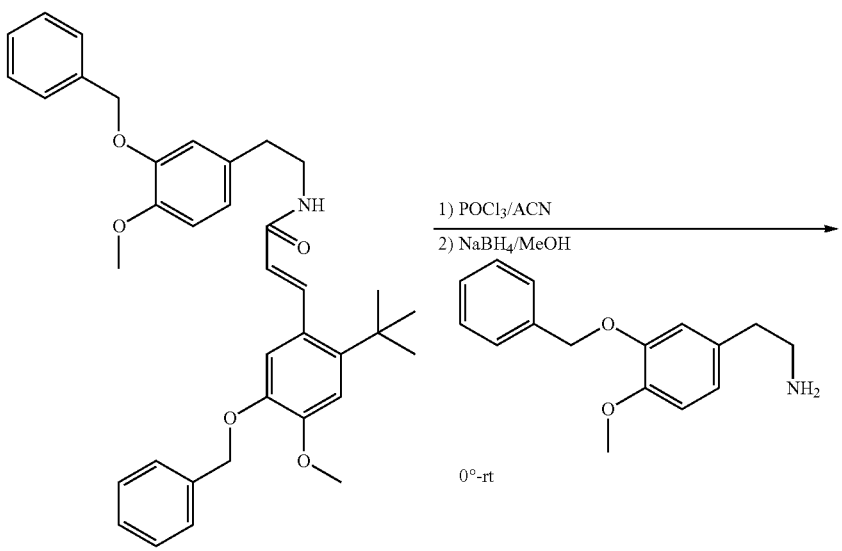

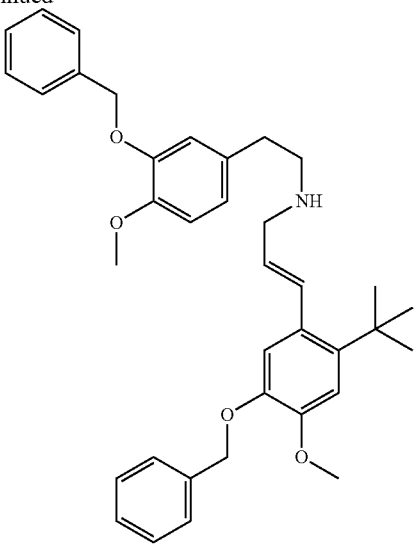

6-Benzyloxy-1-[(E)-2-(5-benzyloxy-2-tert-butyl-4-methoxy-phenyl)vinyl]-7-methoxy-1,2,3,4-tetrahydroisoquinoline: To a solution of (E)-3-(5-benzyloxy-2-tert-butyl-4-methoxy-phenyl)-N-[2-(3-benzyloxy-4-methoxy-phenyl)ethyl]prop-2-enamide [225 mg (0.39 mmol)] in ACN (9 ml) was added, under reflux, $POCl_3$ [300 ul (3.21 mmol)]. The reaction was stirred at reflux for 10 min and then rotary evaporated to dryness. The residue was taken up into 10 ml of chloroform and was then treated with 20 ml of 2N KOH and 50 ml of $Et_2O$. This mixture was rapidly stirred for 30 min at room temperature and the upper organic layer removed, washed with water, dried ($Na_2SO_4$) and the solvent removed. The dark oil was the dissolved into 8 ml of dry EtOH and then treated with NaBH4 [12 mg (0.32 mmol)]. The mixture was stirred for 1 h at room temperature and the resulting solid was carefully filtered off and dried. The solid was triturated with 50/50 ACN/water, filtered and vacuum dried. Yield=50 mg (11% overall) as TFA salt. MS (m/z): 564 [M+H]

Example AT: 6-Benzyloxy-1-[(E)-2-(3,5-dimethoxy-phenyl)vinyl]-7-methoxy-1,2,3,4-tetrahydroisoquinoline

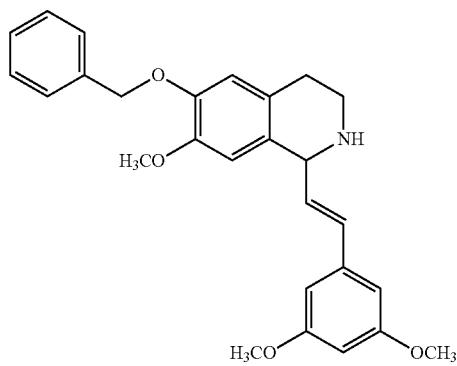 [SMILES: COc1cc(/C=C/C2NCCc3cc(OCc4ccccc4)c(OC)cc32)cc(OC)c1]

Using the same procedure outlined in Example AI at the same scale with the aldehyde 3,5-dimethoxybenzaldehyde the reaction afforded the desired adduct. Yield=30 mg (34%) as TFA salt via prep chrom. MS (m/z): 432 [M+H]

Example AU: 6-benzyloxy-7-methoxy-1-[(E)-2-(2-methoxy-4-pyridyl)vinyl]-1,2,3,4-tetrahydroisoquinoline

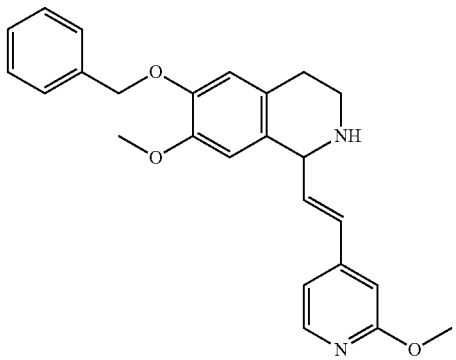

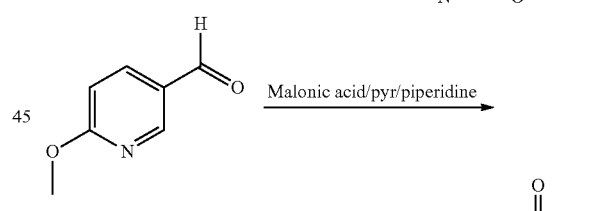

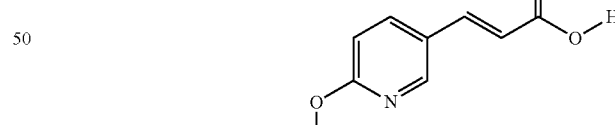

(E)-3-(6-Methoxy-3-pyridyl)prop-2-enoic acid: 6-methoxypyridine-3-carbaldehyde (3 g (0.022 mol)), malonic acid (4.35 g (0.042 mol)), pyridine (15 mL), and piperidine (400 ul, 4 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=2.8 g

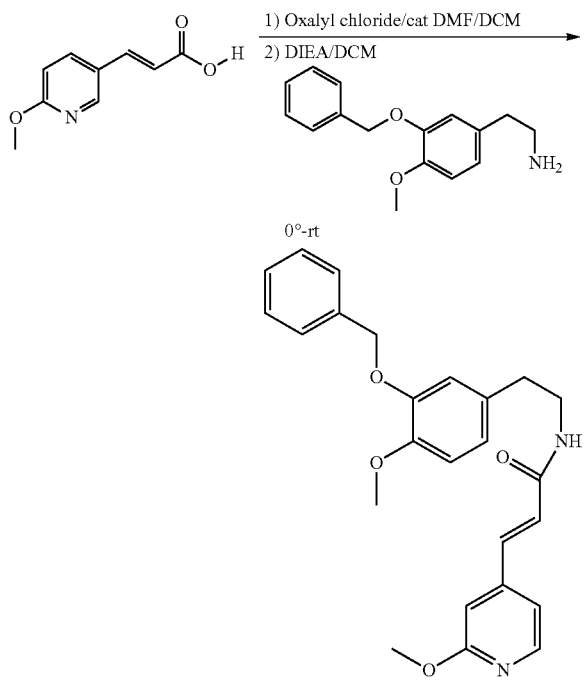

(E)-N-[2-(3-Benzyloxy-4-methoxy-phenyl)ethyl]-3-(2-methoxy-4-pyridyl)prop-2-enamide: To a suspension of (E)-3-(6-Methoxy-3-pyridyl)prop-2-enoic acid [179 mg (1 mmol)] in 10 ml of Dichloromethane was added 2 drops of DMF followed by oxalyl chloride [300 ul (3 mmol)]. After 1 h stirring at room temperature the reaction was rotary evaporated to dryness and the resulting yellow residue was dried in vacuo. To a solution of 2-(3-benzyloxy-4-methoxy-phenyl)ethanamine [257 mg (1 mmol)] and DIEA [500 uL (3 mmol)] in 10 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO$_4$) and the solvent removed. Yield=286 mg (68%) after flash chromatography with 10% MeOH/DCM)

6-Benzyloxy-7-methoxy-1-[(E)-2-(2-methoxy-4-pyridyl)vinyl]-1,2,3,4-tetrahydroisoquinoline: To a solution of (E)-N-[2-(3-benzyloxy-4-methoxy-phenyl)ethyl]-3-(2-methoxy-4-pyridyl)prop-2-enamide [286 mg (0.68 mmol)] in ACN (9 ml) was added, under reflux, POCl$_3$ [600 ul (6.42 mmol)]. The reaction was stirred at reflux for 10 min and then rotary evaporated to dryness. The residue was taken up into 10 ml of chloroform and was then treated with 20 ml of 2N KOH and 50 ml of Et$_2$O. This mixture was rapidly stirred for 30 min at room temperature and the upper organic layer removed, washed with water, dried (Na$_2$SO$_4$) and the solvent removed. The dark oil was the dissolved into 8 ml of dry EtOH and then treated with NaBH4 [12 mg (0.32 mmol)]. The mixture was stirred for 1 h at room temperature and the resulting solid was carefully filtered off and dried. The solid was triturated with 50/50 ACN/water, filtered and vacuum dried. Yield=20 mg (8% overall) as TFA salt. MS (m/z): 403 [M+H]

Example AV: 6-Benzyloxy-1-[(E)-2-(2,4-dimethoxyphenyl)vinyl]-7-methoxy-1,2,3,4-tetrahydroisoquinoline

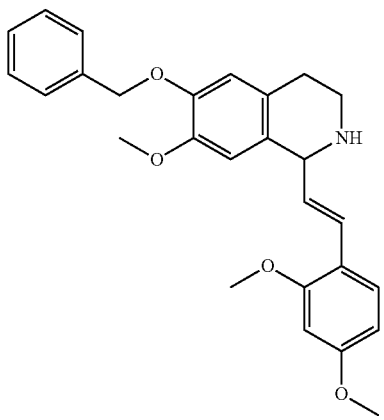

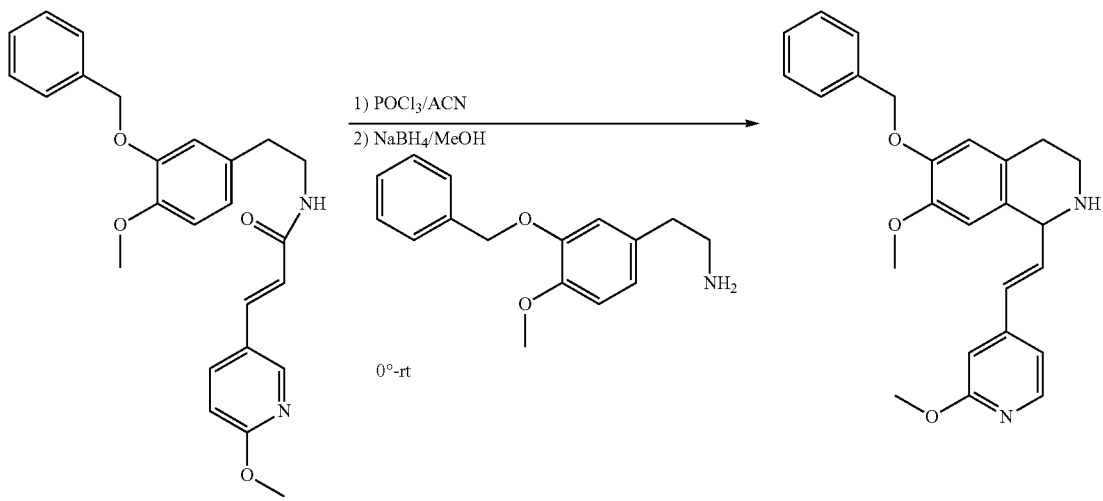 [SMILES: COc1ccc(/C=C/C(=O)NCCc2ccc(OC)c(OCc3ccccc3)c2)cn1 ; COc1ccc(CCN)cc1OCc1ccccc1 ; COc1cc(/C=C/C2NCCc3cc(OCc4ccccc4)c(OC)cc32)ccn1]

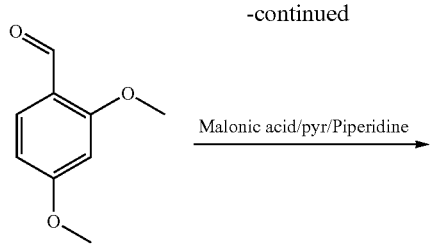

Malonic acid/pyr/Piperidine

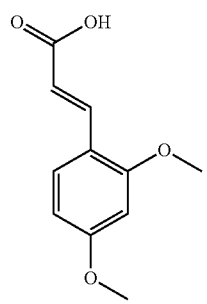

(E)-3-(2,4-Dimethoxyphenyl)prop-2-enoic acid: A mixture or 2,4-dimethoxybenzaldehyde [0.43 g (0.0026 mol)], malonic acid [0.53 g (0.0052 mol)], pyridine (5 mL) and piperidine (0.050 mL) was stirred at 80° C. for 1 h followed by stirring for 3 h at 115° C. The reaction was then poured into water (100 mL) and acidified with conc. HCl. The resulting white ppt., product, was filtered and vacuum dried. Yield=577 mg (99%)]

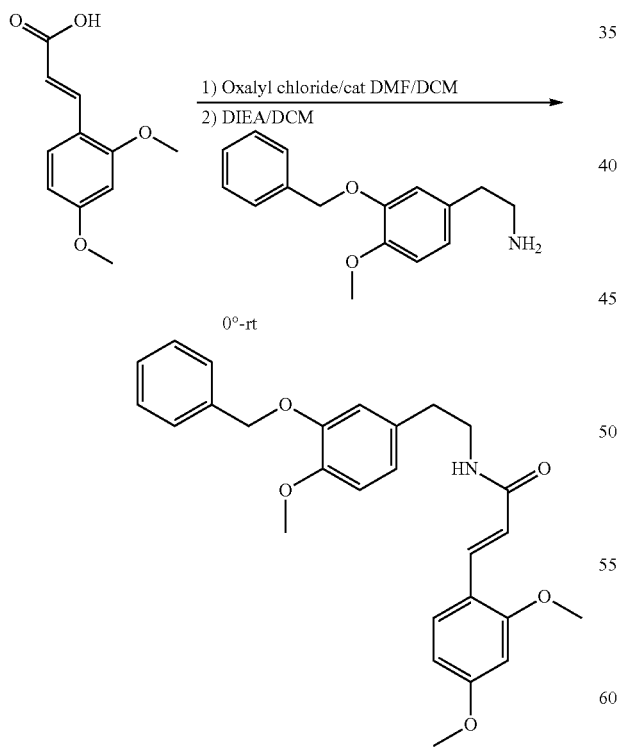

(E)-N-[2-(3-Benzyloxy-4-methoxy-phenyl)ethyl]-3-(3,4,5-trimethoxyphenyl)prop-2-enamide: To a suspension of (E)-3-(3,4,5-trimethoxyphenyl)prop-2-enoic acid [0.577 g (0.0026 mol)] in 20 ml of Dichloromethane was added 2 drops of DMF followed by oxalyl chloride [271 ul (3.2 mol)]. After 1 h stirring at room temperature the reaction was rotary evaporated to dryness and the resulting yellow residue was dried in vacuo. To a solution of 2-(3-benzyloxy-4-methoxy-phenyl)ethanamine [565 mg (2.2 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO4) and the solvent removed. Yield=780 mg (67%) after flash with 10% MeOH/DCM)

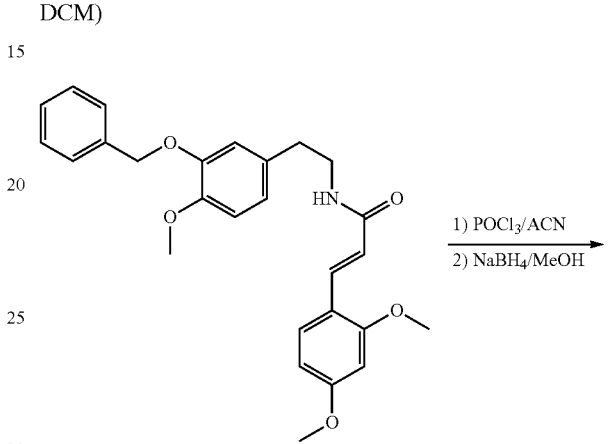

6-Benzyloxy-1-[(E)-2-(2,4-dimethoxyphenyl)vinyl]-7-methoxy-1,2,3,4-tetrahydroisoquinoline: To a solution of (E)-N-[2-(3-benzyloxy-4-methoxy-phenyl)ethyl]-3-(2,4-dimethoxyphenyl)prop-2-enamide [780 mg (1.74 mmol)] in ACN (30 ml) was added, under reflux, POCl3 [1000 ul (11 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na2SO4) and the solvent removed. The dark oil was the dissolved into 24 ml of dry MeOH and then treated with NaBH4 [60 mg (1.65 mmol)]. The mixture was stirred for 1 h at room temperature. A light yellow solid ppt'd out of solution, was filtered off, triturated with 0.1% TFA and then dried in vacuo. Yield=22 mg (3% overall) as TFA salt. MS (m/z): 432 [M+H]

Example AW: 6-Benzyloxy-7-methoxy-1-[(E)-2-(4-pyridyl)vinyl]-1,2,3,4-tetrahydroisoquinoline

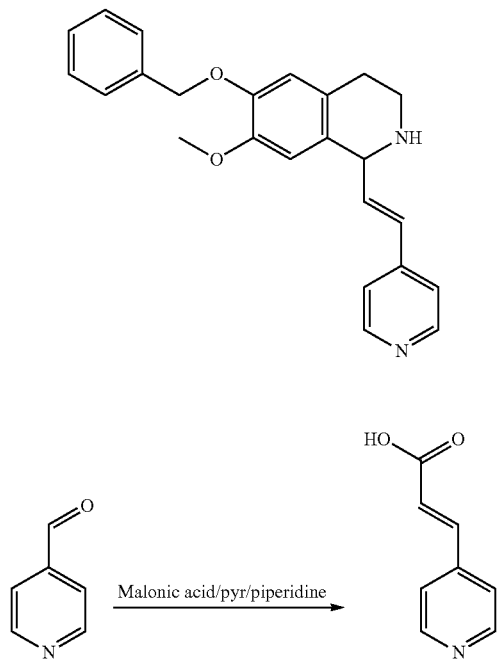

(E)-3-(4-Pyridyl)prop-2-enoic acid: pyridine-4-carbaldehyde (5 g, 0.047 mol), malonic acid (2.2 g (0.094 mol)), pyridine (30 mL), and piperidine (850 ul, 8.5 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=6.9 g.

(E)-N-[2-(3-Benzyloxy-4-methoxy-phenyl)ethyl]-3-(4-pyridyl)prop-2-enamide: To a suspension of (E)-3-(4-pyridyl)prop-2-enoic acid [0.149 g (1 mmol)] in 10 ml of Dichloromethane was added 1 drop of DMF followed by oxalyl chloride [300 ul (3 mmol)]. After 1 h stirring at room temperature the reaction was rotary evaporated to dryness and the resulting yellow residue was dried in vacuo. To a solution of 2-(3-benzyloxy-4-methoxy-phenyl)ethanamine [257 mg (1 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO4) and the solvent removed. Yield=234 mg (60%) after flash with 10% MeOH/DCM)

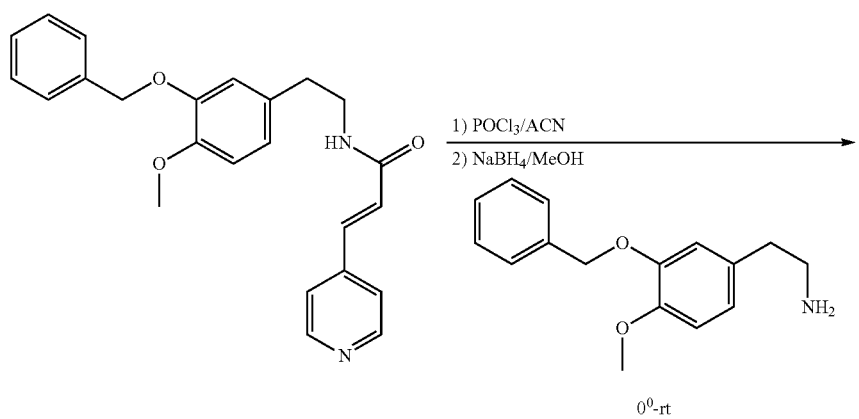

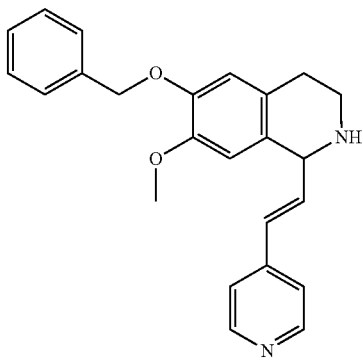

6-Benzyloxy-7-methoxy-1-[(E)-2-(4-pyridyl)vinyl]-1,2,3,4-tetrahydroisoquinoline: To a solution of (E)-N-[2-(3-benzyloxy-4-methoxy-phenyl)ethyl]-3-(4-pyridyl)prop-2-enamide [234 mg (0.6 mmol)] in ACN (15 ml) was added, under reflux, POCl3 [500 ul (5.2 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na2SO4) and the solvent removed. The dark oil was the dissolved into 24 ml of dry MeOH and then treated with NaBH4 [5 mg (0.13 mmol)]. The mixture was stirred for 1 h at room temperature. A light yellow solid ppt'd out of solution, was filtered off, triturated with 0.1% TFA and then dried in vacuo. Yield=130 mg (58% overall) as TFA salt. MS (m/z): 371 [M+H]

Example AX: 6-Benzyloxy-7-methoxy-1-[(E)-2-(6-methoxy-3-pyridyl)vinyl]-1,2,3,4-tetrahydroisoquinoline (E)-3-(6-Methoxy-3-pyridyl)prop-2-enoic acid: 6-methoxypyridine-3-carbaldehyde (1 g (0.007 mol)), malonic acid (1.45 g (0.014 mol)), pyridine (5 mL), and piperidine (100 ul, 1 mmol) were mixed well, heated to 80-85° C. for 1 h and finally refluxed (110-115° C.) for an additional 3 h. The reaction mixture was poured into water and acidified with concentrated HCl. The precipitate obtained was filtered, and washed with cold water repeatedly. The residue was dissolved in NaOH, diluted, again acidified, the precipitate was collected washed with cold water and dried under high vacuum over $P_2O_5$ and used without further purifications. Yield=950 mg.

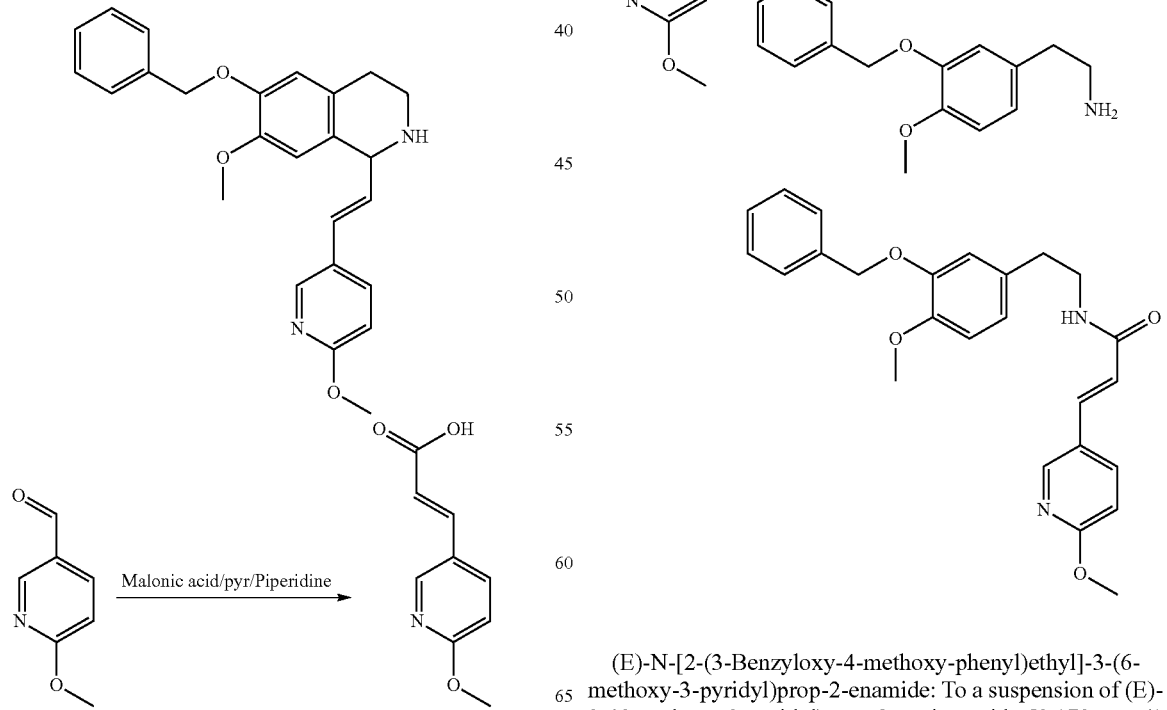

(E)-N-[2-(3-Benzyloxy-4-methoxy-phenyl)ethyl]-3-(6-methoxy-3-pyridyl)prop-2-enamide: To a suspension of (E)-3-(6-methoxy-3-pyridyl)prop-2-enoic acid [0.179 g (1 mmol)] in 10 ml of Dichloromethane was added 1 drop of DMF followed by oxalyl chloride [300 ul (3 mmol)]. After 1 h stirring at room temperature the reaction was rotary evaporated to dryness and the resulting yellow residue was dried in vacuo. To a solution of 2-(3-benzyloxy-4-methoxy-phenyl)ethanamine [257 mg (1 mmol)] and DIEA [1 mL (6 mmol)] in 20 ml of Dichloromethane was added dropwise, at ice bath temperature, the crude yellow acyl chloride dissolved in 4 ml of Dichloromethane. The reaction mix was then stirred at room temperature 2 h then diluted with 50 mL of EtOAc and washed 2× with sat. NaCl aq. The EtOAc layer was dried (MgSO4) and the solvent removed. Yield=395 mg (94%) after flash chromatography with 10% MeOH/DCM)

Example AY: 6-(Benzyloxy)-1-(5-(benzyloxy)-4-methoxy-2-methylphenyl)-7-methoxy-1,2,3,4-tetra-hydroisoquinoline

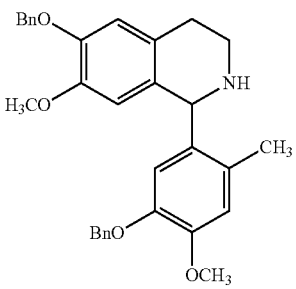

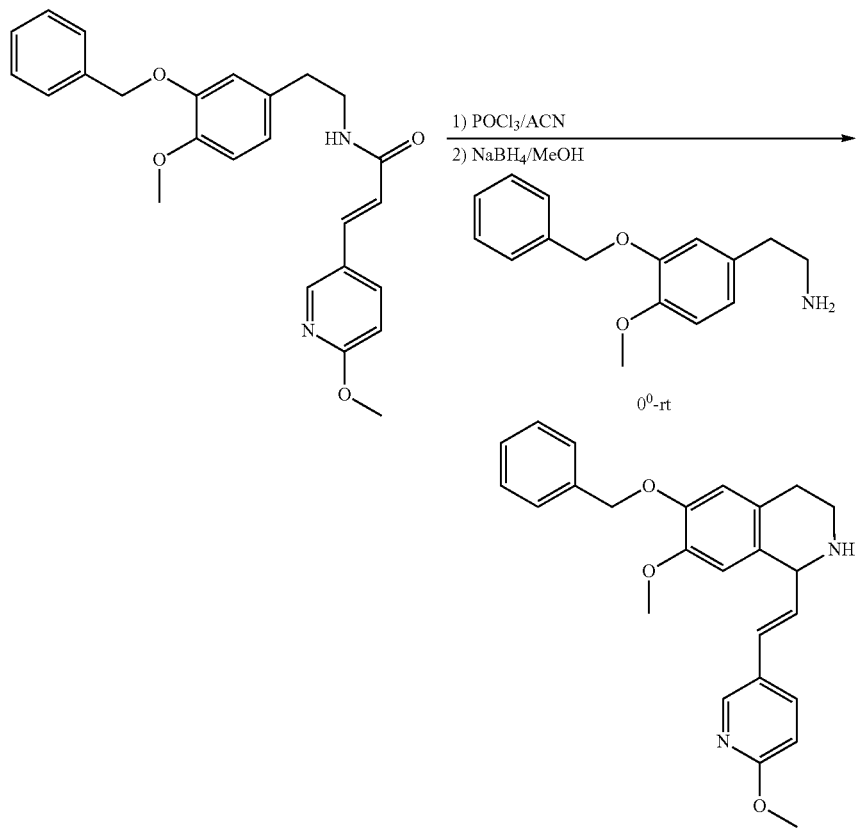

6-Benzyloxy-7-methoxy-1-[(E)-2-(6-methoxy-3-pyridyl) vinyl]-1,2,3,4-tetrahydroisoquinoline: To a solution of (E)-N-[2-(3-benzyloxy-4-methoxy-phenyl)ethyl]-3-(6-methoxy-3-pyridyl)prop-2-enamide [395 mg (0.94 mmol)] in ACN (45 ml) was added, under reflux, POCl3 [1500 ul (16 mmol)]. The reaction was stirred at reflux for 10 min and then rotary evaporated to dryness. The residue was taken up into 10 ml of chloroform and was then treated with 20 ml of 2N KOH and 50 ml of Et2O. This mixture was rapidly stirred for 30 min at room temperature and the upper organic layer removed, washed with water, dried (Na2SO4) and the solvent removed. The dark oil was the dissolved into 15 ml of dry MeOH and then treated with NaBH4 [5 mg (0.14 mmol)]. The mixture was stirred for 1 h at room temperature. A light yellow solid ppt'd out of solution, was filtered off, triturated with 0.1% TFA and then dried in vacuo. Yield=226 mg (60% overall) as TFA salt. MS (m/z): 403 [M+H]

-continued

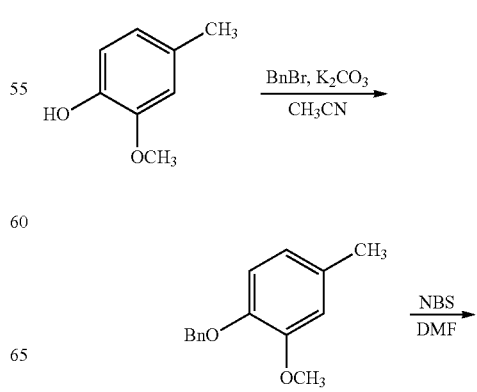

155

-continued

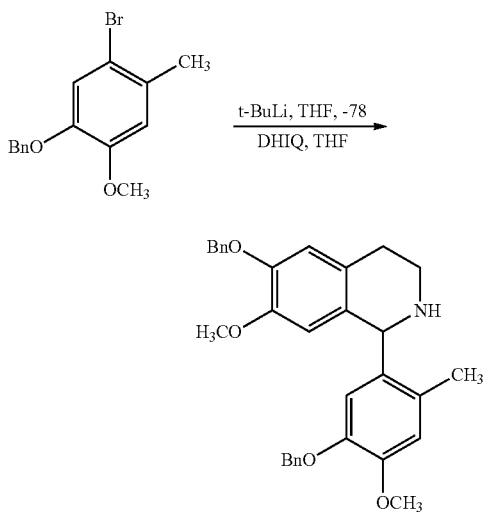

1-(Benzyloxy)-2-methoxy-4-methylbenzene: 2-Methoxy-4-methylphenol (14.9 g, 107.8 mmol) was combined with benzylbromide (37.2 g, 217.5 mmol), K$_2$CO$_3$ (30 g, 217.5 mmol), in acetonitrile (220 mL) and heated at reflux for 18 hours. After TLC analysis showed complete reaction, it was allowed to cool to room temperature. The organic solvent was evaporated to dryness, the residue obtained was extracted with EtOAc and water. The combined organic layers were dried over MgSO$_4$, filtered and evaporated to dryness the crude product obtained was used in the next step without further purification. LCMS: M+1=229.3.

1-(Benzyloxy)-5-bromo-2-methoxy-4-methylbenzene: The 1-(Benzyloxy)-2-methoxy-4-methylbenzene (3.00 g, 13.14 mmol) was dissolved in dry DMF (25 mL) and NBS (2.34 g, 13.14 mmol) was added in portions. The resulting reaction mixture was stirred at room temperature for 18 hours. The reaction was monitored by TLC analysis, upon completion the organic solvent was removed under high vacuum to dryness. The residue obtained was purified by flash chromatography to afford the desired product as a solid. LCMS: M+1=308.2.

6-(Benzyloxy)-1-(5-(benzyloxy)-4-methoxy-2-methylphenyl)-7-methoxy-1,2,3,4-tetrahydroisoquinoline: The 1-(Benzyloxy)-5-bromo-2-methoxy-4-methylbenzene (307 mg, 1.0 mmol) was dissolved in dry THF (10 mL) and cooled to −78° C., under argon. To this solution was added t-BuLi (1.3 mL, 2.2 mmol, 1.7M in pentane) dropwise, as the solution turned light yellow. After the addition, the reaction mixture was stirred for an hour at −78° C. before a solution of 6-(benzyloxy)-7-methoxy-3,4-dihydroisoquinoline (268 mg, 1.0 mmol) in THF (3 mL) was added dropwise. The mixture was allowed to stir at −78° C. for 2 hours, and then immediately quenched with sat. aqueous NH$_4$Cl solution. The reaction mixture was extracted with EtOAc, and the combined organic layers were dried over MgSO$_4$, filtered and evaporated to dryness. The residue obtained was purified by flash chromatography to afford the titled compound. LCMS: M+1=496.

156

Example AZ: tert-Butyl N-[[2-(6-benzyloxy-7-methoxy-1,2,3,4-tetrahydroisoquinolin-1-yl)phenyl]methyl]carbamate

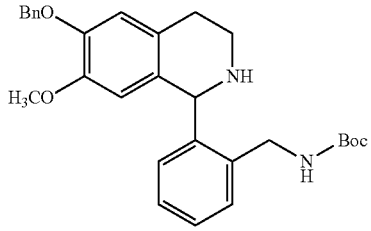 [SMILES: COc1cc2c(cc1OCc1ccccc1)CCNC2c1ccccc1CNC(=O)OC(C)(C)C]

The title compound was obtained from tert-Butyl N-[(2-bromophenyl)methyl]carbamate using the same protocol as described in Example AY above. LC-MS; M+1=475.

Example BA: 6-Benzyloxy-7-methoxy-1-[(E)-2-(4-methoxy-2,6-dimethyl-phenyl)vinyl]-1,2,3,4-tetrahydroisoquinoline

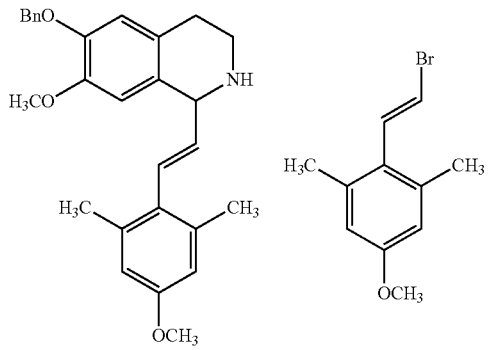

2-[(E)-2-bromovinyl]-5-methoxy-1,3-dimethyl-benzene: This intermediate was obtain first through the alternate cinnamic acid approach protocol (which utilizes ethyl 2-diethoxyphosphanylacetate) to obtain the corresponding cinnamic acid in 2 steps. The conversion to the vinyl bromide followed the same protocol as Example AD.

6-benzyloxy-7-methoxy-1-[(E)-2-(4-methoxy-2,6-dimethyl-phenyl)vinyl]-1,2,3,4-tetrahydroisoquinoline: The title compound was obtained through the same protocol as shown in Example AD above. LC-MS; M+1=430.

Example BB: 6-Benzyloxy-7-methoxy-1-[(E)-2-(6-methyl-1,3-benzodioxol-5-yl)vinyl]-1,2,3,4-tetrahydroisoquinoline

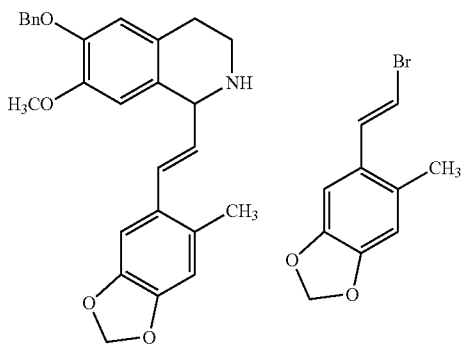 [SMILES: COc1cc2c(cc1OCc1ccccc1)CCNC2/C=C/c1cc2c(cc1C)OCO2 ; Cc1cc2c(cc1/C=C/Br)OCO2]

5-[(E)-2-bromovinyl]-6-methyl-1,3-benzodioxole was obtained from 6-methyl-1,3-benzodioxole-5-carbaldehyde through the two step protocol as shown in Example AD.

6-Benzyloxy-7-methoxy-1-[(E)-2-(6-methyl-1,3-benzodioxol-5-yl)vinyl]-1,2,3,4-tetrahydroisoquinoline was obtained using the same conditions as in Example AD above. LC-MS; M+1=430.

Example BC: 6-Benzyloxy-7-methoxy-1-[(E)-2-(7-methyl-2,3-dihydro-1,4-benzodioxin-6-yl)vinyl]-1,2,3,4-tetrahydroisoquinoline

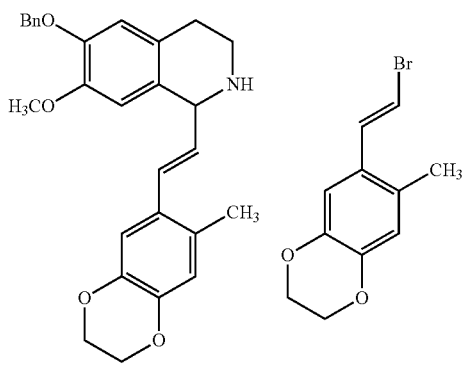 [SMILES: COc1cc2c(cc1OCc1ccccc1)CCNC2/C=C/c1cc2c(cc1C)OCCO2 ; Cc1cc2c(cc1/C=C/Br)OCCO2]

6-[(E)-2-Bromovinyl]-7-methyl-2,3-dihydro-1,4-benzodioxine was obtained from 7-methyl-2,3-dihydro-1,4-benzodioxine-6-carbaldehyde using the protocol in Example AD above.

6-Benzyloxy-7-methoxy-1-[(E)-2-(7-methyl-2,3-dihydro-1,4-benzodioxin-6-yl)vinyl]-1,2,3,4-tetrahydroisoquinoline was obtained using the same procedure as in Example AD above. LC-MS; M+1=444.

Example BD: 6-Benzyloxy-1-[(E)-2-(4-butoxy-3-methoxy-phenyl)vinyl]-7-methoxy-1,2,3,4-tetrahydroisoquinoline

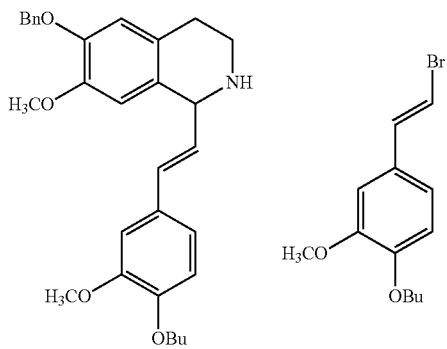

4-[(E)-2-bromovinyl]-1-butoxy-2-methoxy-benzene was obtained from 4-butoxy-3-methoxy-benzaldehyde using the two step protocol above in Example AD.

6-benzyloxy-1-[(E)-2-(4-butoxy-3-methoxy-phenyl)vinyl]-7-methoxy-1,2,3,4-tetrahydroisoquinoline was obtained using the protocol in Example AD above. LC-MS; M+1=474.

Example BE: 6-Benzyloxy-1-[(E)-2-(3-butoxy-4-methoxy-phenyl)vinyl]-7-methoxy-1,2,3,4-tetrahydroisoquinoline

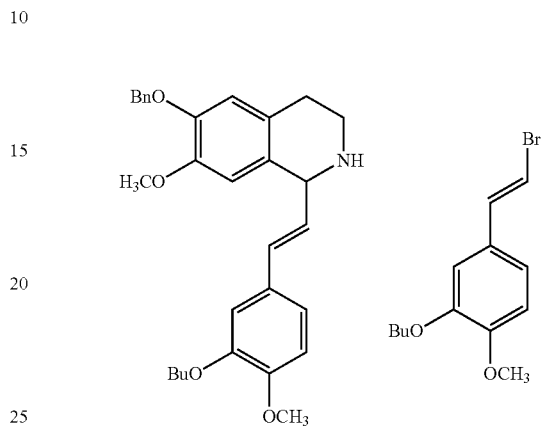

4-[(E)-2-bromovinyl]-2-butoxy-1-methoxy-benzene was obtained from 3-butoxy-4-methoxy-benzaldehyde using the two step protocol in Example AD above.

6-benzyloxy-1-[(E)-2-(3-butoxy-4-methoxy-phenyl)vinyl]-7-methoxy-1,2,3,4-tetrahydroisoquinoline was obtained using the same protocol as Example AD. LC-MS; M+1=474.

Example BF: 6-Benzyloxy-1-[(E)-2-(5-fluoro-4-methoxy-2-methyl-phenyl)vinyl]-7-methoxy-1,2,3,4-tetrahydroisoquinoline

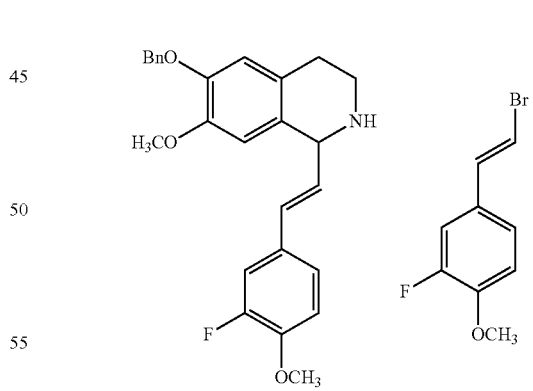

4-[(E)-2-bromovinyl]-2-fluoro-1-methoxy-benzene was obtained from 3-fluoro-4-methoxy-benzaldehyde using the 2 step protocol in Example AD above.

6-benzyloxy-1-[(E)-2-(5-fluoro-4-methoxy-2-methyl-phenyl)vinyl]-7-methoxy-1,2,3,4-tetrahydroisoquinoline was obtained using the same protocol as Example AD above. LC-MS; M+1=434.

Example BG: 4-[(E)-2-(6-benzyloxy-7-methoxy-1,2,3,4-tetrahydroisoquinolin-1-yl)vinyl]-N,N,3-trimethyl-aniline

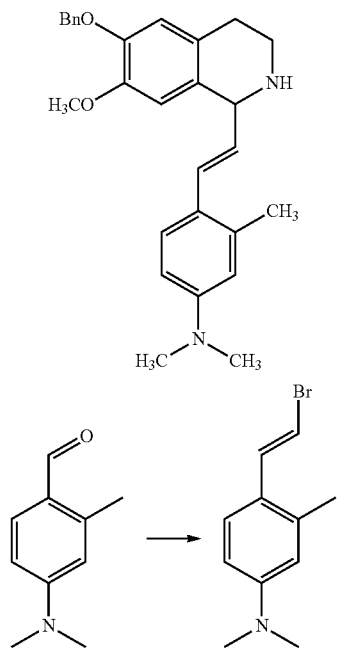

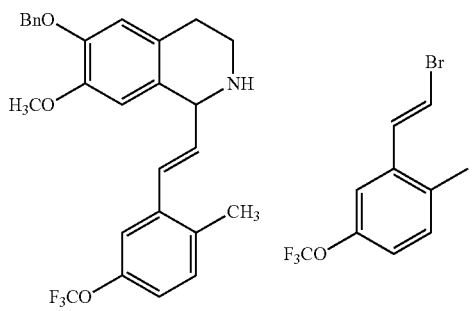 [SMILES: COc1cc2c(cc1OCc1ccccc1)CCNC2/C=C/c1cc(OC(F)(F)F)ccc1C ; Cc1ccc(OC(F)(F)F)cc1/C=C/Br]

4-[(E)-2-bromovinyl]-N,N,3-trimethyl-aniline was obtained from 4-(dimethylamino)-2-methyl-benzaldehyde using ethyl-2-(diethoxyphosphino)acetate in the alternate method for the synthesis of cinnamic acids above. The resulting cinnamic acid was converted to the 4-[(E)-2-bromovinyl]-N,N,3-trimethyl-aniline as in Example AD.

4-[(E)-2-(6-Benzyloxy-7-methoxy-1,2,3,4-tetrahydroisoquinolin-1-yl)vinyl]-N,N,3-trimethyl-aniline was obtained using the same protocol as in Example AD above. LC-MS; M+1=429

Example BH: 6-Benzyloxy-7-methoxy-1-[(E)-2-[2-methyl-5-(trifluoromethoxy)phenyl]vinyl]-1,2,3,4-tetrahydroisoquinoline 2-[(E)-2-bromovinyl]-1-methyl-4-(trifluoromethoxy)benzene was synthesized from 2-methyl-5-(trifluoromethoxy)benzaldehyde using the 2 step protocol in Example AD.

6-Benzyloxy-7-methoxy-1-[(E)-2-[2-methyl-5-(trifluoromethoxy)phenyl]vinyl]-1,2,3,4-tetrahydroisoquinoline was synthesized through the same protocol as Example AD above. LC-MS; M+1=470.

Example BI: 6-Benzyloxy-7-methoxy-1-[(E)-styryl]-1,2,3,4-tetrahydroisoquinoline

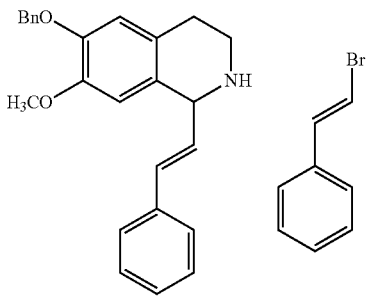 [SMILES: COc1cc2c(cc1OCc1ccccc1)CCNC2/C=C/c1ccccc1 ; Br/C=C/c1ccccc1]

[(E)-2-bromovinyl]benzene was obtained from benzaldehyde in the same manner as Example AD.

6-Benzyloxy-7-methoxy-1-[(E)-styryl]-1,2,3,4-tetrahydroisoquinoline was obtained using the same protocol as shown in Example AD. LC-MS; M+1=372.

Example BJ: 6-Benzyloxy-7-methoxy-1-[(E)-2-(4-methoxyphenyl)vinyl]-1,2,3,4-tetrahydroisoquinoline

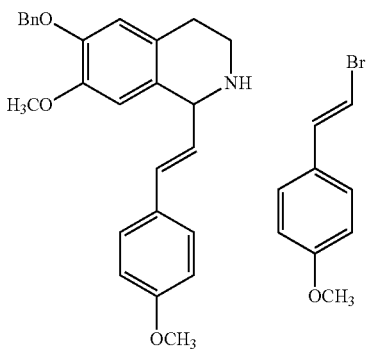 [SMILES: COc1ccc(/C=C/C2NCCc3cc(OCc4ccccc4)c(OC)cc32)cc1 ; COc1ccc(/C=C/Br)cc1]

1-[(E)-2-bromovinyl]-4-methoxy-benzene was obtained from 4-methoxybenzaldehyde in the same manner as Example AD.

6-Benzyloxy-7-methoxy-1-[(E)-2-(4-methoxyphenyl)vinyl]-1,2,3,4-tetrahydroisoquinoline was obtained using the same protocol as shown in Example AD. LC-MS; M+1=402.

Example BK: 6-Benzyloxy-1-[(E)-2-(3-benzyloxy-phenyl)vinyl]-7-methoxy-1,2,3,4-tetrahydroisoquinoline Example BM: 6-Benzyloxy-1-[(E)-2-(2,3-dihydrobenzofuran-5-yl)vinyl]-7-methoxy-1,2,3,4-tetrahydroisoquinoline

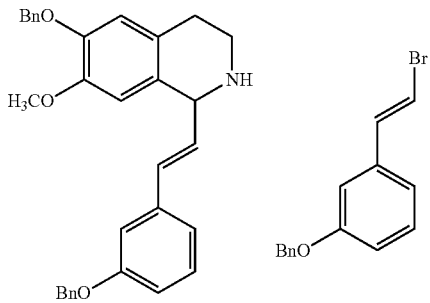 [SMILES: COc1cc2c(cc1OCc1ccccc1)CCNC2/C=C/c1cccc(OCc2ccccc2)c1 ; Br/C=C/c1cccc(OCc2ccccc2)c1]

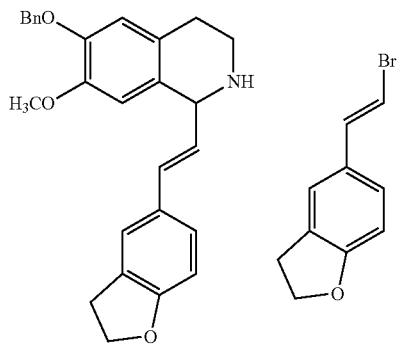

1-Benzyloxy-3-[(E)-2-bromovinyl]benzene was synthesized from 3-benzyloxybenzaldehyde using the two step protocol in Example AD above.

6-Benzyloxy-1-[(E)-2-(3-benzyloxyphenyl)vinyl]-7-methoxy-1,2,3,4-tetrahydroisoquinoline was obtained using the same protocol in Example AD above. LS-MS; M+1=478.

Example BL: 6-Benzyloxy-1-[(E)-2-(5-butoxy-4-methoxy-2-methyl-phenyl)vinyl]-7-methoxy-1,2,3,4-tetrahydroisoquinoline 5-[(E)-2-Bromovinyl]-2,3-dihydrobenzofuran was synthesized from 2,3-dihydrobenzofuran-5-carbaldehyde using the 2 step protocol in Example AD.

6-Benzyloxy-1-[(E)-2-(2,3-dihydrobenzofuran-5-yl)vinyl]-7-methoxy-1,2,3,4-tetrahydroisoquinoline was synthesized using the protocol in Example AD above. LC-MS; M+1=414.

Example BN: 1-[(E)-2-(benzofuran-5-yl)vinyl]-6-benzyloxy-7-methoxy-1,2,3,4-tetrahydroisoquinoline

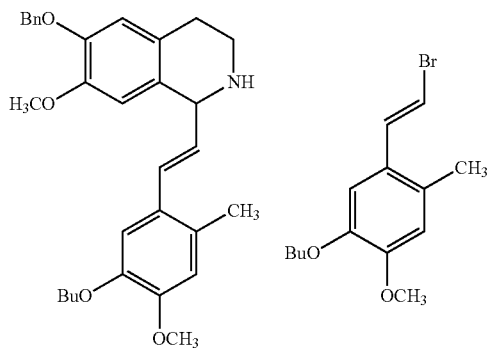

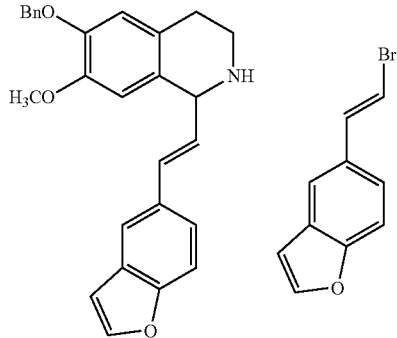 [SMILES: COc1cc2c(cc1OCc1ccccc1)CCNC2/C=C/c1ccc2occc2c1 ; Br/C=C/c1ccc2occc2c1]

1-[(E)-2-bromovinyl]-5-butoxy-4-methoxy-2-methyl-benzene was synthesized from 5-butoxy-4-methoxy-2-methyl-benzaldehyde using the 2 step protocol in Example AD above.

6-Benzyloxy-1-[(E)-2-(5-butoxy-4-methoxy-2-methyl-phenyl)vinyl]-7-methoxy-1,2,3,4-tetrahydroisoquinoline was synthesized using the protocol in Example AD. LC-MS; M+1=488.

5-[(E)-2-bromovinyl]benzofuran was synthesized from benzofuran-5-carbaldehyde using the two step protocol in Example AD above.

1-[(E)-2-(benzofuran-5-yl)vinyl]-6-benzyloxy-7-methoxy-1,2,3,4-tetrahydroisoquinoline was synthesized using the protocol in Example AD above. LC-MS; M+1=412

Example BO: 4-[5-[(E)-2-(B-benzyloxy-7-methoxy-1,2,3,4-tetrahydroisoquinolin-1-yl)vinyl]-2-methoxy-4-methyl-phenoxy]butanoic acid

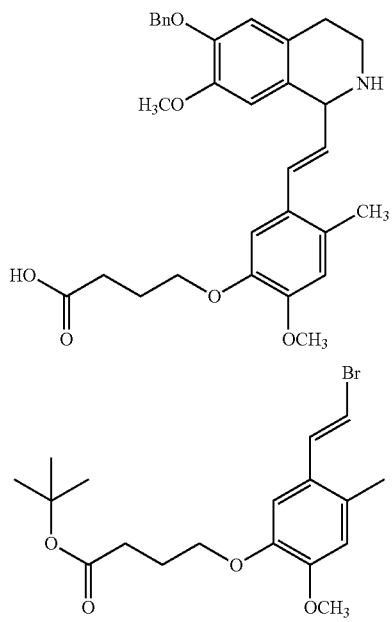

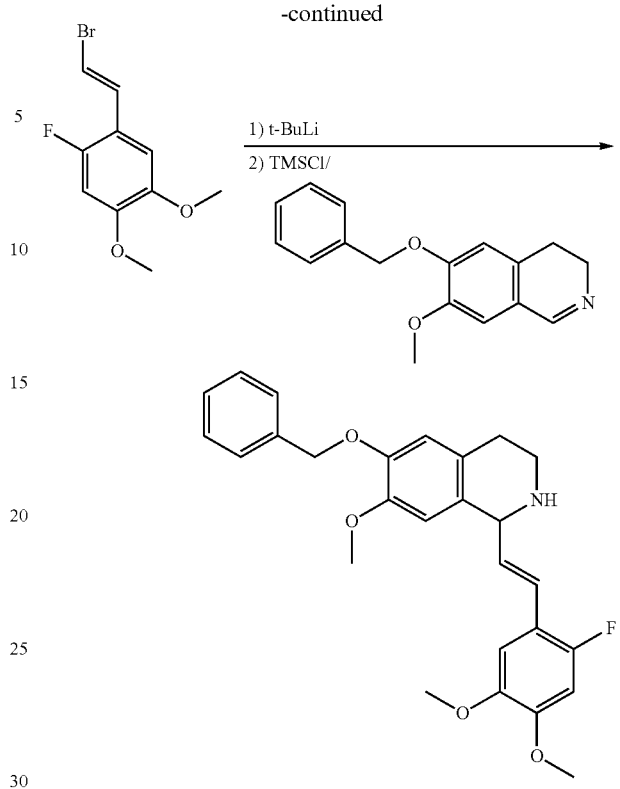

tert-Butyl 4-[5-[(E)-2-bromovinyl]-2-methoxy-4-methyl-phenoxy]butanoate was synthesized from tert-butyl 4-(5-formyl-2-methoxy-4-methyl-phenoxy)butanoate by a 2 step protocol in Example AD above.

4-[5-[(E)-2-(B-benzyloxy-7-methoxy-1,2,3,4-tetrahydroisoquinolin-1-yl)vinyl]-2-methoxy-4-methyl-phenoxy]butanoic acid was synthesized through the protocol above in Example AD. LC-MS; M−1=416

Example BP: 6-Benzyloxy-1-[(E)-2-(2-fluoro-4,5-dimethoxy-phenyl)vinyl]-7-methoxy-1,2,3,4-tetrahydroisoquinoline

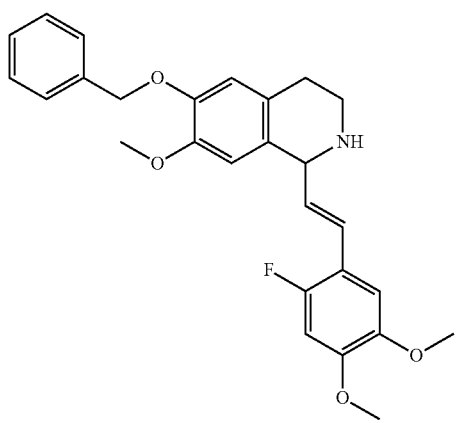

To a solution of 1-[(E)-2-bromovinyl]-2-fluoro-4,5-dimethoxy-benzene[261 mg (1 mmol)] in Ether (15 ml) at −780 C was added 1.7 M t-Butyllithium [1.2 ml (2.2 mmol)]. The mixture was stirred at −780 C for 1 h then treated at −780 with a mix of 6-benzyloxy-7-methoxy-3,4-dihydroisoquinoline [134 mg (0.5 mmol)] and TMSCl [64 ul (0.5 mmol)] in THF (2 ml). The reaction was stirred at −780 C for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=39 mg (9%) as TFA salt via prep chrom. MS (m/z): 450 [M+H]

Example BQ: 6-Benzyloxy-1-[(E)-2-(3,4-dimethoxyphenyl)vinyl]-7-methoxy-1,2,3,4-tetrahydroisoquinoline

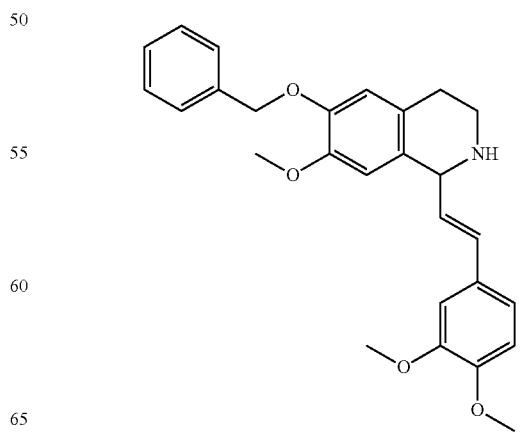

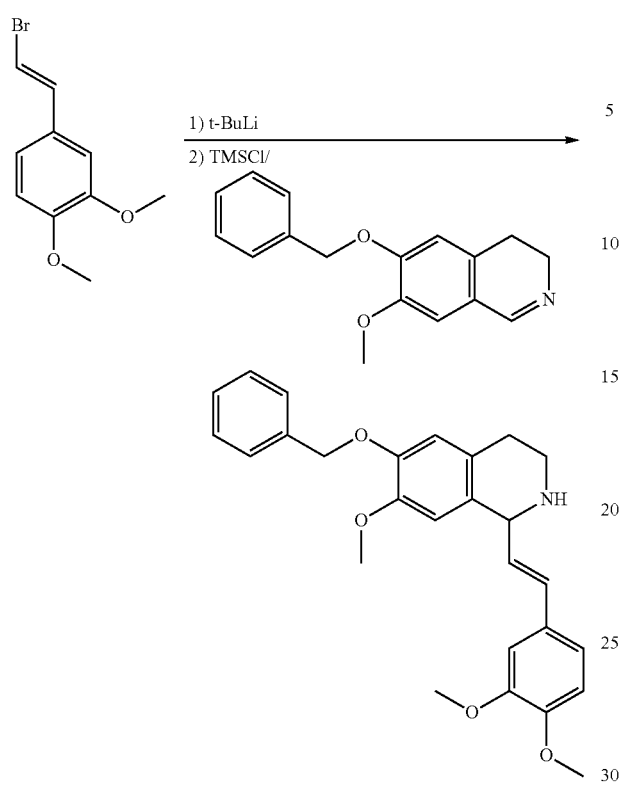

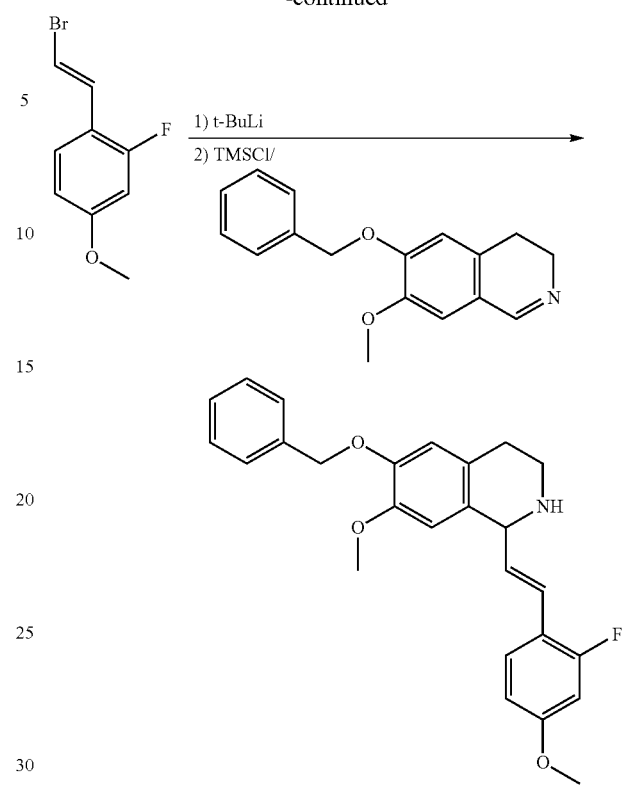

To a solution of 1-[(E)-2-bromovinyl]-2-fluoro-4-methoxy-benzene [486 mg (0.2 mmol)] in Ether (30 ml) at −780 C was added 1.7 M t-Butyllithium [2.4 ml (4.4 mmol)]. The mixture was stirred at −780 C for 1 h then treated at −780 with a mix of 6-benzyloxy-7-methoxy-3,4-dihydroisoquinoline [267 mg (1 mmol)] and TMSCl [127 ul (1 mmol)] in THF (4 ml). The reaction was stirred at −780 C for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=42 mg (5%) as TFA salt via prep chrom. MS (m/z): 432 [M+H]

Example BR: 6-Benzyloxy-1-[(E)-2-(2-fluoro-4-methoxy-phenyl)vinyl]-7-methoxy-1,2,3,4-tetrahydroisoquinoline To a solution of 1-[(E)-2-bromovinyl]-2-fluoro-4-methoxy-benzene [462 mg (0.2 mmol)] in Ether (30 ml) at −780 C was added 1.7 M t-Butyllithium [2.4 ml (4.4 mmol)]. The mixture was stirred at −780 C for 1 h then treated at −780 with a mix of 6-benzyloxy-7-methoxy-3,4-dihydroisoquinoline [267 mg (1 mmol)] and TMSCl [127 ul (1 mmol)] in THF (4 ml). The reaction was stirred at −780 C for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=64 mg (8%) as TFA salt via prep chrom. MS (m/z): 420 [M+H]

Example BS: 6-Benzyloxy-7-methoxy-1-[(E)-2-(3-methyl-2-thienyl)vinyl]-1,2,3,4-tetrahydroisoquinoline

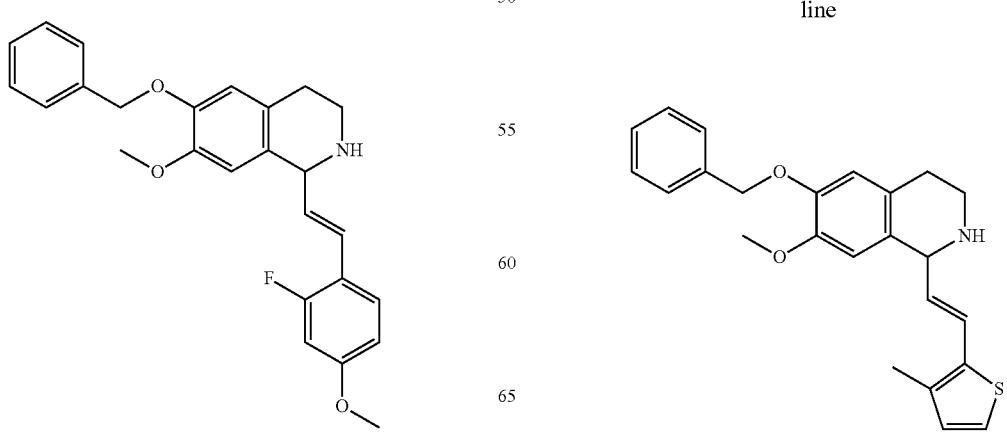

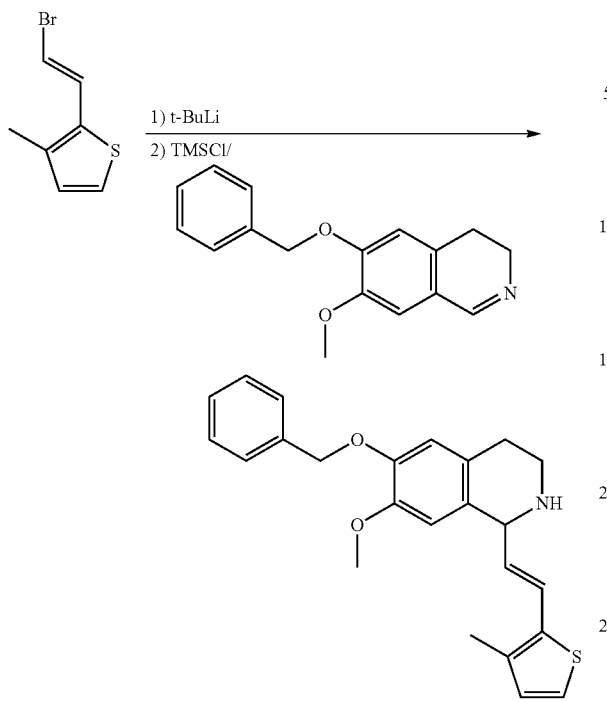

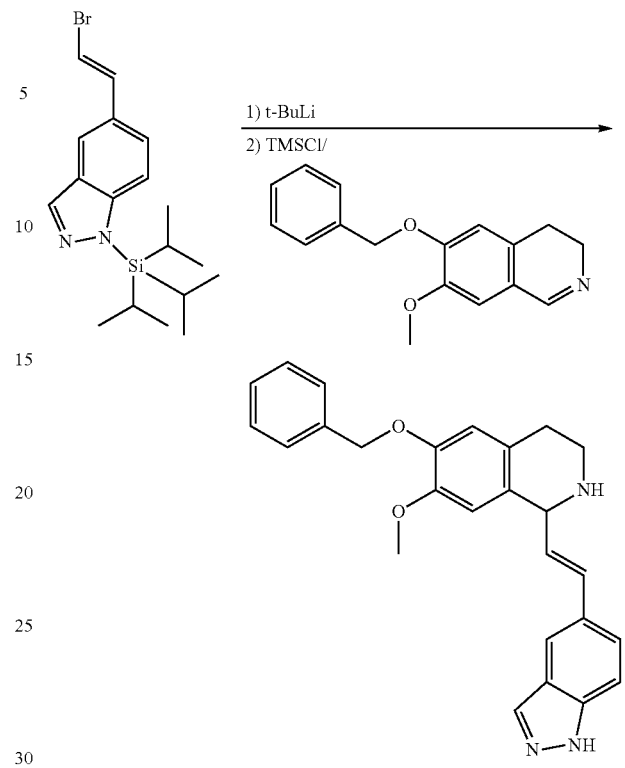

To a solution of 2-[(E)-2-bromovinyl]-3-methyl-thiophene [203 mg (1 mmol)] in Ether (15 ml) at −780 C was added 1.7 M t-Butyllithium [1.2 ml (2.2 mmol)]. The mixture was stirred at −78° C. for 1 h then treated at −780 with a mix of 6-benzyloxy-7-methoxy-3,4-dihydroisoquinoline [134 mg (0.5 mmol)] and TMSCl [64 ul (0.5 mmol)] in THF (2 ml). The reaction was stirred at −780 C for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=15 mg (4%) as TFA salt via prep chrom. MS (m/z): 392 [M+H]

Example BT: 6-Benzyloxy-1-[(E)-2-(1H-indazol-6-yl)vinyl]-7-methoxy-1,2,3,4-tetrahydroisoquinoline To a solution of [5-[(E)-2-bromovinyl]indazol-1-yl]-triisopropyl-silane [379 mg (1 mmol)] in Ether (15 ml) at −780 C was added 1.7 M t-Butyllithium [1.2 ml (2.2 mmol)]. The mixture was stirred at −780 C for 1 h then treated at −780 with a mix of 6-benzyloxy-7-methoxy-3,4-dihydroisoquinoline [134 mg (0.5 mmol)] and TMSCl [64 ul (0.5 mmol)] in THF (2 ml). The reaction was stirred at −780 C for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=15 mg (4%) as TFA salt via prep chrom. MS (m/z): 412 [M+H]

Example BU: 6-Benzyloxy-1-[(E)-2-(2,6-difluoro-4-methoxy-phenyl)vinyl]-7-methoxy-1,2,3,4-tetrahydroisoquinoline

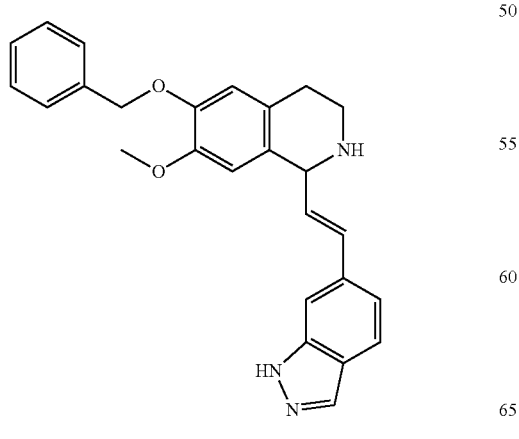

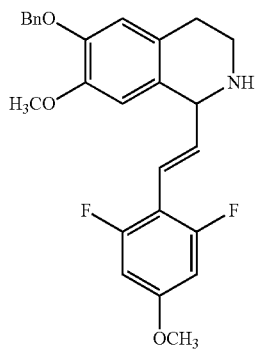

-continued

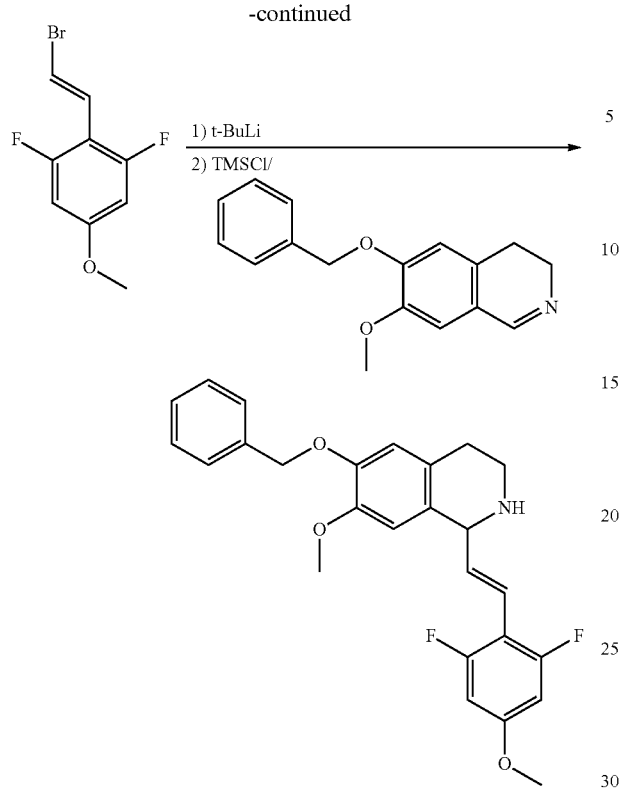

To a solution of 2-[(E)-2-bromovinyl]-1,3-difluoro-5-methoxy-benzene [248 mg (1 mmol)] in Ether (15 ml) at −78°C was added 1.7 M t-Butyllithium [1.2 ml (2.2 mmol)]. The mixture was stirred at −78° C. for 1 h then treated at −78° with a mix of 6-benzyloxy-7-methoxy-3,4-dihydroisoquinoline [134 mg (0.5 mmol)] and TMSCl [64 ul (0.5 mmol)] in THF (2 ml). The reaction was stirred at −78° C. for 1 h and then allowed to come to room temperature overnight. The reaction was then quenched with sat NH4Cl and diluted with 20 ml of EtOAc. The organic layer was removed, washed with water, dried (MgSO4) and the solvent removed. Yield=10 mg (2.3%) as TFA salt via prep chrom. MS (m/z): 249 [M+H]

Example BV: 6-Benzyloxy-7-methoxy-1-[(E)-2-(4-methoxy-2,5-dimethyl-phenyl)vinyl]-1,2,3,4-tetrahydroisoquinoline

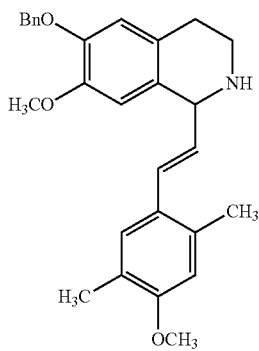 [SMILES: COc1cc(C)c(/C=C/C2NCCc3cc(OCc4ccccc4)c(OC)cc32)cc1C]

A solution of tert-Butyl 6-benzyloxy-7-methoxy-1-[(1-phenyltetrazol-5-yl)sulfonylmethyl]-3,4-dihydro-1H-iso-quinoline-2-carboxylate (100 mg, 0.169 mmol) and the 4-methoxy-2,5-dimethyl-benzaldehyde (125 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=430.

Example BW: 6-Benzyloxy-1-[(E)-2-(5-isopropyl-4-methoxy-2-methyl-phenyl)vinyl]-7-methoxy-1,2,3,4-tetrahydroisoquinoline

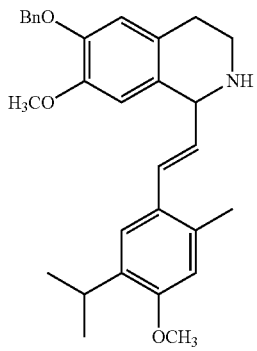 [SMILES: COc1cc2c(cc1OCc1ccccc1)CCNC2/C=C/c1cc(C(C)C)c(OC)cc1C]

A solution of tert-Butyl 6-benzyloxy-7-methoxy-1-[(1-phenyltetrazol-5-yl)sulfonylmethyl]-3,4-dihydro-1H-iso-quinoline-2-carboxylate (100 mg, 0.169 mmol) and 5-isopropyl-4-methoxy-2-methyl-benzaldehyde (164 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=458.

Example BX: 6-Benzyloxy-1-[(E)-2-[5-(2,2-dimethylpropoxy)-4-methoxy-2-methyl-phenyl]vinyl]-7-methoxy-1,2,3,4-tetrahydroisoquinoline

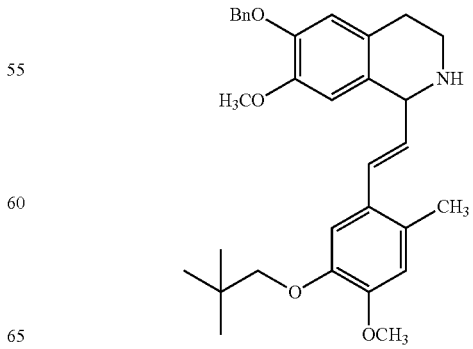

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 5-(2,2-dimethylpropoxy)-4-methoxy-2-methyl-benzaldehyde (196 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=502

Example BY: 6-Benzyloxy-7-methoxy-1-[(E)-2-[4-methoxy-2-methyl-5-(4-piperidylmethoxy)phenyl]vinyl]-1,2,3,4-tetrahydroisoquinoline

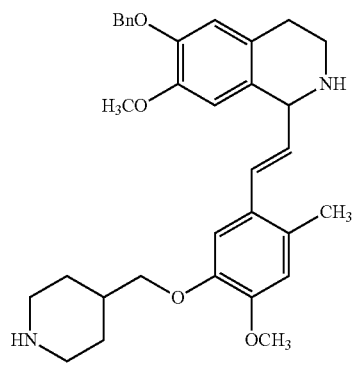 [SMILES: COc1cc2c(cc1OCc1ccccc1)CCNC2/C=C/c1cc(OCC2CCNCC2)c(OC)cc1C]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and isopropyl 4-[(5-formyl-2-methoxy-4-methyl-phenoxy)methyl]piperidine-1-carboxylate (305 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=529

Example BZ: 6-Benzyloxy-7-methoxy-1-[(E)-2-(4-methylsulfonylphenyl)vinyl]-1,2,3,4-tetrahydroisoquinoline

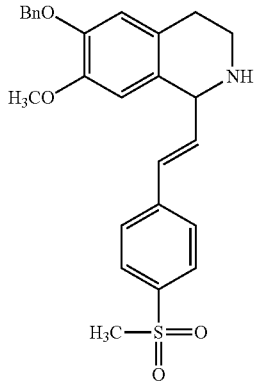 [SMILES: COc1cc2c(cc1OCc1ccccc1)CCNC2/C=C/c1ccc(S(C)(=O)=O)cc1]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 4-methylsulfonylbenzaldehyde (155 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=450.

Example CA: 6-Benzyloxy-1-[(E)-2-(2,6-dimethoxy-3-pyridyl)vinyl]-7-methoxy-1,2,3,4-tetrahydroisoquinoline

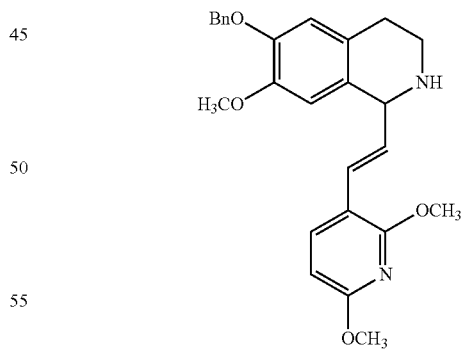

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 2,6-dimethoxypyridine-3-carbaldehyde (140 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=433.

Example CB: 6-Benzyloxy-1-[(E)-2-chroman-6-ylvinyl]-7-methoxy-1,2,3,4-tetrahydroisoquinoline

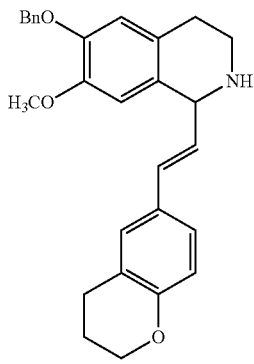 [SMILES: COc1cc2c(cc1OCc1ccccc1)CCNC2/C=C/c1ccc2c(c1)CCCO2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and chromane-6-carbaldehyde (136 mg, 0.84 mmol) in THF (10 mL) was cooled to −35° C. with stirring under argon. To this mixture was added a solution of lithium bis(trimethylsilyl) amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=428

Example CC: 6-Benzyloxy-7-methoxy-1-[(E)-2-(7-methylchroman-8-yl)vinyl]-1,2,3,4-tetrahydroisoquinoline

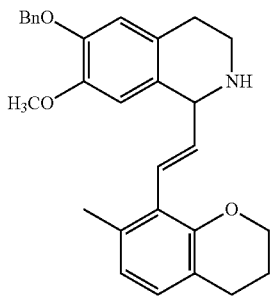 [SMILES: COc1cc2c(cc1OCc1ccccc1)CCNC2/C=C/c1c(C)ccc2c1OCCC2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 7-methylchromane-8-carbaldehyde (148 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=442.

Example CD: 1-[(E)-2-[5-(4-azidobutoxy)-4-methoxy-2-methyl-phenyl]vinyl]-6-benzyloxy-7-methoxy-1,2,3,4-tetrahydroisoquinoline

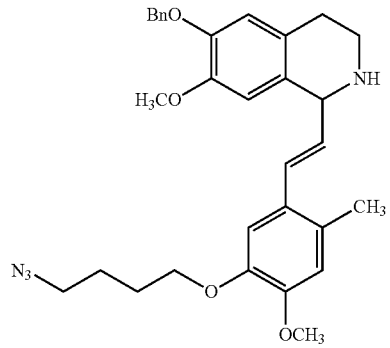 [SMILES: COc1cc(C)c(/C=C/C2NCCc3cc(OCc4ccccc4)c(OC)cc32)cc1OCCCCN=[N+]=[N-]]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 5-(4-azidobutoxy)-4-methoxy-2-methyl-benzaldehyde (221 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=529.

Example CE: 6-Benzyloxy-7-methoxy-1-[(E)-2-(7-methylchroman-6-yl)vinyl]-1,2,3,4-tetrahydroisoquinoline

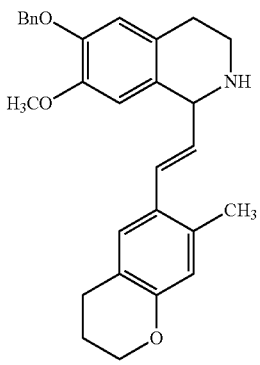 [SMILES: COc1cc2c(cc1OCc1ccccc1)CCNC2/C=C/c1cc2c(cc1C)OCCC2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 7-methylchromane-6-carbaldehyde (148 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=442.

Example CF: 6-Benzyloxy-1-[(E)-2-chroman-8-ylvinyl]-7-methoxy-1,2,3,4-tetrahydroisoquinoline

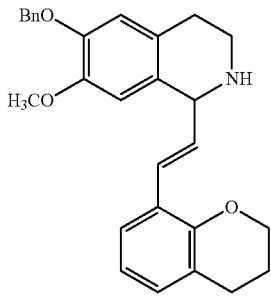 [SMILES: COc1cc2c(cc1OCc1ccccc1)CCNC2/C=C/c1cccc2c1OCCC2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and chromane-8-carbaldehyde (136 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=428.

Example CG: 6-Benzyloxy-7-methoxy-1-[(E)-2-(6-methyl-2,3-dihydrobenzofuran-5-yl)vinyl]-1,2,3,4-tetrahydroisoquinoline

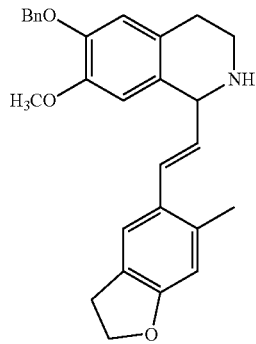 [SMILES: COc1cc2c(cc1OCc1ccccc1)CCNC2/C=C/c1cc2c(cc1C)OCC2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 6-methyl-2,3-dihydrobenzofuran-5-carbaldehyde (136 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=428.

Example CH: tert-Butyl 2-[(E)-2-(6-benzyloxy-7-methoxy-1,2,3,4-tetrahydroisoquinolin-1-yl)vinyl]indole-1-carboxylate

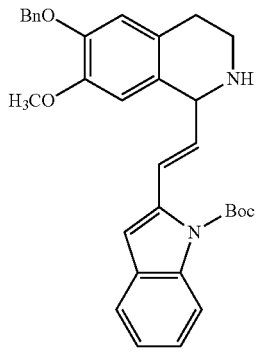 [SMILES: COc1cc2c(cc1OCc1ccccc1)CCNC2/C=C/c1cc2ccccc2n1C(=O)OC(C)(C)C]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 2-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511.

Example CI: tert-Butyl 3-[(E)-2-(6-benzyloxy-7-methoxy-1,2,3,4-tetrahydroisoquinolin-1-yl)vinyl]indole-1-carboxylate

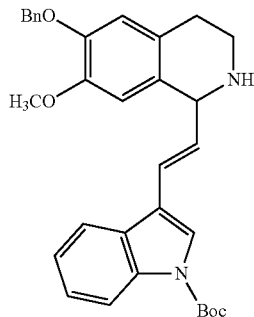 [SMILES: COc1cc2c(cc1OCc1ccccc1)CCNC2/C=C/c1cn(C(=O)OC(C)(C)C)c2ccccc12]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 3-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511

Example CJ: 6-Benzyloxy-1-[(E)-2-(1H-indol-3-yl)vinyl]-7-methoxy-1,2,3,4-tetrahydroisoquinoline

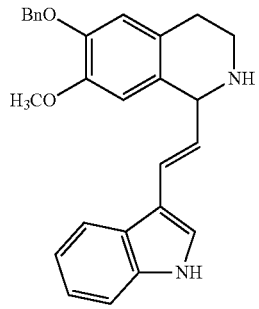 [SMILES: COc1cc2c(cc1OCc1ccccc1)CCNC2/C=C/c1c[nH]c2ccccc12]

The product was obtained from the reaction in Example CI. LC-MS; M+1=411.

Example CK: tert-Butyl 4-[(E)-2-(6-benzyloxy-7-methoxy-1,2,3,4-tetrahydroisoquinolin-1-yl)ethenyl]-1H-indole-1-carboxylate

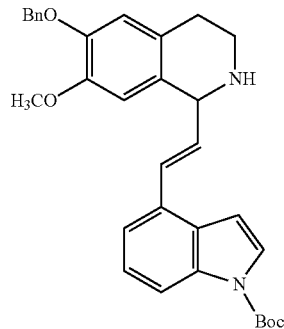 [SMILES: COc1cc2c(cc1OCc1ccccc1)CCNC2/C=C/c1cccc2c1ccn2C(=O)OC(C)(C)C]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 4-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511.

Example CL: 6-Benzyloxy-1-[(E)-2-(1H-indol-4-yl)vinyl]-7-methoxy-L2,3,4-tetrahydroisoquinoline

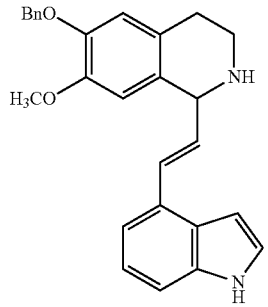 [SMILES: COc1cc2c(cc1OCc1ccccc1)CCNC2/C=C/c1cccc2[nH]ccc12]

The product was obtained from the reaction in Example CK. LC-MS; M+1=411.

Example CM: tert-Butyl 5-[(E)-2-(6-benzyloxy-7-methoxy-1,2,3,4-tetrahydroisoquinolin-1-yl)vinyl]indole-1-carboxylate

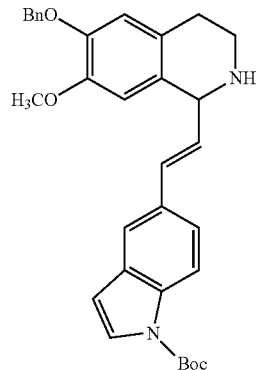 [SMILES: COc1cc2c(cc1OCc1ccccc1)CCNC2/C=C/c1ccc2c(ccn2C(=O)OC(C)(C)C)c1]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 5-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511.

Example CN: tert-Butyl 7-[(E)-2-(6-benzyloxy-7-methoxy-1,2,3,4-tetrahydroisoquinolin-1-yl)vinyl]indole-1-carboxylate

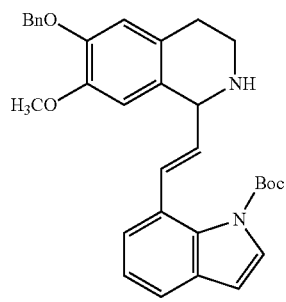 [SMILES: COc1cc2c(cc1OCc1ccccc1)CCNC2/C=C/c1cccc2ccn(C(=O)OC(C)(C)C)c12]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 7-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511.

Example CO: 3-[(E)-2-(6-benzyloxy-7-methoxy-1,2,3,4-tetrahydroisoquinolin-1-yl)vinyl]-2,6-difluorophenol

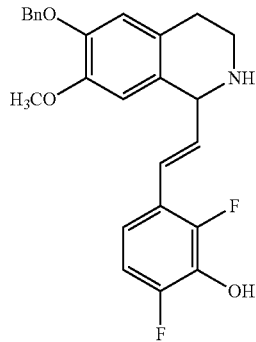 [SMILES: COc1cc2c(cc1OCc1ccccc1)CCNC2/C=C/c1ccc(F)c(O)c1F]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 2,4-difluoro-3-hydroxy-benzaldehyde (133 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=424.

Example CP: 6-Benzyloxy-7-methoxy-1-[(E)-2-(3-methylsulfonylphenyl)vinyl]-1,2,3,4-tetrahydroisoquinoline

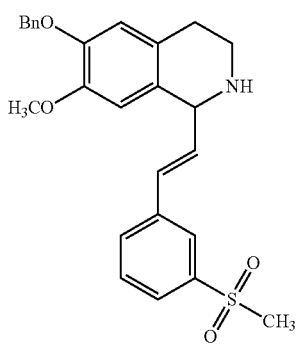 [SMILES: COc1cc2c(cc1OCc1ccccc1)CCNC2/C=C/c1cccc(S(C)(=O)=O)c1]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 3-methylsulfonylbenzaldehyde (155 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=450.

Example CQ: 6-Benzyloxy-7-methoxy-1-[(E)-2-(6-methoxy-2,3-dihydro-1,4-benzodioxin-7-yl)vinyl]-1,2,3,4-tetrahydroisoquinoline

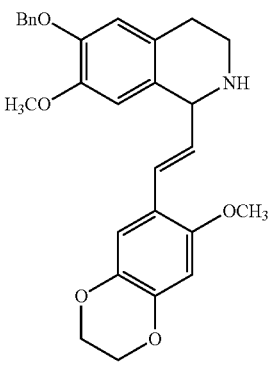 [SMILES: COc1cc2c(cc1/C=C/C1NCCc3cc(OCc4ccccc4)c(OC)cc31)OCCO2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 6-methoxy-2,3-dihydro-1,4-benzodioxine-7-carbaldehyde (163 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=460

Example CR: 6-Benzyloxy-7-methoxy-1-[(E)-2-(6-methoxy-1,3-benzodioxol-5-yl)vinyl]-1,2,3,4-tetrahydroisoquinoline

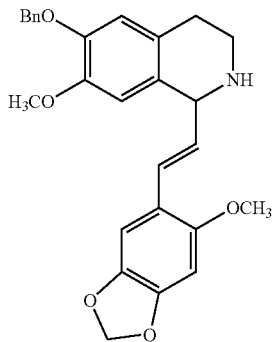 [SMILES: COc1cc2c(cc1/C=C/C1NCCc3cc(OCc4ccccc4)c(OC)cc31)OCO2]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 6-methoxy-1,3-benzodioxole-5-carbaldehyde (151 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=446.

Example CS: tert-Butyl 6-[(E)-2-(6-benzyloxy-7-methoxy-1,2,3,4-tetrahydroisoquinolin-1-yl)vinyl]indole-1-carboxylate

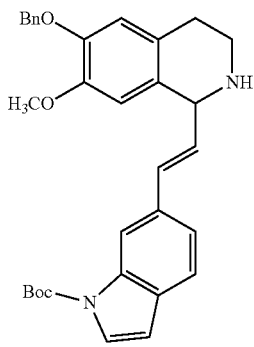 [SMILES: COc1cc2c(cc1OCc1ccccc1)CCNC2/C=C/c1ccc2ccn(C(=O)OC(C)(C)C)c2c1]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl 6-formylindole-1-carboxylate (206 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=511.

Example CT: 2-[(E)-2-(6-benzyloxy-7-methoxy-1,2,3,4-tetrahydroisoquinolin-1-yl)vinyl]-4,5-dimethoxy-N,N-dimethyl-aniline

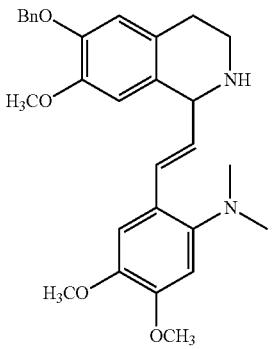 [SMILES: COc1cc(/C=C/C2NCCc3cc(OCc4ccccc4)c(OC)cc32)c(N(C)C)cc1OC]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 2-(dimethylamino)-4,5-dimethoxy-benzaldehyde (176 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=475

Example CU: 3-[(E)-2-(6-benzyloxy-7-methoxy-1,2,3,4-tetrahydroisoquinolin-1-yl)vinyl]-N,N-dimethyl-pyridin-2-amine

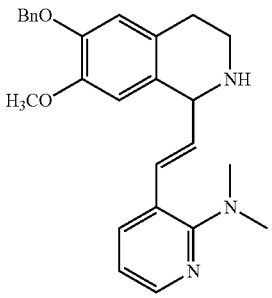 [SMILES: COc1cc2c(cc1OCc1ccccc1)CCNC2/C=C/c1cccnc1N(C)C]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and 2-(dimethylamino)pyridine-3-carbaldehyde (126 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=416

Example CV: Ethyl 4-[5-[(E)-2-(6-benzyloxy-7-methoxy-1,2,3,4-tetrahydroisoquinolin-1-yl)vinyl]-2-methoxy-phenoxy]butanoate

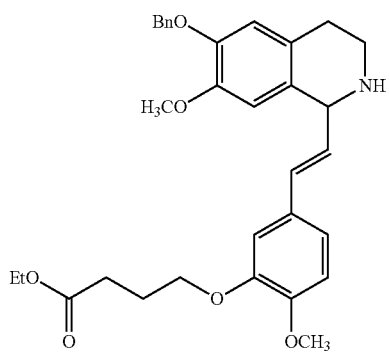 [SMILES: CCOC(=O)CCCOc1cc(/C=C/C2NCCc3cc(OCc4ccccc4)c(OC)cc32)ccc1OC]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and ethyl 4-(5-formyl-2-methoxy-phenoxy)butanoate (223 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=532.

Example CW: tert-Butyl N-[2-[(E)-2-(6-benzyloxy-7-methoxy-1,2,3,4-tetrahydroisoquinolin-1-yl)vinyl]phenyl]carbamate

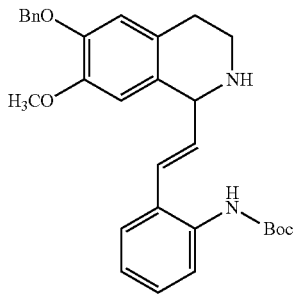 [SMILES: COc1cc2c(cc1OCc1ccccc1)CCNC2/C=C/c1ccccc1NC(=O)OC(C)(C)C]

A solution of tert-Butyl 6-benzyloxy-7-methoxy-1-[(1-phenyltetrazol-5-yl)sulfonylmethyl]-3,4-dihydro-1H-isoquinoline-2-carboxylate (100 mg, 0.169 mmol) and tert-butyl N-(2-formylphenyl)carbamate (186 mg, 0.84 mmol) in THF (10 mL) was cooled to −35° C. with stirring under argon. To this mixture was added a solution of lithium bis(trimethylsilyl)amide (0.68 mL, 0.68 mmol, 1M in THF) and the reaction mixture was stirred for 1 hour at −35° C. The reaction was allowed to warm up to room temperature and the organic solvent was evaporated to give a residue. The residue was dissolved (or suspended) in 4M HCl dioxane (5 mL) and stirred at room temperature until the reaction was completed. The organic layer was evaporated to leave a residue, which was purified by flash or reverse phase preparatory chromatography. LC-MS; M+1=487.

Example CX: 2-[(E)-2-(6-benzyloxy-7-methoxy-1,2,3,4-tetrahydroisoquinolin-1-yl)vinyl]aniline

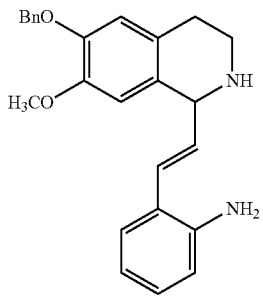 [SMILES: COc1cc2c(cc1OCc1ccccc1)CCNC2/C=C/c1ccccc1N]

The product was obtained from the reaction in Example CW. LC-MS; M+1=387.

Example CY: (E)-6-(Benzyloxy)-7-methoxy-1-(4-methoxy-3-(trifluoromethyl)styryl)-1,2,3,4-tetrahydroisoquinoline

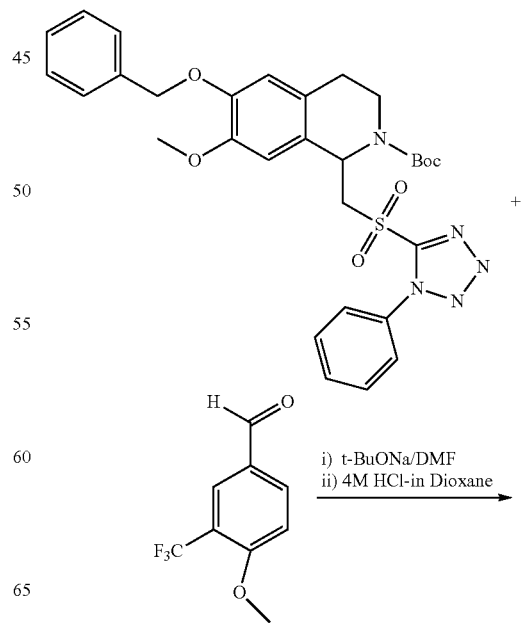

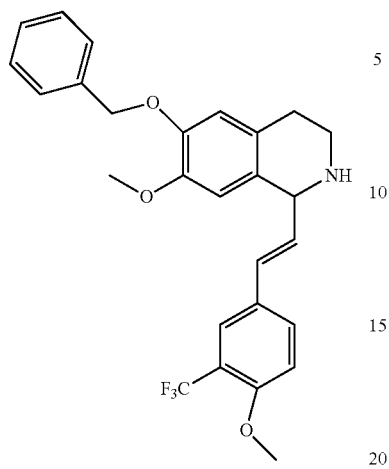

This compound was prepared by the Methylenation reaction for aldehydes and ketones using the new Julia-Kocienski olefination reaction; (Kaori Ando et. al, Organic Letter, Apr. 1, 2015); Raju Jannapu Reddy, et. al, JOC. To the solution of tert-butyl 6-(benzyloxy)-7-methoxy-1-(2-phenyl-2H-tetrazol-5-ylsulfonyl)methyl-3,4-dihydroisoquinoline-2(1H)-carboxylate (0.2016 g, 0,340 mmol) and 4-methoxy-3-(trifluoromethyl) benzaldehyde (58 mgs, 0.284 mmol) in anhydrous DMF (5 ml) under argon was added sodium tert-butoxide (82 mgs, 0.85 mmol) at room temperature. After stirring for 1 hr, the reaction was quenched with aqueous NH₄Cl and the mixture was extracted with EtOAc (2×50 ml), the combined extracts were washed with H2O, brine, dried (MgSO₄), filtered and concentrated to dryness. The crude obtained was treated with 1,2-dichloroethane and 4M HCl-in-Dioxane (v/v) monitored by LCMS, upon completion, it was concentrated to dryness and purified by HPLC to afford the TFA salt of the titled compound. M+H=470.

Example CZ: (E)-6-(benzyloxy)-7-methoxy-1-(4-methoxy-3-methyl-5-(trifluoromethyl)styryl)-1,2,3,4-tetrahydroisoquinoline

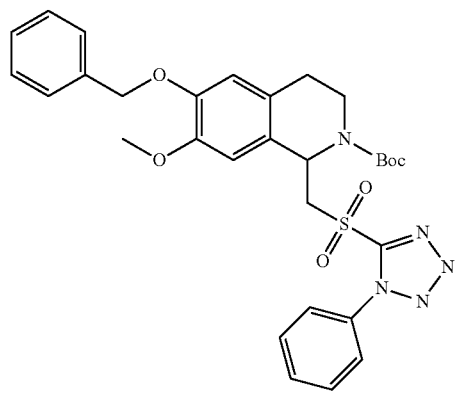

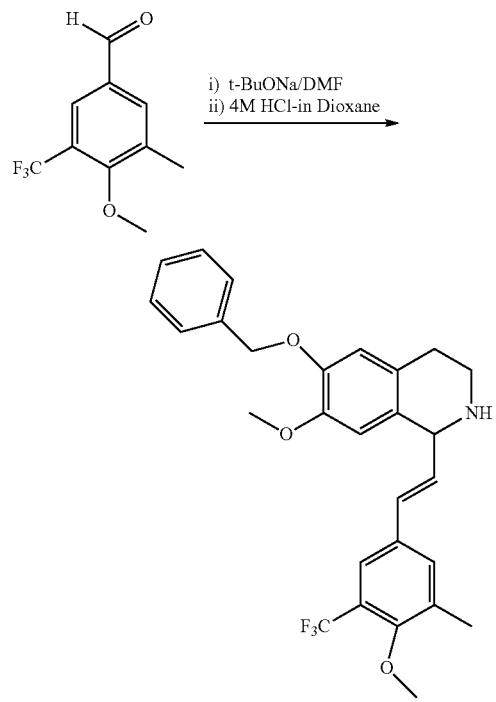

(E)-6-(Benzyloxy)-7-methoxy-1-(4-methoxy-3-methyl-5-(trifluoromethyl)styryl)-1,2,3,4-tetrahydroisoquinoline was prepared as described in detail above using 4-methoxy-3-methyl-5-(trifluoromethyl)benzaldehyde (62 mgs, 0.28 mmol) to afford the titled compound. M+H=484.

Example DA: (E)-6-(benzyloxy)-7-methoxy-1-(2-(trifluoromethyl)styryl)-1,2,3,4-tetrahydroisoquinoline

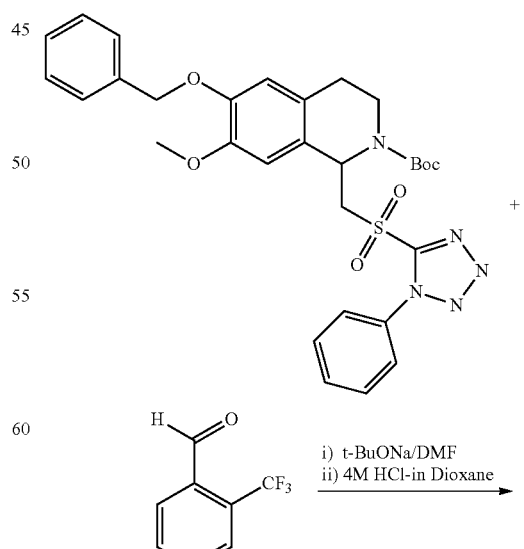

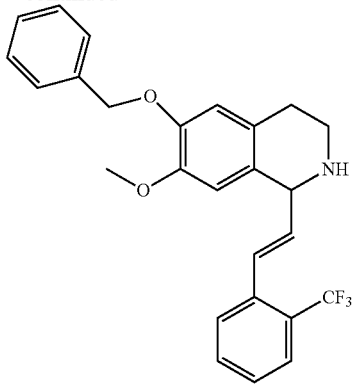

(E)-6-(Benzyloxy)-7-methoxy-1-(2-(trifluoromethyl) styryl)-1,2,3,4-tetrahydroisoquinoline was prepared as described above using 2-(trifluoromethyl)benzaldehyde (0.61 g, 0.35 mmol) to afford the titled compound. M+H=440.

Example DB: (E)-6-(benzyloxy)-7-methoxy-1-(3-(trifluoromethyl)styryl)-1,2,3,4-tetrahydroisoquinolin

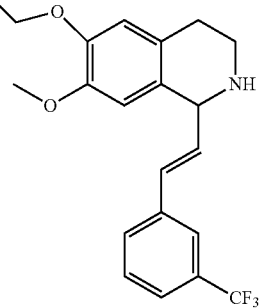

(E)-6-(Benzyloxy)-7-methoxy-1-(3-(trifluoromethyl) styryl)-1,2,3,4-tetrahydroisoquinoline was prepared using 3-(trifluoromethyl)benzaldehyde (0.61 g, 0.35 mmol) to afford the titled compound. M+H=440.

Example DC: (E)-2-(2-(6-(benzyloxy)-methoxy-1,2,3,4-tetrahydroisoquinolin-1-yl)vinyl)-N,N-dimethyl-amine

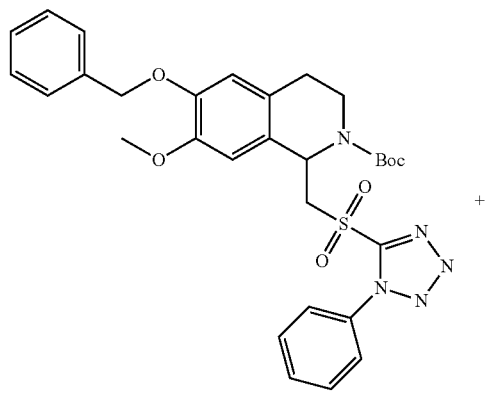

To the stirred solution of 10 (0.2578 g, 0.44 mmol) and 2-(dimethylamino)benzaldehyde (0.2602 g, 1.74 mmol, 5 eq.) in anhydrous THF (10 ml), under argon at −35° C. was added sodium bis(trimethylsilyl)amide (1.0M in THF, 1.7 ml) dropwise. The resulting pale yellow solution was stirred vigorously for an additional 1 hr and diluted with sat. ammonium chloride, and the mixture was extracted with ethyl acetate. The organic layer was washed with water, brine, dried (MgSO4), filtered, concentrated to dryness, residue obtained subjected to boc-deprotection using 4M HCl-in-Dioxane and 1,2-Dichloroethane. The crude after concentration was purified by the Waters LCMS prepsystem to afford the titled compound as the TFA salt. M+H=415.

189

Example DD: (E)-(benzyloxy)-7-methoxy-1-(2-(2-methoxypyrimidin-5-yl)vinyl)-1,2,3,4-tetrahydroisoquinoline

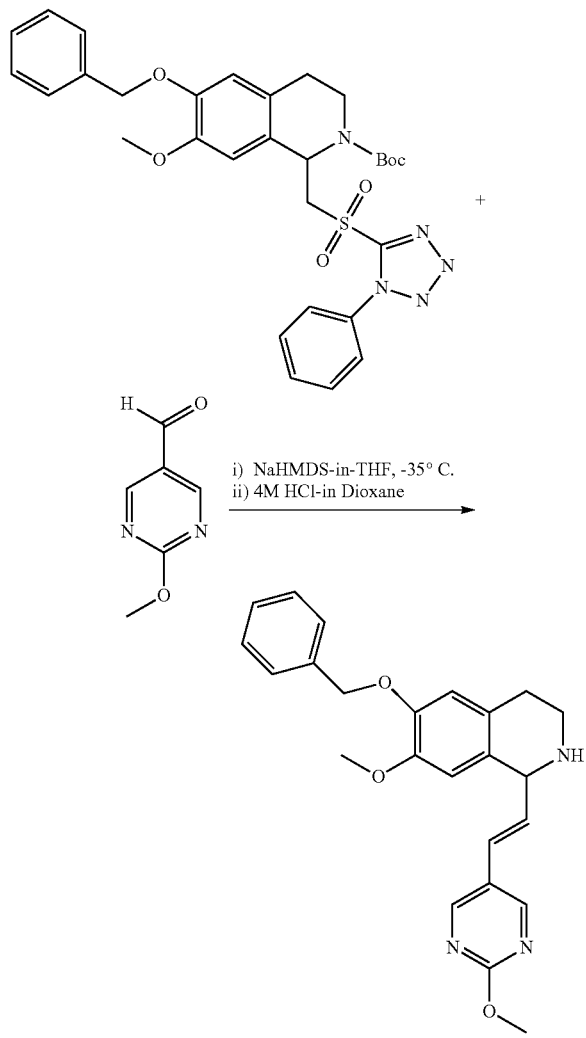

(E)-(Benzyloxy)-7-methoxy-1-(2-(2-methoxypyrimidin-5-yl)vinyl)-1,2,3,4-tetrahydroisoquinoline was prepared as described above using 2-methoxypyrimidine-5-carbaldehyde (0.1940 g, 1.40 mmol) to afford the titled compound. M+H=404.

Example DE: (E)-6-(benzyloxy)-7-methoxy-1-(2-(2-methoxyethoxy)styryl)-1,2,3,4-tetrahydroisoquinoline

190

-continued

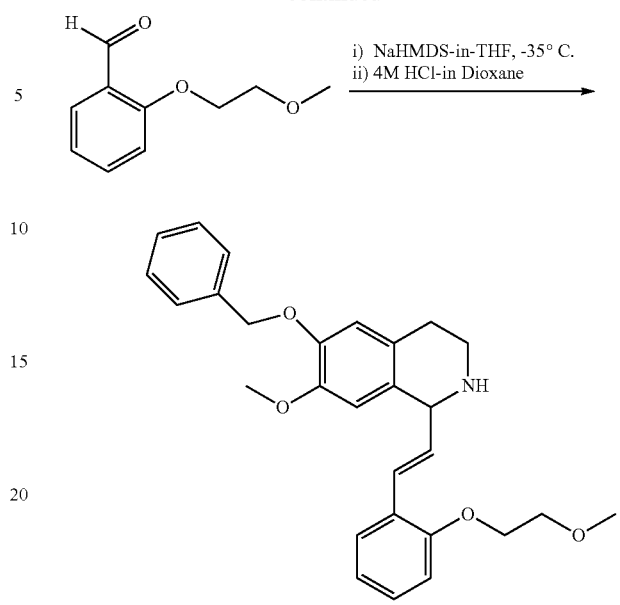

(E)-6-(Benzyloxy)-7-methoxy-1-(2-(2-methoxyethoxy)styryl)-1,2,3,4-tetrahydroisoquinoline was prepared using 2-(2-methoxyethoxy)benzaldehyde (0.2776 g, 1.54 mmol) to afford the titled compound as the TFA salt. M+H=446.

Example DF: (E)-6-(benzyloxy)-1-(2-(2,2-difluorobenzo[d][1,3]dioxol-5-yl)vinyl)-7-methoxy-1,2,3,4-tetrahydroisoquinoline

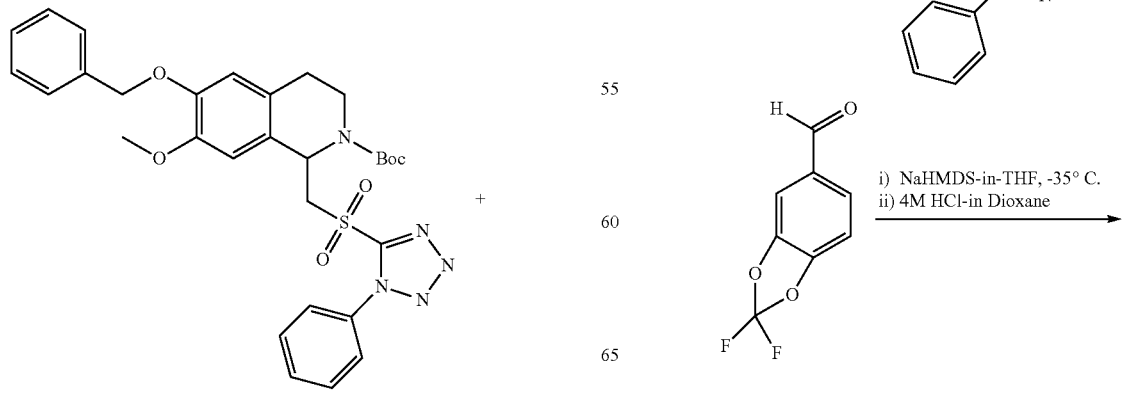

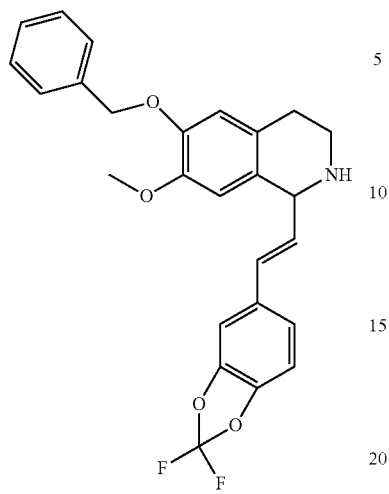

(E)-6-(Benzyloxy)-1-(2-(2,2-difluorobenzo[d][1,3]di-oxol-5-yl)vinyl)-7-methoxy-1,2,3,4-tetrahydroisoquinoline was prepared using 2,2-difluorobenzo[d][1,3]dioxol-5-carbaldehyde (0.2444 g, 1.31 mmol) to afford the titled compound. M+H=452.

Example DG: (E)-6-(benzyloxy)-7-methoxy-1-(2-methoxystyryl)-1,2,3,4-tetrahydroisoquinoline

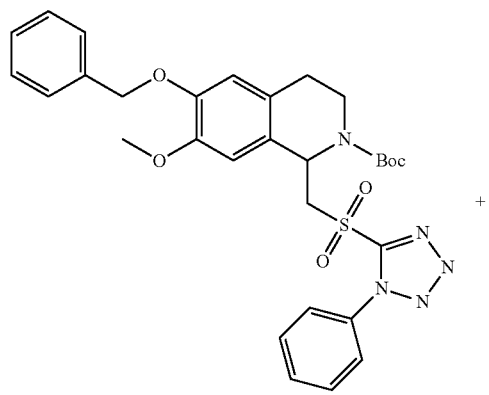

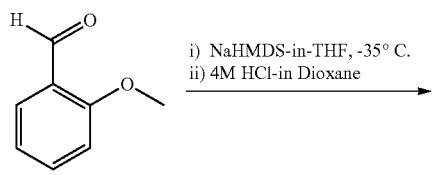

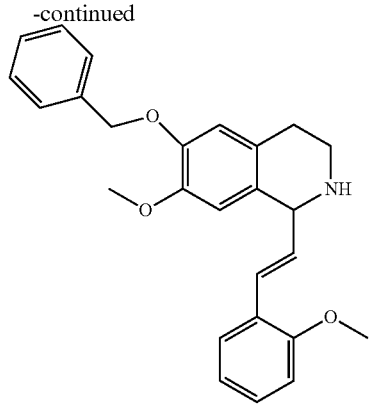

(E)-6-(Benzyloxy)-7-methoxy-1-(2-methoxystyryl)-1,2,3,4-tetrahydroisoquinoline was prepared using 2-methoxybenzaldehyde (0.1985 g, 1.46 mmol) to afford the titled compound. M+H=402.

Example DH: (E)-4-(2-(2-(6-(benzyloxy)-7-methoxy-1,2,3,4-tetrahydroisoquinolin-1-yl)vinyl)phenyl)morpholine

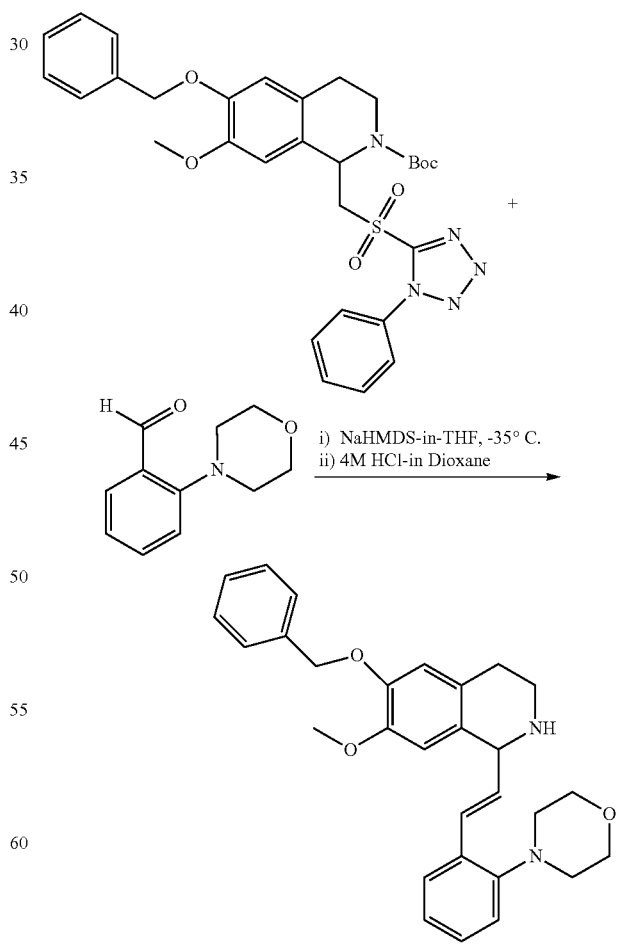

(E)-4-(2-(2-(6-(Benzyloxy)-7-methoxy-1,2,3,4-tetrahydroisoquinolin-1-yl)vinyl)phenyl)morpholine was prepared using 2-morpholinobenzaldehyde (0.2218 g, 1.16 mmol) to afford the titled compound. M+H=457.

Example DI: (E)-6-(benzyloxy)-7-methoxy-1-(2-(6-methoxynaphthalen-2-yl)vinyl)-1,2,3,4-tetrahydroisoquinoline

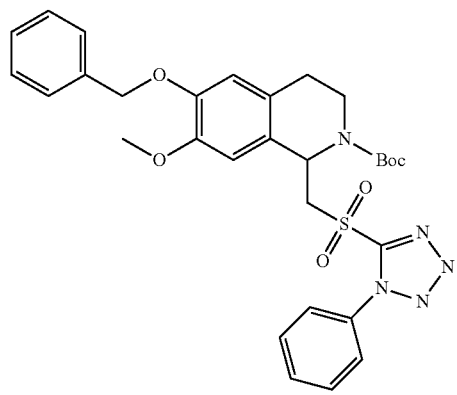

Example DJ: (E)-6-(benzyloxy-7-methoxy-1-(4-(pyridine-3-yl)styryl)-1,2,3,4-tetrahydroisoquinoline

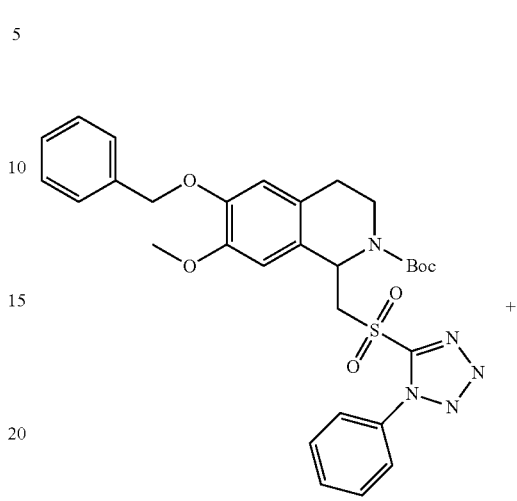

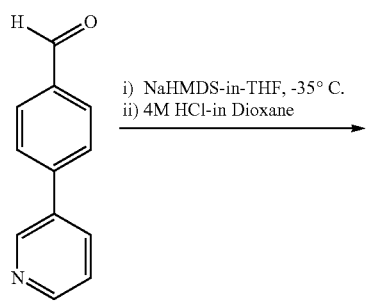

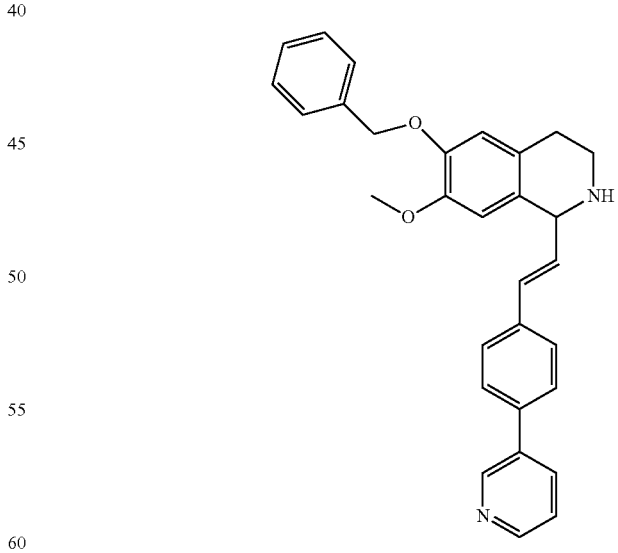

(E)-6-(Benzyloxy)-7-methoxy-1-(2-(6-methoxynaphthalen-2-yl)vinyl)-1,2,3,4-tetrahydroisoquinoline was prepared using 6-methoxy-2-naphthaldehyde (0.2063 g, 1.11 mmol) to afford the titled compound. M+H=452

(E)-6-(Benzyloxy-7-methoxy-1-(4-(pyridine-3-yl)styryl)-1,2,3,4-tetrahydroisoquinoline was prepared using 4-(pyridine-3-yl)benzaldehyde (0.2201 g, 1.201 mmol) to afford the titled compound.

Example DK: (E)-1-(4-(1H-imidazol-1-yl)styryl)-6-(benzyloxy)-7-methoxy-1,2,3,4-tetrahydroisoquinoline

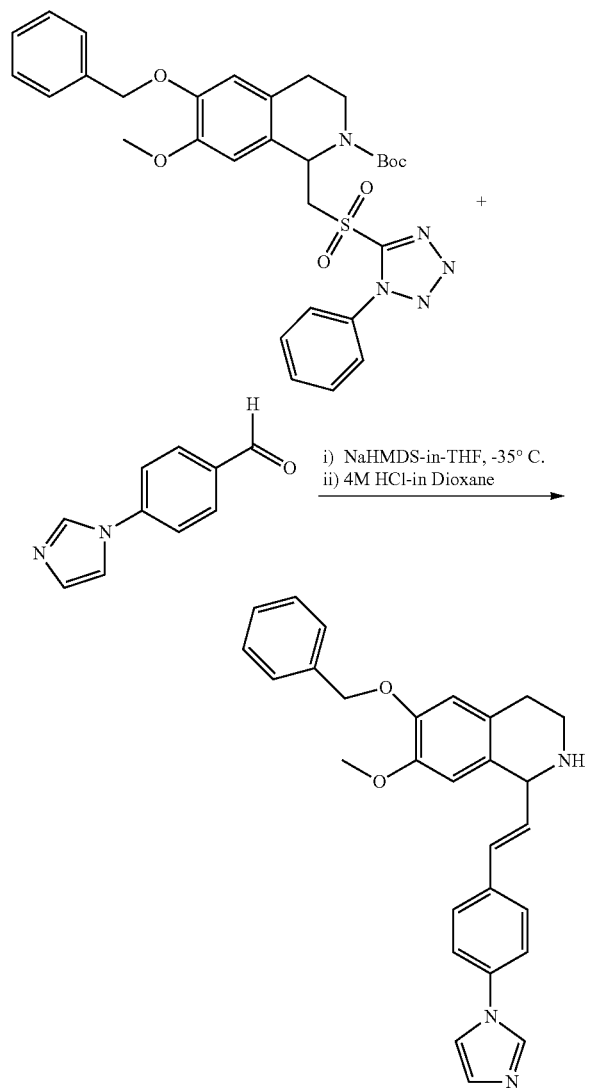

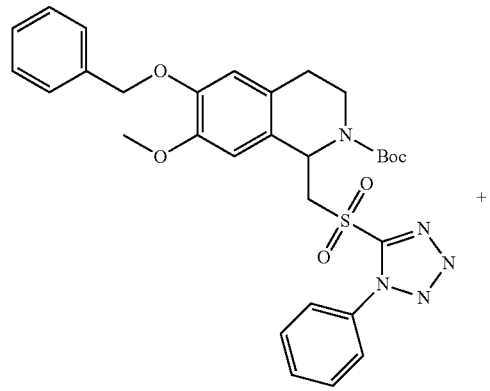

(E)-1-(4-(1H-Imidazol-1-yl)styryl)-6-(benzyloxy)-7-methoxy-1,2,3,4-tetrahydroisoquinoline was prepared using 4-(1H-imidazol-1-yl)benzaldehyde 23 (0.2536 g, 1.5 mmol) to afford the titled compound.

Example DL: (E)-7-(2-(6-(benzyloxy)-7-methoxy-1,2,3,4-tetrahydroisoquinolin-1-yl)vinyl)quinoline

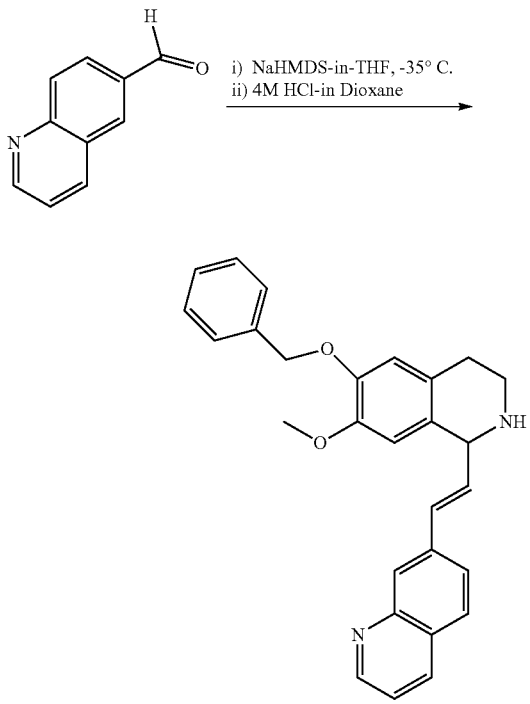

(E)-7-(2-(6-(benzyloxy)-7-methoxy-1,2,3,4-tetrahydroisoquinolin-1-yl)vinyl)quinoline was prepared using quinolone-6-carbaldehyde (0.2789 g, 1.8 mmol) to afford the titled compound. M+H=423

Example DM: (E)-6-(benzyloxy)-7-methoxy-1-(4-(2-methyl-1H-imidazol-1-yl)styryl)-1,2,3,4-tetrahydroisoquinoline

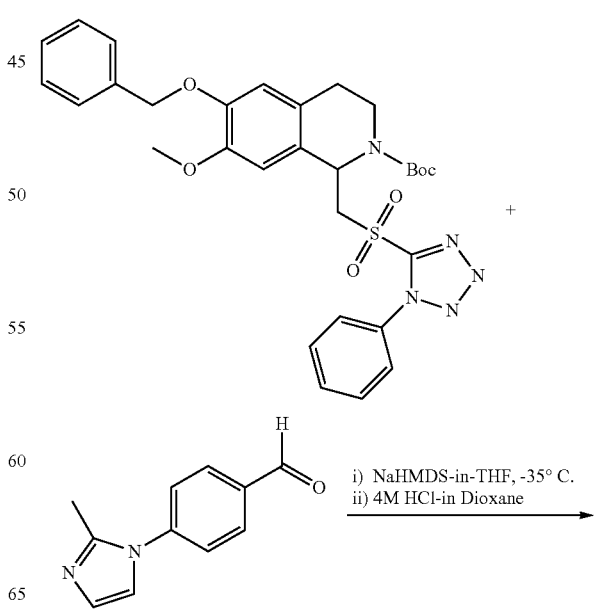

197
-continued

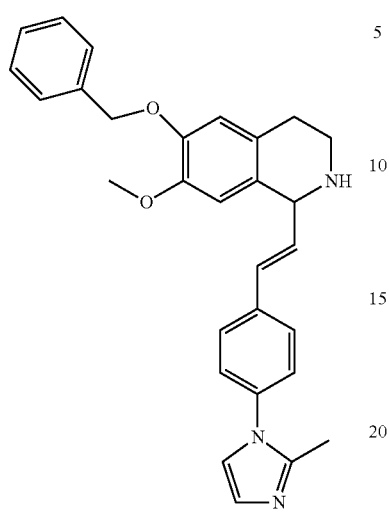

(E)-6-(Benzyloxy)-7-methoxy-1-(4-(2-methyl-1H-imidazol-1-yl)styryl)-1,2,3,4-tetrahydroisoquinoline was prepared using 4-(2-methyl-1H-imidazol-1-yl)benzaldehyde (0.3112 g, 1.67 mmol) to afford the titled compound. M+H=452.

Example DN: (E)-6-(benzyloxy)-7-methoxy-1-(2-(2-(3-methoxyphenyl)pyrimidin-5-yl)vinyl-1,2,3,4-tetrahydroisoquinoline

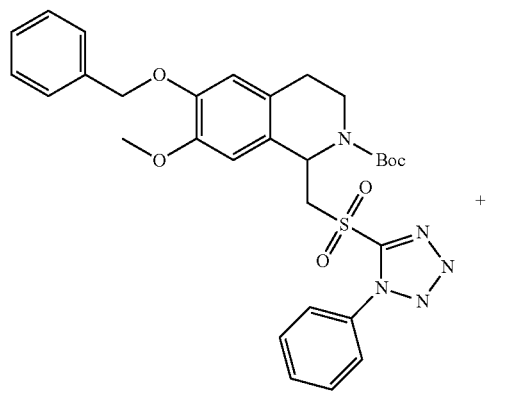

+

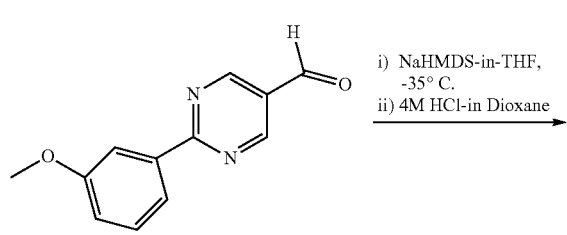

i) NaHMDS-in-THF, -35° C.
ii) 4M HCl-in Dioxane →

198
-continued (E)-6-(Benzyloxy)-7-methoxy-1-(2-(2-(3-methoxyphenyl)pyrimidin-5-yl)vinyl-1,2,3,4-tetrahydroisoquinoline was prepared using 2-(3-methoxyphenyl)pyrimidine-5-carbaldehyde (0.2996 g, 1.40 mmol) to afford the titled compound. M+H=480.

Example DO: (E)-6-(benzyloxy)-1-(4-(4-ethylpyrazin-1-yl)styryl)-7-methoxy-1,2,3,4-tetrahydroisoquinoline

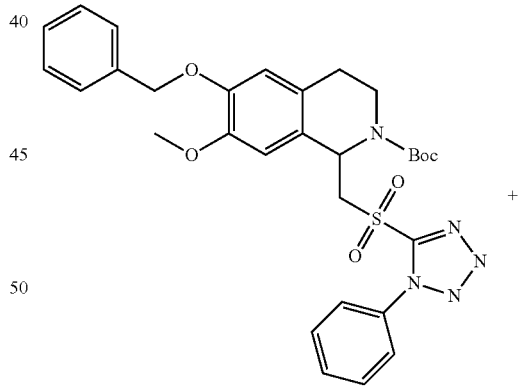

+

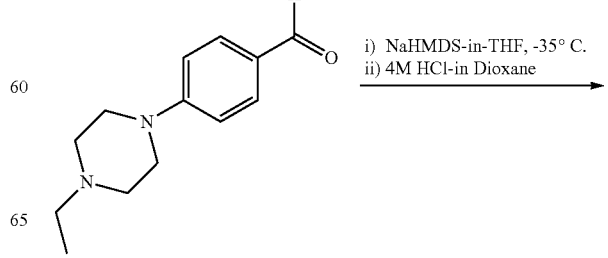

i) NaHMDS-in-THF, -35° C.
ii) 4M HCl-in Dioxane →

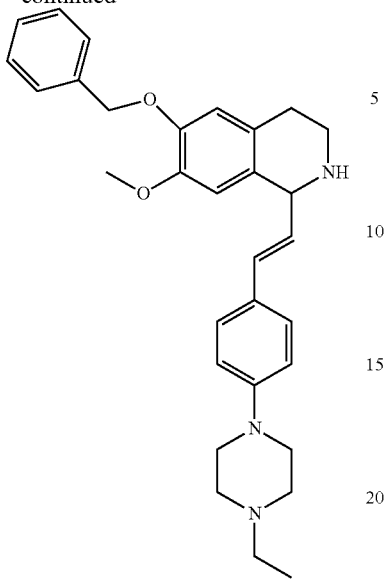

(E)-6-(Benzyloxy)-1-(4-(4-ethylpiperazin-1-yl)styryl)-7-methoxy tetrahydroisoquinoline was prepared using 4-(4-ethylpiperazin-1-yl)benzaldehyde (0.3742 g, 1.71 mmol) to afford the titled compound. M+H=484.

Example DP: 6-(Benzyloxy)-7-methoxy-1-[(E)-2-{1-methyl-1H-pyrrolo[2,3-b]pyridin-3-yl}ethenyl]-1,2,3,4-tetrahydroquinoline

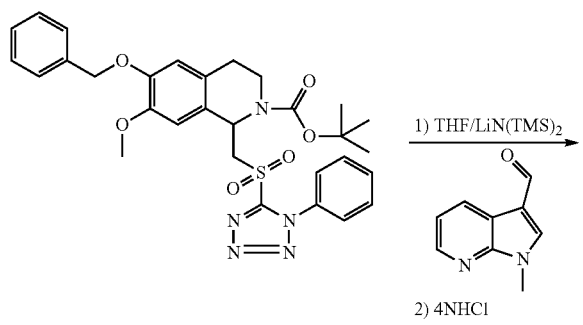

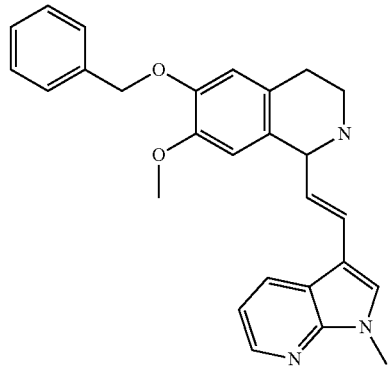

To a solution of tert-butyl 6-benzyloxy-7-methoxy-1-[(1-phenyltetrazol-5-yl)sulfonylmethyl]-3,4-dihydro-1H-isoquinoline-2-carboxylate [118 mg (0.2 mmol)] in THF (5 ml) with 1-methylpyrrolo[2,3-b]pyridine-3-carbaldehyde [96 mg (0.6 mmol)] was added at −38° C. 1M LiN(TMSi)$_2$ [600 ul (0.6 mmol)]. The reaction was stirred at −38° C. for 60 min and then at room temperature for 30 min longer. The reaction was quenched with sat NH$_4$Cl (10 ml), extracted with EtOAc (20 ml), dried (MgSO$_4$) and the solvent removed. The residue was treated with 2 ml of 4NHCl in dioxane for 1 h, rotary evaporated to dryness and chromatographed via reverse phase chromatography. Yield=3 mg (3.5%) as TFA salt via prep chrom. MS (m/z): 426 [M+H]

Example DQ: 6-(Benzyloxy)-7-methoxy-1-[(E)-2-[3-(pyridin-4-yl)phenyl]ethenyl]-1,2,3,4-tetrahydroisoquinoline

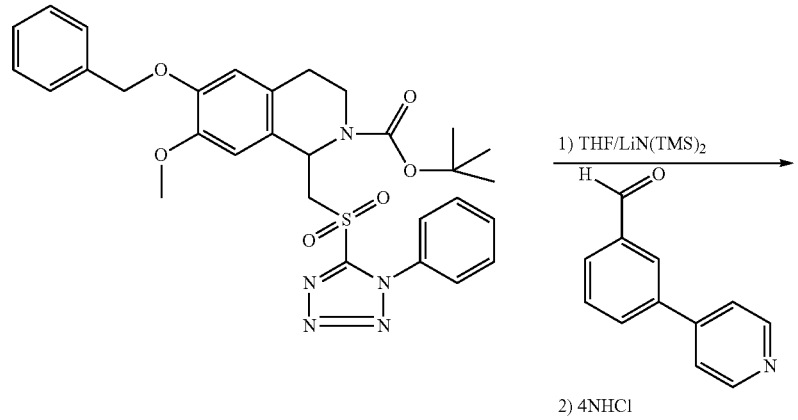

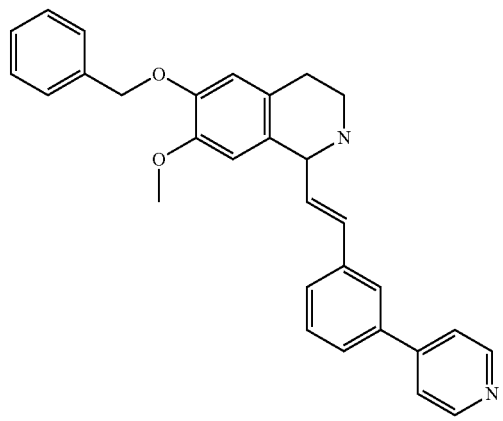

Using the same procedure outlined in Example DP at the same scale with the aldehyde 3-(4-pyridyl)benzaldehyde the reaction afforded the desired adduct. Yield=18 mg (20%) as TFA salt via prep chrom. MS (m/z): 449 [M+H]

Example DR: 6-(Benzyloxy)-7-methoxy-1-[(E)-2-(1,3-thiazol-4-yl)ethenyl]-1,2,3,4-tetrahydroisoquinolin

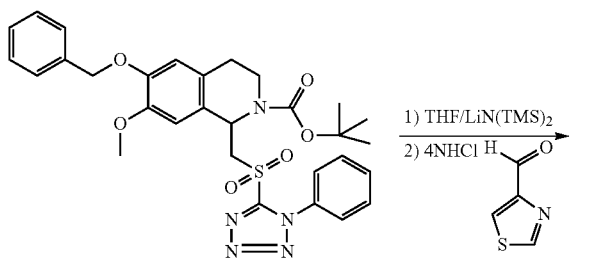

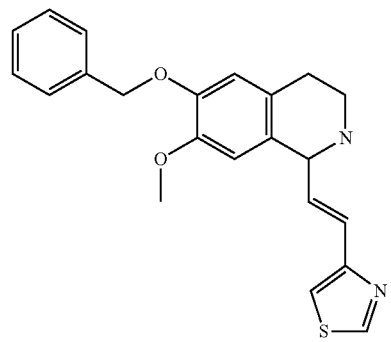

Using the same procedure outlined in Example DP at the same scale with the aldehyde thiazole-4-carbaldehyde the reaction afforded the desired adduct. Yield=11 mg (14%) as TFA salt via prep chrom. MS (m/z): 379 [M+H]

Example DS: 6-(Benzyloxy)-7-methoxy-1-[(E)-2-[4-(pyrimidin-5-yl)phenyl]ethenyl]-1,2,3,4-tetrahydroisoquinoline

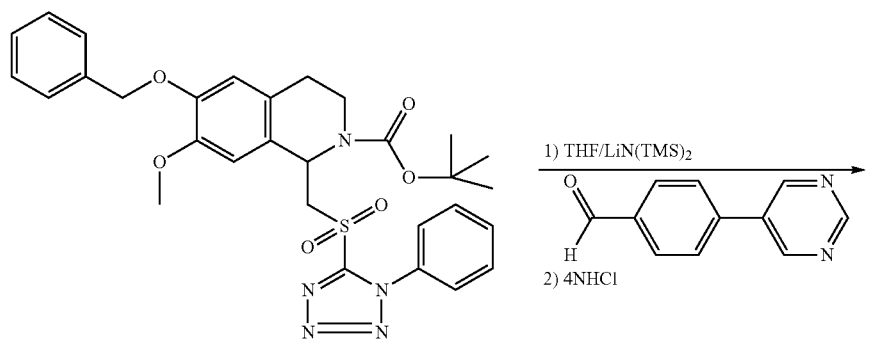

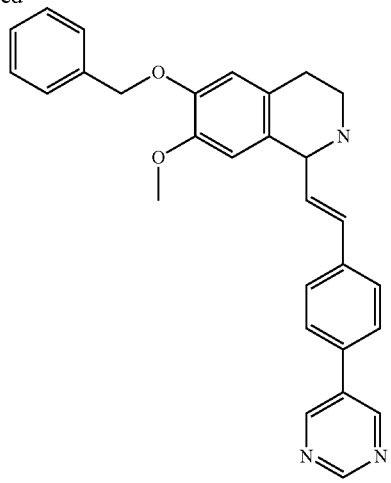

Using the same procedure outlined in Example DP at the same scale with the aldehyde 4-pyrimidin-5-ylbenzaldehyde the reaction afforded the desired adduct. Yield=10 mg (11%) as TFA salt via prep chrom. MS (m/z): 450 [M+H]

Example DT: 6-(Benzyloxy)-7-methoxy-1-[(E)-2-[4-(1H-1,2,4-triazol-1-yl)phenyl]ethenyl]-1,2,3,4-tetrahydroisoquinoline

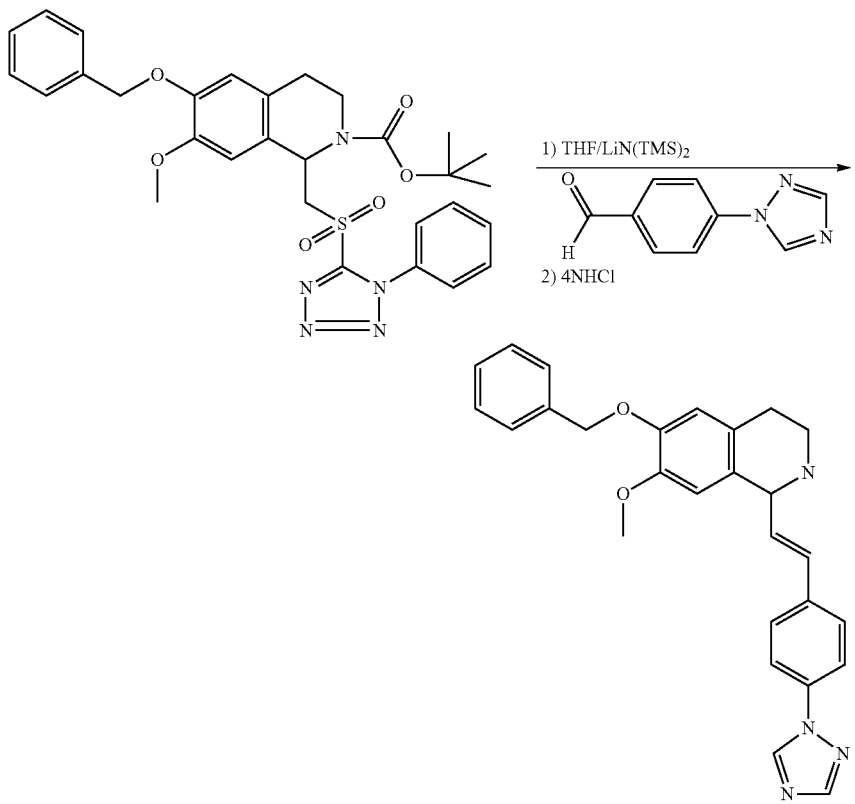

Using the same procedure outlined in Example DP at the same scale with the aldehyde 4-(1,2,4-triazol-1-yl)benzaldehyde the reaction afforded the desired adduct. Yield=10 mg (11%) as TFA salt via prep chrom. MS (m/z): 439 [M+H]

Example DU: 1-[(E)-2-(1-Benzothiophen-2-yl)ethenyl]-6-(benzyloxy)-7-methoxy-1,2,3,4-tetrahydroisoquinoline

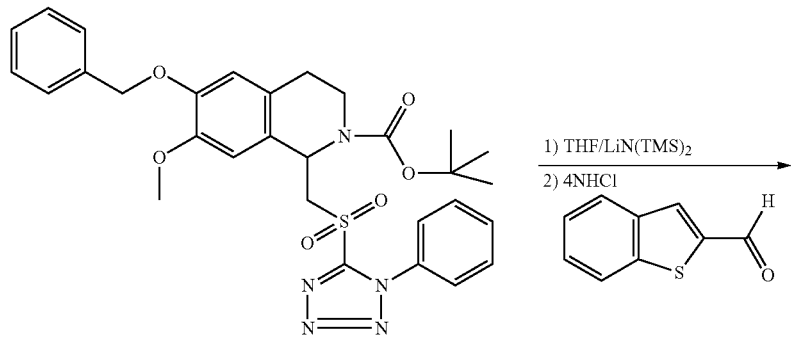

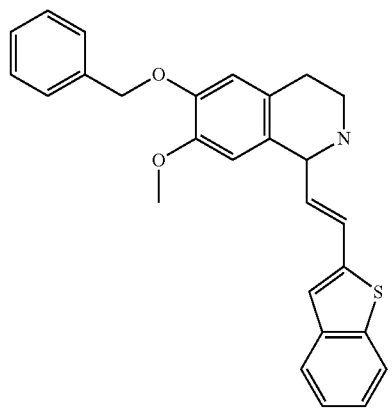

Using the same procedure outlined in Example DP at the same scale with the aldehyde benzothiophene-2-carbaldehyde the reaction afforded the desired adduct. Yield=17 mg (20%) as TFA salt via prep chrom. MS (m/z): 428 [M+H]

Example DV: 6-(Benzyloxy)-7-methoxy-1-[(E)-2-(1,3-thiazol-2-yl)ethenyl]-1,2,3,4-tetrahydroisoquinoline

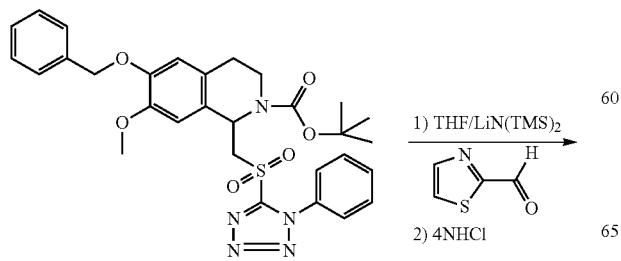

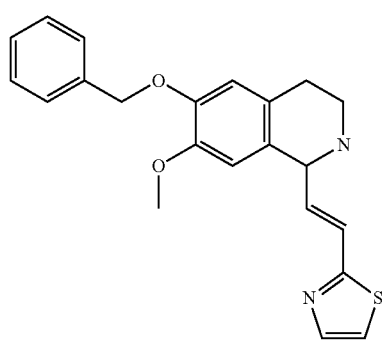

Using the same procedure outlined in Example DP at the same scale with the aldehyde thiazole-2-carbaldehyde the reaction afforded the desired adduct. Yield=15 mg (20%) as TFA salt via prep chrom. MS (m/z): 379 [M+H]

Example DW: 6-(Benzyloxy)-7-methoxy-1-[(E)-2-[4-(4-methylpiperazin-1-yl)phenyl]ethenyl]-1,2,3,4-tetrahydroisoquinoline

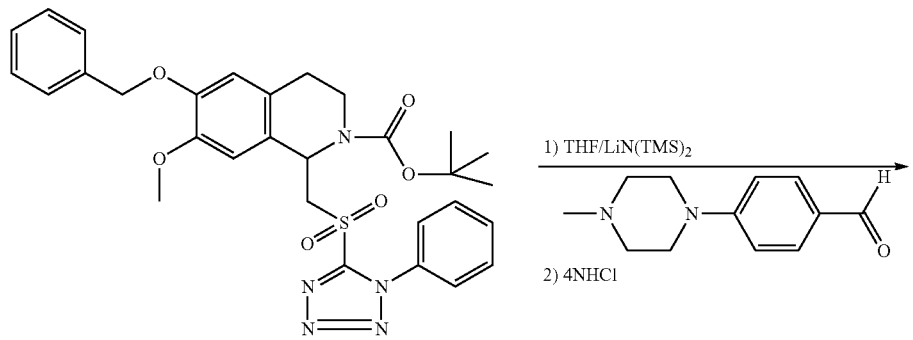

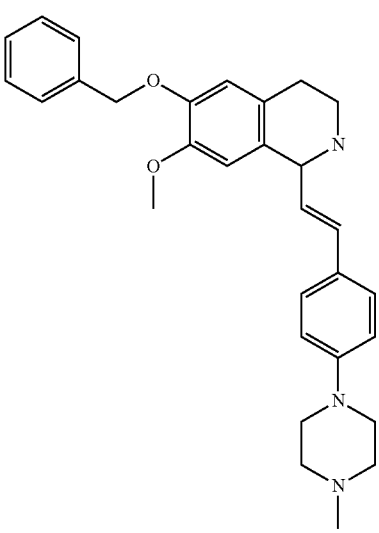

Using the same procedure outlined in Example DP at the same scale with the aldehyde 4-(4-methylpiperazin-1-yl)benzaldehyde the reaction afforded the desired adduct. Yield=3.3 mg (4%) as TFA salt via prep chrom. MS (m/z): 470 [M+H]

Example DX: 6-(Benzyloxy)-7-methoxy-1-[(E)-2-[2-(piperidin-1-yl)phenyl]ethenyl]-1,2,3,4-tetrahydroisoquinoline

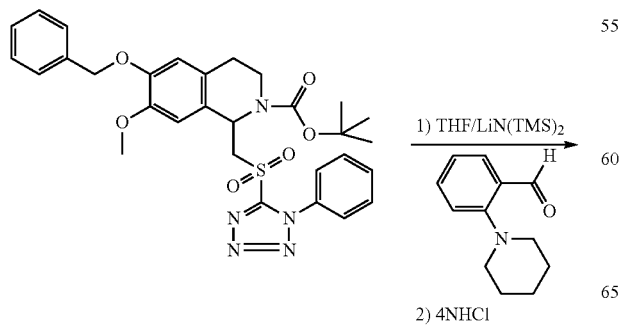

-continued

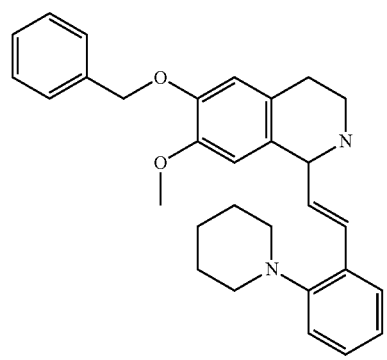

Using the same procedure outlined in Example DP at the same scale with the aldehyde 2-(1-piperidyl)benzaldehyde the reaction afforded the desired adduct. Yield=11 mg (12%) as TFA salt via prep chrom. MS (m/z): 455 [M+H]

Example DY: 5-[(E)-2-(6-Benzyloxy-7-methoxy-1,2,3,4-tetrahydroisoquinolin-1-yl)vinyl]-4-methyl-thiazole

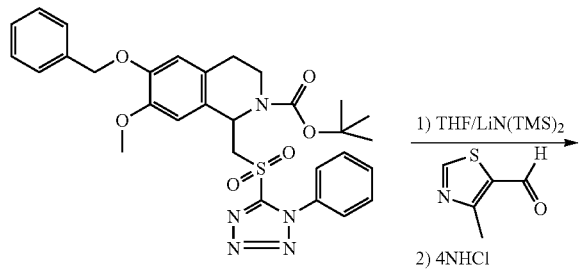
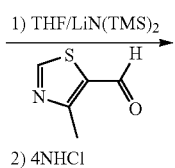
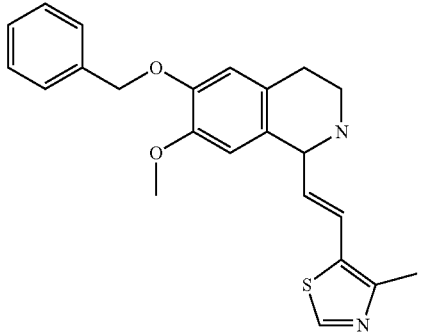

Using the same procedure outlined in Example DP at the same scale with the aldehyde 4-methylthiazole-5-carbaldehyde the reaction afforded the desired adduct. Yield=8 mg (10%) as TFA salt via prep chrom. MS (m/z): 393 [M+H]

Example DZ: 6-Benzyloxy-7-methoxy-1-[(E)-2-[4-(2-pyridyl)phenyl]vinyl]-1,2,3,4-tetrahydroisoquinoline

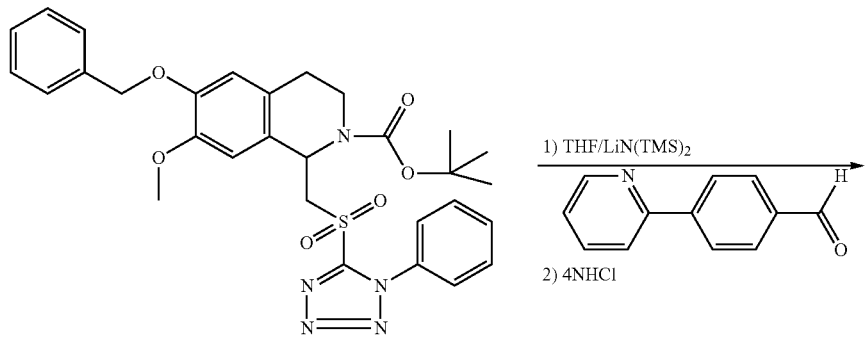
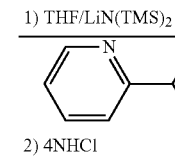
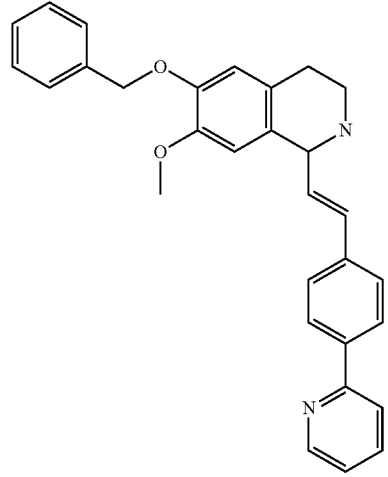

Using the same procedure outlined in Example DP at the same scale with the aldehyde 4-(2-pyridyl)benzaldehyde the reaction afforded the desired adduct. Yield=10 mg (11%) as TFA salt via prep chrom. MS (m/z): 449 [M+H]

Example EA: 6-Benzyloxy-7-methoxy-1-[(E)-2-[4-(1-piperidyl)phenyl]vinyl]-1,2,3,4-tetrahydroisoquinoline

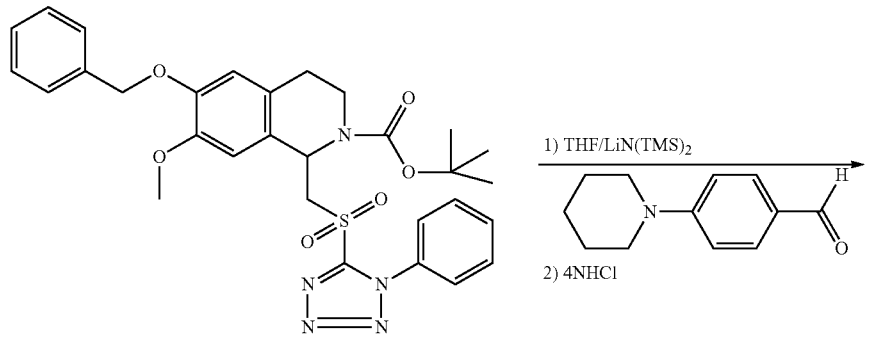

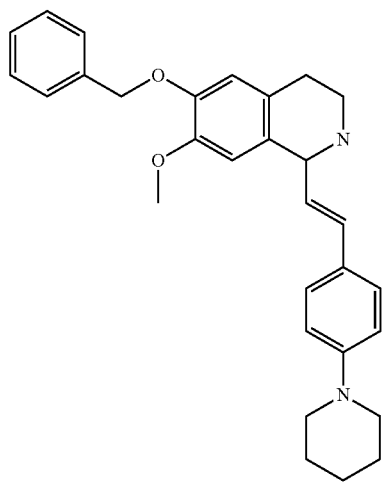

Using the same procedure outlined in Example DP at the same scale with the aldehyde 4-(1-piperidyl)benzaldehyde the reaction afforded the desired adduct. Yield=5 mg (6%) as TFA salt via prep chrom. MS (m/z): 455 [M+H]

Example EB: 6-Benzyloxy-7-methoxy-1-[(E)-2-(6-methoxybenzofuran-5-yl)vinyl]-1,2,3,4-tetrahydroisoquinoline

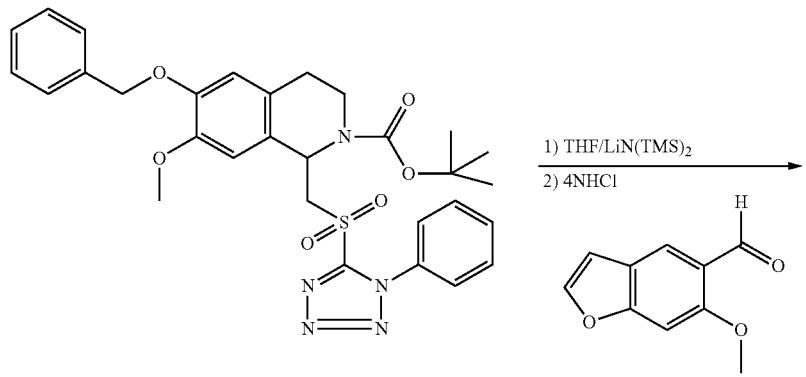

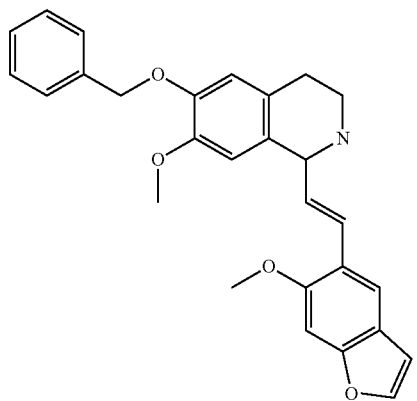

Using the same procedure outlined in Example DP at the same scale with the aldehyde 6-methoxybenzofuran-5-carbaldehyde the reaction afforded the desired adduct. Yield=20 mg (23%) as TFA salt via prep chrom. MS (m/z): 442 [M+H]

Example EC: 2-[3-[(E)-2-(6-Benzyloxy-7-methoxy-1,2,3,4-tetrahydroisoquinolin-1-yl)vinyl]phenyl]oxazole

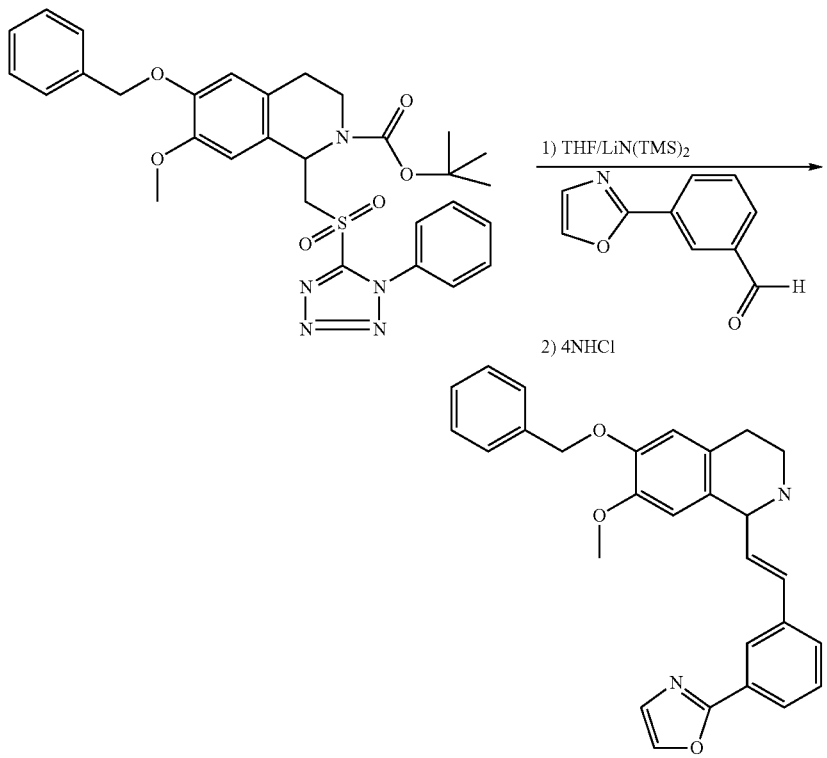

Using the same procedure outlined in Example DP at the same scale with the aldehyde 3-oxazol-2-ylbenzaldehyde the reaction afforded the desired adduct. Yield=20 mg (23%) as TFA salt via prep chrom. MS (m/z): 439 [M+H]

Example ED: 2-[4-[(E)-2-(6-Benzyloxy-7-methoxy-1,2,3,4-tetrahydroisoquinolin-1-yl)vinyl]phenyl]oxazole

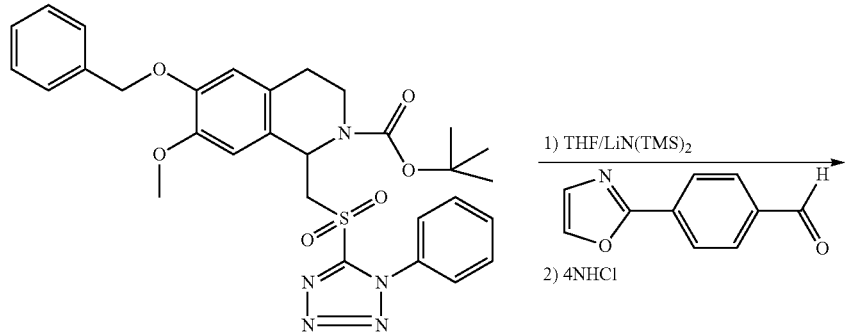

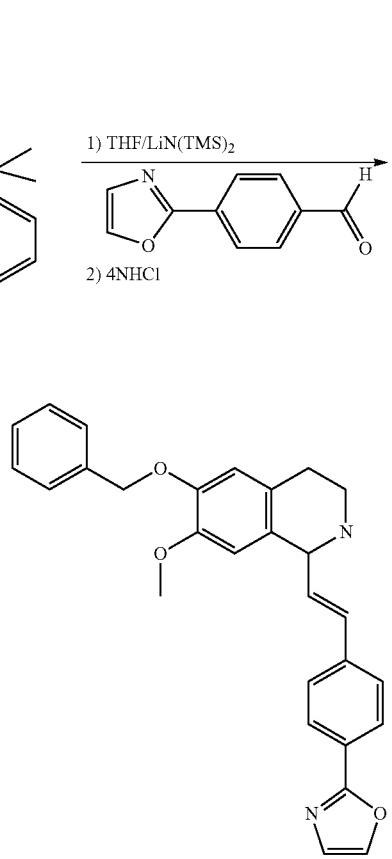

Using the same procedure outlined in Example DP at the same scale with the aldehyde 4-oxazol-2-ylbenzaldehyde the reaction afforded the desired adduct. Yield=10 mg (11%) as TFA salt via prep chrom. MS (m/z): 439 [M+H]

Example EE: Ethyl 2-[4-[(E)-2-(6-benzyloxy-7-methoxy-1,2,3,4-tetrahydroisoquinolin-1-yl)vinyl]phenyl]oxazole-4-carboxylate

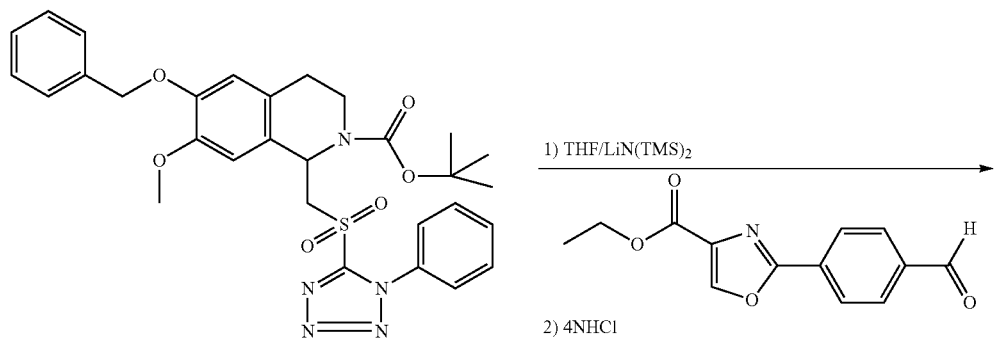

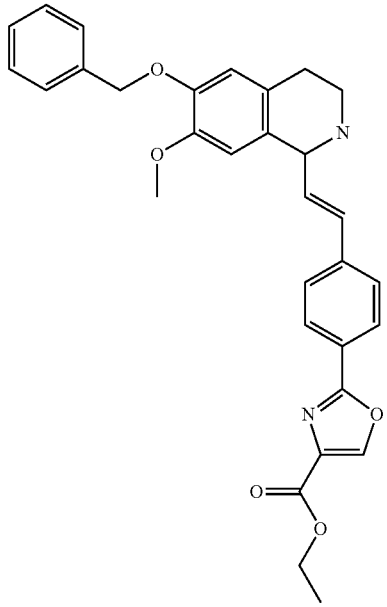
Using the same procedure outlined in Example DP at the same scale with the aldehyde ethyl 2-(4-formylphenyl)oxazole-4-carboxylate the reaction afforded the desired adduct. Yield=20 mg (20%) as TFA salt via prep chrom. MS (m/z): 511 [M+H]
Example EF: Ethyl 2-[3-[(E)-2-(6-benzyloxy-7-methoxy-1,2,3,4-tetrahydroisoquinolin-1-yl)vinyl]phenyl]oxazole-4-carboxylate
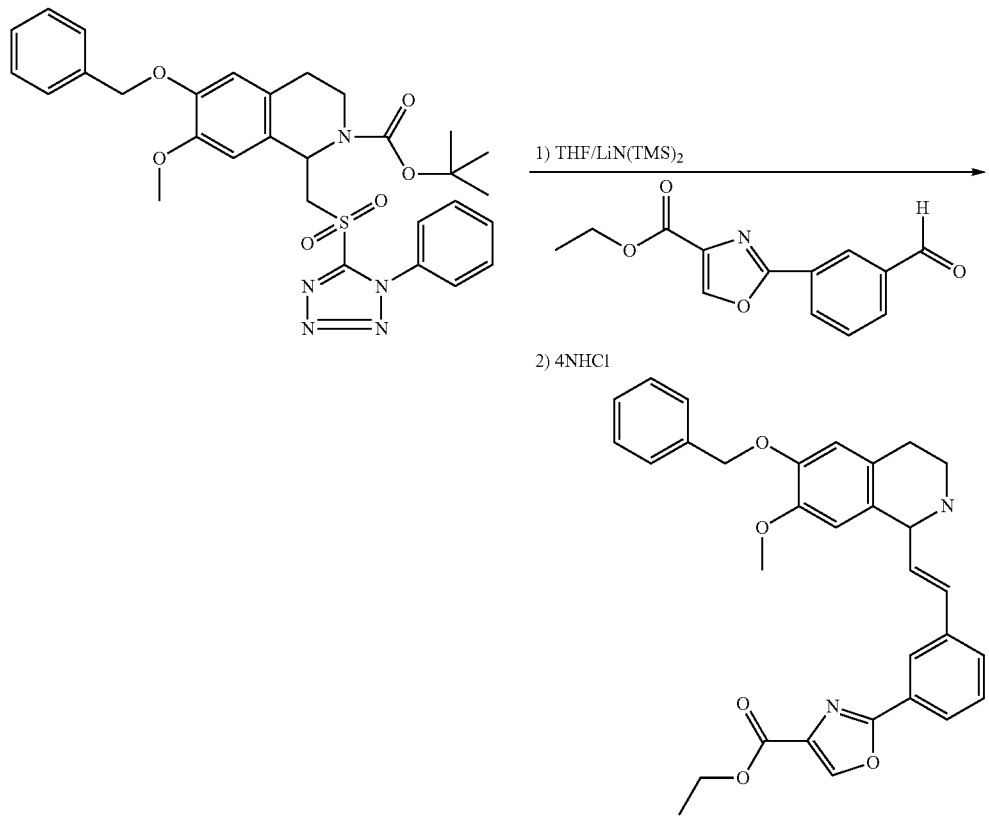

Using the same procedure outlined in Example DP at the same scale with the aldehyde ethyl 2-(3-formylphenyl)oxazole-4-carboxylate the reaction afforded the desired adduct. Yield=25 mg (24%) as TFA salt via prep chrom. MS (m/z): 511 [M+H]

Example EG: 6-Benzyloxy-1-[(E)-2-(2,3-dihydrobenzofuran-6-yl)vinyl]-7-methoxy-1,2,3,4-tetrahydroisoquinoline

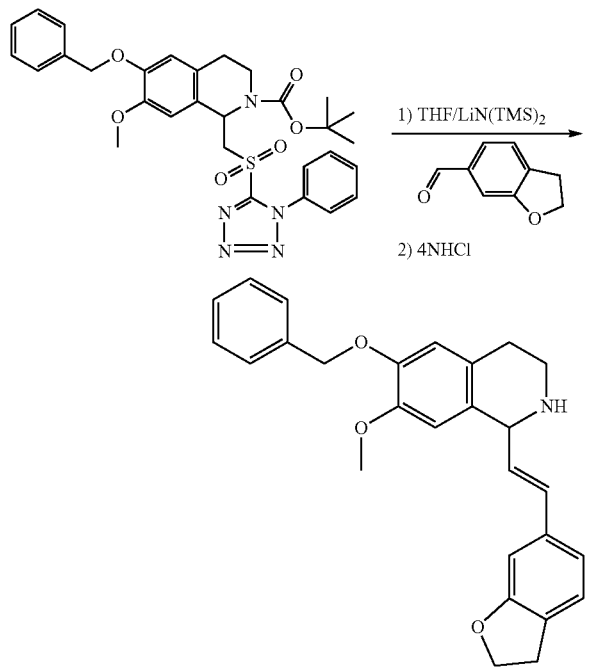

Using the same procedure outlined in Example DP at the same scale with the aldehyde 2,3-dihydrobenzofuran-6-carbaldehyde the reaction afforded the desired adduct. Yield=25 mg (30%) as TFA salt via prep chrom. MS (m/z): 414 [M+H]

Example EH: 6-Benzyloxy-1-[(E)-2-(2,4-dimethoxy-5-methyl-phenyl)vinyl]-7-methoxy-1,2,3,4-tetrahydroisoquinolin

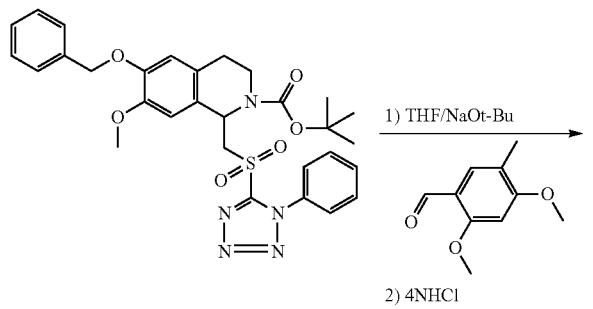

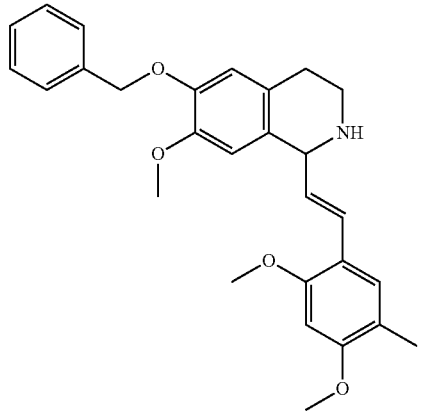

To a solution of tert-butyl 6-benzyloxy-7-methoxy-1-[(1-phenyltetrazol-5-yl)sulfonylmethyl]-3,4-dihydro-1H-isoquinoline-2-carboxylate [118 mg (0.2 mmol)] in THF (5 ml) with 2,4-dimethoxy-5-methyl-benzaldehyde [36 mg (0.2 mmol)] was added at room temperature Na t-butoxide [58 mg (0.6 mmol)]. The reaction was stirred at room temperature for 60 min. The reaction was quenched with sat NH$_4$Cl (10 ml), extracted with EtOAc (20 ml), dried (MgSO$_4$) and the solvent removed. The residue was treated for 1 h with 3NHCl/EtOAc at room temperature then rotary evaporated to a brown oil which was taken up into EtOAc and washed with 2N NaOH. The organic layer was dried (MgSO$_4$) and the solvent removed. The residue was chromatographed via reverse phase chromatography. Yield=3.1 mg (3.5%) as TFA salt via prep chrom. MS (m/z): 446 [M+H]

Example EI: 6-Benzyloxy-7-methoxy-1-[(E)-2-(4-methoxy-3-methyl-phenyl)vinyl]-1,2,3,4-tetrahydroisoquinoline

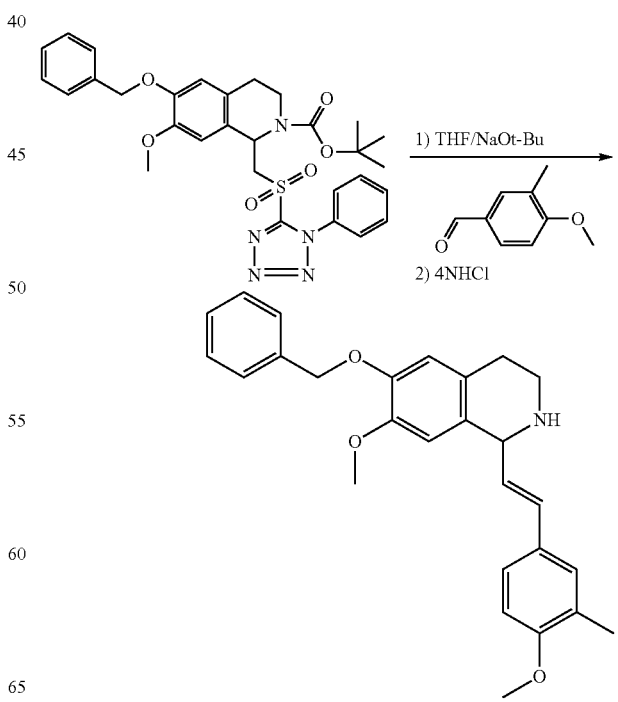

To a solution of tert-butyl 6-benzyloxy-7-methoxy-1-[(1-phenyltetrazol-5-yl)sulfonylmethyl]-3,4-dihydro-1H-isoquinoline-2-carboxylate [118 mg (0.2 mmol)] in THF (5 ml) with 4-methoxy-3-methyl-benzaldehyde [30 mg (0.2 mmol)] was added at room temperature Na t-butoxide [58 mg (0.6 mmol)]. The reaction was stirred at room temperature for 60 min. The reaction was quenched with sat NH₄Cl (10 ml), extracted with EtOAc (20 ml), dried (MgSO4) and the solvent removed. The residue was treated for 1 h with 3NHCl/EtOAc at room temperature then rotary evaporated to a brown oil which was taken up into EtOAc and washed with 2N NaOH. The organic layer was dried (MgSO₄) and the solvent removed. The residue was chromatographed via reverse phase chromatography. Yield=7.2 mg (9%) as TFA salt via prep chrom. MS (m/z): 416 [M+H]

Example EJ: 6-Benzyloxy-7-methoxy-1-[(E)-2-(3-methoxyphenyl)vinyl]-1,2,3,4-tetrahydroisoquinoline

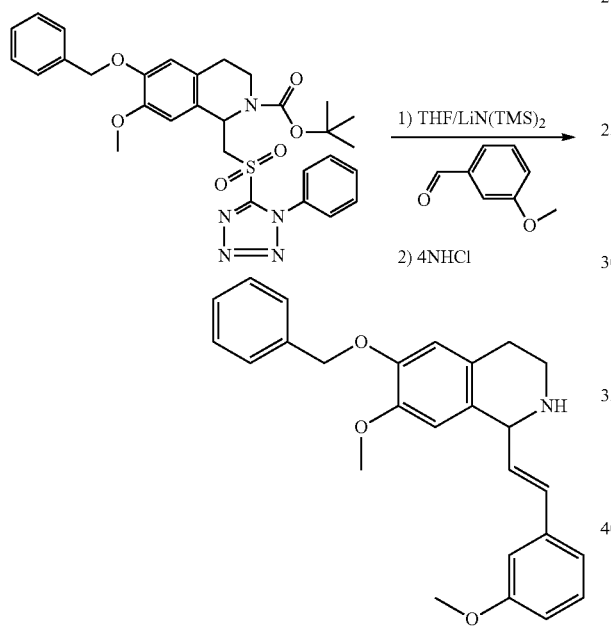

Using the same procedure outlined in Example DP at the same scale with the aldehyde 3-methoxybenzaldehyde the reaction afforded the desired adduct. Yield=37 mg (45%) as TFA salt via prep chrom. MS (m/z): 402 [M+H]

Example EK: 6-Benzyloxy-1-[(E)-2-(2,5-dimethoxyphenyl)vinyl]-7-methoxy-1,2,3,4-tetrahydroisoquinoline

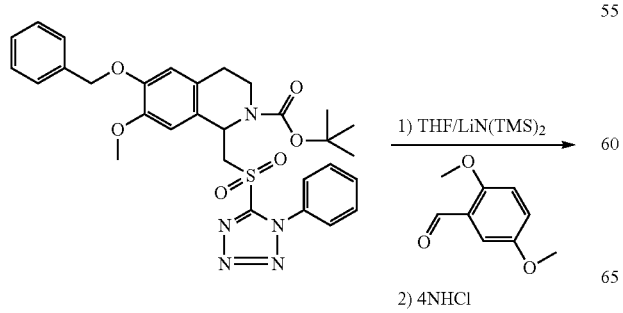

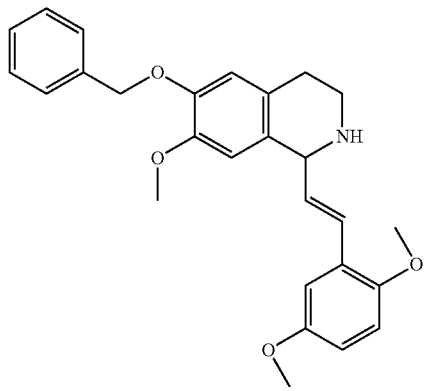

Using the same procedure outlined in Example DP at the same scale with the aldehyde 2,5-dimethoxybenzaldehyde the reaction afforded the desired adduct. Yield=50 mg (57%) as TFA salt via prep chrom. MS (m/z): 432 [M+H]

Example EL: 6-Benzyloxy-7-methoxy-1-[(E)-2-(4-methoxy-2,3-dimethyl-phenyl)vinyl]-1,2,3,4-tetrahydroisoquinoline

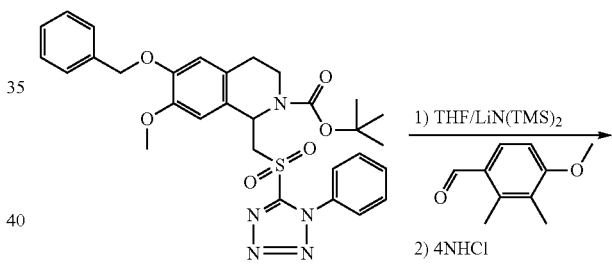

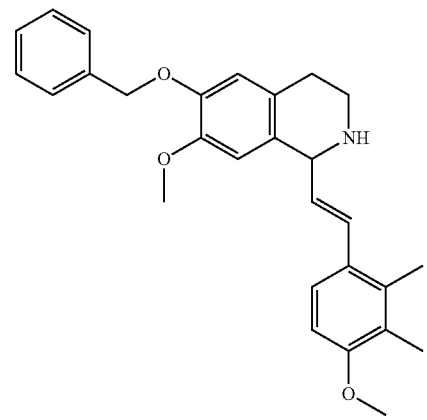

Using the same procedure outlined in Example DP at the same scale with the aldehyde 4-methoxy-2,3-dimethyl-benzaldehyde the reaction afforded the desired adduct. Yield=20 mg (23%) as TFA salt via prep chrom. MS (m/z): 430 [M+H]

Example EM: 6-Benzyloxy-7-methoxy-1-[(E)-2-[4-methoxy-3-(1-piperidylmethyl)phenyl]vinyl]-1,2,3,4-tetrahydroisoquinoline

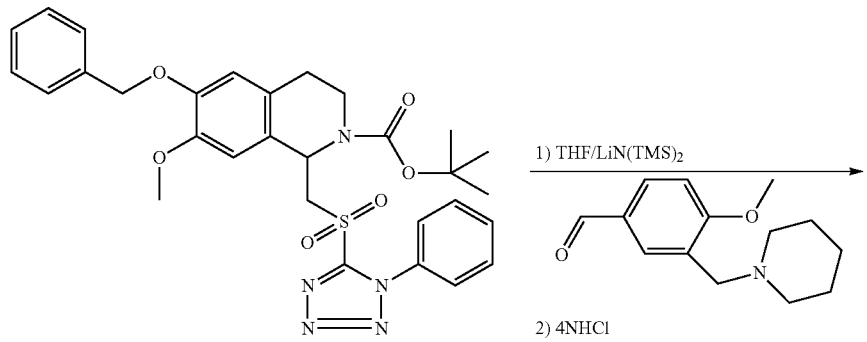

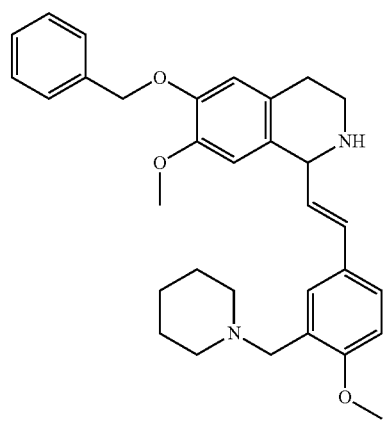

Using the same procedure outlined in Example DP at the same scale with the aldehyde 4-methoxy-2,3-dimethyl-benzaldehyde the reaction afforded the desired adduct. Yield=10 mg (10%) as TFA salt via prep chrom. MS (m/z): 499 [M+H]

Example EN: 6-Benzyloxy-7-methoxy-1-[(E)-2-[4-methoxy-3-[(2-methylimidazol-1-yl)methyl]phenyl]vinyl]-1,2,3,4-tetrahydroisoquinolin

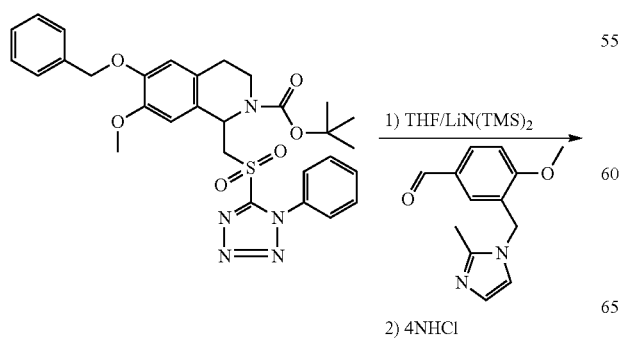

-continued

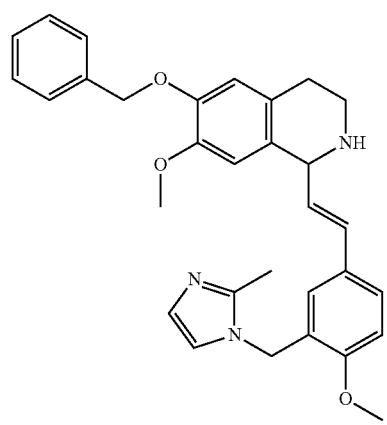

Using the same procedure outlined in Example DP at the same scale with the aldehyde 4-methoxy-3-[(2-methylimidazol-1-yl)methyl]benzaldehyde the reaction afforded the desired adduct. Yield=8.2 mg (8%) as TFA salt via prep chrom. MS (m/z): 496 [M+H]

Example EO: 6-Benzyloxy-7-methoxy-1-[(E)-2-[4-methoxy-3-(2,2,2-trifluoroethoxymethyl)phenyl]vinyl]-1,2,3,4-tetrahydroisoquinoline

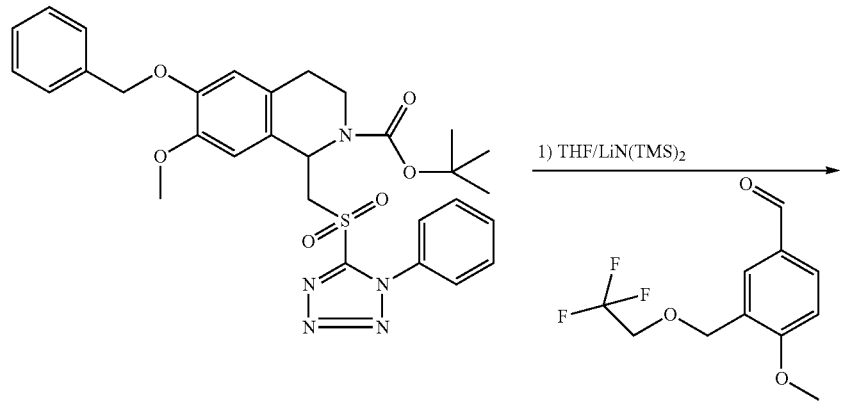

Using the same procedure outlined in Example DP at the same scale with the aldehyde 4-methoxy-3-(2,2,2-trifluoroethoxymethyl)benzaldehyde the reaction afforded the desired adduct. Yield=9 mg (9%) as TFA salt via prep chrom. MS (m/z): 514 [M+H]

Example EP: (E)-6-(benzyloxy)-1-(3-(ethoxymethyl)-4-methoxystyryl)-7-methoxy-1,2,3,4-tetrahydroisoquinoline

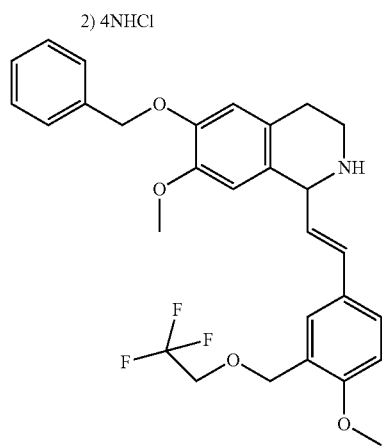

-continued

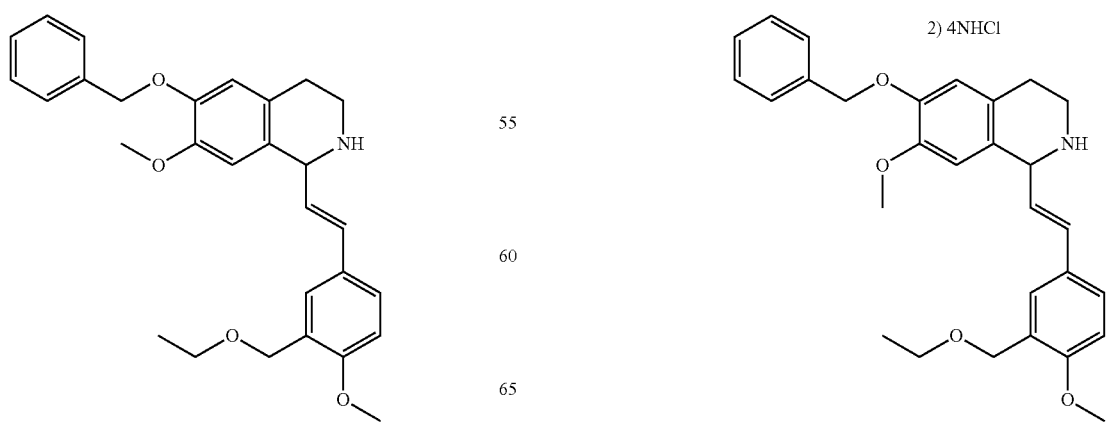

Using the same procedure outlined in Example DP at the same scale with the aldehyde 4-methoxy-3-(methoxymethyl)benzaldehyde the reaction afforded the desired adduct. Yield=11 mg (10%) as TFA salt via prep chrom. MS (m/z): 460 [M+H]

Example EQ: 4-[(E)-2-(6-benzyloxy-7-methoxy-1,2,3,4-tetrahydroisoquinolin-1-yl)vinyl]benzoic acid

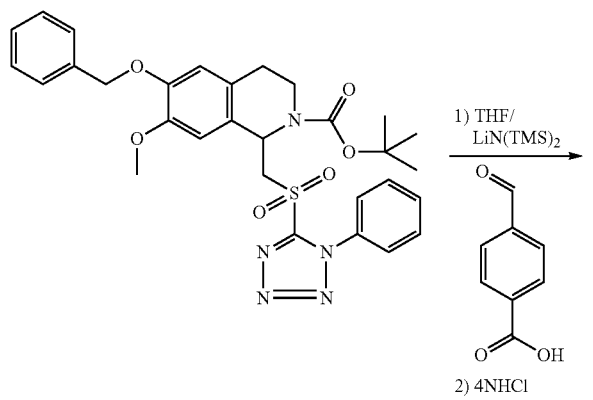

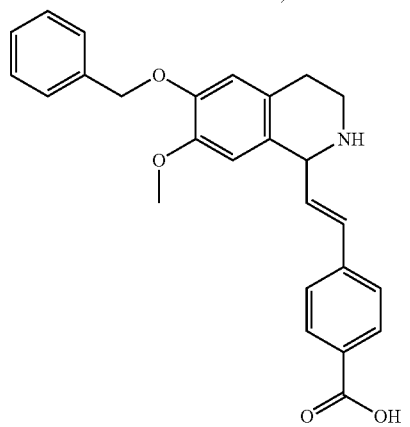

Using the same procedure outlined in Example DP at the same scale with the aldehyde 4-formylbenzoic acid the reaction afforded the desired adduct. Yield=11 mg (13%) as TFA salt via prep chrom. MS (m/z): 416 [M+H]

Example ER: 3-[(E)-2-(6-benzyloxy-7-methoxy-1,2,3,4-tetrahydroisoquinolin-1-yl)vinyl]benzoic acid

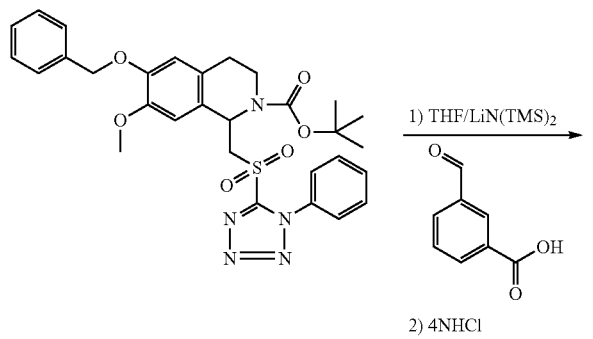

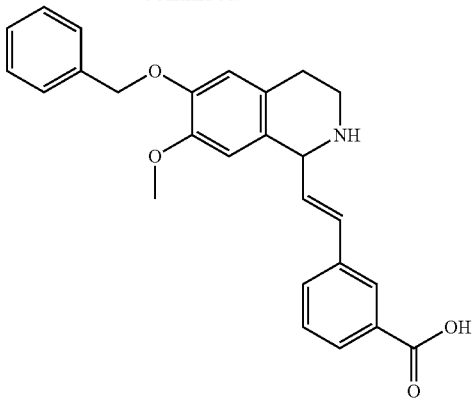

Using the same procedure outlined in Example DP at the same scale with the aldehyde 3-formylbenzoic acid the reaction afforded the desired adduct. Yield=21 mg (25%) as TFA salt via prep chrom. MS (m/z): 416 [M+H]

Example ES: 2-[(E)-2-(6-benzyloxy-7-methoxy-1,2,3,4-tetrahydroisoquinolin-1-yl)vinyl]benzoic acid

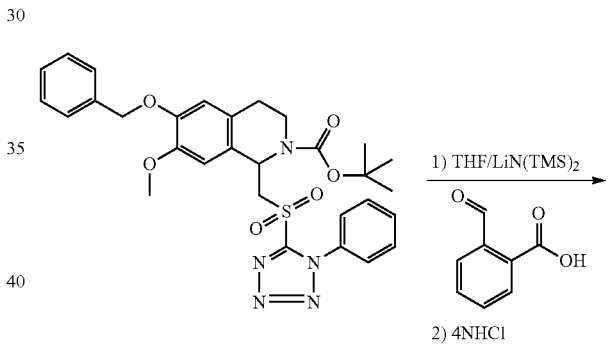

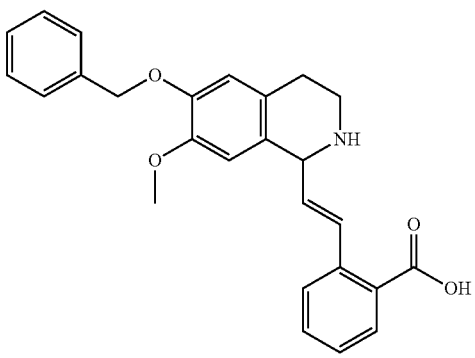

Using the same procedure outlined in Example DP at the same scale with the aldehyde 2-formylbenzoic acid the reaction afforded the desired adduct. Yield=2.6 mg (3% overall) as TFA salt via prep chrom. MS (m/z): 416 [M+H]

Example ET: Ethyl 2-[(E)-2-(6-benzyloxy-7-methoxy-1,2,3,4-tetrahydroisoquinolin-1-yl)vinyl]benzoate

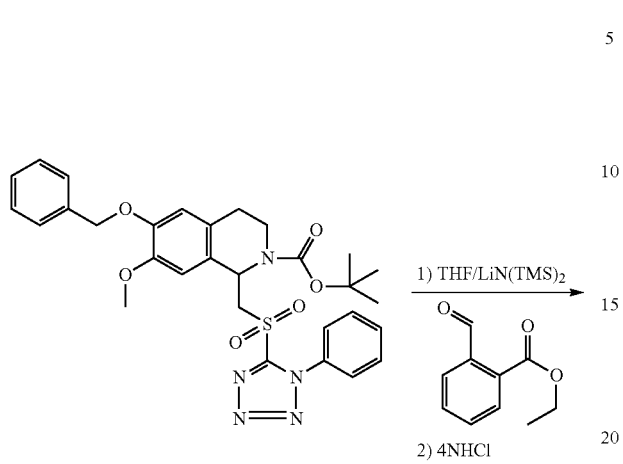

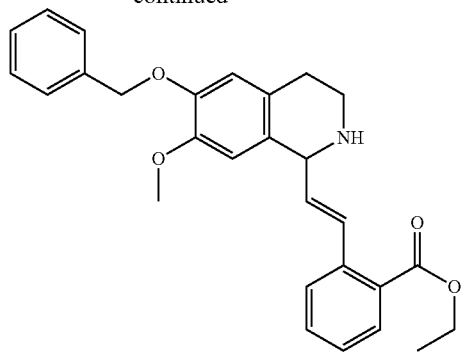

Using the same procedure outlined in Example DP at the same scale with the aldehyde ethyl 2-formylbenzoate the reaction afforded the desired adduct. Yield=11.7 mg (13% overall) as TFA salt via prep chrom. MS (m/z): 444 [M+H]

Example EU: 6-Benzyloxy-7-methoxy-1-[(E)-2-[4-methoxy-3-(phenoxymethyl)phenyl]vinyl]-1,2,3,4-tetrahydroisoquinolin

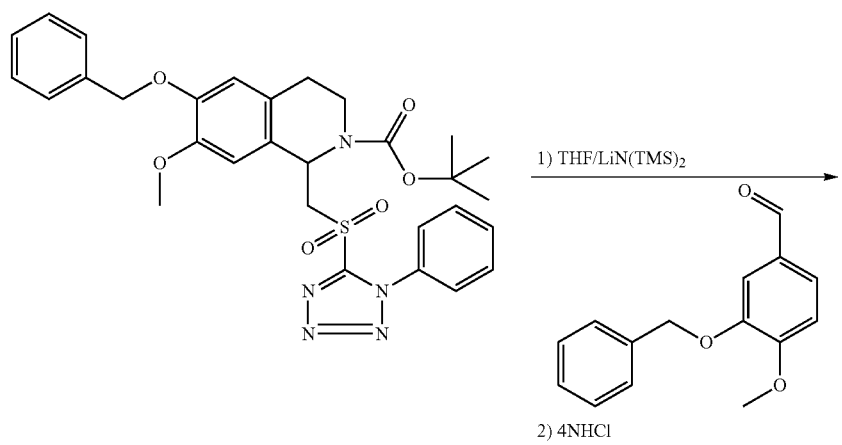

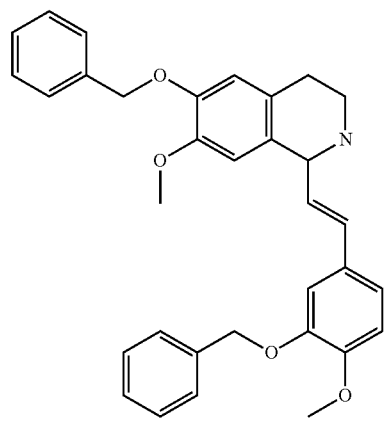

Using the same procedure outlined in Example DP at the same scale with the aldehyde 4-methoxy-3-(phenoxymethyl)benzaldehyde the reaction afforded the desired adduct. Yield=7.3 mg (6% overall) as TFA salt via prep chrom. MS (m/z): 508 [M+H]

Data for Biological Examples
Protocol for MT-2 Spread Assay

The present assay was used to screen candidate antiviral compounds by quantification of virus spread and production over several rounds of infection in vitro. MT-2, a HIV-1 permissive human T-cell line, was seeded in microtiter plates and was simultaneously treated with serially diluted compound and inoculated with a HIV-1 NL4-3 viral clone engineered to express *Renilla* luciferase in place of Nef. Following treatment, the culture was incubated for 96 hours. After the incubation, media was collected and used to estimate relative infectivity on the indicator cell line, TZM-bl. Additionally, viral spread was quantified by measuring luciferase activity via a commercially available luciferase substrate. In parallel, MT-2 cells were seeded and inoculated with mock virus in the presence of serially diluted compound. Compound toxicity was quantified 96 hours after treatment with AlamarBlue.

Compound Treatment and Infection:

MT-2 (NIH Aids reagent program 237) cells were grown and maintained in an incubator at 37° C. with 5% $CO_2$ using a basal medium of RPMI-1640 supplemented with 10% FBS. Cells were seeded in 100 µl at $2\times10^4$ cells/well in white walled 96-well microtiter plates. Candidate compounds were 3-fold serially diluted in the appropriate solvent. Solvent without compound was used as a no drug reference. Cells were inoculated at a multiplicity of 0.027 with an HIV-1 NL4-3 virus stock engineered to express *Renilla* luciferase in place of Nef. Diluted virus stock was first added to serially diluted compound. Compound and virus were delivered to cells in an equal volume (100 µl) and treated cultures were returned to the incubator for 96 hours. In parallel, plates for cytotoxicity estimates were prepared in the same way except cells were plated in clear walled 96-well microtiter plates and were mock infected.

Infectivity Assay:

At 96 hours post infection, 100 µl virus containing culture supernatant was collected from the treated and infected cultures and serially diluted in DMEM supplemented with 10% FBS, 1% sodium pyruvate, and 20 µg/ml DEAE dextran. One day prior, TZM-bl (ATCC PTA-5659) were cultured in basal medium of DMEM supplemented with 10% FBS and 1% sodium pyruvate and seeded at $7.5\times10^3$ cells/well in black walled 96-well microtiter plates. Diluted virus containing culture supernatant was transferred to TZM-bl cultures and incubated for 48 hours at 37° C. with 5% $CO_2$. Infected TZM-bl cultures were fixed for 5 minutes with a 1% formaldehyde/0.2% gluteraldehyde/PBS solution then washed three times with PBS. Fixed cultures were incubated at 37° C. for 25 minutes with a 200 µg/ml MUG (4-Methylumbelliferyl β-D-glucopyranoside)/DMEM solution. The reaction was stopped with an equal volume of 1M sodium carbonate and read at 360, 449 nm on fluorescence plate reader (Biotek).

(Viral Spread) Luciferase Assay:

At 96 hours post infection, 100 µl of culture supernatant was removed from the treated and infected cultures and EnduRen live cell substrate (Promega) was added at a final concentration 1.3 µg/ml. Cells were incubated for 1.5 hours at 37° C. with 5% $CO_2$ then read on a luminescence plate reader (Biotek).

Cytotoxicity Assay:

At 96 hours post treatment, 20 µl AlamarBlue proliferation reagent was added to 200 µl treated and mock infected cultures and incubated for 3 hours at 37° C. with 5% $CO_2$ then read at 545, 590 nm on fluorescence plate reader (Biotek).

Analysis:

For all assays, data was imported into Accelrys Assay Explorer 3.3. In Assay Explorer, % inhibition (antiviral or cytotoxicity) was calculated using the solvent control as a reference by the following equation: $1-(\text{Signal}_{Compound}/\text{Signal}_{Reference})$. The % Inhibition and compound concentration data was fitted using the following 4-parameter logistic model (Assay Explorer model 42):

$$Y = D + \left( \frac{A - d}{1 + \left(\frac{X}{C}\right)^B} \right)$$

where X is compound concentration, Y is % inhibition, D is the maximum % Inhibition (constrained to 100%), C is IC50 value or inflection point, B is the hill slope, and A is the minimum % inhibition (constrained to 0%). The IC50 value is reported as the EC50 or CC50 depending on the assay endpoint. EC50 represents the effective concentration at which virus replication is inhibited by 50 percent. CC50 represents the concentration that results in the death of 50 percent of the host cells. The selectivity or therapeutic index (SI or TI), is the ratio of CC50 over EC50 and represents the relative effectiveness in inhibiting viral replication compared to inducing cell death.

TABLE

| Code | Structure Name | $EC_{50}$, µM | $CC_{50}$, µM | SI |
| --- | --- | --- | --- | --- |
| A | 1-[2-(3,4-dimethoxyphenyl)ethyl]-6,7-dimethoxy-1,2,3,4-tetrahydroisoquinoline | 10 | >10 | 1 |
| B | [6-benzyloxy-1-[(E)-2-(3-benzyloxy-4-methoxy-phenyl)vinyl]-7-methoxy-3,4-dihydro-1H-isoquinolin-2-yl]-pyrazin-2-yl-methanone | 10 | 5 | 0.5 |
| C | 1-[(E)-2-(5-benzyloxy-4-methoxy-2-methyl-phenyl)vinyl]-6,7-dimethoxy-1,2,3,4-tetrahydroisoquinoline | 9.76 | 10.96 | 1.1 |
| D | 7-benzyloxy-1-[(E)-2-(4-benzyloxy-3-methoxy-phenyl)vinyl]-2-butyl-6-methoxy-3,4-dihydro-1H-isoquinoline | 8.92 | >10 | >1.1 |
| E | 6-benzyloxy-1-[(E)-2-(5-benzyloxy-4-methoxy-2-methyl-phenyl)vinyl]- | 8.47 | 7.17 | 0.8 |

TABLE-continued

| Code | Structure Name | EC$_{50}$, μM | CC$_{50}$, μM | SI |
|---|---|---|---|---|
| | 7-methoxy-2-methyl-3,4-dihydro-1H-isoquinoline | | | |
| F | (6-amino-2-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone | 5.05 | 100 | 19.8 |
| G | 6-benzyloxy-1-[(E)-2-(3-benzyloxy-4-methoxy-phenyl)vinyl]-2-butyl-7-methoxy-3,4-dihydro-1H-isoquinoline | 5 | 5 | 1 |
| H | [6-benzyloxy-1-[(E)-2-(5-benzyloxy-4-methoxy-2-methyl-phenyl)vinyl]-7-methoxy-3,4-dihydro-1H-isoquinolin-2-yl]-pyrazin-2-yl-methanone | 4.48 | 100 | 22.3 |
| I | methyl 6-benzyloxy-1-[(E)-2-(4,5-dimethoxy-2-methyl-phenyl)vinyl]-7-methoxy-3,4-dihydro-1H-isoquinoline-2-carboxylate | 4.48 | 100 | 22.3 |
| J | 6-benzyloxy-1-[(E)-2-(5-benzyloxy-2-tert-butyl-4-methoxy-phenyl)vinyl]-7-methoxy-1,2,3,4-tetrahydroisoquinoline | 4.22 | 5.36 | 1.27 |
| K | (2-amino-3-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone | 2.88 | 100 | 34.72 |
| L | methyl 6-benzyloxy-1-[(E)-2-(3-benzyloxy-4-methoxy-phenyl)vinyl]-7-methoxy-3,4-dihydro-1H-isoquinoline-2-carboxylate | 2.81 | >20 | 7.11 |
| M | [6-benzyloxy-1-[(E)-2-(5-benzyloxy-4-methoxy-2-methyl-phenyl)vinyl]-7-methoxy-3,4-dihydro-1H-isoquinolin-2-yl]-(2-pyridyl)methanone | 2.09 | 100 | 47.8 |
| N | (2-amino-4-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone | 2.03 | 100 | 49.3 |
| O | 6-benzyloxy-1-[(E)-2-(5-benzyloxy-4-methoxy-2-methyl-phenyl)vinyl]-N-tert-butyl-7-methoxy-3,4-dihydro-1H-isoquinoline-2-carboxamide | 2.011 | >10 | >5 |
| P | (6-amino-3-pyridyl)-[6-benzyloxy-1-[(E)-2-(5-benzyloxy-4-methoxy-2-methyl-phenyl)vinyl]-7-methoxy-3,4-dihydro-1H-isoquinolin-2-yl]methanone | 1.69 | 100 | 59.17 |
| Q | 6-benzyloxy-1-[2-(5-benzyloxy-4-methoxy-2-methyl-phenyl)ethyl]-7-methoxy-1,2,3,4-tetrahydroisoquinoline | 1.36 | 5.15 | 3.8 |
| R | 6-benzyloxy-1-[(E)-2-(5-benzyloxy-4-methoxy-2-methyl-phenyl)vinyl]-7-methoxy-3,4-dihydro-1H-isoquinoline-2-carboxamide | 1.18 | 39.31 | 33.1 |
| S | 7-benzyloxy-1-[(E)-2-(4-benzyloxy-3-methoxy-phenyl)vinyl]-6-methoxy-1,2,3,4-tetrahydroisoquinoline | 0.992 | 8.25 | 8.3 |
| T | [6-benzyloxy-1-[(E)-2-(5-benzyloxy-4-methoxy-2-methyl-phenyl)vinyl]-7-methoxy-3,4-dihydro-1H-isoquinolin-2-yl]-(3-pyridyl)methanone | 0.93 | 100 | 107 |
| U | [6-benzyloxy-1-[(E)-2-(5-benzyloxy-4-methoxy-2-methyl-phenyl)vinyl]-7-methoxy-3,4-dihydro-1H-isoquinolin-2-yl]-(4-pyridyl)methanone | 0.87 | >100 | >115 |
| V | 6-benzyloxy-1-[(E)-2-(3-benzyloxy-4-methoxy-phenyl)vinyl]-7- | 0.78 | 6.68 | 8.5 |

TABLE-continued

| Code | Structure Name | EC$_{50}$, μM | CC$_{50}$, μM | SI |
|---|---|---|---|---|
| | methoxy-2-methyl-3,4-dihydro-1H-isoquinoline | | | |
| W | 6-benzyloxy-7-methoxy-1-[(E)-2-(o-tolyl)vinyl]-1,2,3,4-tetrahydroisoquinoline | 0.69 | 4 | 5.8 |
| X | 6-benzyloxy-1-[(E)-2-(4-fluoro-2-methyl-phenyl)vinyl]-7-methoxy-1,2,3,4-tetrahydroisoquinoline | 0.62 | 5.3 | 8.53 |
| Y | tert-butyl 6-benzyloxy-1-[(E)-2-(5-benzyloxy-4-methoxy-2-methyl-phenyl)vinyl]-7-methoxy-3,4-dihydro-1H-isoquinoline-2-carboxylate | 0.39 | 28.1 | 71.2 |
| Z | 6-benzyloxy-7-methoxy-1-[(E)-2-[4-methoxy-2-(trifluoromethyl)phenyl]vinyl]-1,2,3,4-tetrahydroisoquinoline | 0.35 | 100 | 17.1 |
| AA | 6-benzyloxy-1-[(E)-2-(5-benzyloxy-2-ethyl-4-methoxy-phenyl)vinyl]-7-methoxy-1,2,3,4-tetrahydroisoquinoline | 0.148 | 3.89 | 26.3 |
| AB | 6-benzyloxy-1-[(E)-2-(3-benzyloxy-4-methoxy-phenyl)vinyl]-7-methoxy-1,2,3,4-tetrahydroisoquinoline | 0.146 | 3.96 | 27.1 |
| AC | 6-benzyloxy-1-[(E)-2-(5-benzyloxy-2-chloro-4-methoxy-phenyl)vinyl]-7-methoxy-1,2,3,4-tetrahydroisoquinoline | 0.0872 | 1.8993 | 21.8 |
| AD | 6-benzyloxy-1-[(E)-2-(5-benzyloxy-2-methyl-phenyl)vinyl]-7-methoxy-1,2,3,4-tetrahydroisoquinoline | 0.084 | 3.22 | 38.1 |
| AE | 6-benzyloxy-1-[(E)-2-(5-benzyloxy-4-methoxy-2-methyl-phenyl)vinyl]-7-methoxy-3,4-dihydroisoquinoline | 0.44 | 33.53 | 76.5 |
| AF | 6-benzyloxy-1-[(E)-2-(5-benzyloxy-4-methoxy-2-methyl-phenyl)vinyl]-7-methoxy-1,2,3,4-tetrahydroisoquinoline | 0.083 | 3.873 | 48.2 |
| AG | 6-benzyloxy-7-methoxy-1-[(E)-2-(4-methoxy-2-methyl-phenyl)vinyl]-1,2,3,4-tetrahydroisoquinoline | 0.0771 | 9.83 | 127.4 |
| AH | 6-benzyloxy-1-[(E)-2-(4,5-dimethoxy-2-methyl-phenyl)vinyl]-7-methoxy-1,2,3,4-tetrahydroisoquinoline | 0.0133 | 2.404 | 180.8 |
| AI | 6-(benzyloxy)-7-methoxy-1-[(E)-2-[4-methoxy-2-(4-methoxybutoxy)phenyl]ethenyl]-1,2,3,4-tetrahydroisoquinoline | 1.5 | 5.6 | 3.9 |
| AJ | 6-(benzyloxy)-7-methoxy-1-[(E)-2-[2-methyl-4-(trifluoromethoxy)phenyl]ethenyl]-1,2,3,4-tetrahydroisoquinoline | 2.74 | 5 | 1.83 |
| AK | 6-(benzyloxy)-7-methoxy-1-[(E)-2-(1-methyl-1H-pyrazol-5-yl)ethenyl]-1,2,3,4-tetrahydroisoquinoline | 8.87 | 10 | 1.1 |
| AL | 6-(benzyloxy)-1-[(E)-2-(1-ethyl-1H-pyrazol-4-yl)ethenyl]-7-methoxy-1,2,3,4-tetrahydroisoquinoline | 2.95 | 24.2 | 8.2 |
| AM | 6-(benzyloxy)-7-methoxy-1-[(E)-2-(3,4,5-trimethoxyphenyl)ethenyl]-1,2,3,4-tetrahydroisoquinoline | 0.22 | 6 | 27.3 |
| AN | 6-(benzyloxy)-7-methoxy-1-[(E)-2-(7-methoxy-1-benzofuran-4-yl)ethenyl]-1,2,3,4-tetrahydroisoquinoline | 0.14 | 3.7 | 26.8 |
| AO | 6-(benzyloxy)-7-methoxy-1-[(E)-2-(4-methoxy-1-benzofuran-7-yl)ethenyl]-1,2,3,4-tetrahydroisoquinoline | 1.13 | 9.94 | 8.8 |
| AP | 6-(benzyloxy)-1-[(E)-2-[4-(benzyloxy)-3,5-dimethoxyphenyl]ethenyl]-7-methoxy-1,2,3,4-tetrahydroisoquinoline | 0.97 | 1.64 | 1.7 |

TABLE-continued

| Code | Structure Name | EC$_{50}$, μM | CC$_{50}$, μM | SI |
|---|---|---|---|---|
| AQ | 6-(benzyloxy)-7-methoxy-1-[(E)-2-(2,4,5-trimethoxyphenyl)ethenyl]-1,2,3,4-tetrahydroisoquinoline | 0.0151 | 1.98 | 131.1 |
| AR | 6-(benzyloxy)-1-[(E)-2-(3-bromo-4-methoxyphenyl)ethenyl]-7-methoxy-1,2,3,4-tetrahydroisoquinoline | 0.8 | 6.2 | 8.2 |
| AS | 6-(benzyloxy)-1-[(E)-2-[5-(benzyloxy)-2-tert-butyl-4-methoxyphenyl]ethenyl]-7-methoxy-1,2,3,4-tetrahydroisoquinoline | 4.22 | 5.36 | 1.3 |
| AT | 6-(benzyloxy)-1-[(E)-2-(3,5-dimethoxyphenyl)ethenyl]-7-methoxy-1,2,3,4-tetrahydroisoquinoline | 0.77 | 4.85 | 6.3 |
| AU | 6-benzyloxy-7-methoxy-1-[(E)-2-(2-methoxy-4-pyridyl)vinyl]-1,2,3,4-tetrahydroisoquinoline | 1.65 | 3.22 | 2 |
| AV | 6-(benzyloxy)-1-[(E)-2-(2,4-dimethoxyphenyl)ethenyl]-7-methoxy-1,2,3,4-tetrahydroisoquinoline | 0.14 | 5.5 | 39.3 |
| AW | 6-(benzyloxy)-7-methoxy-1-[(E)-2-(pyridin-4-yl)ethenyl]-1,2,3,4-tetrahydroisoquinoline | 3.28 | 11.36 | 3.5 |
| AX | 6-benzyloxy-7-methoxy-1-[(E)-2-(6-methoxy-3-pyridyl)vinyl]-1,2,3,4-tetrahydroisoquinoline | 3.28 | 11.36 | 3.5 |
| AY | 6-(benzyloxy)-1-[5-(benzyloxy)-4-methoxy-2-methylphenyl]-7-methoxy-1,2,3,4-tetrahydroisoquinoline | 4.88 | 5.14 | 1.1 |
| AZ | tert-butyl N-({2-[6-(benzyloxy)-7-methoxy-1,2,3,4-tetrahydroisoquinolin-1-yl]phenyl}methyl)carbamate | 2.77 | 9.48 | 12.3 |
| BA | 6-(benzyloxy)-7-methoxy-1-[(E)-2-(4-methoxy-2,6-dimethylphenyl)ethenyl]-1,2,3,4-tetrahydroisoquinoline | 0.497 | 3.33 | 6.7 |
| BB | 6-(benzyloxy)-7-methoxy-1-[(E)-2-(6-methyl-2H-1,3-benzodioxol-5-yl)ethenyl]-1,2,3,4-tetrahydroisoquinoline | 0.0544 | 2.98 | 54.9 |
| BC | 6-(benzyloxy)-7-methoxy-1-[(E)-2-(7-methyl-2,3-dihydro-1,4-benzodioxin-6-yl)ethenyl]-1,2,3,4-tetrahydroisoquinoline | 0.0271 | 2.43 | 90.6 |
| BD | 6-(benzyloxy)-1-[(E)-2-(4-butoxy-3-methoxyphenyl)ethenyl]-7-methoxy-1,2,3,4-tetrahydroisoquinoline | 0.408 | 3.62 | 8.9 |
| BE | 6-(benzyloxy)-1-[(E)-2-(3-butoxy-4-methoxyphenyl)ethenyl]-7-methoxy-1,2,3,4-tetrahydroisoquinoline | 0.0998 | 3.75 | 37.6 |
| BF | 6-(benzyloxy)-1-[(E)-2-(3-fluoro-4-methoxyphenyl)ethenyl]-7-methoxy-1,2,3,4-tetrahydroisoquinoline | 1.02 | 33.507 | 32.85 |
| BG | 4-[(E)-2-[6-(benzyloxy)-7-methoxy-1,2,3,4-tetrahydroisoquinolin-1-yl]ethenyl]-N,N,3-trimethylaniline | 1.65 | 4.44 | 2.69 |
| BH | 6-(benzyloxy)-7-methoxy-1-[(E)-2-[2-methyl-5-(trifluoromethoxy)phenyl]ethenyl]-1,2,3,4-tetrahydroisoquinoline | 1.93 | 5.3 | 2.75 |
| BI | 6-(benzyloxy)-7-methoxy-1-[(E)-2-phenylethenyl]-1,2,3,4-tetrahydroisoquinoline | 2.2 | 10 | 4.5 |
| BJ | 6-(benzyloxy)-7-methoxy-1-[(E)-2-(4-methoxyphenyl)ethenyl]-1,2,3,4-tetrahydroisoquinoline | 0.477 | 20.901 | 43.54 |
| BK | 6-(benzyloxy)-1-[(E)-2-[3-(benzyloxy)phenyl]ethenyl]-7-methoxy-1,2,3,4-tetrahydroisoquinoline | 0.26 | 4 | 15.4 |

TABLE-continued

| Code | Structure Name | EC$_{50}$, μM | CC$_{50}$, μM | SI |
|---|---|---|---|---|
| BL | 6-(benzyloxy)-1-[(E)-2-(5-butoxy-4-methoxy-2-methylphenyl)ethenyl]-7-methoxy-1,2,3,4-tetrahydroisoquinoline | 0.052 | 1.1 | 21.2 |
| BM | 6-(benzyloxy)-1-[(E)-2-(2,3-dihydro-1-benzofuran-5-yl)ethenyl]-7-methoxy-1,2,3,4-tetrahydroisoquinoline | 0.146 | 20.43 | 139.8 |
| BN | 1-[(E)-2-(1-benzofuran-5-yl)ethenyl]-6-(benzyloxy)-7-methoxy-1,2,3,4-tetrahydroisoquinoline | 0.84 | 20.65 | 24.8 |
| BO | 4-{5-[(E)-2-[6-(benzyloxy)-7-methoxy-1,2,3,4-tetrahydroisoquinolin-1-yl]ethenyl]-2-methoxy-4-methylphenoxy}butanoic acid | 0.234 | 8.96 | 38.3 |
| BP | 6-(benzyloxy)-1-[(E)-2-(2-fluoro-4,5-dimethoxyphenyl)ethenyl]-7-methoxy-1,2,3,4-tetrahydroisoquinoline | 2.03 | 5.61 | 2.76 |
| BQ | 6-(benzyloxy)-1-[(E)-2-(3,4-dimethoxyphenyl)ethenyl]-7-methoxy-1,2,3,4-tetrahydroisoquinoline | 0.198 | 8.7 | 43.5 |
| BR | 6-(benzyloxy)-1-[(E)-2-(2-fluoro-4-methoxyphenyl)ethenyl]-7-methoxy-1,2,3,4-tetrahydroisoquinoline | 1.14 | 10 | 8.77 |
| BS | 6-(benzyloxy)-7-methoxy-1-[(E)-2-(3-methylthiophen-2-yl)ethenyl]-1,2,3,4-tetrahydroisoquinoline | 2.87 | 11.31 | 3.94 |
| BT | 6-(benzyloxy)-1-[(E)-2-(1H-indazol-6-yl)ethenyl]-7-methoxy-1,2,3,4-tetrahydroisoquinoline | 0.613 | 7.98 | 13.02 |
| BU | 6-(benzyloxy)-1-[(E)-2-(2,6-difluoro-4-methoxyphenyl)ethenyl]-7-methoxy-1,2,3,4-tetrahydroisoquinoline | 1.02 | 10.56 | 10.4 |
| BV | 6-(benzyloxy)-7-methoxy-1-[(E)-2-(4-methoxy-2,5-dimethylphenyl)ethenyl]-1,2,3,4-tetrahydroisoquinoline | 0.304 | 2.63 | 8.7 |
| BW | 6-(benzyloxy)-7-methoxy-1-[(E)-2-[4-methoxy-2-methyl-5-(propan-2-yl)phenyl]ethenyl]-1,2,3,4-tetrahydroisoquinoline | 0.84 | 1.88 | 2.2 |
| BX | 6-(benzyloxy)-1-[(E)-2-[5-(2,2-dimethylpropoxy)-4-methoxy-2-methylphenyl]ethenyl]-7-methoxy-1,2,3,4-tetrahydroisoquinoline | 0.35 | 3.4 | 9.71 |
| BY | 6-(benzyloxy)-7-methoxy-1-[(E)-2-[4-methoxy-2-methyl-5-(piperidin-4-ylmethoxy)phenyl]ethenyl]-1,2,3,4-tetrahydroisoquinoline | 0.397 | 1.97 | 5 |
| BZ | 6-(benzyloxy)-1-[(E)-2-(4-methanesulfonylphenyl)ethenyl]-7-methoxy-1,2,3,4-tetrahydroisoquinoline | 1 | 1 | 1 |
| CA | 6-(benzyloxy)-1-[(E)-2-(2,6-dimethoxypyridin-3-yl)ethenyl]-7-methoxy-1,2,3,4-tetrahydroisoquinoline | 0.64 | 15.3 | 23.9 |
| CB | 6-(benzyloxy)-1-[(E)-2-(3,4-dihydro-2H-1-benzopyran-6-yl)ethenyl]-7-methoxy-1,2,3,4-tetrahydroisoquinoline | 1.55 | 5.36 | 3.5 |
| CC | 6-(benzyloxy)-7-methoxy-1-[(E)-2-(7-methyl-3,4-dihydro-2H-1-benzopyran-8-yl)ethenyl]-1,2,3,4-tetrahydroisoquinoline | 1.18 | 5.44 | 4.6 |
| CD | 1-[(E)-2-[5-(4-azidobutoxy)-4-methoxy-2-methylphenyl]ethenyl]-6-(benzyloxy)-7-methoxy-1,2,3,4-tetrahydroisoquinoline | 0.088 | 1.63 | 18.5 |

TABLE-continued

| Code | Structure Name | EC$_{50}$, µM | CC$_{50}$, µM | SI |
|---|---|---|---|---|
| CE | 6-(benzyloxy)-7-methoxy-1-[(E)-2-(7-methyl-3,4-dihydro-2H-1-benzopyran-6-yl)ethenyl]-1,2,3,4-tetrahydroisoquinoline | 0.125 | 4.87 | 38.9 |
| CF | 6-(benzyloxy)-1-[(E)-2-(3,4-dihydro-2H-1-benzopyran-8-yl)ethenyl]-7-methoxy-1,2,3,4-tetrahydroisoquinoline | 0.49 | 9.1 | 18.6 |
| CG | 6-(benzyloxy)-7-methoxy-1-[(E)-2-(6-methyl-2,3-dihydro-1-benzofuran-5-yl)ethenyl]-1,2,3,4-tetrahydroisoquinoline | 0.14 | 4.8 | 34.3 |
| CH | tert-butyl 2-[(E)-2-[6-(benzyloxy)-7-methoxy-1,2,3,4-tetrahydroisoquinolin-1-yl]ethenyl]-1H-indole-1-carboxylate | 0.58 | 3.48 | 6 |
| CI | tert-butyl 3-[(E)-2-[6-(benzyloxy)-7-methoxy-1,2,3,4-tetrahydroisoquinolin-1-yl]ethenyl]-1H-indole-1-carboxylate | 0.23 | 4.98 | 21.7 |
| CJ | 6-(benzyloxy)-1-[(E)-2-(1H-indol-3-yl)ethenyl]-7-methoxy-1,2,3,4-tetrahydroisoquinoline | 0.47 | 6.55 | 13.9 |
| CV | ethyl 4-{5-[(E)-2-[6-(benzyloxy)-7-methoxy-1,2,3,4-tetrahydroisoquinolin-1-yl]ethenyl]-2-methoxyphenoxy}butanoate | 0.1 | 2.7 | 20 |
| CW | tert-butyl N-{2-[(E)-2-[6-(benzyloxy)-7-methoxy-1,2,3,4-tetrahydroisoquinolin-1-yl]ethenyl]phenyl}carbamate | 5.4 | 23.6 | 4.3 |
| CX | 2-[(E)-2-[6-(benzyloxy)-7-methoxy-1,2,3,4-tetrahydroisoquinolin-1-yl]ethenyl]aniline | 1.4 | 20.8 | 14 |
| CY | 6-(benzyloxy)-7-methoxy-1-[(E)-2-[4-methoxy-3-(trifluoromethyl)phenyl]ethenyl]-1,2,3,4-tetrahydroisoquinoline | 0.697 | 4 | 5.7 |
| CZ | 6-(benzyloxy)-7-methoxy-1-[(E)-2-[4-methoxy-3-methyl-5-(trifluoromethyl)phenyl]ethenyl]-1,2,3,4-tetrahydroisoquinoline | 2.188 | 4 | 1.8 |
| DA | 6-(benzyloxy)-7-methoxy-1-[(E)-2-[2-(trifluoromethyl)phenyl]ethenyl]-1,2,3,4-tetrahydroisoquinoline | 2.34 | 10 | 4.3 |
| DB | 6-(benzyloxy)-7-methoxy-1-[(E)-2-[3-(trifluoromethyl)phenyl]ethenyl]-1,2,3,4-tetrahydroisoquinoline | 2.67 | 10 | 3.7 |
| DC | 2-[(E)-2-[6-(benzyloxy)-7-methoxy-1,2,3,4-tetrahydroisoquinolin-1-yl]ethenyl]-N,N-dimethylaniline | 0.83 | 10 | 12.1 |
| DD | 6-(benzyloxy)-7-methoxy-1-[(E)-2-(2-methoxypyrimidin-5-yl)ethenyl]-1,2,3,4-tetrahydroisoquinoline | 11.06 | 100 | 9 |
| DE | 6-(benzyloxy)-7-methoxy-1-[(E)-2-[2-(2-methoxyethoxy)phenyl]ethenyl]-1,2,3,4-tetrahydroisoquinoline | 1.44 | 10 | 6.9 |
| DF | 6-(benzyloxy)-1-[(E)-2-(2,2-difluoro-2H-1,3-benzodioxol-5-yl)ethenyl]-7-methoxy-1,2,3,4-tetrahydroisoquinoline | 5.44 | 10 | 1.8 |
| DG | 6-(benzyloxy)-7-methoxy-1-[(E)-2-(2-methoxyphenyl)ethenyl]-1,2,3,4-tetrahydroisoquinoline | 2.2 | 9 | 4.1 |
| DH | 6-(benzyloxy)-7-methoxy-1-[(E)-2-[2-(morpholin-4-yl)phenyl]ethenyl]-1,2,3,4-tetrahydroisoquinoline | 5.26 | 17.8 | 3.4 |
| DI | 6-(benzyloxy)-7-methoxy-1-[(E)-2-(6-methoxynaphthalen-2-yl)ethenyl]-1,2,3,4-tetrahydroisoquinoline | 0.628 | 5.84 | 9.2 |
| DJ | 6-(benzyloxy)-7-methoxy-1-[(E)-2-[4-(pyridin-3-yl)phenyl]ethenyl]-1,2,3,4-tetrahydroisoquinoline | 0.393 | 5.86 | 15 |

TABLE-continued

| Code | Structure Name | EC$_{50}$, μM | CC$_{50}$, μM | SI |
|---|---|---|---|---|
| DK | 6-(benzyloxy)-1-[(E)-2-[4-(1H-imidazol-1-yl)phenyl]ethenyl]-7-methoxy-1,2,3,4-tetrahydroisoquinoline | 0.107 | 9.13 | 85 |
| DL | 7-[(E)-2-[6-(benzyloxy)-7-methoxy-1,2,3,4-tetrahydroisoquinolin-1-yl]ethenyl]quinoline | 0.0969 | 7 | 72 |
| DM | 6-(benzyloxy)-7-methoxy-1-[(E)-2-[4-(2-methyl-1H-imidazol-1-yl)phenyl]ethenyl]-1,2,3,4-tetrahydroisoquinoline | 1.52 | 21.1 | 14 |
| DN | 6-(benzyloxy)-7-methoxy-1-[(E)-2-[2-(3-methoxyphenyl)pyrimidin-5-yl]ethenyl]-1,2,3,4-tetrahydroisoquinoline | 2.4 | 17.1 | 7.1 |
| DO | 6-(benzyloxy)-1-[(E)-2-[4-(4-ethylpiperazin-1-yl)phenyl]ethenyl]-7-methoxy-1,2,3,4-tetrahydroisoquinoline | 0.496 | 3.61 | 7.3 |
| DP | 6-(benzyloxy)-7-methoxy-1-[(E)-2-{1-methyl-1H-pyrrolo[2,3-b]pyridin-3-yl}ethenyl]-1,2,3,4-tetrahydroisoquinoline | 0.015 | 1.3 | 92 |
| DQ | 6-(benzyloxy)-7-methoxy-1-[(E)-2-[3-(pyridin-4-yl)phenyl]ethenyl]-1,2,3,4-tetrahydroisoquinoline | 0.126 | 4.4 | 35 |
| DR | 6-(benzyloxy)-7-methoxy-1-[(E)-2-(1,3-thiazol-4-yl)ethenyl]-1,2,3,4-tetrahydroisoquinoline | 4.82 | 25.4 | 5.3 |
| DS | 6-(benzyloxy)-7-methoxy-1-[(E)-2-[4-(pyrimidin-5-yl)phenyl]ethenyl]-1,2,3,4-tetrahydroisoquinoline | 0.116 | 7.39 | 64 |
| DT | 6-(benzyloxy)-7-methoxy-1-[(E)-2-[4-(1H-1,2,4-triazol-1-yl)phenyl]ethenyl]-1,2,3,4-tetrahydroisoquinoline | 0.157 | 7.39 | 47 |
| DU | 1-[(E)-2-(1-benzothiophen-2-yl)ethenyl]-6-(benzyloxy)-7-methoxy-1,2,3,4-tetrahydroisoquinoline | 10.1 | 16.3 | 1.6 |
| DV | 6-(benzyloxy)-7-methoxy-1-[(E)-2-(1,3-thiazol-2-yl)ethenyl]-1,2,3,4-tetrahydroisoquinoline | 29.5 | 21.8 | 0.74 |
| DW | 6-(benzyloxy)-7-methoxy-1-[(E)-2-[4-(4-methylpiperazin-1-yl)phenyl]ethenyl]-1,2,3,4-tetrahydroisoquinoline | 1.24 | 2.31 | 1.9 |
| DX | 6-(benzyloxy)-7-methoxy-1-[(E)-2-[2-(piperidin-1-yl)phenyl]ethenyl]-1,2,3,4-tetrahydroisoquinoline | 4.2 | 5.38 | 1.3 |
| DY | 6-(benzyloxy)-7-methoxy-1-[(E)-2-(4-methyl-1,3-thiazol-5-yl)ethenyl]-1,2,3,4-tetrahydroisoquinoline | 5.51 | 21.6 | 3.9 |
| DZ | 6-(benzyloxy)-7-methoxy-1-[(E)-2-[4-(pyridin-2-yl)phenyl]ethenyl]-1,2,3,4-tetrahydroisoquinoline | 0.65 | 5.8 | 8.9 |
| EA | 6-(benzyloxy)-7-methoxy-1-[(E)-2-[4-(piperidin-1-yl)phenyl]ethenyl]-1,2,3,4-tetrahydroisoquinoline | 2.1 | 4.8 | 2.3 |
| EB | 6-(benzyloxy)-7-methoxy-1-[(E)-2-(6-methoxy-1-benzofuran-5-yl)ethenyl]-1,2,3,4-tetrahydroisoquinoline | 0.3 | 6 | 20 |
| EC | 6-(benzyloxy)-7-methoxy-1-[(E)-2-[3-(1,3-oxazol-2-yl)phenyl]ethenyl]-1,2,3,4-tetrahydroisoquinoline | 0.93 | 7.5 | 8 |
| ED | 6-(benzyloxy)-7-methoxy-1-[(E)-2-[4-(1,3-oxazol-2-yl)phenyl]ethenyl]-1,2,3,4-tetrahydroisoquinoline | 0.58 | 7.5 | 13 |
| EE | ethyl 2-{4-[(E)-2-[6-(benzyloxy)-7-methoxy-1,2,3,4-tetrahydroisoquinolin-1-yl]ethenyl]phenyl}-1,3-oxazole-4-carboxylate | 0.99 | 5.9 | 2.8 |
| EF | ethyl 2-{3-[(E)-2-[6-(benzyloxy)-7-methoxy-1,2,3,4- | 1 | 5.9 | 6 |

TABLE-continued

| Code | Structure Name | EC$_{50}$, μM | CC$_{50}$, μM | SI |
|---|---|---|---|---|
| | tetrahydroisoquinolin-1-yl]ethenyl]phenyl}-1,3-oxazole-4-carboxylate | | | |
| EG | 6-(benzyloxy)-1-[(E)-2-(2,3-dihydro-1-benzofuran-6-yl)ethenyl]-7-methoxy-1,2,3,4-tetrahydroisoquinoline | 0.9 | 19.3 | 21.4 |
| EH | 6-(benzyloxy)-1-[(E)-2-(2,4-dimethoxy-5-methylphenyl)ethenyl]-7-methoxy-1,2,3,4-tetrahydroisoquinoline | 0.066 | 3.59 | 54.5 |
| EI | 6-(benzyloxy)-7-methoxy-1-[(E)-2-(4-methoxy-3-methylphenyl)ethenyl]-1,2,3,4-tetrahydroisoquinoline | 0.34 | 11.8 | 35.3 |
| EJ | 6-(benzyloxy)-7-methoxy-1-[(E)-2-(3-methoxyphenyl)ethenyl]-1,2,3,4-tetrahydroisoquinoline | 2.98 | 10 | 3.3 |
| EK | 6-(benzyloxy)-1-[(E)-2-(2,5-dimethoxyphenyl)ethenyl]-7-methoxy-1,2,3,4-tetrahydroisoquinoline | 0.38 | 3.6 | 9.5 |
| EL | 6-(benzyloxy)-7-methoxy-1-[(E)-2-(4-methoxy-2,3-dimethylphenyl)ethenyl]-1,2,3,4-tetrahydroisoquinoline | 0.15 | 3.25 | 21.7 |
| EM | 6-(benzyloxy)-7-methoxy-1-[(E)-2-[4-methoxy-3-(piperidin-1-ylmethyl)phenyl]ethenyl]-1,2,3,4-tetrahydroisoquinoline | 0.32 | 1.8 | 5.6 |
| EN | 6-(benzyloxy)-7-methoxy-1-[(E)-2-{4-methoxy-3-[(2-methyl-1H-imidazol-1-yl)methyl]phenyl}ethenyl]-1,2,3,4-tetrahydroisoquinoline | 0.189 | 4.03 | 21.3 |
| EO | 6-(benzyloxy)-7-methoxy-1-[(E)-2-{4-methoxy-3-[(2,2,2-trifluoroethoxy)methyl]phenyl}ethenyl]-1,2,3,4-tetrahydroisoquinoline | 0.504 | 1.94 | 3.8 |
| EP | 6-(benzyloxy)-7-methoxy-1-[(E)-2-[4-methoxy-3-(methoxymethyl)phenyl]ethenyl]-1,2,3,4-tetrahydroisoquinoline | 0.846 | 4 | 4.7 |
| EQ | 4-[(E)-2-[6-(benzyloxy)-7-methoxy-1,2,3,4-tetrahydroisoquinolin-1-yl]ethenyl]benzoic acid | 7.04 | 10 | 1.4 |
| ER | 3-[(E)-2-[6-(benzyloxy)-7-methoxy-1,2,3,4-tetrahydroisoquinolin-1-yl]ethenyl]benzoic acid | 10 | 10 | 1 |
| ES | 2-[(E)-2-[6-(benzyloxy)-7-methoxy-1,2,3,4-tetrahydroisoquinolin-1-yl]ethenyl]benzoic acid | 8.62 | 10 | 1.2 |
| ET | ethyl 2-[(E)-2-[6-(benzyloxy)-7-methoxy-1,2,3,4-tetrahydroisoquinolin-1-yl]ethenyl]benzoate | 2.48 | 9.9 | 4 |
| EU | 6-(benzyloxy)-7-methoxy-1-[(E)-2-[4-methoxy-3-(phenoxymethyl)phenyl]ethenyl]-1,2,3,4-tetrahydroisoquinoline | 0.24 | 5.1 | 21.3 |

It is understood that the examples and embodiments described herein are for illustrative purposes only and that various modifications or changes in light thereof will be suggested to persons skilled in the art and are to be included within the spirit and purview of this application and scope of the appended claims. It is to be understood that the present invention covers all combinations of aspects and/or embodiments, as well as suitable, convenient and preferred groups described herein. All publications, patents, and patent applications cited herein are hereby incorporated by reference in their entirety for all purposes.

The invention is further illustrated by the Examples that follow. The Examples are not intended to define or limit the scope of the invention.

What is claimed is:

1. A compound which is:

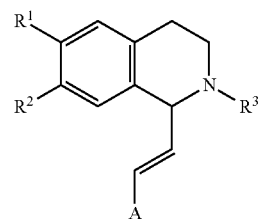

in which R¹ is H or unsubstituted alkoxy or phenyl substituted alkoxy;
R² is H or CF₃ or unsubstituted alkoxy or phenyl substituted alkoxy;
R³ is H or —C(O)OR⁴ or —C(O)R⁴ or —C(O)NR⁴R⁵ wherein R⁴ and R⁵ are independently selected from unsubstituted alkyl, unsubstituted phenyl, or unsubstituted pyridinyl;
A is substituted or unsubstituted pyrazole or substituted pyridinyl
or substituted thienyl or substituted or unsubstituted pyrimidinyl
or substituted or unsubstituted pyrrole or substituted or unsubstituted thiazolyl or a hydrate, solvate, or salt thereof.

2. The compound of claim 1, which is:

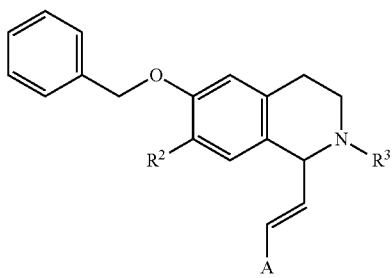

or a hydrate, solvate, or salt thereof.

3. The compound of claim 1, which is:

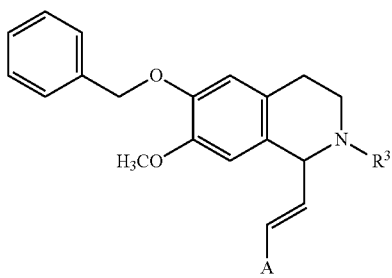

or a hydrate, solvate, or salt thereof.

4. The compound of claim 1, which is:

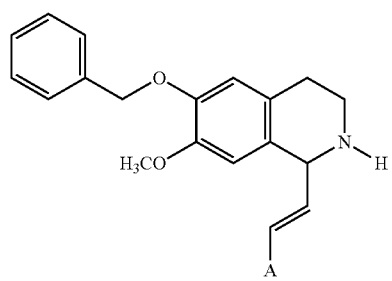

or a hydrate, solvate, or salt thereof.

5. A pharmaceutical formulation comprising:
a) a compound of claim 1, or a pharmaceutically acceptable salt thereof; and
b) a pharmaceutically acceptable excipient.

6. A method of inhibiting the replication of a virus in an animal, comprising:

a) administering a compound of claim 1 or a pharmaceutical formulation of claim 5
to the animal, wherein the animal is in need of treatment thereof thereby inhibiting the replication of the virus in an animal.

7. The method of claim 6, wherein the virus is a member of the Orthoretroviridae family.

8. The method of claim 6, wherein the virus is HIV.

9. A method of treating AIDS in an animal, comprising: a) administering a compound of claim 1 or a pharmaceutical formulation of a claim 5 to the animal, wherein the animal is in need of treatment thereof thereby treating the disease in the animal.

10. The method of claim 9, wherein the animal is a human.

11. A method of treating an HIV infection in a human, the method comprising administering to said human a therapeutically effective amount of a compound according to claim 1.

12. The compound of claim 1, wherein R¹ is H or —CH₃ or

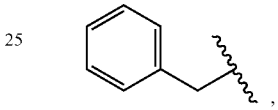

or a hydrate, solvate, or salt thereof.

13. The compound of claim 1, wherein R² is H or —CH₃ or

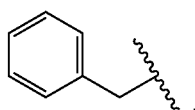

or a hydrate, solvate, or salt thereof.

14. The compound of claim 1, wherein R³ is selected from the group consisting of H, —C(O)OCH₃, —C(O)OC(CH₃)₃, —C(O)NH₂, —C(O)NHC(CH₃)₃, and —(CH₂)ₙCH₃, wherein n is an integer selected from 0-10, or a hydrate, solvate, or salt thereof.

15. The compound of claim 1, wherein R³ is selected from the group consisting of

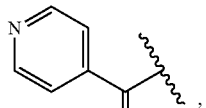 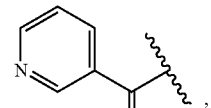

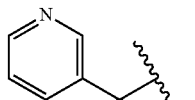 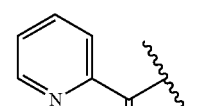

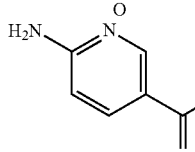 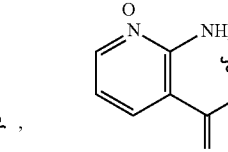

-continued

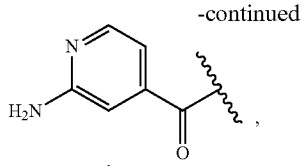

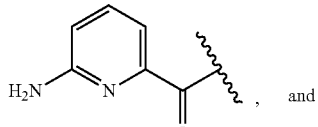
and

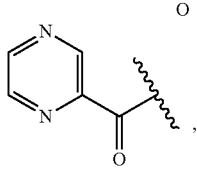

or a hydrate, solvate, or salt thereof.

16. The compound of claim 1, wherein A is unsubstituted pyrazolyl, or a hydrate, solvate, or salt thereof.

17. The compound of claim 1, wherein A is substituted pyrazolyl, or a hydrate, solvate, or salt thereof.

18. The compound of claim 1, wherein A is pyrazolyl substituted with $C_1$-$C_3$ alkyl, or a hydrate, solvate, or salt thereof.

19. The compound of claim 1, wherein A is pyrazolyl substituted with methyl, or a hydrate, solvate, or salt thereof.

20. The compound of claim 1, wherein A is

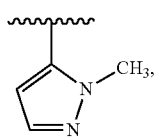 [SMILES: *c1ccnn1C]

or a hydrate, solvate, or salt thereof.

21. The compound of claim 1, wherein A is unsubstituted pyridinyl, or a hydrate, solvate, or salt thereof.

22. The compound of claim 1, wherein A is substituted pyridinyl or substituted pyridin-4-yl or substituted pyridin-3-yl or pyridinyl substituted with $C_1$-$C_3$ alkyloxy or pyridinyl substituted with two $C_1$-$C_3$ alkyloxy or is pyridinyl substituted with methoxy or pyridin-3-yl substituted with methoxy or pyridin-4-yl substituted with methoxy or pyridin-3-yl substituted with two methoxy or pyridin-4-yl substituted with two methoxy or

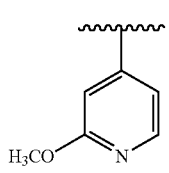 or 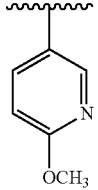 or

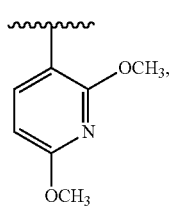

or a hydrate, solvate, or salt thereof.

23. The compound of claim 1, wherein A is
pyridinyl substituted with $NR^{10}R^{11}$, wherein $R^{10}$ and $R^{11}$ are each independently selected from H or unsubstituted $C_1$-$C_3$ alkyl, or
pyridinyl substituted with two $NR^{10}R^{11}$, wherein $R^{10}$ and $R^{11}$ are each independently selected from H or unsubstituted $C_1$-$C_3$ alkyl, or
pyridinyl substituted with $N(CH_3)_2$, or
pyridinyl substituted with $NH_2$, or
pyridin-3-yl substituted with $N(CH_3)_2$, or
pyridin-4-yl substituted with $N(CH_3)_2$, or
pyridin-3-yl substituted with $NH_2$, or
pyridin-4-yl substituted with $NH_2$, or

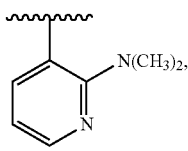 [SMILES: *c1cccnc1N(C)C]

or a hydrate, solvate, or salt thereof.

24. The compound of claim 1, wherein A is unsubstituted pyrimidinyl
or unsubstituted pyrimidin-5-yl,
or unsubstituted pyrimidin-4-yl,
or substituted pyrimidinyl,
or substituted pyrimidin-5-yl,
or substituted pyrimidin-4-yl,
or pyrimidinyl substituted with $C_1$-$C_3$ alkyloxy,
or pyrimidinyl substituted with two $C_1$-$C_3$ alkyloxy,
or pyrimidinyl substituted with methoxy,
or pyrimidin-5-yl substituted with methoxy,
or pyrimidin-4-yl substituted with methoxy,
or

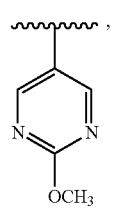

or pyrimidinyl substituted with substituted phenyl,
or pyrimidinyl substituted with unsubstituted phenyl,
or pyrimidinyl substituted with unsubstituted phenyl substituted with $C_1$-$C_3$ alkyloxy
or pyrimidinyl substituted with unsubstituted phenyl substituted with methoxy,
or

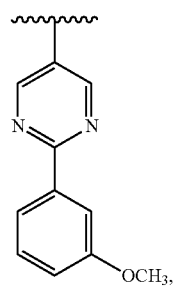 [SMILES: *c1cnc(-c2cccc(OC)c2)nc1]

or a hydrate, solvate, or salt thereof.

25. The compound of claim 1, wherein A is thienyl substituted with $C_1$-$C_3$ alkyl or thien-2-yl substituted with $C_1$-$C_3$ alkyl or thien-3-yl substituted with $C_1$-$C_3$ alkyl, or a hydrate, solvate, or salt thereof.

26. The compound of claim 1, wherein A is unsubstituted thiazolyl or unsubstituted thiazol-4-yl or unsubstituted thiazol-5-yl or unsubstituted thiazol-2-yl or thiazolyl substituted with $C_1$-$C_3$ alkyl or thiazol-4-yl substituted with $C_1$-$C_3$ alkyl or thiazol-5-yl substituted with $C_1$-$C_3$ alkyl or thiazol-2-yl substituted with $C_1$-$C_3$ alkyl, or a hydrate, solvate, or salt thereof.

27. The compound of claim 1, wherein the compound has a formula which is:

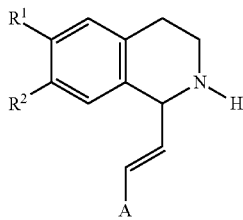

wherein $R^2$, $R^1$ and A are as described herein, or a hydrate, solvate, or salt thereof.

28. The compound of claim 1, wherein the compound has a formula which is:

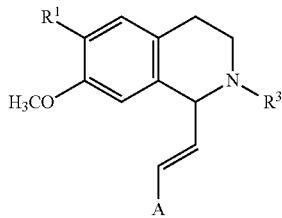

wherein $R^1$, $R^3$ and A are as described herein, or a hydrate, solvate, or salt thereof.

29. The compound of claim 1, wherein the compound has a formula which is:

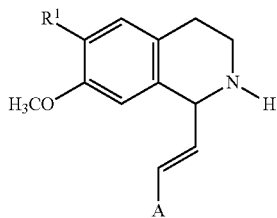

wherein $R^1$, $R^3$ and A are as described herein, or a hydrate, solvate, or salt thereof.

30. The compound of claim 1, wherein the compound is 6-benzyloxy-7-methoxy-1-[(E)-2-(2-methylpyrazol-3-yl)vinyl]-1,2,3,4-tetrahydroisoquinoline or 6-benzyloxy-1-[(E)-2-(1-ethylpyrazol-4-yl)vinyl]-7-methoxy-1,2,3,4-tetrahydroisoquinoline or 6-benzyloxy-1-[(E)-2-(1-methylpyrazol-4-yl)vinyl]-7-methoxy-1,2,3,4-tetrahydroisoquinoline or 6-benzyloxy-7-methoxy-1-[(E)-2-(2-methoxy-4-pyridyl)vinyl]-1,2,3,4-tetrahydroisoquinoline or 6-benzyloxy-7-methoxy-1-[(E)-2-(6-methoxy-3-pyridyl)vinyl]-1,2,3,4-tetrahydroisoquinoline or 6-benzyloxy-7-methoxy-1-[(E)-2-(3-methyl-2-thienyl)vinyl]-1,2,3,4-tetrahydroisoquinoline or 6-benzyloxy-1-[(E)-2-(2,6-dimethoxy-3-pyridyl)vinyl]-7-methoxy-1,2,3,4-tetrahydroisoquinoline or tert-butyl 2-[(E)-2-(6-benzyloxy-7-methoxy-1,2,3,4-tetrahydroisoquinolin-1-yl)vinyl]indole-1-carboxylate or tert-butyl 3-[(E)-2-(6-benzyloxy-7-methoxy-1,2,3,4-tetrahydroisoquinolin-1-yl)vinyl]indole-1-carboxylate or 6-benzyloxy-1-[(E)-2-(1H-indol-3-yl)vinyl]-7-methoxy-1,2,3,4-tetrahydroisoquinoline or 3-[(E)-2-(6-benzyloxy-7-methoxy-1,2,3,4-tetrahydroisoquinolin-1-yl)vinyl]-N,N-dimethyl-pyridin-2-amine or (E)-(benzyloxy)-7-methoxy-1-(2-(2-methoxypyrimidin-5-yl)vinyl)-1,2,3,4-tetrahydroisoquinoline or (E)-6-(benzyloxy)-7-methoxy-1-(2-(2-(3-methoxyphenyl)pyrimidin-5-yl)vinyl-1,2,3,4-tetrahydroisoquinoline or 6-(benzyloxy)-7-methoxy-1-[(E)-2-{1-methyl-1H-pyrrolo[2,3-b]pyridin-3-yl}ethenyl]-1,2,3,4-tetrahydroisoquinoline or 6-(benzyloxy)-7-methoxy-1-[(E)-2-(1,3-thiazol-4-yl)ethenyl]-1,2,3,4-tetrahydroisoquinoline or 1-[(E)-2-(1-benzothiophen-2-yl)ethenyl]-6-(benzyloxy)-7-methoxy-1,2,3,4-tetrahydroisoquinoline or 6-(benzyloxy)-7-methoxy-1-[(E)-2-(1,3-thiazol-2-yl)ethenyl]-1,2,3,4-tetrahydroisoquinoline or 5-[(E)-2-(6-benzyloxy-7-methoxy-1,2,3,4-tetrahydroisoquinolin-1-yl)vinyl]-4-methyl-thiazole, or a hydrate, solvate, or salt thereof.

31. The compound of claim 1, wherein the compound is 6-(benzyloxy)-7-methoxy-1-[(E)-2-{1-methyl-1H-pyrrolo[2,3-b]pyridin-3-yl}ethenyl]-1,2,3,4-tetrahydroisoquinoline, or a hydrate, solvate, or salt thereof.

* * * * *